(12) United States Patent
Watnick et al.

(10) Patent No.: US 11,071,779 B2
(45) Date of Patent: Jul. 27, 2021

(54) BIOFILM MATRIX-BOOSTED VACCINE

(71) Applicant: Children's Medical Center Corporation, Boston, MA (US)

(72) Inventors: Paula I. Watnick, Waban, MA (US); Szu Yu Liao, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 214 days.

(21) Appl. No.: 16/310,544

(22) PCT Filed: Jun. 16, 2017

(86) PCT No.: PCT/US2017/038045
§ 371 (c)(1),
(2) Date: Dec. 17, 2018

(87) PCT Pub. No.: WO2017/219004
PCT Pub. Date: Dec. 21, 2017

(65) Prior Publication Data
US 2020/0268867 A1 Aug. 27, 2020

Related U.S. Application Data

(60) Provisional application No. 62/351,895, filed on Jun. 17, 2016.

(51) Int. Cl.
*A61K 39/02* (2006.01)
*A61K 39/00* (2006.01)
*A61K 39/39* (2006.01)
*C07K 14/28* (2006.01)
*C12N 1/20* (2006.01)

(52) U.S. Cl.
CPC ............ *A61K 39/107* (2013.01); *C07K 14/28* (2013.01); *C12N 1/20* (2013.01); *A61K 39/39* (2013.01); *A61K 2039/522* (2013.01); *A61K 2039/542* (2013.01); *A61K 2039/55544* (2013.01)

(58) Field of Classification Search
None
See application file for complete search history.

(56) References Cited

U.S. PATENT DOCUMENTS

| 8,642,534 | B2 | 2/2014 | Yildiz |
| 10,722,569 | B2 | 7/2020 | Watnick |
| 2006/0235206 | A1 | 10/2006 | Pier et al. |
| 2011/0003734 | A1 | 1/2011 | Yildiz |
| 2011/0287443 | A1 | 11/2011 | Retallack et al. |
| 2015/0150959 | A1 | 6/2015 | Watnick |
| 2015/0165019 | A1 | 6/2015 | Del Giudice et al. |

FOREIGN PATENT DOCUMENTS

| WO | WO 2008/018903 A2 | 2/2008 |
| WO | WO 2012/014073 A2 | 2/2012 |
| WO | WO 2014/128555 A2 | 8/2014 |
| WO | WO 2015/095335 A1 | 6/2015 |

OTHER PUBLICATIONS

Kiereketal. Appl. Environ. Microbiol. 5079-5088, 2003.*
Lazar et al. Mol. Cellular Biol. 8: 1247-1252, 1988.*
Skolnick et al. Trends in Biotechnology 18: 34-39, 2000.*
U.S. Appl. No. 14/411,647, filed Dec. 29, 2014, Watnick et al.
EP 13813283.2, Dec. 4, 2015, Supplementary European Search Report.
EP 13813283.2, Mar. 14, 2019, European Office Action.
EP 13813283.2, Sep. 16, 2019, Further European Exam Report.
PCT/US2013/049337, Dec. 18, 2013, Invitation to Pay Additional Fees.
PCT/US2013/049337, Mar. 4, 2014, International Search Report and Written Opinion
PCT/US2013/049337, Jan. 15, 2015, International Preliminary Report on Patentability.
PCT/US2017/038045, Dec. 22, 2017, International Search Report and Written Opinion.
PCT/US2017/038045, Dec. 27, 2018, International Preliminary Report on Patentability.
[No Author Listed] GenBank Accession No. NP-231522. Heidelberg et al., DNA sequence of both chromosomes of the cholera pathogen Vibrio cholera. Nature. 2000;406(6795):477-483. Dec. 17, 2014.
Absalon et al., A communal bacterial adhesin anchors biofilm and bystander cells to surfaces. PLoS Pathog. Aug. 2011;7(8):e1002210. doi: 10.1371/journal.ppat.1002210. Epub Aug. 25, 2011.
Absalon et al., The bacterial biofilm matrix as a platform for protein delivery. MBio. Jul. 17, 2012;3(4):e00127-2. doi: 10.1128/mBio.00127-12.
Chen et al., A recombinant live attenuated strain of *Vibrio cholerae* induces immunity against tetanus toxin and *Bordetella pertussis* tracheal colonization factor. Infection and Immunity. Apr. 19, 1998; 66(4): 1648.
Dasgupta et al., Recombinant derivative of a naturally occurring non-toxinogenic *Vibrio cholerae* 01 expressing the B subunit of cholera toxin: a potential oral vaccine strain. Vaccine. 1994; 12(4):359.

(Continued)

*Primary Examiner* — Sarvamangala Devi
(74) *Attorney, Agent, or Firm* — Wolf, Greenfield & Sacks, P.C.

(57) ABSTRACT

Some aspects of this disclosure provide engineered exopolysaccharide-associated proteins, engineered bacteria expressing such proteins, and engineered biofilms comprising such proteins. Some aspects of this disclosure provide methods for engineering exopolysaccharide-associated proteins, and for the generation of engineered bacteria and biofilms expressing or comprising such proteins. Some aspects of this disclosure provide compositions and methods useful for the generation of vaccines and the vaccination of subjects, for delivering molecules of interest to a target site, for example, a surface, for purification of molecules of interest, for example, from bioreactors comprising engineered bacteria as provided herein, and for bioremediation applications, such as the cleanup of environmental pollutants.

12 Claims, 19 Drawing Sheets
Specification includes a Sequence Listing.

(56) References Cited

OTHER PUBLICATIONS

Giglio et al., Structural basis for biofilm formation via the Vibrio cholerae matrix protein RbmA. J Bacteriol. Jul. 2013;195(14):3277-86. doi: 10.1128/JB.00374-13. Epub May 17, 2013.
Heidelberg et al., DNA sequence of both chromosomes of the cholera pathogen Vibrio cholerae. Nature. Aug. 3, 2000;406(6795):477-84.
Kaper et al., Recombinant nontoxinogenic Vibrio cholerae strains as attenuated cholera vaccine candidates. Nature. Apr. 12-18, 1984;308(5960):655-8.
Krzych et al., Repertoires of T cells directed against a large protein antigen, beta-galactosidase. II. Only certain T helper or T suppressor cells are relevant in particular regulatory interactions. J Exp Med. Jul. 1, 1985;162(1):311-23.
Levine et al., Evaluation in humans of attenuated Vibrio cholerae E1 Tor Ogawa strain Texas Star-SR as a live oral vaccine. Infect Immun. Feb. 1984;43(2):515-22.
Silva et al., Vibrio cholerae Biofilms and Cholera Pathogenesis. PLoS Negl Trop Dis. Feb. 4, 2016;10(2):e0004330. doi: 10.1371/journal.pntd.0004330. eCollection Feb. 2016 Review.
Svennerholm., From cholera to enterotoxigenic *Escherichia coli* (ETEC) vaccine development. Indian J Med Res. Feb. 2011;133:188-96.

\* cited by examiner

FIGURE 2

| | Vibriocidal titer | | | |
|---|---|---|---|---|
| | Condition | Day 14 | Day 28 | Day 56 |
| Killed whole-cell vaccine | PBS | n.d. | n.d. | < 2 |
| | V. cholerae | n.d. | n.d. | 64 |
| | + CTB | n.d. | n.d. | 64 |
| Live-attenuated | RbmA-CtxB | 2 | 16 | 64 |

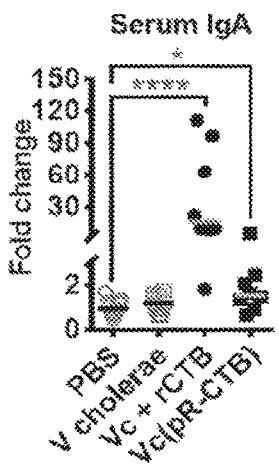
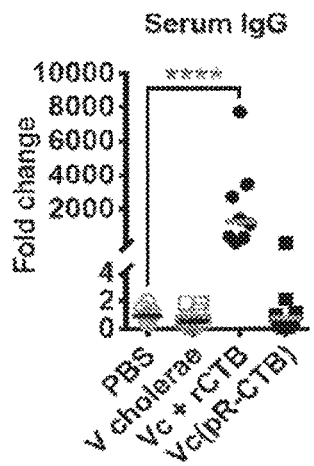
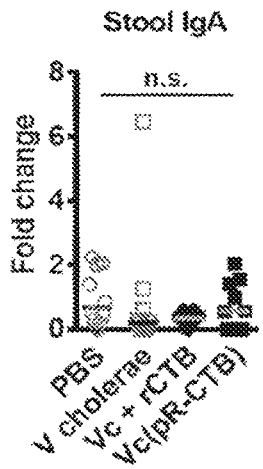
FIGURE 18A          FIGURE 18B          FIGURE 18C
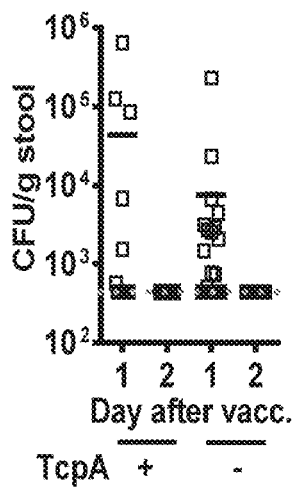
FIGURE 19

SEQUENCE LISTING

<160> NUMBER OF SEQ ID NOS: 66

<210> SEQ ID NO 1
<211> LENGTH: 691
<212> TYPE: PRT
<213> ORGANISM: Artificial Sequence
<220> FEATURE:
<223> OTHER INFORMATION: Synthetic Polypeptide

<400> SEQUENCE: 1

```
Met Lys Gln Thr Lys Thr Leu Thr Ala Ile Ser Val Leu Ala Leu Ser
1               5                   10                  15

His Leu Met Thr Gln Ser Thr Ala Phe Ala Ser Ser Ser Ser Asp Ile
            20                  25                  30

Gln Thr Lys Leu Lys Trp Ser Trp Ser Thr Ser Val Phe His Pro Glu
        35                  40                  45

Ser Asn Gln Val Met Ala Ala Pro Ile Val Val Gln Leu Asn Asp Asp
    50                  55                  60

Asn Gly Asp Gly Lys Ile Asp Glu Lys Asp Val Ala Asp Ile Ile Val
65                  70                  75                  80

Val Thr Phe Glu Gly Asn Lys Tyr Ala Asn Gly Gly Tyr Ile Arg Ala
                85                  90                  95

Leu Ser Gly Val Asp Gly Ser Glu Leu Trp Ser Tyr Ser Asn Gly Gly
            100                 105                 110

Val Ile Ala Asp Ala Arg Tyr Ala Pro Ala Ala Asp Leu Asp Gly
        115                 120                 125

Asp Gly Leu Ile Glu Ile Val Ser Thr Ser Ala Leu Thr Pro Tyr Ile
    130                 135                 140

Asn Ile Leu Asp His Gln Gly Asn Ile Lys Lys Gln Leu Leu Lys Ser
145                 150                 155                 160

Ala Ser Gly Trp Arg Ser Val Gly Asp Ile Ala Leu Ala Asp Ile Asn
                165                 170                 175

Gly Asp Gly Asn Ile Glu Ile Leu Ala Ala Asp Gly Val Tyr Ser Tyr
            180                 185                 190

Glu Ser Gly Leu Leu Phe Ser His Asp Trp Ala Pro Ser Ser Ile Ala
        195                 200                 205

Phe Asp Ser Asn Gly Asp Gly Gln Arg Glu Val Phe Ala Asn Gly Thr
    210                 215                 220

Leu Tyr Gln Asn Asn Gly Ala Tyr Leu Trp Gln Tyr Gln Ala Asn Asp
225                 230                 235                 240

Thr Val Trp Phe Ser Ser Val Ala Asn Leu Asp Gly Asp Lys Pro
                245                 250                 255

Glu Leu Val Val Ser Val Pro Ala Ser Leu Ser Thr Pro Glu Asn Ser
            260                 265                 270

Glu Ile Ala Val Leu Glu His Asp Gly Ser Val Lys Trp Arg Val Asn
        275                 280                 285

Asn Leu Ser Asn Pro Gly Gly Ser Val Gln Ala Val Ser Ser Phe Leu
    290                 295                 300

Gly Lys Pro Ser Ser Ser Ala Thr Thr Val Asp Ala Gln Ser Ala Val
305                 310                 315                 320

Tyr Gly Tyr Thr Asp Trp Ala His Gln Gln Arg Val Leu Ala Glu Asn
                325                 330                 335

His Gln Leu Ala Ile Arg Ser Gly Ala Val Val Asp Ala Ile Gly Ala
            340                 345                 350

Asn Ser Gln Asn Met Ile Gly Gly Ser Gly Gly Ser Leu Ser Thr Ile
```

```
                355                 360                 365
Asp Thr Ser Lys Val Arg Ala Ile Asp Val Thr Tyr Gly Lys Asn Lys
    370                 375                 380

Tyr Thr Trp Lys Tyr Gly Val Leu Glu Met Ser Phe Thr Leu Asp Asn
385                 390                 395                 400

Gly Ala Lys Val Thr Val Gly Ser Lys Asp Ser Ala Phe Thr Tyr Leu
                405                 410                 415

Gly Leu Glu Trp Lys Thr Lys Thr Val Pro Tyr Leu Gly Val Glu Trp
            420                 425                 430

Arg Thr Lys Thr Val Ser Tyr Trp Phe Phe Gly Trp His Thr Lys Gln
        435                 440                 445

Val Ala Tyr Leu Ala Pro Val Trp Lys Glu Lys Thr Ile Pro Tyr Ala
    450                 455                 460

Val Pro Val Thr Leu Ser Lys Ser Thr Thr Val Arg Tyr Asp Ile Pro
465                 470                 475                 480

Gln Gly Ser Gln Leu Leu Gly Met Asn Val Trp Ser Lys Glu Lys His
                485                 490                 495

Leu Phe Lys His Lys Gln Gln Val Asn Ala Val Gln Phe Leu Val Gly
            500                 505                 510

Lys Val Thr Ala Asp Gln Ser His Met Gly Ile Val Tyr Ala Gly Tyr
        515                 520                 525

Tyr Ala Val Asp Met Tyr Asp Ala Gln Gly Asn Lys Val Trp Ser Val
    530                 535                 540

Ala Asn Asp Asp Leu Asn Ser Gly Lys Ile Gly Val Ser Ala Tyr Asp
545                 550                 555                 560

Phe Thr Gly Asp Gly Ile Asp Glu Val Leu Val Gln Asp Arg Leu Arg
                565                 570                 575

Met Arg Ile Leu Asp Gly Gln Thr Gly Arg Val Met Gly Ile Ile Ala
            580                 585                 590

Asn Ser Ser Gly Thr Leu Trp Glu Tyr Pro Val Ala Asp Leu Glu
        595                 600                 605

Gly Asn Asn Asn Ala Ser Leu Ile Met Val Ala Asn Asp Tyr Asp Arg
    610                 615                 620

Glu Ser Gln Val Asn His Gly Val Phe Val Tyr Glu Ser Ala Asn Pro
625                 630                 635                 640

Ser Lys Pro Trp Arg Asn Ala Thr Arg Ile Trp Asn Gln Tyr Ala Phe
                645                 650                 655

Asn Phe Ser Asp Ile Asn Ala Asn Gly Thr Ile Pro Thr Asn Ala Gln
            660                 665                 670

Pro Ser Trp Leu Thr His Asn Ser Phe Arg Ser Ala Thr Ile Arg Val
        675                 680                 685

Pro Leu Lys
    690

<210> SEQ ID NO 2
<211> LENGTH: 271
<212> TYPE: PRT
<213> ORGANISM: Artificial Sequence
<220> FEATURE:
<223> OTHER INFORMATION: Synthetic Polypeptide

<400> SEQUENCE: 2

Met Ser Asn Phe Lys Gly Ser Ile Met Asn Lys Arg His Tyr Tyr Leu
1               5                   10                  15

Ala Ser Cys Leu Ala Leu Leu Phe Ser Thr Ala Ser Tyr Ala Glu Val
```

-continued

```
                20                  25                  30
Asp Cys Glu Leu Gln Pro Val Ile Glu Ala Asn Leu Ser Leu Asn Gln
            35                  40                  45
Asn Gln Leu Ala Ser Asn Gly Gly Tyr Ile Ser Ser Gln Leu Gly Ile
        50                  55                  60
Arg Asn Glu Ser Cys Glu Thr Val Lys Phe Lys Tyr Trp Leu Ser Ile
65                  70                  75                  80
Lys Gly Pro Glu Gly Ile Tyr Phe Pro Ala Lys Ala Val Val Gly Val
                85                  90                  95
Asp Thr Ala Gln Gln Glu Ser Asp Ala Leu Thr Asp Gly Arg Met Leu
            100                 105                 110
Asn Val Thr Arg Gly Phe Trp Val Pro Glu Tyr Met Ala Asp Gly Lys
        115                 120                 125
Tyr Thr Val Ser Leu Gln Val Val Ala Glu Asn Gly Lys Val Phe Lys
        130                 135                 140
Ala Asn Gln Glu Phe Val Lys Gly Val Asp Leu Asn Ser Leu Pro Glu
145                 150                 155                 160
Leu Asn Gly Leu Thr Ile Asp Ile Lys Asn Gln Phe Gly Ile Asn Ser
                165                 170                 175
Val Glu Ser Thr Gly Gly Phe Val Pro Phe Thr Val Asp Leu Asn Asn
            180                 185                 190
Gly Arg Glu Gly Glu Ala Asn Val Glu Phe Trp Met Thr Ala Val Gly
        195                 200                 205
Pro Asp Gly Leu Ile Ile Pro Val Asn Ala Arg Glu Lys Trp Val Ile
        210                 215                 220
Ala Ser Gly Asp Thr Tyr Ser Lys Val Arg Gly Ile Asn Phe Asp Lys
225                 230                 235                 240
Ser Tyr Pro Ala Gly Glu Tyr Thr Ile Asn Ala Gln Val Val Asp Ile
                245                 250                 255
Val Ser Gly Glu Arg Val Glu Gln Ser Met Thr Val Val Lys Lys
            260                 265                 270
```

<210> SEQ ID NO 3
<211> LENGTH: 957
<212> TYPE: PRT
<213> ORGANISM: Artificial Sequence
<220> FEATURE:
<223> OTHER INFORMATION: Synthetic Polypeptide

<400> SEQUENCE: 3

```
Met Thr Ser His Tyr Ile Ala Leu Ala Val Gly Leu Leu Ser Leu Ser
1               5                   10                  15
Ser Asn Val Val Gln Ala Thr Thr Asn Glu Ala Glu Gly Cys Ile Ile
            20                  25                  30
Ser Arg Leu Asn Gly Glu Lys Tyr Cys Leu Lys Val Gly Glu Arg Ser
        35                  40                  45
Gly Tyr Ser Leu Pro Ser Trp Ile Tyr Ala His Pro Val Asp Val Gln
        50                  55                  60
Ala Pro Ser Gly Val Ser Val Met Leu Ser Asp Trp Asp Asn Leu Ser
65                  70                  75                  80
Tyr Asn Arg Leu Ala Val Phe Asp Arg Tyr Thr Gly Asn Glu Asp Leu
                85                  90                  95
Lys Asn Val Lys Ala Tyr Asn Gly Ala Tyr Leu Asp Phe Ser Lys Pro
            100                 105                 110
Arg Ser Met Arg Val Leu Ala Ser Glu Thr Tyr Pro Glu Ala Cys Ile
```

```
            115                 120                 125
Val Ser Arg Gln Thr Gly Glu Arg Phe Cys Leu Lys Glu Gly Glu Arg
130                 135                 140

Ser Gly Tyr Ser Leu Pro Ala Tyr Ile Tyr Gly His Glu Val Asp Val
145                 150                 155                 160

Glu Ala Pro Leu Gly Leu Gly Val Met Leu Ser Asp Trp Asp Asn Leu
                    165                 170                 175

Ser Tyr Asn Arg Leu Ala Val Phe Gly Gly Asn Thr Gln Asn Glu Gln
                180                 185                 190

Met Arg Ala Val Lys Ala Tyr Asn Gly Glu Thr Leu Asp Phe Ser Lys
            195                 200                 205

Pro Arg Ser Met Arg Val Val Pro Tyr Asp Gly Asp Ser Ser Ala Leu
210                 215                 220

Asn Met Lys Leu Lys Trp Ser Trp Gln Gly Ser Ala Phe Gln Pro Asn
225                 230                 235                 240

Ser Asn Gln Val Met Val Thr Pro Ile Val Ala Gln Leu Asn Asp Asp
                    245                 250                 255

Asn Gly Asp Gly Lys Ile Asp Glu Lys Asp Val Ala Asp Leu Ile Val
                260                 265                 270

Val Thr Phe Glu Gly Asn Lys Tyr Ala Asn Gly Gly Leu Val Arg Ala
            275                 280                 285

Leu Ser Gly Val Asp Gly Ser Glu Leu Trp Ser Tyr Ala Asn Gly Gly
290                 295                 300

Val Ile Ala Asp Ala Arg Tyr Ser Pro Ala Val Gly Asp Leu Asp Gly
305                 310                 315                 320

Asp Gly Ile Val Glu Ile Val Thr Thr Asn Asn Arg Asp Gln Phe Ile
                    325                 330                 335

Thr Ile Leu Asp Asn Gln Gly Asn Ile Lys Lys Gln Ile Pro Thr Thr
                340                 345                 350

Glu Ser Gly Trp Arg Ile Val Gly Asp Ile Thr Leu Ala Asp Leu Asp
            355                 360                 365

His Asp Gly Ser Val Glu Ile Leu Ala Ala Asp Gly Val Tyr Asn Tyr
370                 375                 380

His Ser Gly Leu Val Phe Asn His Pro Trp Ala Pro Ser Ser Ile Asn
385                 390                 395                 400

Val Asp Val Asp Gly Asp Gln Gln Gln Glu Val Phe Ser Gly Gly Thr
                    405                 410                 415

Leu Phe Gln Asn Asn Gly Ala Ile Asn Trp Gln Tyr Gln Ala Asn Asp
                420                 425                 430

Ala Val Trp Phe Ser Ser Leu Val Asn Leu Asp Asn Asp Ala Glu Pro
            435                 440                 445

Glu Ile Val Ala Ser Val Pro Ala Thr Phe Ala Thr Gly Asp Asn Ala
450                 455                 460

Arg Phe Ala Val Leu Glu His Asp Gly Thr Ile Lys Trp Glu Ile Asn
465                 470                 475                 480

Asn Thr Ala Asn Pro Gly Gly Val Gln Ala Val Ser Asn Phe Leu
                    485                 490                 495

Gly Lys Ala Gln Ala Val Glu Thr Ser Glu Phe Ser Lys Val Tyr Gly
                500                 505                 510

Tyr Gln Pro Asn Asn Pro Ala Ser Ile Ala Leu Ala Val Asp Gly
            515                 520                 525

Lys Ile Ser Val Arg Ser Gly Phe Ala Ile Asp Ala Ile Gly Ala Ser
530                 535                 540
```

```
Ala Ser Thr Leu Val Gly Gly Thr Gly Gly Asn Leu Asn Ala Ala Val
545                 550                 555                 560

Asn Val Lys Asp Ile Lys Ala Ile Asp Leu Thr Trp Gly Lys Tyr Tyr
            565                 570                 575

Trp Gly Gly Tyr His Leu Leu Ala Leu Asp Phe Arg Met Ser Asn Gly
            580                 585                 590

Ser Val Ile Ser Met Gly Ser Lys Asn Tyr Ala Tyr Ser Lys Gln Thr
            595                 600                 605

Glu Arg Phe Thr Val Pro Ala Gly Ser Arg Ile Lys Gly Ile Lys Ala
610                 615                 620

Trp Thr Ala Gly Trp Leu Leu Asp Gly Val Gln Phe Glu Leu Ala Thr
625                 630                 635                 640

Gln Asn Gly Thr Asn Asp Leu Asp Val Lys Gly Ile Val Tyr Ala Gly
                645                 650                 655

Tyr Ala Ala Val Asp Met Tyr Asn Ser Lys Gly Glu Arg Val Trp Ser
                660                 665                 670

Val Ala Asn Asp Asp Thr Gly Ser Gly Lys Ile Gly Val Ser Ala Tyr
            675                 680                 685

Asp Phe Asp Asn Asp Gly Ile Asp Glu Val Leu Val Gln Asp His Ala
            690                 695                 700

Arg Val Arg Val Leu Asp Gly Lys Thr Gly Lys Glu Arg Ala Ser Leu
705                 710                 715                 720

Ala His Ser Thr Ala Thr Leu Trp Glu Tyr Pro Ile Val Val Asp Leu
                725                 730                 735

Glu Gly Asp Asn Asn Ala Glu Leu Ile Val Ala Ala Asn Asp Phe Asp
                740                 745                 750

Arg Gln Tyr Ser Ile Asn His Gly Val Tyr Val Tyr Gln Ser Ala Asp
            755                 760                 765

Ser Ser Lys Pro Trp Lys Asn Ala Thr Arg Ile Trp Asn Gln His Ala
            770                 775                 780

Phe His Leu Thr Asn Ile Asn Gln Asp Gly Thr Leu Pro Thr Phe Val
785                 790                 795                 800

Glu Pro Ser Trp Leu Ser His Asn Thr Tyr Arg Ser Ser Thr Leu Arg
                805                 810                 815

Ala Ala Val Gly Gly Glu Ser Pro Ile Phe Gly Tyr Ser Asn Thr Gln
                820                 825                 830

Gln Ser Gln Arg Val Val Thr Ala Asp Asn Leu Met Tyr Leu Arg Ser
            835                 840                 845

Gly Phe Ala Ile Asp Ala Ile Gly Thr Thr Val Asn Asn Leu Val Gly
            850                 855                 860

Gly Pro Val Gln Gly Thr Asn Gly Gly Val Leu Arg Ala Pro Ile Ala
865                 870                 875                 880

Leu Asp Gln Leu Gln Ser Val Glu Val Thr Ser Gly Leu Tyr Asn Trp
                885                 890                 895

Gly Gly Tyr His Ile Val Ala Ile Lys Phe Thr Met Lys Asp Gly Ser
                900                 905                 910

Ser Val Leu Leu Gly Ser Thr His Tyr Ala Ser Asn Lys Lys Val Glu
            915                 920                 925

Thr Tyr Thr Val Pro Gln Gly Lys Arg Ile Lys Gln Ile Asn Val Trp
            930                 935                 940

Thr Gly Gly Trp Leu Val Glu Gly Phe Gln Phe Val Tyr
945                 950                 955
```

<210> SEQ ID NO 4
<211> LENGTH: 741
<212> TYPE: PRT
<213> ORGANISM: Artificial Sequence
<220> FEATURE:
<223> OTHER INFORMATION: Synthetic Polypeptide

<400> SEQUENCE: 4

```
Met Pro Lys Leu Asn Arg Cys Ala Ile Ala Ile Phe Thr Ile Leu Ser
1               5                   10                  15

Ala Ile Ser Ser Pro Thr Leu Leu Ala Asn Ile Asn Glu Pro Ser Gly
            20                  25                  30

Glu Ala Ala Asp Ile Ile Ser Gln Val Ala Asp Ser His Ala Ile Lys
        35                  40                  45

Tyr Tyr Asn Ala Ala Asp Trp Gln Ala Glu Asp Asn Ala Leu Pro Ser
    50                  55                  60

Leu Ala Glu Leu Arg Asp Leu Val Ile Asn Gln Gln Lys Arg Val Leu
65                  70                  75                  80

Val Asp Phe Ser Gln Ile Ser Asp Ala Glu Gly Gln Ala Glu Met Gln
                85                  90                  95

Ala Gln Phe Arg Lys Ala Tyr Gly Val Gly Phe Ala Asn Gln Phe Ile
            100                 105                 110

Val Ile Thr Glu His Lys Gly Glu Leu Leu Phe Thr Pro Phe Asp Gln
        115                 120                 125

Ala Glu Glu Val Asp Pro Gln Leu Leu Glu Ala Pro Arg Thr Ala Arg
    130                 135                 140

Leu Leu Ala Arg Ser Gly Phe Ala Ser Pro Ala Asn Ser Glu
145                 150                 155                 160

Thr Asn Thr Leu Pro His Val Ala Phe Tyr Ile Ser Val Asn Arg Ala
                165                 170                 175

Ile Ser Asp Glu Glu Cys Thr Phe Asn Asn Ser Trp Leu Trp Lys Asn
            180                 185                 190

Glu Lys Gly Ser Arg Pro Phe Cys Lys Asp Ala Asn Ile Ser Leu Ile
        195                 200                 205

Tyr Arg Val Asn Leu Glu Arg Ser Leu Gln Tyr Gly Ile Val Gly Ser
    210                 215                 220

Ala Thr Pro Asp Ala Lys Ile Val Arg Ile Ser Leu Asp Asp Ser
225                 230                 235                 240

Thr Gly Ala Gly Ile His Leu Asn Asp Gln Leu Gly Tyr Arg Gln Phe
                245                 250                 255

Gly Ala Ser Tyr Thr Thr Leu Asp Ala Tyr Phe Arg Glu Trp Ser Thr
            260                 265                 270

Asp Ala Ile Ala Gln Asp Tyr Arg Phe Val Phe Asn Ala Ser Asn Asn
        275                 280                 285

Lys Ala Gln Ile Leu Lys Thr Phe Pro Val Asp Asn Ile Asn Glu Lys
    290                 295                 300

Phe Glu Arg Lys Glu Val Ser Gly Phe Glu Leu Gly Val Thr Gly Gly
305                 310                 315                 320

Val Glu Val Ser Gly Asp Gly Pro Lys Ala Lys Leu Glu Ala Arg Ala
                325                 330                 335

Ser Tyr Thr Gln Ser Arg Trp Leu Thr Tyr Asn Thr Gln Asp Tyr Arg
            340                 345                 350

Ile Glu Arg Asn Ala Lys Asn Ala Gln Ala Val Ser Phe Thr Trp Asn
        355                 360                 365
```

-continued

```
Arg Gln Gln Tyr Ala Thr Ala Glu Ser Leu Leu Asn Arg Ser Thr Asp
    370                 375                 380
Ala Leu Trp Val Asn Thr Tyr Pro Val Asp Val Asn Arg Ile Ser Pro
385                 390                 395                 400
Leu Ser Tyr Ala Ser Phe Val Pro Lys Met Asp Val Ile Tyr Lys Ala
                405                 410                 415
Ser Ala Thr Glu Thr Gly Ser Thr Asp Phe Ile Ile Asp Ser Ser Val
            420                 425                 430
Asn Ile Arg Pro Ile Tyr Asn Gly Ala Tyr Lys His Tyr Tyr Val Val
        435                 440                 445
Gly Ala His Gln Phe Tyr His Gly Phe Glu Asp Thr Pro Arg Arg Arg
450                 455                 460
Ile Thr Lys Ser Ala Ser Phe Thr Val Asp Trp Asp His Pro Val Phe
465                 470                 475                 480
Thr Gly Gly Arg Pro Val Asn Leu Gln Leu Ala Ser Phe Asn Asn Arg
                485                 490                 495
Cys Ile Gln Val Asp Ala Gln Gly Arg Leu Ala Ala Asn Thr Cys Asp
            500                 505                 510
Ser Gln Gln Ser Ala Gln Ser Phe Ile Tyr Asp Gln Leu Gly Arg Tyr
        515                 520                 525
Val Ser Ala Ser Asn Thr Lys Leu Cys Leu Asp Gly Glu Ala Leu Asp
530                 535                 540
Ala Leu Gln Pro Cys Asn Gln Asn Leu Thr Gln Arg Trp Glu Trp Arg
545                 550                 555                 560
Lys Gly Thr Asp Glu Leu Thr Asn Val Tyr Ser Gly Glu Ser Leu Gly
                565                 570                 575
His Asp Lys Gln Thr Gly Glu Leu Gly Leu Tyr Ala Ser Ser Asn Asp
            580                 585                 590
Ala Val Ser Leu Arg Thr Ile Thr Ala Tyr Thr Asp Val Phe Asn Ala
        595                 600                 605
Gln Glu Ser Ser Pro Ile Leu Gly Tyr Thr Gln Gly Lys Met Asn Gln
610                 615                 620
Gln Arg Val Gly Gln Asp His Arg Leu Tyr Val Arg Ala Gly Ala Ala
625                 630                 635                 640
Ile Asp Ala Leu Gly Ser Ala Ser Asp Leu Leu Val Gly Asn Gly
                645                 650                 655
Gly Ser Leu Ser Ser Val Asp Leu Ser Gly Val Lys Ser Ile Thr Ala
            660                 665                 670
Thr Ser Gly Asp Phe Gln Tyr Gly Gly Gln Gln Leu Val Ala Leu Thr
        675                 680                 685
Phe Thr Tyr Gln Asp Gly Arg Gln Gln Thr Val Gly Ser Lys Ala Tyr
690                 695                 700
Val Thr Asn Ala His Glu Asp Arg Phe Asp Leu Pro Ala Ala Ala Lys
705                 710                 715                 720
Ile Thr Gln Leu Lys Ile Trp Ser Asp Asp Trp Leu Val Lys Gly Val
                725                 730                 735
Gln Phe Asp Leu Asn
            740
```

<210> SEQ ID NO 5
<211> LENGTH: 124
<212> TYPE: PRT
<213> ORGANISM: Artificial Sequence
<220> FEATURE:
<223> OTHER INFORMATION: Synthetic Polypeptide

<400> SEQUENCE: 5

Met Ile Lys Leu Lys Phe Gly Val Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile Tyr Thr Leu Asn Asp Lys Ile Phe Ser Tyr
            35                  40                  45

Thr Glu Ser Leu Ala Gly Lys Arg Glu Met Ala Ile Ile Thr Phe Lys
        50                  55                  60

Asn Gly Ala Ile Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120

<210> SEQ ID NO 6
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 6

Met Asn Ile Phe Lys Gln Thr Cys Val Gly Ala Phe Ala Val Ile Phe
1               5                   10                  15

Gly Ala Thr Ser Ile Ala Pro Thr Met Ala
            20                  25

<210> SEQ ID NO 7
<211> LENGTH: 46
<212> TYPE: PRT
<213> ORGANISM: Artificial Sequence
<220> FEATURE:
<223> OTHER INFORMATION: Synthetic Polypeptide

<400> SEQUENCE: 7

Met Lys Phe Leu Gln Gln Met Arg Lys Leu Phe Gly Leu Ala Ala Lys
1               5                   10                  15

Phe Pro Ala Arg Leu Thr Ile Ala Val Ile Gly Thr Ala Leu Leu Ala
            20                  25                  30

Gly Leu Val Gly Val Val Gly Asp Thr Ala Ile Ala Val Ala
        35                  40                  45

<210> SEQ ID NO 8
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 8

Met Asn Pro Met Thr Arg Arg His Thr Trp Thr Arg Leu Ala Cys Ala
1               5                   10                  15

Leu Ser Leu Gly Val Ala Ala Phe Ala Ala Gln Ala
            20                  25

```
<210> SEQ ID NO 9
<211> LENGTH: 34
<212> TYPE: PRT
<213> ORGANISM: Artificial Sequence
<220> FEATURE:
<223> OTHER INFORMATION: Synthetic Polypeptide

<400> SEQUENCE: 9

Met Ser Thr Phe Lys Leu Leu Lys Thr Leu Thr Ser Arg Arg Gln Val
1               5                   10                  15

Leu Lys Thr Gly Leu Ala Ala Leu Thr Leu Ser Gly Met Ser His Ala
            20                  25                  30

Val Ala

<210> SEQ ID NO 10
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 10

Met Lys Leu Ala Ala Cys Phe Leu Thr Leu Leu Pro Gly Phe Ala Val
1               5                   10                  15

Ala

<210> SEQ ID NO 11
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 11

Met His Pro Ser Thr Ser Arg Pro Ser Arg Arg Thr Leu Leu Thr Ala
1               5                   10                  15

Thr Ala Gly Ala Ala Leu Ala Ala Ala Thr Leu Val Pro Gly Thr Ala
            20                  25                  30

His Ala Ser Ser Gly Gly Arg
        35

<210> SEQ ID NO 12
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 12

Met Arg Phe Arg His Lys Ala Ala Ala Leu Ala Ala Thr Leu Ala Leu
1               5                   10                  15

Pro Leu Ala Gly Leu Val Gly Leu Ala Ser Pro Ala Gln Ala
            20                  25                  30

<210> SEQ ID NO 13
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 13

Ile Leu Pro Trp Lys Trp Pro Trp Trp Pro Trp Arg Arg
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 14

Val Phe Leu Arg Arg Ile Arg Val Ile Val Ile Arg
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 15

Val Phe Trp Arg Arg Ile Arg Val Trp Val Ile Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 16

Val Gln Leu Arg Ala Ile Arg Val Arg Val Ile Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 17

Val Gln Leu Arg Arg Ile Arg Val Trp Val Ile Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 18

Val Gln Trp Arg Ala Ile Arg Val Arg Val Ile Arg
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 19

Val Gln Trp Arg Arg Ile Arg Val Trp Val Ile Arg
1               5                   10

```
<210> SEQ ID NO 20
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 20

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
            20                  25

<210> SEQ ID NO 21
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 21

Gly Gly Leu Arg Ser Leu Gly Arg Lys Ile Leu Arg Ala Trp Lys Lys
1               5                   10                  15

Tyr Gly Pro Ile Ile Val Pro Ile Ile Arg Ile Gly
            20                  25

<210> SEQ ID NO 22
<211> LENGTH: 49
<212> TYPE: PRT
<213> ORGANISM: Artificial Sequence
<220> FEATURE:
<223> OTHER INFORMATION: Synthetic Polypeptide

<400> SEQUENCE: 22

Arg Leu Ala Arg Ile Val Val Ile Arg Val Ala Arg Leu Leu Gly Asp
1               5                   10                  15

Phe Phe Arg Lys Ser Lys Glu Lys Ile Gly Lys Glu Phe Lys Arg Ile
            20                  25                  30

Val Gln Arg Ile Lys Asp Phe Leu Arg Asn Leu Val Pro Arg Thr Glu
        35                  40                  45

Ser

<210> SEQ ID NO 23
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 23

Val Gln Leu Arg Ile Arg Val Ala Val Ile Arg Ala
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 24

Val Gln Arg Trp Leu Ile Val Trp Arg Ile Arg Lys
1               5                   10
```

-continued

```
<210> SEQ ID NO 25
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 25

Val Arg Leu Ile Val Ala Val Arg Ile Trp Arg Arg
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 26

Ile Trp Val Ile Trp Arg Arg
1               5

<210> SEQ ID NO 27
<211> LENGTH: 27
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(2)
<223> OTHER INFORMATION: Modified by dehydrobutyrine
<220> FEATURE:
<221> NAME/KEY: MISC_FEATURE
<222> LOCATION: (3)..(4)
<223> OTHER INFORMATION: Modified by dehydroalanine
<220> FEATURE:
<221> NAME/KEY: MISC_FEATURE
<222> LOCATION: (5)..(6)
<223> OTHER INFORMATION: Modified by 2-aminobutyric acid
<220> FEATURE:
<221> NAME/KEY: MISC_FEATURE
<222> LOCATION: (9)..(10)
<223> OTHER INFORMATION: Modified by 2-aminobutyric acid
<220> FEATURE:
<221> NAME/KEY: MISC_FEATURE
<222> LOCATION: (18)..(19)
<223> OTHER INFORMATION: Modified by 2-aminobutyric acid
<220> FEATURE:
<221> NAME/KEY: MISC_FEATURE
<222> LOCATION: (19)..(20)
<223> OTHER INFORMATION: Modified by 2-aminobutyric acid
<220> FEATURE:
<221> NAME/KEY: MISC_FEATURE
<222> LOCATION: (26)..(27)
<223> OTHER INFORMATION: Modified by dehydroalanine

<400> SEQUENCE: 27

Ile Ala Ile Leu Ala Pro Gly Ala Lys Gly Ala Leu Met Gly Ala Asn
1               5                   10                  15

Met Lys Ala Ala Asn Ala Ser Ile Asn Val Leu
            20                  25

<210> SEQ ID NO 28
<211> LENGTH: 12
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
```

```
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid

<400> SEQUENCE: 28

Val Xaa Xaa Arg Xaa Ile Arg Val Xaa Val Ile Arg
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 29

Ile Leu Lys Trp Lys Trp Pro Trp Trp Pro Trp Arg Arg
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 30

Ile Leu Pro Trp Lys Lys Pro Trp Trp Pro Trp Arg Arg
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 31

Ile Leu Lys Trp Lys Trp Pro Trp Trp Lys Trp Arg Arg
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 32

Ile Leu Arg Trp Lys Trp Arg Trp Trp Arg Trp Arg Arg
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified by [RbmA]-[CtxB]
```

<400> SEQUENCE: 33

Ile Leu Pro Trp Lys Trp Pro Trp Trp Pro Trp Arg Arg
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: Modified by [RbmC]

<400> SEQUENCE: 34

Ile Leu Lys Trp Lys Trp Pro Trp Trp Pro Trp Arg Arg
1               5                   10

<210> SEQ ID NO 35
<211> LENGTH: 279
<212> TYPE: PRT
<213> ORGANISM: Artificial Sequence
<220> FEATURE:
<223> OTHER INFORMATION: Synthetic Polypeptide

<400> SEQUENCE: 35

Met Ser Asn Phe Lys Gly Ser Ile Met Asn Lys Arg His Tyr Tyr Leu
1               5                   10                  15

Ala Ser Cys Leu Ala Leu Leu Phe Ser Thr Ala Ser Tyr Ala Glu Val
            20                  25                  30

Asp Cys Glu Leu Gln Pro Val Ile Glu Ala Asn Leu Ser Leu Asn Gln
        35                  40                  45

Asn Gln Leu Ala Ser Asn Gly Gly Tyr Ile Ser Ser Gln Leu Gly Ile
    50                  55                  60

Arg Asn Glu Ser Cys Glu Thr Val Lys Phe Lys Tyr Trp Leu Ser Ile
65                  70                  75                  80

Lys Gly Pro Glu Gly Ile Tyr Phe Pro Ala Lys Ala Val Val Gly Val
                85                  90                  95

Asp Thr Ala Gln Gln Glu Ser Asp Ala Leu Thr Asp Gly Arg Met Leu
            100                 105                 110

Asn Val Thr Arg Gly Phe Trp Val Pro Glu Tyr Met Ala Asp Gly Lys
        115                 120                 125

Tyr Thr Val Ser Leu Gln Val Val Ala Glu Asn Gly Lys Val Phe Lys
    130                 135                 140

Ala Asn Gln Glu Phe Val Lys Gly Val Asp Leu Asn Ser Leu Pro Glu
145                 150                 155                 160

Leu Asn Gly Leu Thr Ile Asp Ile Lys Asn Gln Phe Gly Ile Asn Ser
                165                 170                 175

Val Glu Ser Thr Gly Gly Phe Val Pro Phe Thr Val Asp Leu Asn Asn
            180                 185                 190

Gly Arg Glu Gly Glu Ala Asn Val Glu Phe Trp Met Thr Ala Val Gly
        195                 200                 205

Pro Asp Gly Leu Ile Ile Pro Val Asn Ala Arg Glu Lys Trp Val Ile
    210                 215                 220

Ala Ser Gly Asp Thr Tyr Ser Lys Val Arg Gly Ile Asn Phe Asp Lys
225                 230                 235                 240

Ser Tyr Pro Ala Gly Glu Tyr Thr Ile Asn Ala Gln Val Val Asp Ile

```
                    245                 250                 255
Val Ser Gly Glu Arg Val Glu Gln Ser Met Thr Val Val Lys Lys Asp
                260                 265                 270

Tyr Lys Asp Asp Asp Lys
        275

<210> SEQ ID NO 36
<211> LENGTH: 395
<212> TYPE: PRT
<213> ORGANISM: Artificial Sequence
<220> FEATURE:
<223> OTHER INFORMATION: Synthetic Polypeptide

<400> SEQUENCE: 36

Met Ser Asn Phe Lys Gly Ser Ile Met Asn Lys Arg His Tyr Tyr Leu
1               5                   10                  15

Ala Ser Cys Leu Ala Leu Leu Phe Ser Thr Ala Ser Tyr Ala Glu Val
                20                  25                  30

Asp Cys Glu Leu Gln Pro Val Ile Glu Ala Asn Leu Ser Leu Asn Gln
            35                  40                  45

Asn Gln Leu Ala Ser Asn Gly Gly Tyr Ile Ser Ser Gln Leu Gly Ile
        50                  55                  60

Arg Asn Glu Ser Cys Glu Thr Val Lys Phe Lys Tyr Trp Leu Ser Ile
65                  70                  75                  80

Lys Gly Pro Glu Gly Ile Tyr Phe Pro Ala Lys Ala Val Val Gly Val
                85                  90                  95

Asp Thr Ala Gln Gln Glu Ser Asp Ala Leu Thr Asp Gly Arg Met Leu
            100                 105                 110

Asn Val Thr Arg Gly Phe Trp Val Pro Glu Tyr Met Ala Asp Gly Lys
        115                 120                 125

Tyr Thr Val Ser Leu Gln Val Val Ala Glu Asn Gly Lys Val Phe Lys
130                 135                 140

Ala Asn Gln Glu Phe Val Lys Gly Val Asp Leu Asn Ser Leu Pro Glu
145                 150                 155                 160

Leu Asn Gly Leu Thr Ile Asp Ile Lys Asn Gln Phe Gly Ile Asn Ser
                165                 170                 175

Val Glu Ser Thr Gly Gly Phe Val Pro Phe Thr Val Asp Leu Asn Asn
            180                 185                 190

Gly Arg Glu Gly Glu Ala Asn Val Glu Phe Trp Met Thr Ala Val Gly
        195                 200                 205

Pro Asp Gly Leu Ile Ile Pro Val Asn Ala Arg Glu Lys Trp Val Ile
    210                 215                 220

Ala Ser Gly Asp Thr Tyr Ser Lys Val Arg Gly Ile Asn Phe Asp Lys
225                 230                 235                 240

Ser Tyr Pro Ala Gly Glu Tyr Thr Ile Asn Ala Gln Val Val Asp Ile
                245                 250                 255

Val Ser Gly Glu Arg Val Glu Gln Ser Met Thr Val Val Lys Lys Met
                260                 265                 270

Ile Lys Leu Lys Phe Gly Val Phe Phe Thr Val Leu Leu Ser Ser Ala
            275                 280                 285

Tyr Ala His Gly Thr Pro Gln Asn Ile Thr Asp Leu Cys Ala Glu Tyr
        290                 295                 300

His Asn Thr Gln Ile Tyr Thr Leu Asn Asp Lys Ile Phe Ser Tyr Thr
305                 310                 315                 320

Glu Ser Leu Ala Gly Lys Arg Glu Met Ala Ile Ile Thr Phe Lys Asn
```

```
                    325                 330                 335
Gly Ala Ile Phe Gln Val Glu Val Pro Gly Ser Gln His Ile Asp Ser
                340                 345                 350
Gln Lys Lys Ala Ile Glu Arg Met Lys Asp Thr Leu Arg Ile Ala Tyr
            355                 360                 365
Leu Thr Glu Ala Lys Val Glu Lys Leu Cys Val Trp Asn Asn Lys Thr
        370                 375                 380
Pro His Ala Ile Ala Ala Ile Ser Met Ala Asn
385                 390                 395

<210> SEQ ID NO 37
<211> LENGTH: 1128
<212> TYPE: PRT
<213> ORGANISM: Artificial Sequence
<220> FEATURE:
<223> OTHER INFORMATION: Synthetic Polypeptide

<400> SEQUENCE: 37

Met Ser Asn Phe Lys Gly Ser Ile Met Asn Lys Arg His Tyr Tyr Leu
1               5                   10                  15
Ala Ser Cys Leu Ala Leu Leu Phe Ser Thr Ala Ser Tyr Ala Glu Val
                20                  25                  30
Asp Cys Glu Leu Gln Pro Val Ile Glu Ala Asn Leu Ser Leu Asn Gln
            35                  40                  45
Asn Gln Leu Ala Ser Asn Gly Gly Tyr Ile Ser Ser Gln Leu Gly Ile
        50                  55                  60
Arg Asn Glu Ser Cys Glu Thr Val Lys Phe Lys Tyr Trp Leu Ser Ile
65                  70                  75                  80
Lys Gly Pro Glu Gly Ile Tyr Phe Pro Ala Lys Ala Val Gly Val
                85                  90                  95
Asp Thr Ala Gln Gln Glu Ser Asp Ala Leu Thr Asp Gly Arg Met Leu
                100                 105                 110
Asn Val Thr Arg Gly Phe Trp Val Pro Glu Tyr Met Ala Asp Gly Lys
            115                 120                 125
Tyr Thr Val Ser Leu Gln Val Val Ala Glu Asn Gly Lys Val Phe Lys
        130                 135                 140
Ala Asn Gln Glu Phe Val Lys Gly Val Asp Leu Asn Ser Leu Pro Glu
145                 150                 155                 160
Leu Asn Gly Leu Thr Ile Asp Ile Lys Asn Gln Phe Gly Ile Asn Ser
                165                 170                 175
Val Glu Ser Thr Gly Gly Phe Val Pro Phe Thr Val Asp Leu Asn Asn
            180                 185                 190
Gly Arg Glu Gly Glu Ala Asn Val Glu Phe Trp Met Thr Ala Val Gly
        195                 200                 205
Pro Asp Gly Leu Ile Ile Pro Val Asn Ala Arg Glu Lys Trp Val Ile
210                 215                 220
Ala Ser Gly Asp Thr Tyr Ser Lys Val Arg Gly Ile Asn Phe Asp Lys
225                 230                 235                 240
Ser Tyr Pro Ala Gly Glu Tyr Thr Ile Asn Ala Gln Val Val Asp Ile
                245                 250                 255
Val Ser Gly Glu Arg Val Glu Gln Ser Met Thr Val Val Lys Lys Met
            260                 265                 270
Asn Arg Met Thr Leu Cys Ala Ala Ser Ile Ala Cys Ala Leu Ala Ser
        275                 280                 285
Thr Ala Met Ala Ala Pro Ser Ala Pro Ser Val Asp Val Tyr Gly Ser
```

```
            290                 295                 300
Asn Asn Leu Gln Phe Ser Lys Ile Glu Leu Ala Met Glu Thr Thr Ala
305                 310                 315                 320

Gly Tyr Asn Gln Met Val Lys Tyr His Glu Ala Pro Ile Thr Leu
                325                 330                 335

Lys Phe Asn Gln Trp Ser Gly Val Thr Gly Asn Thr Tyr Lys Ile Tyr
                340                 345                 350

Phe Asp Gly Val Glu Val Ala Thr Gly Pro Ile Ser Gly Ser Gln Thr
                355                 360                 365

Thr Ala Gln Phe Thr Tyr Pro Lys Gly Val Tyr Gln Leu Val Ile
        370                 375                 380

Glu Ala Cys Asp Ala Thr Gly Cys Thr Lys Ser Ala Pro Ser Glu Ile
385                 390                 395                 400

Thr Ile Ala Asp Thr Asp Gly Ser His Leu Lys Pro Leu Lys Met Asn
                405                 410                 415

Val Asp Pro Asn Asn Lys Ser Tyr Thr Ile Pro Gln Asn Thr Val Ile
                420                 425                 430

Gly Thr Tyr Phe Val Glu Trp Ser Ile Tyr Asp Arg Lys Phe Thr Val
                435                 440                 445

Asp Asn Ile Pro Gly Gln Asn Leu Thr His Ile Leu Tyr Gly Phe Ile
                450                 455                 460

Pro Ile Cys Gly Pro Asn Glu Ser Leu Lys Ser Val Gly Gly Asn Ser
465                 470                 475                 480

Phe Asn Ala Leu Gln Thr Ala Cys Lys Gly Val Pro Asp Phe Glu Val
                485                 490                 495

Val Ile His Asp Pro Trp Ala Ala Tyr Gln Lys Ser Phe Pro Gln Ala
                500                 505                 510

Gly His Gln Tyr Ser Ser Pro Ile Lys Gly Asn Tyr Ala Met Leu Met
                515                 520                 525

Ala Leu Lys Lys Thr Tyr Pro Asp Leu Lys Ile Ile Pro Ser Ile Gly
        530                 535                 540

Gly Trp Thr Leu Ser Asp Pro Phe Phe Ser Phe Thr Asp Lys Ala Lys
545                 550                 555                 560

Arg Asp Val Phe Val Ala Ser Val Lys Arg Phe Leu Lys Thr Trp Lys
                565                 570                 575

Phe Tyr Asp Gly Val Asp Ile Asp Trp Glu Tyr Pro Gly Gly Gly Gly
                580                 585                 590

Gln Ala Ala Asp Leu Gly Asp Pro Val Lys Asp Gly Pro Ala Tyr Val
        595                 600                 605

Ala Leu Met Ala Glu Leu Arg Ala Met Leu Asp Glu Leu Glu Ala Glu
        610                 615                 620

Thr Gly Arg Lys Tyr Glu Leu Thr Ser Ala Ile Gly Val Gly His Asp
625                 630                 635                 640

Lys Ile Glu Asp Val Asn Tyr Gly Gln Ala Val Gln Tyr Met Asp Tyr
                645                 650                 655

Ile Phe Ala Met Thr Tyr Asp Phe Tyr Gly Gly Trp Asn Asn Val Leu
                660                 665                 670

Gly His Gln Thr Ala Leu Tyr Cys Gly Ser Phe Met Arg Pro Gly Gln
                675                 680                 685

Cys Asp Gly Lys Gly Val Asp Glu Asn Gly Glu Pro Tyr Lys Gly Pro
        690                 695                 700

Ala Tyr Thr Thr Asp Asn Gly Ile Gln Leu Leu Leu Ala Gln Gly Val
705                 710                 715                 720
```

```
Pro Pro Ser Lys Leu Val Val Gly Ala Ala Met Tyr Gly Arg Gly Trp
            725                 730                 735

Glu Gly Val Thr Pro Ala Ser Leu Lys Asp Pro Asn Asp Pro Met Thr
            740                 745                 750

Gly Val Gly Asn Gly Lys Leu Lys Gly Thr Thr Ala Gln Gly Val Trp
            755                 760                 765

Glu Ala Gly Val Ile Asp Tyr Lys Gly Val Lys Asn Phe Met Leu Gly
            770                 775                 780

Ala Asn Lys Thr Gly Val Asn Gly Phe Glu Tyr Gly Tyr Asp Glu Gln
785                 790                 795                 800

Ala Glu Ala Pro Trp Val Trp Asn Arg Thr Thr Gly Gln Leu Val Thr
            805                 810                 815

Phe Asp Asp Arg Ser Val Lys Ala Lys Gly Ala Tyr Val Arg Asn
            820                 825                 830

Leu Gly Leu Ala Gly Leu Phe Ser Trp Glu Ile Asp Ala Asp Asn Gly
            835                 840                 845

Asp Ile Leu Asn Ala Met His Glu Gly Leu Ala Gly Gly Thr Thr Thr
850                 855                 860

Pro Pro Val Asn Lys Ala Pro Val Ala Asn Ala Gly Ala Asp Ile Thr
865                 870                 875                 880

Val Thr Gly Pro Ala Ala Val Ser Leu Asp Gly Ser Ala Ser Lys Asp
            885                 890                 895

Ser Asp Gly Ser Ile Ala Ser Tyr Leu Trp Glu Gln Thr Ala Gly Pro
            900                 905                 910

Ala Val Thr Leu Thr Gly Ala Asn Ser Ala Lys Ala Ser Phe Asn Ala
            915                 920                 925

Ala Glu Val Thr Glu Lys Gln Thr Phe Thr Phe Lys Leu Thr Val Thr
            930                 935                 940

Asp Asn Lys Gly Ala Thr Ala Thr Asp Thr Val Val Val Thr Val Asn
945                 950                 955                 960

Pro Lys Ser Thr Thr Pro Val Asn Thr Ala Pro Val Ala Ala Leu Ser
            965                 970                 975

Ala Pro Ala Ser Val Lys Ala Gly Ala Thr Val Val Val Asp Ala Ser
            980                 985                 990

Ala Ser Ser Asp Ala Asp Gln Asp Pro Leu Ser Phe Thr Trp Asp Leu
            995                 1000                1005

Pro Val Gly Val Asn Ala Thr Val Gln Gly Ala Lys Val Thr Phe
            1010                1015                1020

Val Ala Gly Glu Tyr Thr Gln Asp Thr Thr Leu Asp Phe Thr Val
            1025                1030                1035

Thr Val Ser Asp Gly Lys Ala Thr Ser Lys Ala Ser Ala Ser Val
            1040                1045                1050

Leu Val Glu Lys Lys Ala Gly Thr Gly Gly Asp Ala Cys Thr Asn
            1055                1060                1065

Leu Trp Asn Ala Glu Ser Ile Tyr Thr Gly Gly Gln Gln Val Thr
            1070                1075                1080

Trp Ala Gly Lys Thr Trp Glu Ala Lys Trp Trp Thr Arg Gly Glu
            1085                1090                1095

Asp Pro Ser Lys Ser Gly Gln Trp Gly Val Trp Lys Asp Leu Gly
            1100                1105                1110

Ala Ala Ser Cys Ser Thr His Asp Tyr Lys Asp Asp Asp Asp Lys
            1115                1120                1125
```

```
<210> SEQ ID NO 38
<211> LENGTH: 271
<212> TYPE: PRT
<213> ORGANISM: Artificial Sequence
<220> FEATURE:
<223> OTHER INFORMATION: Synthetic Polypeptide

<400> SEQUENCE: 38

Met Ser Asn Phe Lys Gly Ser Ile Met Asn Lys Arg His Tyr Tyr Leu
1               5                   10                  15

Ala Ser Cys Leu Ala Leu Leu Phe Ser Thr Ala Ser Tyr Ala Glu Val
            20                  25                  30

Asp Cys Glu Leu Gln Pro Val Ile Glu Ala Asn Leu Ser Leu Asn Gln
        35                  40                  45

Asn Gln Leu Ala Ser Asn Gly Gly Tyr Ile Ser Ser Gln Leu Gly Ile
    50                  55                  60

Arg Asn Glu Ser Cys Glu Thr Val Lys Phe Lys Tyr Trp Leu Ser Ile
65                  70                  75                  80

Lys Gly Pro Glu Gly Ile Tyr Phe Pro Ala Lys Ala Val Val Gly Val
                85                  90                  95

Asp Thr Ala Gln Gln Glu Ser Asp Ala Leu Thr Asp Gly Arg Met Leu
            100                 105                 110

Asn Val Thr Arg Gly Phe Trp Val Pro Glu Tyr Met Ala Asp Gly Lys
        115                 120                 125

Tyr Thr Val Ser Leu Gln Val Val Ala Glu Asn Gly Lys Val Phe Lys
    130                 135                 140

Ala Asn Gln Glu Phe Val Lys Gly Val Asp Leu Asn Ser Leu Pro Glu
145                 150                 155                 160

Leu Asn Gly Leu Thr Ile Asp Ile Lys Asn Gln Phe Gly Ile Asn Ser
                165                 170                 175

Val Glu Ser Thr Gly Gly Phe Val Pro Phe Thr Val Asp Leu Asn Asn
            180                 185                 190

Gly Arg Glu Gly Glu Ala Asn Val Glu Phe Trp Met Thr Ala Val Gly
        195                 200                 205

Pro Asp Gly Leu Ile Ile Pro Val Asn Ala Arg Glu Lys Trp Val Ile
    210                 215                 220

Ala Ser Gly Asp Thr Tyr Ser Lys Val Ala Gly Ile Asn Phe Asp Lys
225                 230                 235                 240

Ser Tyr Pro Ala Gly Glu Tyr Thr Ile Asn Ala Gln Val Val Asp Ile
                245                 250                 255

Val Ser Gly Glu Arg Val Glu Gln Ser Met Thr Val Val Lys Lys
            260                 265                 270

<210> SEQ ID NO 39
<211> LENGTH: 271
<212> TYPE: PRT
<213> ORGANISM: Artificial Sequence
<220> FEATURE:
<223> OTHER INFORMATION: Synthetic Polypeptide

<400> SEQUENCE: 39

Met Ser Asn Phe Lys Gly Ser Ile Met Asn Lys Arg His Tyr Tyr Leu
1               5                   10                  15

Ala Ser Cys Leu Ala Leu Leu Phe Ser Thr Ala Ser Tyr Ala Glu Val
            20                  25                  30

Asp Cys Glu Leu Gln Pro Val Ile Glu Ala Asn Leu Ser Leu Asn Gln
        35                  40                  45
```

Asn Gln Leu Ala Ser Asn Gly Gly Tyr Ile Ser Ser Gln Leu Gly Ile
            50                  55                  60

Arg Asn Glu Ser Cys Glu Thr Val Lys Phe Lys Tyr Trp Leu Ser Ile
 65                  70                  75                  80

Lys Gly Pro Glu Gly Ile Tyr Phe Pro Ala Lys Ala Val Val Gly Val
                    85                  90                  95

Asp Thr Ala Gln Gln Glu Ser Asp Ala Leu Thr Asp Gly Arg Met Leu
                100                 105                 110

Asn Val Thr Arg Gly Phe Trp Val Pro Glu Tyr Met Ala Asp Gly Lys
            115                 120                 125

Tyr Thr Val Ser Leu Gln Val Val Ala Glu Asn Gly Lys Val Phe Lys
            130                 135                 140

Ala Asn Gln Glu Phe Val Lys Gly Val Asp Leu Asn Ser Leu Pro Glu
145                 150                 155                 160

Leu Asn Gly Leu Thr Ile Asp Ile Lys Asn Gln Phe Gly Ile Asn Ser
                165                 170                 175

Val Glu Ser Thr Gly Gly Phe Val Pro Phe Thr Val Asp Leu Asn Asn
                180                 185                 190

Gly Arg Glu Gly Glu Ala Asn Val Glu Phe Trp Met Thr Ala Val Gly
            195                 200                 205

Pro Asp Gly Leu Ile Ile Pro Val Asn Ala Ala Glu Lys Trp Val Ile
210                 215                 220

Ala Ser Gly Asp Thr Tyr Ser Lys Val Arg Gly Ile Asn Phe Asp Lys
225                 230                 235                 240

Ser Tyr Pro Ala Gly Glu Tyr Thr Ile Asn Ala Gln Val Val Asp Ile
                245                 250                 255

Val Ser Gly Glu Arg Val Glu Gln Ser Met Thr Val Val Lys Lys
            260                 265                 270

<210> SEQ ID NO 40
<211> LENGTH: 271
<212> TYPE: PRT
<213> ORGANISM: Artificial Sequence
<220> FEATURE:
<223> OTHER INFORMATION: Synthetic Polypeptide

<400> SEQUENCE: 40

Met Ser Asn Phe Lys Gly Ser Ile Met Asn Lys Arg His Tyr Tyr Leu
 1               5                  10                  15

Ala Ser Cys Leu Ala Leu Leu Phe Ser Thr Ala Ser Tyr Ala Glu Val
            20                  25                  30

Asp Cys Glu Leu Gln Pro Val Ile Glu Ala Asn Leu Ser Leu Asn Gln
            35                  40                  45

Asn Gln Leu Ala Ser Asn Gly Gly Tyr Ile Ser Ser Gln Leu Gly Ile
            50                  55                  60

Arg Asn Glu Ser Cys Glu Thr Val Lys Phe Lys Tyr Trp Leu Ser Ile
 65                  70                  75                  80

Lys Gly Pro Glu Gly Ile Tyr Phe Pro Ala Lys Ala Val Val Gly Val
                    85                  90                  95

Asp Thr Ala Gln Gln Glu Ser Asp Ala Leu Thr Asp Gly Arg Met Leu
                100                 105                 110

Asn Val Thr Ala Gly Phe Trp Val Pro Glu Tyr Met Ala Asp Gly Lys
            115                 120                 125

Tyr Thr Val Ser Leu Gln Val Val Ala Glu Asn Gly Lys Val Phe Lys
            130                 135                 140

Ala Asn Gln Glu Phe Val Lys Gly Val Asp Leu Asn Ser Leu Pro Glu
145                 150                 155                 160

Leu Asn Gly Leu Thr Ile Asp Ile Lys Asn Gln Phe Gly Ile Asn Ser
            165                 170                 175

Val Glu Ser Thr Gly Gly Phe Val Pro Phe Thr Val Asp Leu Asn Asn
        180                 185                 190

Gly Arg Glu Gly Glu Ala Asn Val Glu Phe Trp Met Thr Ala Val Gly
            195                 200                 205

Pro Asp Gly Leu Ile Ile Pro Val Asn Ala Arg Glu Lys Trp Val Ile
        210                 215                 220

Ala Ser Gly Asp Thr Tyr Ser Lys Val Arg Gly Ile Asn Phe Asp Lys
225                 230                 235                 240

Ser Tyr Pro Ala Gly Glu Tyr Thr Ile Asn Ala Gln Val Val Asp Ile
            245                 250                 255

Val Ser Gly Glu Arg Val Glu Gln Ser Met Thr Val Val Lys Lys
        260                 265                 270

<210> SEQ ID NO 41
<211> LENGTH: 271
<212> TYPE: PRT
<213> ORGANISM: Artificial Sequence
<220> FEATURE:
<223> OTHER INFORMATION: Synthetic Polypeptide

<400> SEQUENCE: 41

Met Ser Asn Phe Lys Gly Ser Ile Met Asn Lys Arg His Tyr Tyr Leu
1               5                   10                  15

Ala Ser Cys Leu Ala Leu Leu Phe Ser Thr Ala Ser Tyr Ala Glu Val
            20                  25                  30

Asp Cys Glu Leu Gln Pro Val Ile Glu Ala Asn Leu Ser Leu Asn Gln
        35                  40                  45

Asn Gln Leu Ala Ser Asn Gly Gly Tyr Ile Ser Ser Gln Leu Gly Ile
    50                  55                  60

Arg Asn Glu Ser Cys Glu Thr Val Lys Phe Lys Tyr Trp Leu Ser Ile
65                  70                  75                  80

Lys Gly Pro Glu Gly Ile Tyr Phe Pro Ala Lys Ala Val Val Gly Val
            85                  90                  95

Asp Thr Ala Gln Gln Glu Ser Asp Ala Leu Thr Asp Gly Arg Met Leu
        100                 105                 110

Asn Val Thr Arg Gly Phe Trp Val Pro Glu Tyr Met Ala Asp Gly Lys
    115                 120                 125

Tyr Thr Val Ser Leu Gln Val Val Ala Glu Asn Gly Lys Val Phe Lys
130                 135                 140

Ala Asn Gln Glu Phe Val Lys Gly Val Asp Leu Asn Ser Leu Pro Glu
145                 150                 155                 160

Leu Asn Gly Leu Thr Ile Asp Ile Lys Asn Gln Phe Gly Ile Asn Ser
            165                 170                 175

Val Glu Ser Thr Gly Gly Phe Val Pro Phe Thr Val Asp Leu Asn Asn
        180                 185                 190

Gly Arg Glu Gly Glu Ala Asn Val Glu Phe Trp Met Thr Ala Val Gly
            195                 200                 205

Pro Asp Gly Leu Ile Ile Pro Val Asn Ala Ala Glu Lys Trp Val Ile
        210                 215                 220

Ala Ser Gly Asp Thr Tyr Ser Lys Val Ala Gly Ile Asn Phe Asp Lys
225                 230                 235                 240

Ser Tyr Pro Ala Gly Glu Tyr Thr Ile Asn Ala Gln Val Val Asp Ile
            245                 250                 255

Val Ser Gly Glu Arg Val Glu Gln Ser Met Thr Val Val Lys Lys
            260                 265                 270

<210> SEQ ID NO 42
<211> LENGTH: 271
<212> TYPE: PRT
<213> ORGANISM: Artificial Sequence
<220> FEATURE:
<223> OTHER INFORMATION: Synthetic Polypeptide

<400> SEQUENCE: 42

Met Ser Asn Phe Lys Gly Ser Ile Met Asn Lys Arg His Tyr Tyr Leu
1               5                   10                  15

Ala Ser Cys Leu Ala Leu Leu Phe Ser Thr Ala Ser Tyr Ala Glu Val
                20                  25                  30

Asp Cys Glu Leu Gln Pro Val Ile Glu Ala Asn Leu Ser Leu Asn Gln
            35                  40                  45

Asn Gln Leu Ala Ser Asn Gly Gly Tyr Ile Ser Ser Gln Leu Gly Ile
        50                  55                  60

Arg Asn Glu Ser Cys Glu Thr Val Lys Phe Lys Tyr Trp Leu Ser Ile
65                  70                  75                  80

Lys Gly Pro Glu Gly Ile Tyr Phe Pro Ala Lys Ala Val Val Gly Val
                85                  90                  95

Asp Thr Ala Gln Gln Glu Ser Asp Ala Leu Thr Asp Gly Arg Met Leu
            100                 105                 110

Asn Val Thr Ala Gly Phe Trp Val Pro Glu Tyr Met Ala Asp Gly Lys
        115                 120                 125

Tyr Thr Val Ser Leu Gln Val Val Ala Glu Asn Gly Lys Val Phe Lys
    130                 135                 140

Ala Asn Gln Glu Phe Val Lys Gly Val Asp Leu Asn Ser Leu Pro Glu
145                 150                 155                 160

Leu Asn Gly Leu Thr Ile Asp Ile Lys Asn Gln Phe Gly Ile Asn Ser
                165                 170                 175

Val Glu Ser Thr Gly Gly Phe Val Pro Phe Thr Val Asp Leu Asn Asn
            180                 185                 190

Gly Arg Glu Gly Glu Ala Asn Val Glu Phe Trp Met Thr Ala Val Gly
        195                 200                 205

Pro Asp Gly Leu Ile Ile Pro Val Asn Ala Arg Glu Lys Trp Val Ile
    210                 215                 220

Ala Ser Gly Asp Thr Tyr Ser Lys Val Ala Gly Ile Asn Phe Asp Lys
225                 230                 235                 240

Ser Tyr Pro Ala Gly Glu Tyr Thr Ile Asn Ala Gln Val Val Asp Ile
                245                 250                 255

Val Ser Gly Glu Arg Val Glu Gln Ser Met Thr Val Val Lys Lys
            260                 265                 270

<210> SEQ ID NO 43
<211> LENGTH: 271
<212> TYPE: PRT
<213> ORGANISM: Artificial Sequence
<220> FEATURE:
<223> OTHER INFORMATION: Synthetic Polypeptide

<400> SEQUENCE: 43

Met Ser Asn Phe Lys Gly Ser Ile Met Asn Lys Arg His Tyr Tyr Leu

```
            1               5                  10                 15
Ala Ser Cys Leu Ala Leu Leu Phe Ser Thr Ala Ser Tyr Ala Glu Val
            20                 25                 30
Asp Cys Glu Leu Gln Pro Val Ile Glu Ala Asn Leu Ser Leu Asn Gln
            35                 40                 45
Asn Gln Leu Ala Ser Asn Gly Gly Tyr Ile Ser Ser Gln Leu Gly Ile
            50                 55                 60
Arg Asn Glu Ser Cys Glu Thr Val Lys Phe Lys Tyr Trp Leu Ser Ile
65                 70                 75                 80
Lys Gly Pro Glu Gly Ile Tyr Phe Pro Ala Lys Ala Val Val Gly Val
                85                 90                 95
Asp Thr Ala Gln Gln Glu Ser Asp Ala Leu Thr Asp Gly Arg Met Leu
            100                105                110
Asn Val Thr Ala Gly Phe Trp Val Pro Glu Tyr Met Ala Asp Gly Lys
            115                120                125
Tyr Thr Val Ser Leu Gln Val Val Ala Glu Asn Gly Lys Val Phe Lys
            130                135                140
Ala Asn Gln Glu Phe Val Lys Gly Val Asp Leu Asn Ser Leu Pro Glu
145                150                155                160
Leu Asn Gly Leu Thr Ile Asp Ile Lys Asn Gln Phe Gly Ile Asn Ser
                165                170                175
Val Glu Ser Thr Gly Gly Phe Val Pro Phe Thr Val Asp Leu Asn Asn
            180                185                190
Gly Arg Glu Gly Glu Ala Asn Val Glu Phe Trp Met Thr Ala Val Gly
            195                200                205
Pro Asp Gly Leu Ile Ile Pro Val Asn Ala Ala Glu Lys Trp Val Ile
            210                215                220
Ala Ser Gly Asp Thr Tyr Ser Lys Val Arg Gly Ile Asn Phe Asp Lys
225                230                235                240
Ser Tyr Pro Ala Gly Glu Tyr Thr Ile Asn Ala Gln Val Val Asp Ile
                245                250                255
Val Ser Gly Glu Arg Val Glu Gln Ser Met Thr Val Val Lys Lys
            260                265                270
```

<210> SEQ ID NO 44
<211> LENGTH: 1767
<212> TYPE: PRT
<213> ORGANISM: Artificial Sequence
<220> FEATURE:
<223> OTHER INFORMATION: Synthetic Polypeptide

<400> SEQUENCE: 44

```
Met Asn Arg Ile Tyr Lys Leu Lys Phe Asp Lys Arg Arg Asn Glu Leu
1               5                  10                 15
Val Val Val Ser Glu Ile Thr Thr Gly Val Gly Asn Ala Lys Ala Thr
            20                 25                 30
Gly Ser Val Glu Gly Glu Lys Ser Pro Arg Arg Gly Val Arg Ala Met
            35                 40                 45
Ala Leu Ser Leu Leu Ser Gly Met Met Ile Met Ala His Pro Ala Met
            50                 55                 60
Ser Ala Asn Leu Pro Thr Gly Gly Gln Ile Val Ala Gly Ser Gly Ser
65                 70                 75                 80
Ile Gln Thr Pro Ser Gly Asn Gln Met Asn Ile His Gln Asn Ser Gln
                85                 90                 95
Asn Met Val Ala Asn Trp Asn Ser Phe Asp Ile Gly Lys Gly Asn Thr
```

```
                100                 105                 110
Val Gln Phe Asp Gln Pro Ser Ser Ser Ala Val Ala Leu Asn Arg Val
            115                 120                 125

Val Gly Gly Gly Glu Ser Gln Ile Met Gly Asn Leu Lys Ala Asn Gly
130                 135                 140

Gln Val Phe Leu Val Asn Pro Asn Gly Val Leu Phe Gly Glu Gly Ala
145                 150                 155                 160

Ser Val Ser Thr Ser Gly Phe Val Ala Ser Thr Arg Asp Ile Lys Asn
                165                 170                 175

Asp Asp Phe Met Asn Arg Arg Tyr Thr Phe Ser Gly Gly Gln Lys Ala
            180                 185                 190

Gly Ala Ala Ile Val Asn Gln Gly Glu Leu Thr Thr Asn Ala Gly Gly
            195                 200                 205

Tyr Ile Val Leu Ala Ala Asp Arg Val Ser Asn Ser Gly Thr Ile Arg
        210                 215                 220

Thr Pro Gly Gly Lys Thr Val Leu Ala Ala Ser Glu Arg Ile Thr Leu
225                 230                 235                 240

Gln Leu Asp Asn Gly Gly Leu Met Ser Val Gln Val Thr Gly Asp Val
                245                 250                 255

Val Asn Ala Leu Val Glu Asn Arg Gly Leu Val Ser Ala Arg Asp Gly
                260                 265                 270

Gln Val Tyr Leu Thr Ala Leu Gly Arg Gly Met Leu Met Asn Thr Val
            275                 280                 285

Leu Asn Val Ser Gly Val Val Glu Ala Ser Gly Met His Arg Gln Asp
        290                 295                 300

Gly Asn Ile Val Leu Asp Gly Gly Asp Ser Gly Val Val His Leu Ser
305                 310                 315                 320

Gly Thr Leu Gln Ala Asp Asn Ala Ser Gly Gln Gly Gly Lys Val Val
                325                 330                 335

Val Gln Gly Lys Asn Ile Leu Leu Asp Lys Gly Ser Asn Ile Thr Ala
                340                 345                 350

Thr Gly Gly Gln Gly Gly Gly Glu Val Tyr Val Gly Gly Gly Trp Gln
            355                 360                 365

Gly Lys Asp Ser Asn Ile Arg Asn Ala Asp Lys Val Val Met Gln Gly
        370                 375                 380

Gly Ala Arg Ile Asp Val Ser Ala Thr Gln Gln Gly Asn Gly Gly Thr
385                 390                 395                 400

Ala Val Leu Trp Ser Asp Ser Tyr Thr Asn Phe His Gly Gln Ile Ser
                405                 410                 415

Ala Lys Gly Gly Glu Thr Gly Gly Asn Gly Gly Arg Val Glu Thr Ser
                420                 425                 430

Ser His Gly Asn Leu Gln Ala Phe Gly Thr Val Ser Ala Ser Ala Lys
            435                 440                 445

Lys Gly Lys Ala Gly Asn Trp Leu Leu Asp Ser Ala Asp Ile Thr Ile
        450                 455                 460

Val Asn Gly Ser Asn Val Ser Lys Thr Glu Thr Thr Gln Ser Pro Pro
465                 470                 475                 480

His Thr Gln Phe Ala Pro Thr Ala Ala Gly Ser Ala Val Ser Asn Thr
                485                 490                 495

Ser Ile Asn Asn Arg Leu Asn Asn Gly Thr Ser Val Thr Ile Leu Thr
            500                 505                 510

His Arg Thr Arg Thr Gly Thr Ala Gln Gly Gly Asn Ile Thr Val Asn
        515                 520                 525
```

Ala Ala Ile Asn Lys Ser Asn Gly Ser Asp Val Asn Leu Thr Leu Gln
        530                 535                 540

Ala Gly Gly Asn Ile Thr Val Asn Asn Ser Ile Thr Ser Thr Glu Gly
545                 550                 555                 560

Lys Leu Asn Val Asn Leu Ser Gly Ala Arg Thr Ser Asn Gly Ser Ile
                565                 570                 575

Thr Ile Ser Asn Asn Ala Asn Ile Thr Thr Asn Gly Gly Asp Ile Thr
                580                 585                 590

Val Gly Thr Thr Asn Thr Ser Asn Arg Val Asn Ile Ser Ile Asn Asn
            595                 600                 605

Thr Thr Leu Asn Ala Ser Gly Asn Ile Gln Leu Thr Gly Thr Gly
    610                 615                 620

Thr Asp Ser Gly Ile Leu Phe Ala Gly Asn Asn Arg Leu Thr Ala Ser
625                 630                 635                 640

Asn Ile Ala Leu Thr Gly Asn Ser Thr Ser Gly Asn Ala Ile Asn Leu
                645                 650                 655

Thr Gly Thr Ala Thr Leu Asn Ala Thr Asn Asn Ile Thr Leu Thr Gly
                660                 665                 670

Ser Ser Thr Ser Gly Asn Ala Ile Asn Leu Lys Gly Asn Asn Thr Leu
            675                 680                 685

Thr Ala Ser Asn Ile Thr Leu Thr Gly Glu Ser Thr Ser Gly Asn Ala
    690                 695                 700

Ile Asn Leu Thr Asp Thr Thr Gly Thr Thr Thr Leu Asn Ala Thr Asn
705                 710                 715                 720

Asn Ile Thr Met Gln Gly Thr Arg Val Gln Ile Lys His Ser Asn Ile
                725                 730                 735

Thr Ala Gly Asn Phe Ala Leu Asn Ala Thr Val Ala Gly Ser Glu Ile
                740                 745                 750

Ser Asn Thr Thr Leu Thr Ala Thr Asn Asn Ile Asn Leu Ala Ala Lys
            755                 760                 765

Thr Asn Ser Ala Ser Ser Gly Val Tyr Leu Lys Asp Ala Arg Ile Thr
    770                 775                 780

Ser Thr Asn Gly Ser Ile Thr Ala Asn Gly Thr Ala Thr Ala Asn Gly
785                 790                 795                 800

Lys Ala Thr His Leu Asp Gly Asn Val Thr Leu Asn Ala Ser Asn Gly
                805                 810                 815

Arg Ile Lys Leu Thr Gly Asn Gly His Gly Ser Ala Ser Gly Ile Leu
                820                 825                 830

Phe Ala Gly Asn Asn Arg Leu Thr Ala Ser Asn Ile Ala Leu Thr Gly
            835                 840                 845

Asn Ser Thr Ser Gly Asn Ala Ile Asn Leu Thr Gly Thr Ala Thr Leu
    850                 855                 860

Asn Ala Thr Asn Asp Ile Thr Leu Thr Gly Ser Ser Thr Ser Gly Asn
865                 870                 875                 880

Ala Ile Asn Leu Thr Gly Thr Ala Thr Leu Asn Ala Thr Asn Asn Ile
                885                 890                 895

Thr Leu Thr Gly Ser Ser Thr Ser Gly Asn Ala Ile Asn Leu Lys Gly
                900                 905                 910

Asn Asn Thr Leu Thr Ala Ser Asn Ile Thr Leu Thr Gly Glu Ser Thr
            915                 920                 925

Ser Gly Asn Ala Ile Asn Leu Thr Asp Thr Thr Gly Thr Thr Thr Leu
    930                 935                 940

```
Asn Ala Thr Asn Asn Ile Thr Met Gln Gly Thr Arg Val Gln Ile Lys
945                 950                 955                 960

His Ser Asn Ile Thr Ala Gly Asn Phe Ala Leu Asn Ala Thr Val Ala
                965                 970                 975

Gly Ser Glu Ile Ser Asn Thr Thr Leu Thr Ala Thr Asn Asn Ile Asn
            980                 985                 990

Leu Ala Ala Lys Thr Asn Ser Ala Ser Ser Gly Val Tyr Leu Lys Asp
        995                 1000                1005

Ala Arg Ile Thr Ser Thr Asn Gly Ser Ile Thr Ala Asn Gly Thr
    1010                1015                1020

Ala Thr Ala Asn Gly Lys Ala Thr His Leu Asp Gly Asn Val Thr
    1025                1030                1035

Leu Asn Ala Ser Asn Gly Arg Ile Lys Leu Thr Gly Asn Gly His
    1040                1045                1050

Gly Ser Ala Ser Gly Ile Leu Phe Ala Gly Asn Asn Arg Leu Thr
    1055                1060                1065

Ala Ser Asn Ile Ala Leu Thr Gly Asn Ser Thr Ser Gly Asn Ala
    1070                1075                1080

Ile Asn Leu Thr Gly Thr Ala Thr Leu Asn Ala Thr Asn Asp Ile
    1085                1090                1095

Thr Leu Thr Gly Ser Ser Thr Ser Gly Asn Ala Ile Asn Leu Thr
    1100                1105                1110

Gly Thr Ala Thr Leu Asn Ala Thr Asn Asn Ile Thr Leu Thr Gly
    1115                1120                1125

Ser Ser Thr Ser Gly Asn Ala Ile Asn Leu Lys Gly Asn Asn Thr
    1130                1135                1140

Leu Thr Ala Ser Asn Ile Thr Leu Thr Gly Glu Ser Thr Ser Gly
    1145                1150                1155

Asn Ala Ile Asn Leu Thr Asp Thr Thr Gly Thr Thr Thr Leu Asn
    1160                1165                1170

Ala Thr Asn Asn Ile Thr Met Gln Gly Thr Arg Val Gln Ile Lys
    1175                1180                1185

His Ser Asn Ile Thr Ala Gly Asn Phe Ala Leu Asn Ala Thr Val
    1190                1195                1200

Ala Gly Ser Glu Ile Ser Asn Thr Thr Leu Thr Ala Thr Asn Asn
    1205                1210                1215

Ile Asn Leu Ala Ala Lys Thr Asn Ser Ala Ser Ser Gly Val Tyr
    1220                1225                1230

Leu Lys Asp Ala Arg Ile Thr Ser Thr Asn Gly Ser Ile Thr Ala
    1235                1240                1245

Asn Gly Thr Ala Thr Ala Asn Gly Lys Ala Thr His Leu Asp Gly
    1250                1255                1260

Asn Val Thr Leu Asn Ala Ser Asn Gly Arg Ile Lys Leu Thr Gly
    1265                1270                1275

Asn Gly His Gly Ser Ala Ser Gly Ile Leu Phe Ala Gly Asn Asn
    1280                1285                1290

Arg Leu Thr Ala Ser Asn Ile Ala Leu Thr Gly Asn Ser Thr Ser
    1295                1300                1305

Gly Asn Ala Ile Asn Leu Thr Gly Thr Ala Thr Leu Asn Ala Thr
    1310                1315                1320

Asn Asp Ile Thr Leu Thr Gly Ser Ser Thr Ser Gly Asn Ala Ile
    1325                1330                1335

Asn Leu Thr Gly Thr Ala Thr Leu Asn Ala Thr Asn Asn Ile Thr
```

-continued

```
                1340                1345                1350

Leu Thr Gly Ser Ser Thr Ser Gly Asn Ala Ile Asn Leu Lys Gly
    1355                1360                1365

Asn Asn Thr Leu Thr Ala Ser Asn Ile Thr Leu Thr Gly Glu Ser
    1370                1375                1380

Thr Ser Gly Asn Ala Ile Asn Leu Thr Asp Thr Thr Gly Thr Thr
    1385                1390                1395

Thr Leu Asn Ala Thr Asn Asn Ile Thr Met Gln Gly Thr Arg Val
    1400                1405                1410

Gln Ile Lys His Ser Asn Ile Thr Ala Gly Asn Phe Ala Leu Asn
    1415                1420                1425

Ala Thr Val Ala Gly Ser Glu Ile Ser Asn Thr Thr Leu Thr Ala
    1430                1435                1440

Thr Asn Asn Ile Asn Leu Ala Ala Lys Thr Asn Ser Ala Ser Ser
    1445                1450                1455

Gly Val Tyr Leu Lys Asp Ala Arg Ile Thr Ser Thr Asn Gly Ser
    1460                1465                1470

Ile Thr Thr Asn Gly Thr Ala Thr Ala Asn Gly Lys Ala Thr His
    1475                1480                1485

Leu Asp Gly Asn Val Thr Leu Asn Ala Ser Asn Gly Arg Ile Lys
    1490                1495                1500

Leu Thr Gly Asn Gly His Gly Ser Ala Ser Gly Ile Leu Phe Ala
    1505                1510                1515

Gly Asn Asn Arg Leu Thr Ala Ser Asn Ile Ala Leu Thr Gly Asn
    1520                1525                1530

Ser Thr Ser Gly Asn Ala Ile Asn Leu Thr Gly Thr Ala Thr Leu
    1535                1540                1545

Asn Ala Thr Asn Asp Ile Thr Leu Thr Gly Ser Ser Thr Ser Gly
    1550                1555                1560

Asn Ala Ile Asn Leu Thr Gly Thr Ala Thr Leu Asn Ala Thr Asn
    1565                1570                1575

Asn Ile Thr Leu Thr Gly Ser Ser Thr Ser Gly Asn Ala Ile Asn
    1580                1585                1590

Leu Lys Gly Asn Asn Thr Leu Thr Ala Ser Asn Ile Thr Leu Thr
    1595                1600                1605

Gly Glu Ser Thr Ser Gly Asn Ala Ile Asn Leu Thr Asp Thr Thr
    1610                1615                1620

Gly Thr Thr Thr Leu Asn Ala Thr Asn Asn Ile Thr Met Gln Gly
    1625                1630                1635

Thr Arg Val Gln Ile Lys His Ser Asn Ile Thr Ala Gly Asn Phe
    1640                1645                1650

Ala Leu Asn Ala Thr Val Ala Gly Ser Glu Ile Ser Asn Thr Thr
    1655                1660                1665

Leu Thr Ala Thr Asn Asn Ile Asn Leu Ala Ala Lys Thr Asn Ser
    1670                1675                1680

Ala Ser Ser Gly Val Tyr Leu Lys Asp Ala Arg Ile Thr Ser Thr
    1685                1690                1695

Asn Gly Ser Ile Thr Ala Asn Gly Thr Ala Pro Ala Asn Asp Asn
    1700                1705                1710

Ala Thr Tyr Leu Asp Gly Asn Val Thr Leu Asn Ala Ser Asn Gly
    1715                1720                1725

Ser Ile Lys Leu Thr Gly Asn Gly Asn Gly Ser Thr Ser Gly Ile
    1730                1735                1740
```

Leu Phe Ala Gly Asn Asn Thr Leu Thr Ala Ser Asn Ile Thr Leu
    1745                1750                1755

Thr Gly Asn Ser Glu Val Tyr Trp Gln
    1760                1765

<210> SEQ ID NO 45
<211> LENGTH: 1049
<212> TYPE: PRT
<213> ORGANISM: Artificial Sequence
<220> FEATURE:
<223> OTHER INFORMATION: Synthetic Polypeptide

<400> SEQUENCE: 45

Ser Phe Ser Pro Phe Val Val Gly Ala Ser Leu Leu Gly Gly Pro
1               5                   10                  15

Ile Ala Phe Ala Ile Pro Leu Ser Gly Thr Gln Glu Leu His Phe Ser
            20                  25                  30

Glu Asp Asn Tyr Glu Lys Leu Leu Thr Pro Val Asp Gly Leu Ser Pro
        35                  40                  45

Leu Gly Ala Gly Glu Asp Gly Met Asp Ala Trp Tyr Ile Thr Ser Ser
    50                  55                  60

Asn Pro Ser His Ala Ser Arg Thr Lys Leu Arg Ile Asn Ser Asp Ile
65                  70                  75                  80

Met Ile Ser Ala Gly His Gly Ala Gly Asp Asn Asn Asp Gly Asn
                85                  90                  95

Ser Cys Gly Gly Asn Gly Gly Asp Ser Ile Thr Gly Ser Asp Leu Ser
            100                 105                 110

Ile Ile Asn Gln Gly Met Ile Leu Gly Gly Ser Gly Ser Gly Ala
        115                 120                 125

Asp His Asn Gly Asp Gly Gly Glu Ala Val Thr Gly Asp Asn Leu Phe
    130                 135                 140

Ile Ile Asn Gly Glu Ile Ile Ser Gly Gly His Gly Gly Asp Ser Tyr
145                 150                 155                 160

Ser Asp Ser Asp Gly Gly Asn Gly Gly Asp Ala Val Thr Gly Val Asn
                165                 170                 175

Leu Pro Ile Ile Asn Lys Gly Thr Ile Ser Gly Gly Asn Gly Gly Asn
            180                 185                 190

Asn Tyr Gly Glu Gly Asp Gly Gly Asn Gly Gly Asp Ala Ile Thr Gly
        195                 200                 205

Ser Ser Leu Ser Val Ile Asn Lys Gly Thr Phe Ala Gly Gly Asn Gly
    210                 215                 220

Gly Ala Ala Tyr Gly Tyr Gly Tyr Asp Gly Tyr Gly Gly Asn Ala Ile
225                 230                 235                 240

Thr Gly Asp Asn Leu Ser Ile Ile Asn Asn Gly Ala Ile Leu Gly Gly
                245                 250                 255

Asn Gly Gly His Trp Gly Asp Ala Ile Asn Gly Ser Asn Met Thr Ile
            260                 265                 270

Ala Asn Ser Gly Tyr Ile Ile Ser Gly Lys Glu Asp Gly Thr Gln
        275                 280                 285

Asn Val Ala Gly Asn Ala Ile His Ile Thr Gly Asn Asn Ser Leu
    290                 295                 300

Ile Leu His Glu Gly Ser Val Ile Thr Gly Asp Val Gln Val Asn Asn
305                 310                 315                 320

Ser Ser Ile Leu Lys Ile Ile Asn Asn Asp Tyr Thr Gly Thr Thr Pro
                325                 330                 335

```
Thr Ile Glu Gly Asp Leu Cys Ala Gly Asp Cys Thr Val Ser Leu
            340                 345                 350

Ser Gly Asn Lys Phe Thr Val Ser Gly Asp Val Ser Phe Gly Glu Asn
            355                 360                 365

Ser Ser Leu Asn Leu Ala Gly Ile Ser Ser Leu Glu Ala Ser Gly Asn
            370                 375                 380

Met Ser Phe Gly Asn Asn Val Lys Val Glu Ala Ile Ile Asn Asn Trp
385                 390                 395                 400

Ala Gln Lys Asp Tyr Lys Leu Leu Ser Ala Asp Lys Gly Ile Thr Ser
            405                 410                 415

Asn Ile Ser Ile Ile Asn Pro Leu Leu Thr Thr Gly Ala Ile Asp Tyr
            420                 425                 430

Thr Lys Ser Tyr Ile Ser Asp Gln Asn Lys Leu Ile Tyr Gly Leu Ser
            435                 440                 445

Trp Asn Asp Thr Asp Gly Asp Ser His Gly Glu Phe Asn Leu Lys Glu
            450                 455                 460

Asn Ala Glu Leu Thr Val Ser Thr Ile Leu Ala Asp Asn Leu Ser His
465                 470                 475                 480

His Asn Ile Asn Ser Trp Asp Gly Lys Ser Leu Thr Lys Ser Gly Glu
            485                 490                 495

Gly Thr Leu Ile Leu Ala Glu Lys Asn Thr Tyr Ser Gly Phe Thr Asn
            500                 505                 510

Ile Asn Ala Gly Ile Leu Lys Met Gly Thr Val Glu Ala Met Thr Arg
            515                 520                 525

Thr Ala Gly Val Ile Val Asn Lys Gly Ala Thr Leu Asn Phe Ser Gly
            530                 535                 540

Met Asn Gln Thr Val Asn Ser Leu Leu Asn Ser Gly Thr Val Leu Ile
545                 550                 555                 560

Asn Asn Ile Asn Ala Pro Phe Leu Pro Asp Pro Val Ile Val Thr Gly
            565                 570                 575

Asn Met Thr Leu Glu Lys Asn Gly His Val Ile Leu Asn Asn Ser Ser
            580                 585                 590

Ser Asn Val Gly Gln Thr Tyr Val Gln Lys Gly Asn Trp His Gly Lys
            595                 600                 605

Gly Gly Ile Leu Ser Leu Gly Ala Val Leu Gly Asn Asp Asn Ser Lys
            610                 615                 620

Thr Asp Arg Leu Glu Ile Thr Gly His Ala Ser Gly Ile Thr Tyr Val
625                 630                 635                 640

Ala Val Thr Asn Glu Gly Gly Ser Gly Asp Lys Thr Leu Glu Gly Val
            645                 650                 655

Gln Ile Ile Ser Thr Asp Ser Ser Asp Lys Asn Ala Phe Ile Gln Lys
            660                 665                 670

Gly Arg Ile Val Ala Gly Ser Tyr Asp Tyr Arg Leu Lys Gln Gly Thr
            675                 680                 685

Val Ser Gly Leu Asn Thr Asn Lys Trp Tyr Leu Thr Ser Gln Met Asp
            690                 695                 700

Asn Gln Glu Ser Lys Gln Met Ser Asn Gln Glu Ser Thr Gln Met Ser
705                 710                 715                 720

Ser Arg Arg Ala Ser Ser Gln Leu Val Ser Leu Asn Leu Gly Glu
            725                 730                 735

Gly Ser Ile His Thr Trp Arg Pro Glu Ala Gly Ser Tyr Ile Ala Asn
            740                 745                 750
```

-continued

Leu Ile Ala Met Asn Thr Met Phe Ser Pro Ser Leu Tyr Asp Arg His
        755                 760                 765

Gly Ser Thr Ile Val Asp Pro Thr Thr Gly Gln Leu Ser Glu Thr Thr
    770                 775                 780

Met Trp Ile Arg Thr Val Gly Gly His Asn Glu His Asn Leu Ala Asp
785                 790                 795                 800

Arg Gln Leu Lys Thr Thr Ala Asn Arg Met Val Tyr Gln Ile Gly Gly
            805                 810                 815

Asp Ile Leu Lys Thr Asn Phe Thr Asp His Asp Gly Leu His Val Gly
            820                 825                 830

Ile Met Gly Ala Tyr Gly Tyr Gln Asp Ser Lys Thr His Asn Lys Tyr
        835                 840                 845

Thr Ser Tyr Ser Ser Arg Gly Thr Val Ser Gly Tyr Thr Ala Gly Leu
    850                 855                 860

Tyr Ser Ser Trp Phe Gln Asp Glu Lys Glu Arg Thr Gly Leu Tyr Met
865                 870                 875                 880

Asp Ala Trp Leu Gln Tyr Gly Trp Phe Asn Asn Thr Val Lys Gly Asp
            885                 890                 895

Gly Leu Thr Gly Glu Lys Tyr Ser Ser Lys Gly Ile Thr Gly Ala Leu
            900                 905                 910

Glu Ala Gly Tyr Ile Tyr Pro Thr Ile Arg Trp Thr Ala His Asn Asn
        915                 920                 925

Ile Asp Asn Ala Leu Tyr Leu Asn Pro Gln Val Gln Ile Thr Arg His
        930                 935                 940

Gly Val Lys Ala Asn Asp Tyr Ile Glu His Asn Gly Thr Met Val Thr
945                 950                 955                 960

Ser Ser Gly Val Asn Asn Ile Gln Ala Lys Leu Gly Leu Arg Thr Ser
            965                 970                 975

Leu Ile Ser Gln Ser Cys Ile Asp Lys Glu Thr Leu Arg Lys Phe Glu
            980                 985                 990

Pro Phe Leu Glu Val Asn Trp Lys Trp Ser Ser Lys Gln Tyr Gly Val
        995                 1000                1005

Ile Met Asn Gly Met Ser Asn His Gln Ile Gly Asn Arg Asn Val
    1010                1015                1020

Ile Glu Leu Lys Thr Gly Val Gly Gly Arg Leu Ala Asp Asn Leu
    1025                1030                1035

Ser Ile Trp Gly Asn Val Ser Gln Gln Leu Val
    1040                1045

<210> SEQ ID NO 46
<211> LENGTH: 240
<212> TYPE: PRT
<213> ORGANISM: Artificial Sequence
<220> FEATURE:
<223> OTHER INFORMATION: Synthetic Polypeptide

<400> SEQUENCE: 46

Asn Asp Asp Lys Leu Tyr Arg Ala Asp Ser Arg Pro Pro Asp Glu Ile
1               5                   10                  15

Lys Gln Ser Gly Gly Leu Met Pro Arg Gly Gln Ser Glu Tyr Phe Asp
            20                  25                  30

Arg Gly Thr Gln Met Asn Ile Asn Leu Tyr Asp His Ala Arg Gly Thr
        35                  40                  45

Gln Thr Gly Phe Val Arg His Asp Asp Gly Tyr Val Ser Thr Ser Ile
    50                  55                  60

Ser Leu Arg Ser Ala His Leu Val Gly Gln Thr Ile Leu Ser Gly His
 65                  70                  75                  80

Ser Thr Tyr Tyr Ile Tyr Val Ile Ala Thr Ala Pro Asn Met Phe Asn
                 85                  90                  95

Val Asn Asp Val Leu Gly Ala Tyr Ser Pro His Pro Asp Glu Gln Glu
            100                 105                 110

Val Ser Ala Leu Gly Gly Ile Pro Tyr Ser Gln Ile Tyr Gly Trp Tyr
        115                 120                 125

Arg Val His Phe Gly Val Leu Asp Glu Gln Leu His Arg Asn Arg Gly
    130                 135                 140

Tyr Arg Asp Arg Tyr Tyr Ser Asn Leu Asp Ile Ala Pro Ala Ala Asp
145                 150                 155                 160

Gly Tyr Gly Leu Ala Gly Phe Pro Pro Glu His Arg Ala Trp Arg Glu
                165                 170                 175

Glu Pro Trp Ile His His Ala Pro Pro Gly Cys Gly Asn Ala Pro Arg
            180                 185                 190

Ser Ser Met Ser Asn Thr Cys Asp Glu Lys Thr Gln Ser Leu Gly Val
        195                 200                 205

Lys Phe Leu Asp Glu Tyr Gln Ser Lys Val Lys Arg Gln Ile Phe Ser
    210                 215                 220

Gly Tyr Gln Ser Asp Ile Asp Thr His Asn Arg Ile Lys Asp Glu Leu
225                 230                 235                 240

<210> SEQ ID NO 47
<211> LENGTH: 125
<212> TYPE: DNA
<213> ORGANISM: Artificial Sequence
<220> FEATURE:
<223> OTHER INFORMATION: Synthetic Polynucleotide

<400> SEQUENCE: 47
gtatcgatta aataaggagg aataaaccat ggtaaagata atcttcgtgt tcttcatctt    60
cctgagcagc ttttcgtacg ctaacgatga taagctctat cgcgcagata gtcgcccgcc   120
cgacg                                                              125

<210> SEQ ID NO 48
<211> LENGTH: 522
<212> TYPE: DNA
<213> ORGANISM: Artificial Sequence
<220> FEATURE:
<223> OTHER INFORMATION: Synthetic Polynucleotide

<400> SEQUENCE: 48
gagtggaaca gtcaatgaca gtggtaaaga agatgaataa agtaaaatgt tatgttttat    60
ttacggcgtt actatcctct ctatgtgcat acggagctcc ccagtctatt acagaactat   120
gttcggaata tcgcaacaca caaatatata cgataaatga caagatacta tcatatacgg   180
aatcgatggc aggcaaaaga gaaatggtta tcattacatt taagagcggc gcaacatttc   240
aggtcgaagt cccgggcagt caacatatag actcccaaaa aaaagccatt gaaaggatga   300
aggacacatt aagaatcaca tatctgaccg agaccaaaat tgataaatta tgtgtatgga   360
ataataaaac ccccaattca attgcggcaa tcagtatgga aaacgatccc cgggtaccga   420
gctcgaatag tagcaattac tgctgtgaat tgtgttgtaa tcctcattgt accgggtgct   480
attaaattta cctagtcact tagtcgtatg tataaaaaac cg                     522

<210> SEQ ID NO 49

<210> SEQ ID NO 49
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 49
gatcatttgg taataggtat cgattaaata aggagg                              36

<210> SEQ ID NO 50
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 50
tgctttattt cgtcgggcgg gcgactatc                                      29

<210> SEQ ID NO 51
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 51
ccgcccgacg aaataaagca gtcaggtggt cttatgc                             37

<210> SEQ ID NO 52
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 52
ataaccatct gctgctggag caatatctaa gttactg                             37

<210> SEQ ID NO 53
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 53
attgctccag cagcagatgg ttatggattg gcaggtttc                           39

<210> SEQ ID NO 54
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 54
atcacccgtg attgttccgc tactatcccc acaacccggc ggtgcatgat g             51

<210> SEQ ID NO 55
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 55
gatagtagcg gaacaatcac gggtgatact tgcgatgaaa aaacccaaag tc    52

<210> SEQ ID NO 56
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 56
gattggtatt cgtcagcgaa ttttacacct agactttg    38

<210> SEQ ID NO 57
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 57
gtaaaattcg ctgacgaata ccaatctaaa gttaaaagac    40

<210> SEQ ID NO 58
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 58
gtattgcaca ggttaatttg ccatactaat tgcg    34

<210> SEQ ID NO 59
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 59
gcgcgcgcga gctcaagcct tacatacagg ccagcg    36

<210> SEQ ID NO 60
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 60
cgatacctat taccaaatga tcacacaagg gtg    33

<210> SEQ ID NO 61
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 61
gcaaattaac ctgtgcaata cgaaggggc    30

<210> SEQ ID NO 62
<211> LENGTH: 41
<212> TYPE: DNA

```
<213> ORGANISM: Artificial Sequence
<220> FEATURE:
<223> OTHER INFORMATION: Synthetic Polynucleotide

<400> SEQUENCE: 62
gcgcgcgcga gctcgctgga cttttttgac ttcatgtaat g                41

<210> SEQ ID NO 63
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 63
attgggtacc gggcccccc ctcttactga tggtcgtatg                   40

<210> SEQ ID NO 64
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 64
ccactgtcat tgactgttcc                                         20

<210> SEQ ID NO 65
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 65
gtcgtatgta taaaaaaccg                                         20

<210> SEQ ID NO 66
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 66
cttatcgata ccgtcgacct cgatagcatc aatgacccaa ac               42
```

BIOFILM MATRIX-BOOSTED VACCINE

RELATED APPLICATIONS

This application is a national stage filing under 35 U.S.C. § 371 of international application number PCT/US2017/038045, filed Jun. 16, 2017, which claims the benefit under 35 U.S.C. § 119(e) of U.S. provisional application No. 62/351,895, filed Jun. 17, 2016, each of which is incorporated by reference herein in its entirety.

GOVERNMENT LICENSE RIGHTS

This invention was made with government support under grant number AI 050032 awarded by the National Institutes of Health (NIH). The government has certain rights in the invention.

BACKGROUND

Bacterial biofilm formation is the process by which bacteria adhere to surfaces to form single or multilayer structures. These biofilm structures are found on biotic surfaces such as the epithelia of animals and on abiotic surfaces such as those of mineral deposits, soil, walls of bioreactors, and air-water interfaces. The bacterial biofilm matrix is comprised of exopolysaccharide, proteins, and DNA.

SUMMARY

Bacterial biofilms, which are often described as "slime," have been vilified in medicine and industry. While much research has been performed to develop methods and materials that avoid the formation of biofilms on surfaces, e.g., on surfaces of medical devices or bioreactors, some aspects of this disclosure are based on the recognition that biofilms can be engineered to be useful in a number of biomedical and biotechnological applications.

In contrast to the conventional paradigm that biofilm exopolysaccharides function as the adhesive material that cements cell-surface and intercellular interactions, some aspects of this disclosure provide that biofilm exopolysaccharides actually serve as a scaffold for cellular proteins which mediate these adhesive interactions. Some aspects of this disclosure are based on the recognition that the cellular proteins mediating cell adhesion in biofilms are abundant in biofilms, and that these cellular proteins can be used to deliver heterologous molecules, e.g., enzymes, antigens, binding agents, detection agents, or small molecules, to biofilms in order to engineer novel biofilm functionalities.

Some aspects of this disclosure relate to the identification of several secreted proteins that are retained in the bacterial biofilm matrix by their association with the biofilm exopolysaccharide scaffold. As described in more detail elsewhere herein, these exopolysaccharide-associated proteins show different spatial distribution patterns within the biofilm. Some aspects of this disclosure are based on the recognition that such exopolysaccharide-associated proteins can be used to engineer biofilms for various applications, e.g., to serve as reservoirs for surface-active secreted proteins of biomedical, bioengineering, or biotechnological importance. Accordingly, some aspects of this disclosure provide that the biofilm matrix can be exploited, among other uses, as a vehicle for concentration of molecules, e.g., enzymes or antigens, on the surfaces of cells and as a delivery system targeting abiotic surfaces. Because of their affinity for surfaces, biofilms engineered according to aspects of this disclosure are also ideal vehicles for presentation of vaccine antigens and for delivery of enzymes of therapeutic or bioremediative importance to surfaces.

The technology described herein is broadly applicable, with envisioned applications ranging from vaccine development, treatment of digestive dysfunction, biotechnology (e.g., concentration, isolation, or purification of recombinant proteins from bioreactors), bioremediation (e.g., oil spill clean-up), molecular biology, and others.

Some aspects of this disclosure provide compositions comprising: (i) a bacterium associated with an exopolysaccharide; (ii) a RbmA protein, and (iii) a heterologous molecule conjugated to the exopolysaccharide-associated protein, or an exopolysaccharide-binding fragment thereof.

In some embodiments, the heterologous molecule is a heterologous protein. In some embodiments, the heterologous protein is an enzyme, or an antigen. In some embodiments, the heterologous protein is fused to the exopolysaccharide-associated protein, or to the exopolysaccharide-binding fragment thereof, thus forming a fusion protein. In some embodiments, the fusion protein is encoded by a recombinant nucleic acid comprised in the bacterium.

In some embodiments, the RbmA protein comprises an amino acid sequence of SEQ ID NO: 2. In some embodiments, the RbmA protein is a RbmA variant comprising one or more substitution mutations in a surface groove of the RbmA protein. In some embodiments, the one or more substitution mutations are in positions R234, R219, or R116 in SEQ ID NO: 2. In some embodiments, the one or more mutations are R234A, R219A, or R116A in SEQ ID NO: 2. In some embodiments, the RbmA variant comprises an amino acid sequence of any one of SEQ ID NOs: 38-43.

In some embodiments, the heterologous molecule comprises an antigen. In some embodiments, the antigen comprises an antigen of a pathogen. In some embodiments, the antigen comprises an antigen of a bacterial toxin. In some embodiments, the bacterial toxin is a cholera toxin. In some embodiments, the cholera toxin is the B subunit of cholera toxin (e.g., MIKLKFGVFFTVLLSSAYAHGTPQNITDL-CAEYHNTQIYTLNDKIFSYTESLAGKRE MAIITFKN-GAIFQVEVPGSQHIDSQKKAIERMKDTLRIAYL-TEAKVEKLCVWNNKTP HAIAASMAN (SEQ ID NO: 5)). In some embodiments, the antigen comprises a colonization factor antigen. In some embodiments, the colonization factor antigen is from Enterotoxigenic *Escherichia coli* (ETEC). In some embodiments, the colonization factor antigen is EtpA. In some embodiments, the EtpA comprise the amino acid sequence of SEQ ID NO: 44. In some embodiments, the antigen comprises a bacterial virulence factor antigen. In some embodiments, the bacterial virulence factor antigen is from *Shigella*. In some embodiments, the bacterial virulence factor antigen is VirG. In some embodiments, the VirG comprises an amino acid sequence of SEQ ID NO: 45.

In some embodiments, the heterologous molecule comprises an enzyme. In some embodiments, the enzyme is a therapeutic enzyme. In some embodiments, the enzyme is selected from the group consisting of lactase, a pancreatic enzyme, an oil-degrading enzyme, beta-galactosidase, mucinase, cellulase, isomaltase, or alginase.

In some embodiments, the heterologous molecule comprises a binding agent. In some embodiments, the binding agent is selected from the group comprising an antibody, an antigen-binding antibody fragment, a nanobody, an ScFv, an adnectin, a lectin, a ligand, or an affinity tag. In some embodiments, the heterologous molecule comprises a detection agent.

In some embodiments, the compositions disclosed herein further comprises a signal peptide fused to the exopolysaccharide-associated protein, or exopolysaccharide-binding fragment thereof, or to the heterologous molecule, wherein the signal peptide targets the exopolysaccharide-associated protein, or exopolysaccharide-binding fragment thereof, conjugated to the heterologous molecule for secretion.

In some embodiments, the bacterium is a gram-negative bacterium. In some embodiments, the bacterium is a gram-positive bacterium. In some embodiments, the bacterium is a non-pathogenic bacterium. In some embodiments, the bacterium is a *Vibrio* sp. bacterium. In some embodiments, the bacterium is a *Vibrio cholerae* bacterium. In some embodiments, the bacterium is an *E. coli* bacterium.

In some embodiments, the bacteria toxin comprises a non-toxic heat-stable toxoid (STa) variant and a B subunit of heat-labile toxin (LTB) from Enterotoxigenic *Escherichia coli* (ETEC). In some embodiments, the non-toxic STa variant comprises a A14H mutation ($STa^{A14H}$). In some embodiments, the $STa^{A14H}$, LTB, and RbmA forms a fusion protein in an order of RmbA-LTB-$STa^{A14H}$. In some embodiments, wherein the fusion protein is encoded by an nucleotide sequence comprising the nucleotide sequence of SEQ ID NO: 48.

Other aspects of this disclosure provide compositions comprising: (i) a RbmA protein, and (ii) a heterologous molecule conjugated to the exopolysaccharide-associated protein, or an exopolysaccharide-binding fragment thereof.

In some embodiments, the heterologous molecule comprises a heterologous protein. In some embodiments, the heterologous protein is an enzyme, or an antigen. In some embodiments, the heterologous protein is fused to the exopolysaccharide-associated protein, or to the exopolysaccharide-binding fragment thereof, thus forming a fusion protein.

In some embodiments, the RbmA protein comprises an amino acid sequence of SEQ ID NO: 2. In some embodiments, the RbmA protein is a RbmA variant comprising one or more substitution mutations in a surface groove of the RmbA protein. In some embodiments, the one or more substitution mutations are in positions R234, R219, or R116 in SEQ ID NO: 2. In some embodiments, the one or more mutations are R234A, R219A, or R116A in SEQ ID NO: 2. In some embodiments, the RbmA variant comprises an amino acid sequence of any one of SEQ ID NOs: 38-43.

In some embodiments, the heterologous molecule comprises an antigen. In some embodiments, the antigen comprises an antigen of a pathogen. In some embodiments, the antigen comprises an antigen of a bacteria toxin. In some embodiments, the bacterial toxin is a cholera toxin. In some embodiments, the cholera toxin is the B subunit of cholera toxin. In some embodiments, the B subunit of cholera toxin comprises the sequence of (SEQ ID NO: 5). In some embodiments, antigen comprises a colonization factor antigen. In some embodiments, the colonization factor antigen is from Enterotoxigenic *Escherichia coli* (ETEC). In some embodiments, the colonization factor antigen is EtpA. In some embodiments, the EtpA comprise the amino acid sequence of SEQ ID NO: 44. In some embodiments, the antigen comprises a bacterial virulence factor antigen. In some embodiments, the bacterial virulence factor antigen is from *Shigella*. In some embodiments, the bacterial virulence factor antigen is VirG. In some embodiments, the VirG comprises an amino acid sequence of SEQ ID NO: 45.

In some embodiments, the heterologous molecule comprises an enzyme. In some embodiments, the enzyme is a therapeutic enzyme. In some embodiments, the enzyme is selected from the group consisting of lactase, a pancreatic enzyme, an oil-degrading enzyme, beta-galactosidase, mucinase, cellulase, isomaltase, or alginase.

In some embodiments, the heterologous molecule comprises a binding agent. In some embodiments, the binding agent is selected from the group comprising an antibody, an antigen-binding antibody fragment, a nanobody, an ScFv, an adnectin, a lectin, a ligand, or an affinity tag. In some embodiments, the heterologous molecule comprises a detection agent.

In some embodiments, the compositions disclosed herein further comprise a signal peptide fused to the exopolysaccharide-associated protein, or exopolysaccharide-binding fragment thereof, or to the heterologous molecule, wherein the signal peptide targets the exopolysaccharide-associated protein, or exopolysaccharide-binding fragment thereof, conjugated to the heterologous molecule for secretion.

In some embodiments, the bacteria toxin comprises a non-toxic heat-stable toxoid (STa) variant and a B subunit of heat-labile toxin (LTB) from Enterotoxigenic *Escherichia coli* (ETEC). In some embodiments, the non-toxic STa variant comprises a A14H mutation ($STa^{A14H}$). In some embodiments, the $STa^{A14H}$, LTB, and RbmA forms a fusion protein in an order of RmbA-LTB-$STa^{A14H}$. In some embodiments, wherein the fusion protein is encoded by an nucleotide sequence comprising the nucleotide sequence of SEQ ID NO: 48.

Further provided herein are vaccines comprising the composition described herein. In some embodiments, the fusion protein is expressed by the bacterium. In some embodiments, the exopolysaccharide is an exopolysaccharide secreted by the bacterium. In some embodiments, the exopolysaccharide is bound by the bacterium. In some embodiments, the fusion protein is bound by the exopolysaccharide. In some embodiments, the antigen is an antigen of a pathogen.

In some embodiments, the vaccine further comprises an adjuvant. In some embodiments, the adjuvant is a Cholera toxin subunit A (CtxA) variant. In some embodiments, the CtxA variant comprises mutations corresponding to N189D, A190S, P191S, R192G, S193T, S1941, M195T, S196G, N197, N197D, or L211A in SEQ ID NO: 46. In some embodiments, the CtxA variant has reduced activity. In some embodiments, the CtxA variant activity is reduced by at least 10-100 fold. In some embodiments, the CtxA variant is expressed by the bacterium. In some embodiments, the CtxA variant is constitutively expressed.

In some embodiments, the adjuvant is a multiple-mutated Cholera toxin (mmCT). In some embodiments, the mmCT is encoded by a polynucleotide comprising the nucleotide sequence of SEQ ID NO: 47.

In some embodiments, the vaccine is a killed whole cell vaccine. In some embodiments, the vaccine is a live attenuated vaccine.

In some embodiments, the bacterium is a pathogenic bacterium. In some embodiments, the bacterium is *V. Cholerae*. In some embodiments, the bacterium is *E. Coli*. In some embodiments, the *V. cholerae* is inactivated in ctxA. In some embodiments, the ctxA is deleted from the *C. cholerae* genome.

Other aspects of this disclosure provide methods of vaccinating a subject against a pathogen, the methods comprising administering to the subject an effective amount of the vaccine described herein.

In some embodiments, the vaccine is administered in an amount sufficient to elicit an immune response against the bacterium and/or against the antigen. In some embodiments, the vaccine is administered in an amount sufficient to immunize the subject against the bacterium and/or against the antigen. In some embodiments, the vaccine is administered sublingually. In some embodiments, the vaccine is administered orally.

In some embodiments, the subject is 0-13 years of age.

In some embodiments, the vaccine stimulates systemic immune response to the antigen. In some embodiments, the vaccine stimulates mucosal immune response to the antigen. In some embodiments, the vaccine elicits antigen-specific antibodies in the subject. In some embodiments, the antigen-specific antibody is IgG. In some embodiments, the antigen-specific antibody is IgA.

Further provided herein are methods for delivering a molecule to a target site, the method comprising delivering to the target site a bacterium associated with an exopolysaccharide that binds a RbmA protein, wherein the exopolysaccharide-associated protein, or an exopolysaccharide-binding fragment thereof, binds the molecule. In some embodiments, the target site is a surface. In some embodiments, the target site is an air/water interface. In some embodiments, the heterologous molecule comprises a polypeptide. In some embodiments, the polypeptide is fused to the exopolysaccharide-associated protein or the exopolysaccharide binding protein fragment.

In some embodiments, the bacterium comprises a recombinant nucleic acid encoding the polypeptide fused to the exopolysaccharide-associated protein or the exopolysaccharide binding protein fragment. In some embodiments, the molecule comprises a therapeutic protein. In some embodiments, the method comprises administering an effective amount of the bacterium to a subject. In some embodiments, the bacterium is a non-pathogenic bacterium. In some embodiments, the molecule is an enzyme and wherein the target site is a digestive organ of the subject. In some embodiments, the target site is the intestinal tract of the subject.

In some embodiments, the molecule is lactase, a pancreatic enzyme, beta-galactosidase, mucinase, cellulase, isomaltase, or alginase. In some embodiments, the bacterium can colonize the intestinal tract of the subject. In some embodiments, the bacterium is administered orally. In some embodiments, the molecule is a mucus-digesting enzyme, and wherein the target site is the lung of the subject. In some embodiments, the mucus-digesting enzyme is mucinase or alginase.

In some embodiments, the bacterium can colonize the lung of the subject. In some embodiments, the bacterium is administered via an aerosol. In some embodiments, the molecule is an enzyme that can digest a contaminant. In some embodiments, the contaminant is oil. In some embodiments, the molecule is an oil-digesting enzyme. In some embodiments, the target site is an environmental water-air interface.

Also provided herein are biofilms comprising the bacterium described herein.

Yet other aspects of this disclosure provide methods for modifying the surface of a bacterium, the method comprising contacting a bacterium associated with an exopolysaccharide with a composition comprising a heterologous molecule conjugated to a RbmA protein, wherein the RbmA protein binds to the exopolysaccharide. In some embodiments, the composition is the composition disclosed herein.

Yet another aspect of the present disclosure provides methods of targeting a molecule to a biofilm, the method comprising contacting a biofilm that comprises an exopolysaccharide with a RmbA protein, conjugated to the molecule. In some embodiments, the biofilm comprises a pathogen and the molecule comprises a polypeptide toxic to the pathogen.

Other aspects of the present disclosure provide vaccines comprising: (i) a *Vibrio cholerae* bacterium associated with an exopolysaccharide; (ii) a RbmA protein; and (iii) an antigen conjugated to the RbmA protein, or an exopolysaccharide-binding fragment thereof. In some embodiments, the RbmA protein comprises the amino acid sequence of SEQ ID NO: 2.

In some embodiments, the antigen is a bacterial toxin. In some embodiments, the bacterial toxin is a cholera toxin. In some embodiments, the cholera toxin is the B subunit of cholera toxin (CtxB). In some embodiments, the CtxB comprises the amino acid sequence of (SEQ ID NO: 5).

In some embodiments, the bacterial toxin comprises a non-toxic heat-stable toxoid (STa) variant and a B subunit of heat-labile toxin (LTB) from Enterotoxigenic *Escherichia coli* (ETEC). In some embodiments, the bacterial toxin comprises a non-toxic heat-stable toxoid (STa) variant and a B subunit of heat-labile toxin (LTB) from Enterotoxigenic *Escherichia coli* (ETEC).

In some embodiments, the non-toxic STa variant comprises a A14H mutation ($STa^{A14H}$). In some embodiments, the $STa^{A14H}$, LTB, and RbmA forms a fusion protein in an order of RmbA-LTB-$STa^{A14H}$. In some embodiments, the fusion protein is encoded by an nucleotide sequence comprising the nucleotide sequence of SEQ ID NO: 48.

In some embodiments, the antigen is bacterial lipopolysaccharide (LPS). In some embodiments, the LPS is from *Vibrio cholerae*.

In some embodiments, the vaccine further comprises an adjuvant. In some embodiments, the adjuvant is a Cholera toxin subunit A (CtxA) variant. In some embodiments, the CtxA variant comprises mutations corresponding to N189D, A190S, P191S, R192G, S193T, S1941, M195T, S196G, N1971, N197D, or L211A in SEQ ID NO: 46. In some embodiments, the CtxA variant has reduced activity. In some embodiments, the adjuvant is a multiple-mutated Cholera toxin (mmCT). In some embodiments, the mmCT is encoded by a polynucleotide comprising the nucleotide sequence of SEQ ID NO: 47. In some embodiments, the adjuvant is expressed by the *Vibrio cholera* bacterium. In some embodiments, the adjuvant is constitutively expressed. In some embodiments, the adjuvant is under the control of a LacZ promoter. In some embodiments, the RbmA protein and the antigen conjugated to the RbmA protein are under the control of a native RbmA promoter.

In some embodiments, the *Vibrio cholera* bacterium lacks endogenous CtxA. In some embodiments, the vaccine is a live attenuated vaccine.

Further provided herein are methods of vaccinating a subject against a pathogen, the method comprising administering to the subject an effective amount of the vaccine described herein. In some embodiments, the vaccine is administered in an amount sufficient to elicit an immune response against the bacterium and/or against the antigen. In some embodiments, the vaccine is administered sublingually. In some embodiments, the vaccine is administered orally.

In some embodiments, the subject is 0-13 years of age.

In some embodiments, the vaccine stimulates systemic immune response to the antigen. In some embodiments, the vaccine stimulates mucosal immune response to the antigen. In some embodiments, the vaccine elicits antigen-specific antibodies in the subject. In some embodiments, the antigen-specific antibody is IgG. In some embodiments, the antigen-specific antibody is IgA.

The summary above is meant to illustrate, in a non-limiting manner, some of the embodiments, advantages, features, and uses of the technology disclosed herein. Other embodiments, advantages, features, and uses of the technology disclosed herein will be apparent from the Detailed Description, the Drawings, the Examples, and the Claims.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A. Immunofluorescent imaging of the distribution of RbmA-FLAG (RbmA), ChiA-2-FLAG, RbmA-ChiA-2-FLAG, or RbmA-CtxB fusion protein (RbmA-CtxB) in a biofilm formed by wild-type $V.$ $cholerae$ carrying a plasmid encoding this protein. RbmA-FLAG and the fusion protein were visualized with anti-FLAG and anti-CtxB antibodies, respectively. Bacterial DNA was stained with DAPI. FLAG-tagged ChiA does not stay associated with the cells, while the RbmA-Chia12 and RbmA-CTB fusion proteins remained cell-associated. FIG. 1B. An expanded view of the distributions of RbmA-FLAG and RbmA-CtxB in the biofilm. RbmA-CTB fusion protein co-localizes with the cells.

FIG. 2. An enzymatically active RbmA-ChiA-2-FLAG fusion protein is retained in the biofilm matrix. (A) Immunofluorescent imaging of the distribution of ChiA-2-FLAG or RbmA-ChiA-2-FLAG in a biofilm formed by wild-type *V. cholerae* carrying a plasmid encoding each of these proteins. The proteins were visualized with an anti-FLAG antibody. Bacterial DNA was stained with DAPI. As a control, a biofilm formed by wildtype *V. cholerae* carrying an empty vector was developed with an anti-FLAG antibody (CTL). (B) An expanded view of the distribution of RbmA-ChiA-2-FLAG in the biofilm. Chitinase activity measured in the biofilms (C) and supernatants (D) of wild-type *V. cholerae* carrying an empty vector (CTL) or a plasmid encoding RbmA-CtxB (RbmACtxB), ChiA-2-FLAG (ChiA-2), or RbmA-ChiA-2-FLAG (RbmA-ChiA-2). The chitinase activity in the biofilm of the strain expressing RbmA-ChiA-2-FLAG was approximately 40 times higher. This difference was statistically significantly different from that in all other biofilms ($p \leq 0.0003$). Similarly, chitinase activity in the supernatants of strains expressing either RbmA-ChiA-2-FLAG or ChiA-2-FLAG was significantly different from that of strains carrying the control vector ($p=0.007$ and $p=0.0215$, respectively) or the RbmA-CtxB fusion ($p=0.0025$ or $p=0.0149$, respectively). The difference in chitinase activity between the supernatants of the strains expressing RbmA-ChiA-2-FLAG and ChiA-2-FLAG was not significantly different ($p=0.07$). Using a commercial kit for chitinase activity, chitinase activity was found in the supernatant (F) of both a strain expressing ChiA, a normally secreted protein, and a strain expressing RbmA-ChiA, indicating that there are some RbmA-ChiA fusion proteins in the supernatant that either did not stick onto the cell or become dissociated from the cell surface. Chitinase activity was only detected in the cell pellet of a strain expressing RbmA-ChiA fusion protein on a plasmid, but not in the pellets of strains only expressing unconjugated ChiA (E).

FIG. 3. A *V. cholerae* Δbap1ΔrbmAΔrbmC triple mutant does not make a biofilm but can recruit the chitinase activity of RbmA-ChiA-2-FLAG to the cell surface. (A) Quantification of biofilms formed by wild-type *V. cholerae* (WT), an exopolysaccharide mutant (ΔvpsL), and a Δbap1ΔrbmAΔrbmC mutant (triple) carrying either an empty vector (pCTL) or a plasmid encoding RbmA (pRbmA), and (B) the pellicle formed by a Δbap1ΔrbmAΔrbmC mutant carrying either an empty vector (CTL) or plasmids encoding RbmA-FLAG (RbmA), RbmA-CtxB (RbmA-CtxB), ChiA-2-FLAG (ChiA-2), or RbmA-ChiA-2-FLAG (RbmA-ChiA-2). Chitinase activity in the cellular fraction (C) and supernatants (D) of *V. cholerae* Δbap1ΔrbmAΔrbmC mutant carrying an empty vector or a plasmid encoding RbmA-CtxB. ChiA-2-FLAG, or RbmA-ChiA-2-FLAG. Chitinase activity in the cellular fraction of the mutant expressing RbmA-ChiA-2-FLAG was significantly different from strains expressing all other recombinant proteins ($p<0.001$). The chitinase activity in the supernatants of mutants expressing ChiA-2-FLAG and RbmA-ChiA-2-FLAG was significantly different from those of the mutant carrying an empty vector ($p=0.034$ and $p=0.0172$) and the mutant expressing RbmA-CtxB ($p=0.039$ and $p=0.0215$). The difference in chitinase activity between the supernatants of the strains expressing RbmA-ChiA-2-FLAG and ChiA-2-FLAG was not significantly different ($p=0.535$).

FIG. 4. Structures of β-prism domain proteins: (A) In Bap1 and RbmC, the β-prism domain is surrounded by FG-GAP domains that likely form a β-propeller. HlyA consists of spatially separated cytolysin, β-trefoil, and β-prism domains. (B) Crystal structure of HlyA.

FIG. 5. Bap1 and RbmC are required for anchoring of the biofilm to a surface, while RbmA stabilizes intercellular attachments. Wild-type *V. cholerae* as well as ΔvpsL, ΔrbmA, Δbap1ΔrbmC, and rescued Δbap1ΔrbmC mutant biofilms undisturbed (U), after shaking (S), or after vortexing (V). A ΔrbmA biofilm is dispersed by vortexing, while the Δbap1 ΔrbmC mutant falls to the bottom of the tube when shaken gently.

FIG. 6. Distinct distributions of the proteins RbmA and Bap1 in the biofilm matrix: Immunofluorescent analysis of biofilms formed by strains containing a chromosomally encoded affinity tag at the C-terminus of RbmA (A) or Bap1 (B). Immunofluorescence shows that RbmA is distributed throughout the biofilm, while Bap1 is concentrated at the surface. (C) Fluorescent intensity plotted as a function of biofilm height (Z-axis) for each of these biofilms.

FIG. 7. RbmA mediates cell-cell interactions in the biofilm. RbmA contains two Fn III domains and functions as a homodimer (bottom panel). It is secreted and attaches to the outside of cells to mediate cell-cell interactions. There are two grooves in an RbmA dimer: the wide groove and the narrow groove. The wide groove, which has a net negative charge, is important in recruiting VPS (planktonic) cells into biofilm. The narrow groove, which has a net positive charge, is important in cell-cell adhesion within the biofilm, and key arginine residues within the groove have been found to be key contributors to this charge and cell adhesion property. Knocking out RmbA impairs biofilm formation. When the wild-type biofilm is vortexed, it breaks up into small aggregates of cells; RbmA mutant biofilms are easily dispersed by vortexing (top panel). Adding purified protein exogenously to the RbmA mutant during biofilm formation results in the vortex-resistant aggregate phenotype seen in WT biofilm (middle panel). RbmA mediates cell-cell interactions.

FIG. 8. Confirmation that RbmA-CTB fusion protein co-localizes with cells. A prototype formalin-killed whole cell vaccine that carries RbmA-CTB on the surface of the cell was developed. The Western blot shows that cholera toxin B (CTB) is expressed by itself from a plasmid is only detected in the supernatant; however, when it is linked to RbmA, the fusion protein is found in the cellular fraction. Furthermore, in a simple whole cell vaccine, the RbmA-CTB fusion protein is found at levels equivalent to the amount of purified recombinant CTB added to the Dukoral® vaccine, showing that the CTB protein antigen is effectively incorporated into the whole cell vaccine. The RbmA protein presentation platform may be an efficient way to achieve antigen presentation.

Figure 9:
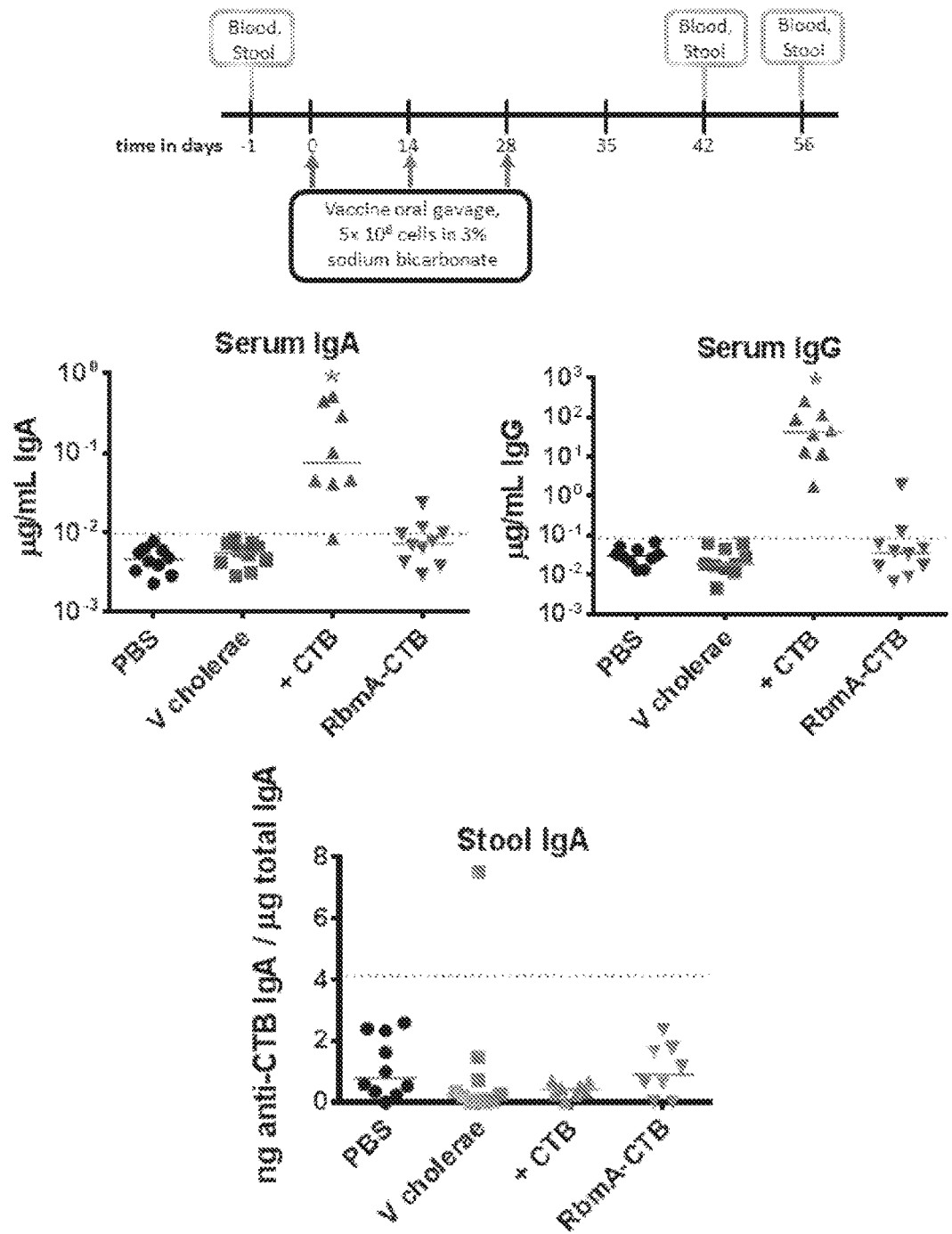

FIG. 9. Schematic and results of the initial vaccine trial with prototype vaccine. BALB/c mice were administered formalin-killed whole cell vaccines by oral gavage, followed by a regimen of one initial inoculation and two boosters spaces two weeks apart. For comparison, formalin-killed *V. cholera* whole cells, similar to Shanchol™, and formalin-killed whole cells given with purified CTB, similar to Dukoral®, were also studied. The primary outcome was the presence of CTB-specific antibodies in serum and stool. As shown in the graphs, four weeks after the final booster, only the test group similar to Dukoral®, which contains purified CTB, shows a CTB-specific response in erum. Not CTB-specific antibodies were detected in stool in any of the groups. * p<0.02

Figure 10:
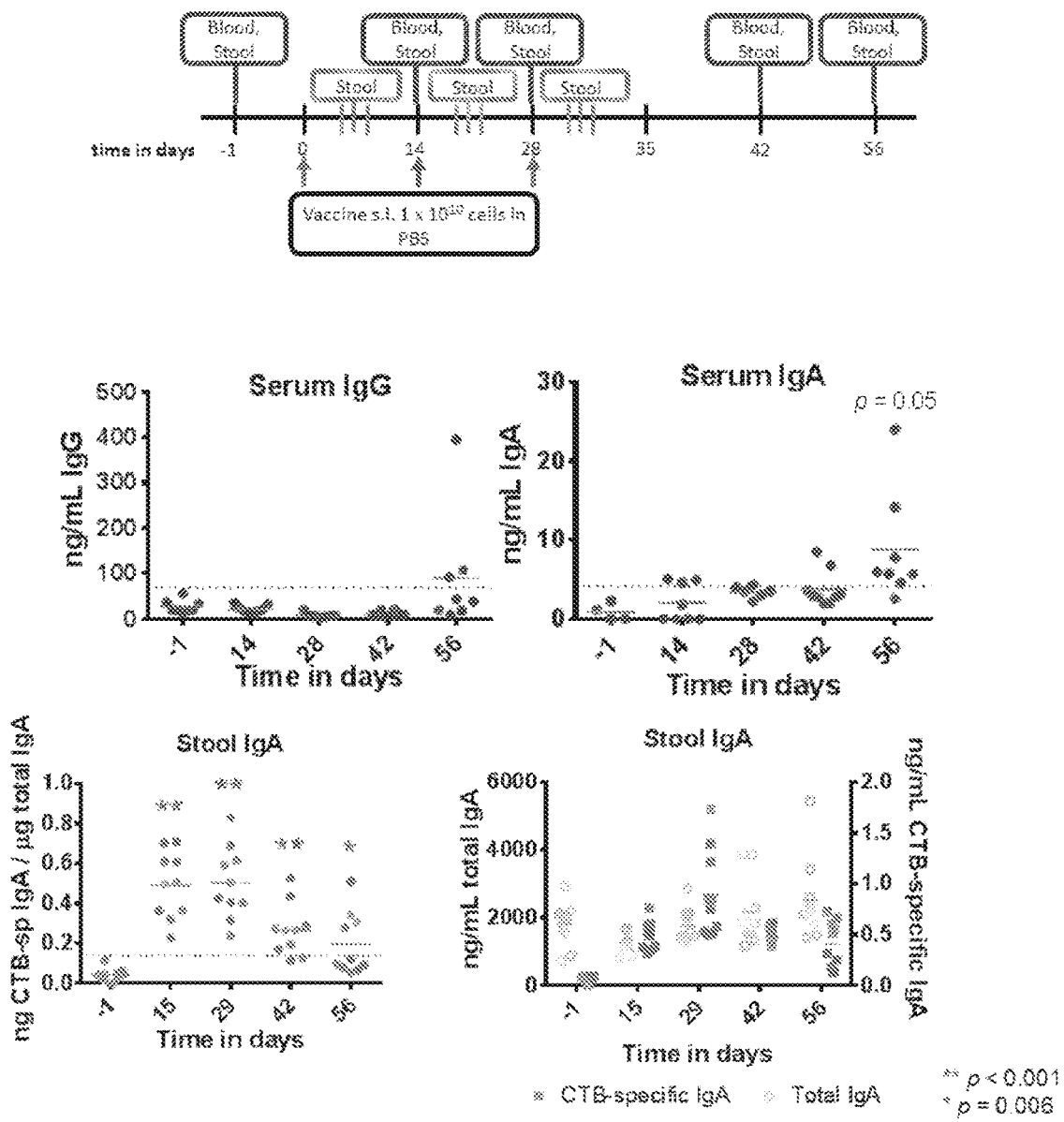

FIG. 10. Schematic and results of a test of a live-attenuated version of the whole cell vaccine. Live-attenuated vaccines have several advantages over an inactivated vaccine, including having documented better responses in young children, a single dose of live-attenuated vaccine can be sufficient to induce an adequate and sustained immune response. The vaccine was delivered sublingually to avoid the use of bicarbonate and to bypass the stomach completely. The strain used, ΔctxA/prbmA-ctxB, does not express ctxA, the effector subunit of the cholera toxin. The study included 10 mice, and serum and stool were collected every two weeks to measure the presence of CTB-specific antibodies. The results, lower panel, show that CTB-specific IgG was not detected in the serum, while the serum levels of CTB-specific IgA showed a slightly increasing trend by four weeks after administration of the final booster. In contrast to the inactivated vaccine, there was a significant rise in the secretory IgA specific to CTB, which waned by four weeks after the final booster. While the level of CTB-specific secretory IgA is low, it is statistically significant compared with levels of non-specific antibody detection before vaccination. Furthermore, levels of total IgA can be seen to have remained constant while the CTB-specific IgA levels increased, therefore, the live-attenuated vaccine may show more promise than the inactivated vaccine.

Figure 11:
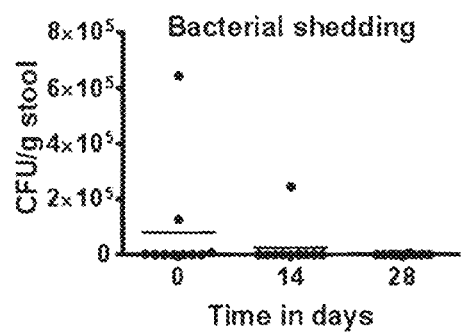

FIG. 11. Both the live-attenuated and the killed whole-cell vaccine generated vibriocidal antibodies. Serum levels of vibriocidal antibodies have been recognized as an indication of protection, both in cases of cholera infection and vaccination. To determine if the vaccines were properly administered, the levels of vibriocidal antibodies in the serum were examined. They were present in both the formalin-killed and live-attenuated vaccines. In particular, the increase in vibriocidal antibody titer for the live-attenuated vaccine corresponded well with a decrease in the number of live *vibrio* shedding in the stool post-vaccination.

Figure 12:
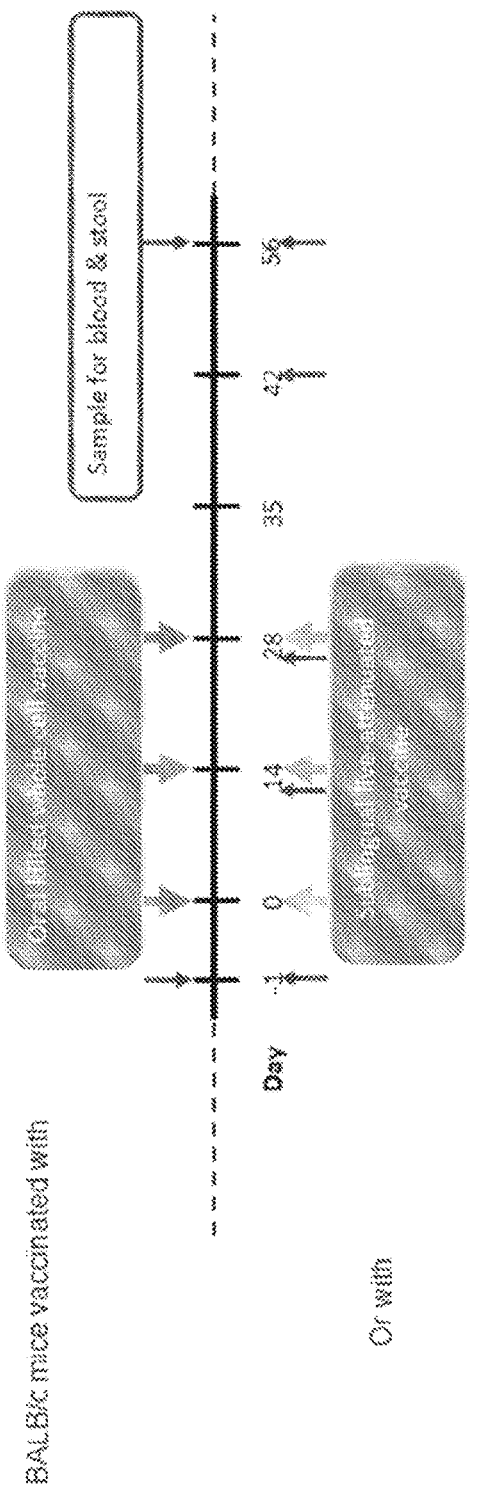
Figure 13A:
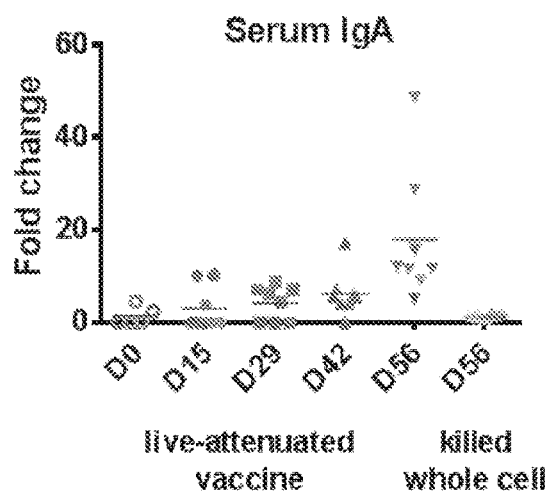
Figure 13B:
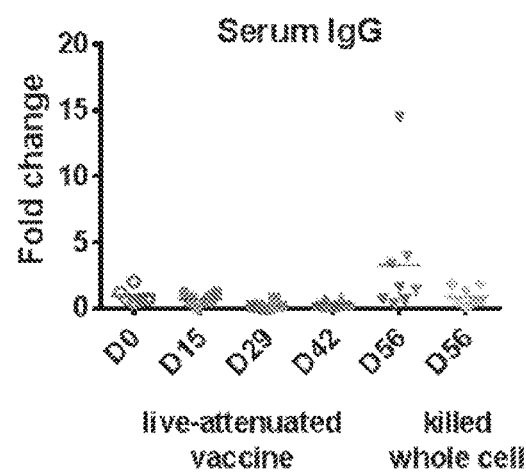
Figure 13C:
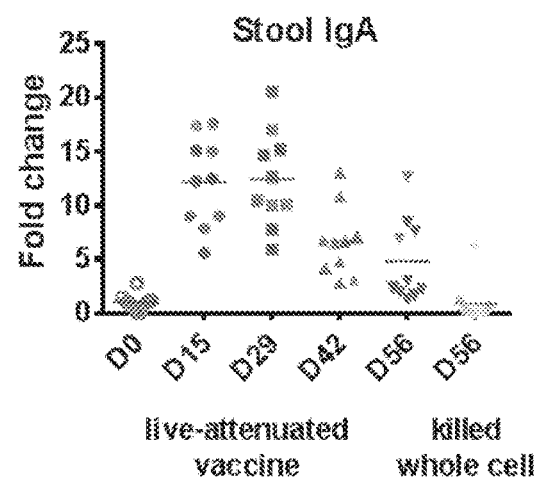
Figure 14A:
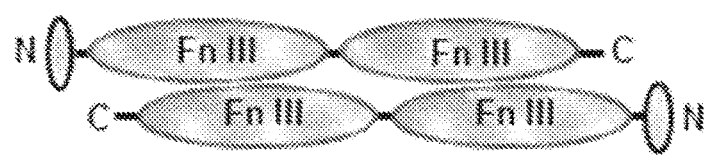
Figure 14B:
Figure 14C:
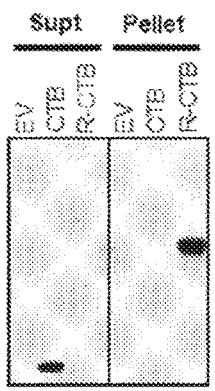
Figure 14D:
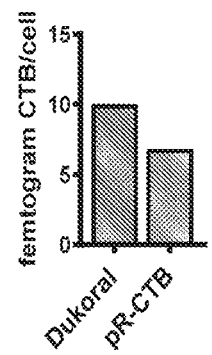
Figures 16A, 16B, 16C:
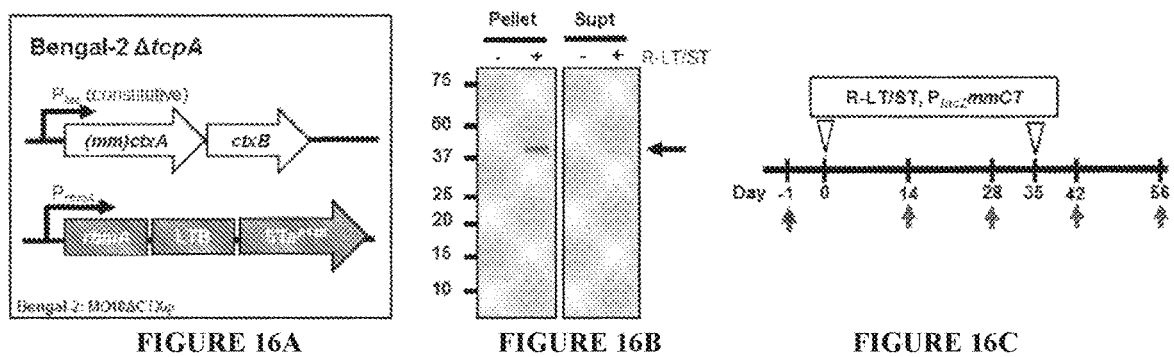
Figures 16D, 16E, 16F:
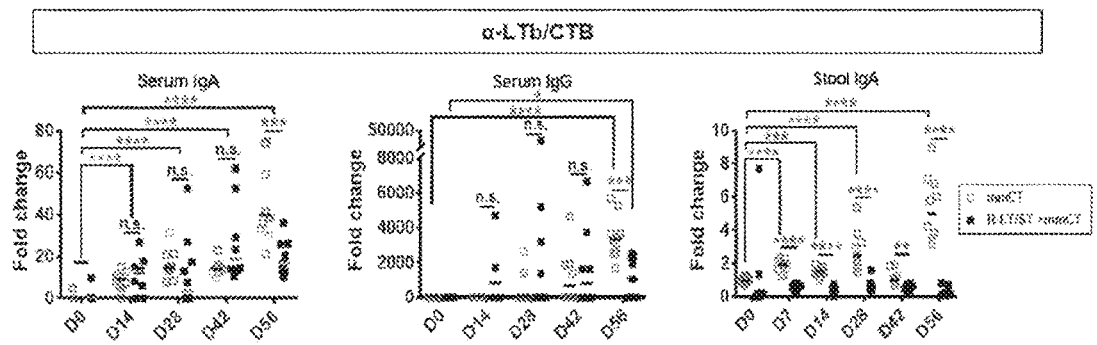
Figures 16G, 16H, 16I:
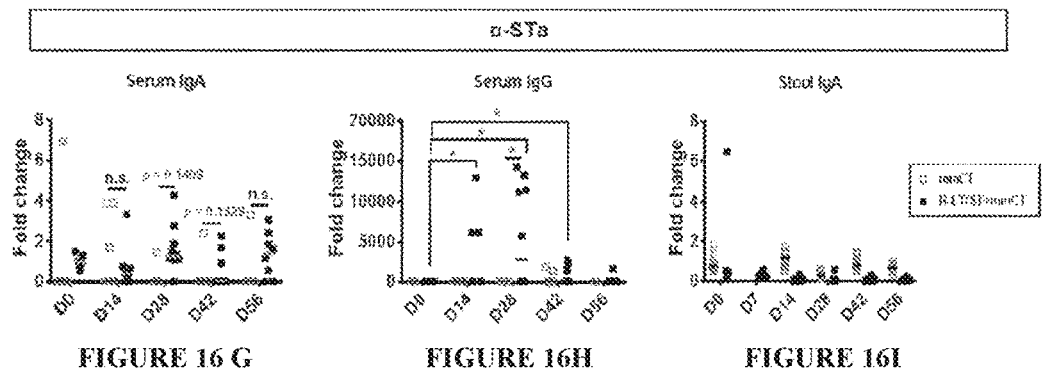

FIG. 12. Schematic of the treatment protocol to test the immunogenicity of a whole cell vaccine expressing RbmA-CTB. BALB/c mice were vaccinated with either an oral killed whole cell vaccine (similar to the current cholera vaccine Shanchol™), or with a live-attenuated strain (ΔctxA) that expresses RbmA-CTB but not ctxA (the effector subunit of cholera toxin) via the sublingual route. Each protocol included an initial vaccination followed by two boosters, each two weeks apart. Immune responses were then examined four weeks after the final booster for the oral killed vaccine group, and every two weeks during vaccination for the live-attenuated vaccine group.

FIGS. 13A to 13C. Antigen-specific antibody responses. No CTB-specific immune response was seen in the control group given the oral killed whole cell vaccine, but the live attenuated vaccine, administered sublingually, induced an antigen-specific response in the serum, dominated by IgA (FIG. 13A). The live-attenuated vaccine also induced the production of antigen-specific secretory IgA at the intestinal mucosa (FIG. 13C). The rise in antigen-specific secretory IgA is seen by the first booster, suggesting that a single dose of the sublingual vaccine may be sufficient to induce this response.

FIGS. 14A-14D. Generation of a prototype biofilm matrix protein vaccine. RbmA contains two fibronectin III (Fn III) domains and functions as a homodimer (FIG. 14A). Schematic of how cholera toxin B subunit (CTB), a secreted protein, can be anchored to the surface of the cell when linked to the C terminus of RbmA (FIG. 14B). The RbmA-CTB fusion protein (R-CTB) is detected by Western blot in the cellular fraction using antibodies against CTB, whereas unfused CTB is detected only in the supernatant (FIG. 14C). The amount of R-CTB in a Vc(pR-CTB) prototype whole cell vaccine is comparable to the amount of purified CTB included in the Dukoral® (WC-rBS) vaccine (FIG. 14D).

FIGS. 15A-15N. The prototype vaccine elicits LPS-specific antibodies, protects against cholera challenge, and generates antigen-specific mucosal antibodies. Vaccination study scheme. Open triangles indicate vaccination. Arrows indicate blood and stool collection (FIG. 15A). Fold change in serum antibodies against O139 or 01 LPS compared against PBS immunization sera (inactivated) or pre-immune sera (live-attenuated) (FIG. 15B). Serum vibriocidal antibody titer at day 42 against wild-type MO10 (O139) (FIG. 15C). Colonization of the small and large intestines in suckling mice challenged with wild-type MO10. Pups were born to unvaccinated dams (Ctrl) or to dams that received the live-attenuated vaccine (Vacc) (FIG. 15D). Weight of the small and large intestines of pups after challenge (FIG. 15E). Fluid accumulation in the large intestine and cecum (triangle) is visible in the control pups and absent in protected pups (FIG. 15F). Reduced skin turgor present in control pups and absent in protected pups. Scale bars=10 cm (FIG. 15G). Fold change of CTB-specific antibodies after immunization with a control strain or vaccine strain expressing R-CTB (FIGS. 15H-15J). Components of the detoxified cholera toxin in the supernatant after overnight culture in LB broth (FIG. 15K). LPS-specific antibodies in vaccine strains with and without mmCT. * $p\leq0.05$,  $p\leq0.01$, * $p\leq0.001$, ** $p\leq0.0001$, n.s. $p\geq0.05$ using unpaired, two-tailed Mann-Whitney rank-sum test. Horizontal bars mark the median (FIGS. 15L-15**N). Each vaccination group included ten mice. Vaccinated and unvaccinated litters included 16 and 11 pups, respectively. Fold change calculated against pre-immune background levels unless otherwise stated.

FIGS. 16A-16. A live-attenuated vaccine delivering ETEC antigens and a detoxified cholera toxin elicits antigen-specific antibodies and enhances LPS-specific antibody response. Schematic of the vaccine strain, based on an O139 strain where CTX phage elements, including the recombination sites, have been deleted. The ETEC antigens LTB and STa was cloned to the 3' end of rbmA on the chromosome to create a chimeric protein expressed from the native rbmA promoter. Additionally, the vaccine strain harbors a deletion of the major colonization factor, tcpA, and expresses mmCT (FIG. 16A). The RbmA-LTB-STa protein (R-LT/ST) detected by anti-STa Western blot in the cell pellet, and not the supernatant, after overnight growth (FIG. 16B). Vaccination scheme for the ETEC antigen-boosted whole cell vaccine. Open triangles indicate vaccination. Arrows indicate blood and stool collection (FIG. 16C). Fold change of LTB/CTB-specific antibodies after immunization with a control strain expressing only mmCT or vaccine strain co-expressing R-LT/ST and mmCT (FIGS. 16D-16F). Fold change of STa-specific antibodies after immunization with the control strain or the R-LT/ST vaccine strain. * $p \leq 0.05$,  $p \leq 0.01$, * $p \leq 0.001$, **** $p \leq 0.0001$, n.s. $p \geq 0.05$ using unpaired, two-tailed Mann-Whitney rank-sum test. Horizontal bars mark the median (FIGS. 16G-16I). Each vaccination group included ten mice. Fold change calculated against pre-immune background levels unless otherwise stated.

Figure 17:
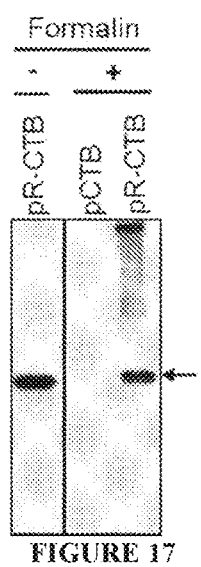

FIG. 17. Western blot analysis of cell-associated R-CTB after formalin treatment. Formalin treatment of the prototype vaccine expressing pR-CTB resulted in protein cross-linking. R-CTB (arrow), but not native CTB, is detected in the cellular fraction after formalin treatment.

FIGS. 18A-18C. Inactivated prototype vaccine given orogastrically did not elicit antigen-specific antibody responses. a-c. Fold change of CTB-specific IgA and IgG in the serum and CTB-specific IgA in the stool. Antibody levels were measured four weeks after the second vaccine booster. Fold change calculated against background levels in PBS immunized sera. Each vaccination group included ten mice. Horizontal bars mark the median. * $p \leq 0.5$, **** $p \leq 0.0001$, n.s. not significant using unpaired, two-tailed Mann-Whitney test.

FIG. 19. Dissemination of live bacteria after sublingual immunization occurs at low levels. Live *V. cholerae* recovered from stool pellets after sublingual immunization. Bacterial shedding ceased after 24 hours. The limit of detection was estimated to be 440 CFU/g and is denoted by the dotted line. Groups that received vaccine strains with tcpA and vaccine strains without tcpA included 20 and 40 mice, respectively. Horizontal bars mark the median.

Figures 20A, 20B:
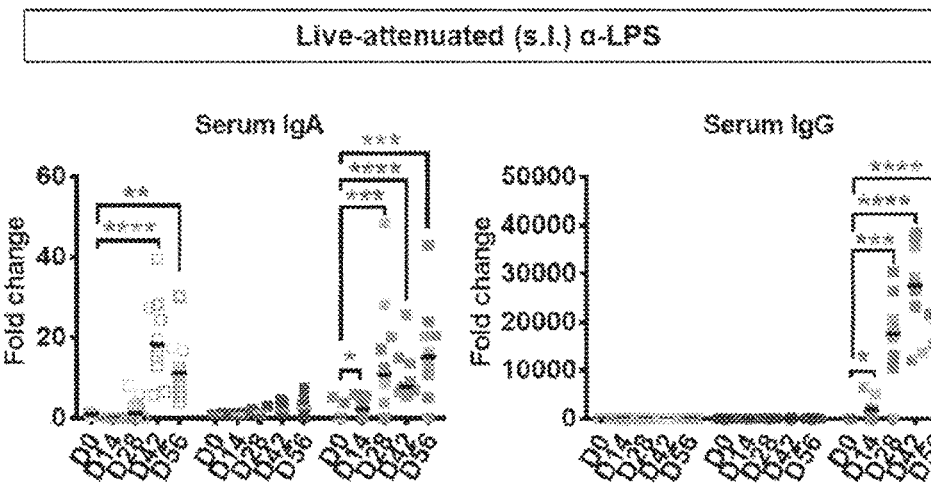
Figure 20C:
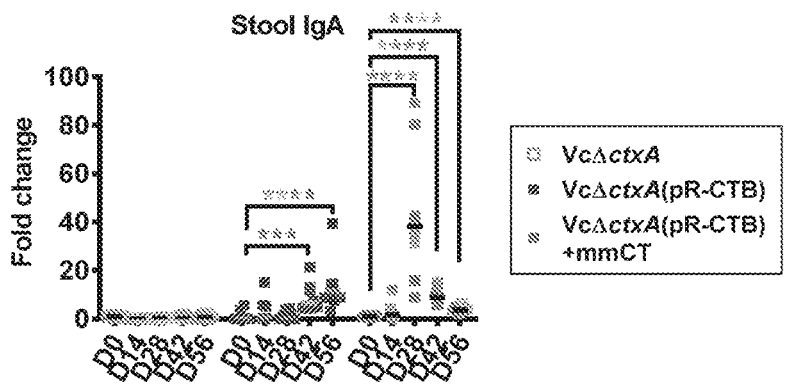

FIGS. 20A-20C. Expression of mmCT by the prototype vaccine significantly enhances production of antibodies against the β-antigen. Fold change of IgA and IgG specific to β-antigen in the serum and IgA against the O-antigen in the stool. Fold change calculated against pre-immune sera. Each vaccination group included ten mice. Horizontal bars mark the median. * $p \leq 0.05$  $p \leq 0.01$, * $p \leq 0.001$, **** $p \leq 0.0001$, n.s. $p \geq 0.05$ using unpaired, two-tailed Mann-Whitney test.

Figures 21A, 21B, 21C:
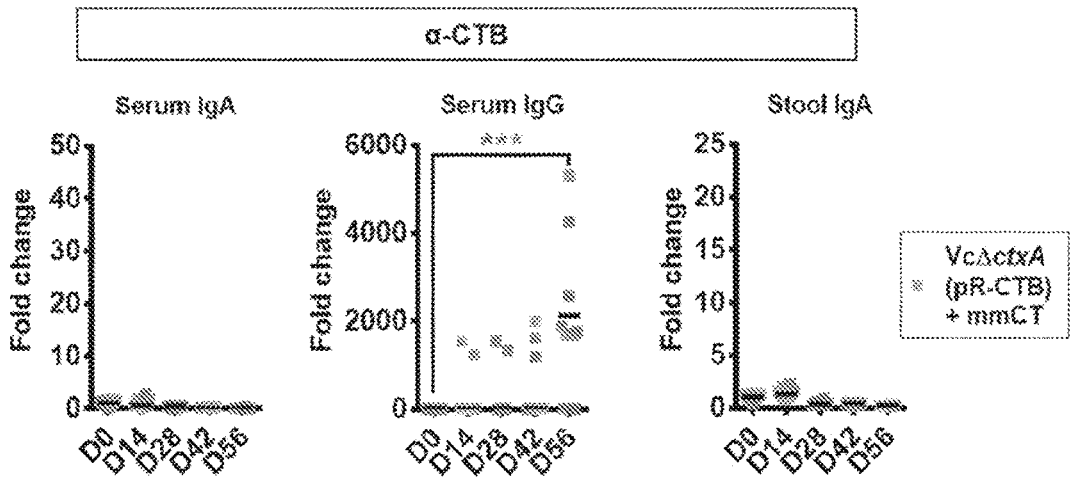

FIGS. 21A-21C. Inclusion of the adjuvant, mmCT, in the prototype R-CTB vaccine abrogated the immune response to CTB. Fold change of CTB-specific antibodies after immunization with a vaccine strain expressing R-CTB and mmCT. *** $p \leq 0.001$, n.s. $p \geq 0.05$ using unpaired, two-tailed Mann-Whitney test. Horizontal bars mark the median. Each vaccination group included ten mice. Fold change calculated against pre-immune background levels.

Figures 22, 23:
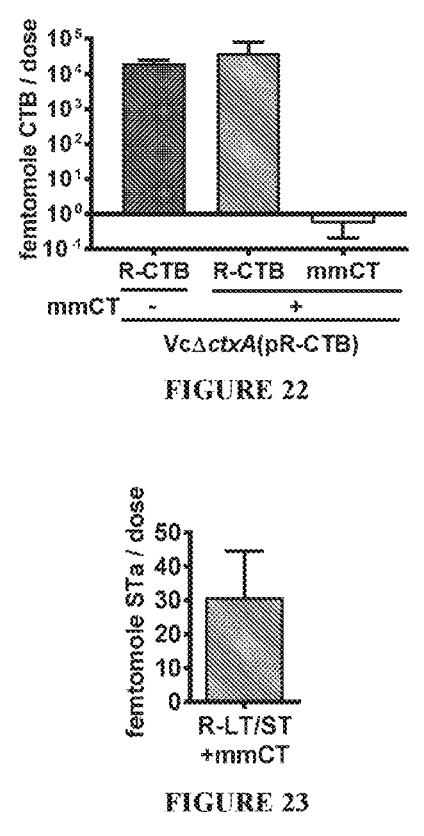

FIG. 22. The mmCT adjuvant does not contribute significantly to the amount of CTB delivered in a vaccine dose. Quantification of the amount of CTB delivered as R-CTB and as part of mmCT. Error bars denote standard deviation.

FIG. 23. Each dose of the R-LT/STa$^{414H}$ vaccine delivers 30 femtomoles of STa. Quantification of the amount of STa delivered as part of R-LT/STa$^{414H}$. Error bar denotes standard error.

DETAILED DESCRIPTION

Introduction

The occurrence of surface-associated bacterial structures known as biofilms is viewed as an undesirable phenomenon in the context of many biomedical and biotechnological applications. Biofilm formation can lead to failure of biomedical devices, to greatly reduced continuous production times and yields in production-scale bioreactors, and to many other detrimental consequences. Accordingly, biofilms are the target of intense antimicrobial research efforts.

In contrast to the conventional paradigm that biofilms are undesirable contaminants, some aspect of this disclosure provide that biofilms can be engineered to confer novel structural and/or functional characteristics upon them, making them useful tools in many biomedical and biotechnological applications. For example, as described in more detail herein, engineered biofilms, bacteria, and biofilm-associated proteins provided herein are useful for vaccine development and production, isolation and purification of bioreactor products, delivery of molecules to a target site in vivo, and bioremediation applications, such as cleaning up environmental pollutants.

This paradigm shift away from the view that biofilms are undesirable contaminants and towards the view that biofilms can be engineered to serve highly desirable purposes in a variety of applications is based, in part, on the recognition of how biofilms form and maintain their structure and their adhesion to surfaces. In contrast to the conventional view that exopolysaccharides shed by bacteria in a biofilm function as the "glue" that mediates adhesion of the cells within the biofilm to each other and also adhesion of the biofilm to a surface, some aspects of this disclosure provide that biofilm exopolysaccharides function in a different way. Namely, as described in more detail herein, biofilm exopolysaccharides provide a scaffold to which cellular proteins, secreted by or expressed on the surface of the cells within the biofilm, adhere. These cellular proteins are referred to herein as exopolysaccharide-associated proteins.

Some aspects of this disclosure are based on the recognition that the cellular proteins mediating cell adhesion in biofilms, exopolysaccharide-associated proteins, are abundant in biofilms, and that different exopolysaccharide-associated proteins exhibit different spatial distributions throughout a given biofilm. Some aspects of this disclosure relate to the identification and characterization of several secreted or extracytoplasmic proteins that are retained in the bacterial biofilm matrix by their association with the biofilm exopolysaccharide scaffold. Some aspects of this disclosure provide engineered exopolysaccharide-associated proteins, for example conjugated with a heterologous molecule, e.g., a protein, an enzyme, antigen, binding agent, detection agent, or small molecules. Such engineered exopolysaccharide-associated proteins can be used to deliver heterologous molecules to biofilms, for example, in order to engineer novel biofilm functionalities and structures. Depending on the spatial distribution of a given exopolysaccharide-associated protein, a heterologous molecule can be delivered to the surface, the interior, or evenly throughout a given biofilm according to some aspects of this disclosure.

Some aspects of this disclosure are based on the recognition that engineered exopolysaccharide-associated proteins in bacteria, as provided herein, can be used to engineer biofilms for various applications, e.g., to serve as reservoirs for surface-active secreted proteins of biomedical, bioengineering, or biotechnological importance. Accordingly, some aspects of this disclosure provide that the biofilm matrix can be exploited, among other uses, as a vehicle for concentration of molecules, e.g., enzymes or antigens, on the surfaces of cells and as a delivery system targeting abiotic surfaces. Because of their affinity for surfaces, biofilms engineered according to aspects of this disclosure are also ideal vehicles for presentation of vaccine antigens and for delivery of enzymes of therapeutic or bioremediative importance to surfaces.

Some aspects of this disclosure provide engineered exopolysaccharide-associated proteins, engineered bacteria expressing such proteins, and engineered biofilms comprising such proteins. Some aspects of this disclosure provide methods for engineering exopolysaccharide-associated proteins, and for the generation of engineered bacteria and biofilms expressing or comprising such proteins. Some aspects of this disclosure provide compositions and methods useful for the generation of vaccines and the vaccination of subjects, for delivering molecules of interest to a target site, for example, a surface, for purification of molecules of interest, for example, from bioreactors comprising engineered bacteria as provided herein, and for bioremediation applications, such as the cleanup of environmental pollutants.

The technology described herein is broadly applicable to any biofilm comprising an exopolysaccharide scaffold and exopolysaccharide-associated proteins mediating cell-cell adhesion and/or cell-surface adhesion within the biofilm. Accordingly, exemplary envisioned applications range from, without limitation, therapeutic and prophylactic medical uses, e.g., vaccine development and treatment of digestive dysfunction, to biotechnological uses (e.g., concentration, isolation, or purification of recombinant proteins or other products from bioreactors), to bioremediation (e.g., oil spill clean-up), to molecular biology, and others. For example, the technology described herein represents an economical and versatile new platform for delivery of protein antigens or immune adjuvants in whole cell vaccines. For another example, the technology described herein can be used to deliver functional proteins to surfaces. For instance, a commensal bacterium such as *E. coli* or a commonly used probiotic might be used to deliver a digestive enzyme, for example, lactase or a pancreatic enzyme, to the intestinal brush border of a subject with a deficiency in the digestive enzyme, (e.g., subjects with lactase deficiency or cystic fibrosis). A nonpathogenic bacterium colonizing the lung of a cystic fibrosis patient might be re-engineered according to some aspects of this disclosure to deliver mucinase or alginase, thus helping to clear biofilm-associated *Pseudomonas aeruginosa* from the lung. For another example, the technology described herein can be used to deliver enzymes that are useful in the digestion of an environmental pollutant, e.g., oil, to contaminated surfaces, e.g., polluted water-air surfaces of lakes or oceans. For yet another example, secreted proteins destined for purification, e.g., from a culture in a production-scale bioreactor, could be fused to an exopolysaccharide-associated protein. Cells expressing such a fusion protein would retain the secreted protein and could be used as a "biocolumn." Such cells could be grown, either in suspension or as a biofilm, and subsequently pelleted to isolate the secreted protein of interest. If the fusion protein comprises a protease cleavage site separating the secreted protein of interest from the exopolysaccharide-associated protein, the protein of interest can be released from the bacterial pellet by protease digestion and subsequent elution.

Some aspects of this disclosure demonstrate the feasibility of an application of the bacterial biofilm matrix exopolysaccharide as a scaffold for localization and presentation of proteins and for delivery of functional enzymes to surfaces. The "proof of principle" experiments in the diarrheal pathogen *V. cholerae* described in more detail in the Examples section herein can be extended to other bacteria that also form biofilms incorporating structural exopolysaccharides and exopolysaccharide-associated proteins. Such bacteria include, for example, other biofilm-forming diarrheal pathogens [10-13]. However, it will be understood by those of skill in the art that the inventive concepts described herein can be applied to any biofilm matrix exhibiting similar characteristics to the biofilms specifically described. Additional applications of the technology provided herein will be apparent to those of skill in the art based on the instant disclosure. The exemplary embodiments listed above serve to illustrate the versatility of the instantly disclosed technology. The disclosure is not limited in this respect.

The term bacterium refers to a prokaryotic microorganism from the taxon Bacteria. Names of bacteria described herein are provided according to international rules for the naming of bacteria and taxonomic categories and for the ranking of them in the International Code of Nomenclature of Bacteria by the International Committee on Systematic Bacteriology (ICSB).

The term Gram staining refers to a method of staining bacteria developed by Hans Christian Gram, which allows differentiating bacterial species into two large groups (Gram-positive and Gram-negative, see, e.g., Gram, H C (1884). Über die isolierte Färbung der Schizomvceten in Schnitt-und Trockenpräparaten (German). Fortschritte der Medizin 2: 185-189. English translation in: Brock, T. D. (1999). Milestones in Microbiology 1546-1940 (2 ed.). ASM Press. pp. 215-218. ISBN 1-55581-142-6.); the contents of each of which are incorporated herein in their entirety). Gram staining detects peptidoglycan in Gram positive bacteria via crystal violet staining. Gram-positive bacteria retain crystal violet, resulting in a purple/blue color. In some embodiments, Gram staining also utilizes a counter stain, e.g., fuchsine or safranin, for detecting Gram-negative bacteria, typically resulting in a pink/red color.

The term gram-negative, in the context of bacteria, refers to bacteria that are not stained dark blue or violet by Gram staining, because they cannot retain the crystal-violet stain used in Gram staining. In some embodiments of Gram staining, a counterstain is used (e.g., safranin or fuchsine) that is retained by Gram-negative bacteria, staining them red or pink. Some Gram-negative bacteria are pathogens in humans, for example, some species of *Escherichia* sp., *Enterobacter* sp. (e.g., *Enterobacter cloacae*), *Salmonella* sp. (e.g., *Salmonella enterindis, Salmonella typhi*), *Shigella* sp., *Pseudomonas* sp. (e.g., *Pseudomonas aeruginosa*), *Moraxella* sp. (e.g., *Moraxella catarrhalis*), *Neisseria* sp. (e.g., *Neisseria gonorrhoeae, Neisseria meningitidis*), *Helicobacter* sp., (e.g., *Helicobacter pylori*) *Stenotrophomonas* sp., *Vibrio* sp. (e.g., *Vibrio cholerae*), *Legionella* sp. (*Legionella pneumophila*), *Hemophilus* sp. (e.g., *Hemophilus influenzae*), *Klebsiella* sp. (e.g., *Klebsiella pneumoniae*), *Proteus* sp. (e.g., *Proteus mirabilis*), *Serratia* sp. (*Serratia marcescens*).

The term Gram-positive, in the context of bacteria, refers to bacteria that are stained dark blue or violet by Gram staining. Gram-positive bacteria retain the crystal violet stain because of the high amount of peptidoglycan in the cell wall. The cell walls of Gram-positive bacteria typically lack the outer membrane found in Gram-negative bacteria Some Gram-positive bacteria are pathogens in humans, for example, some species of *Streptococcus* sp., *Staphylococcus* sp., *Corynebacterium* sp., *Listeria* sp., and *Clostridium* sp., The term non-pathogenic refers to a microorganism, e.g., a bacterium, that does not typically cause a disease in a subject exposed to it. In some embodiments, whether or not a bacterium is pathogenic depends on the type of exposure or administration of the bacterium to the subject. For example, a bacterium may be non-pathogenic or even beneficial if administered into the gastrointestinal tract, but may be pathogenic, e.g., causing inflammation or other disease or disorder, upon exposure of an open wound, administration into the bloodstream, or inhalation. In some embodiments, a non-pathogenic bacterium is a bacterium that does not cause a disease or disorder in a subject, e.g., a human subject, when administered orally, parenterally, subcutaneously, intravenously, intramuscularly, into the lung, into the blood, topically, or into the respiratory tract.

The term pathogen refers to an agent or organism that causes a disease or disorder in a subject, e.g., a human subject. In some embodiments, the pathogen is a bacterium. Bacterial pathogens are well known to those of skill in the art. Bacterial genera comprising bacterial pathogens and exemplary bacterial pathogens include, without limitation, *Bacillus* sp. (e.g., *Bacillus anthracis*) *Bordetella* sp. (e.g., *Bordetella pertussis*): *Borrelia* sp. (e.g., *Borrelia burgdorferi*); *Brucella* sp. (e.g., *Brucella abortus*, *Brucella canis*, *Brucella melitensis*, *Brucella suis*): *Campylobacter* sp. (e.g., *Campylobacter jejuni*): *Chlamydia* sp. and *Chlamydophila* sp. (e.g., *Chlamydia pneumoniae*, *Chlamydia trachomatis*, *Chlamydophila psittaci*); *Clostridium* sp. (e.g., *Clostridium botulinum*, *Clostridium difficile*, *Clostridium perfringens*, *Clostridium tetani*); *Corynebacterium* sp. (e.g., *Corynebacterium diphtheriae*); *Enterococcus* sp. (e.g., *Enterococcus faecalis Enterococcus faecium*); *Escherichia* sp. (e.g., *Escherichia coli*, Enterotoxic *E. coli*, enteropathogenic *E. coli*: *E. coli* O157: H7); *Francisella* sp. (e.g., *Francisella tularensis*); *Haemophilus* sp. (e.g., *Haemophilus influenzae*): *Helicobacter* sp. (e.g., *Helicobacter pylori*): *Legionella* sp. (e.g., *Legionella pneumophila*); *Leptospira* sp. (e.g., *Leptospira interrogans*); *Listeria* sp. (e.g., *Listeria monocytogenes*); *Mycobacterium* sp. (e.g., *Mycobacterium leprae*, *Mycobacterium tuberculosis*, *Mycobacterium ulcerans*); *Mycoplasma* sp. (e.g., *Mycoplasma pneumoniae*); *Neisseria* sp. (e.g., *Neisseria gonorrhoeae*, *Neisseria meningitidis*); *Pseudomonas* sp. (e.g., *Pseudomonas aeruginosa*); *Rickettsia* sp. (e.g., *Rickettsia rickettsii*); *Salmonella* sp. (e.g., *Salmonella typhi*, *Salmonella typhimurium*); *Shigella* sp. (e.g., *Shigella sonnei*); *Staphylococcus* sp. (e.g., *Staphylococcus aureus*, *Staphylococcus epidermidis*, *Staphylococcus saprophyticus*): *Streptococcus* sp. (e.g., *Streptococcus agalactiae Streptococcus pneumoniae*, *Streptococcus pyogenes*); *Treponema* sp. (e.g., *Treponema pallidum*): *Vibrio* sp. (e.g., *Vibrio cholerae*); *Yersinia* sp. (e.g., *Yersinia pestis*).

The term biofilm refers to an aggregate of microorganisms, e.g., bacteria, on a surface. In some embodiments, a biofilm comprises bacterial cells that are embedded within an extracellular matrix comprising extracellular polysaccharides, also sometimes referred to as EPS. Extracellular polysaccharides are also referred to herein as exopolysaccharides. In some embodiments, extracellular matrix components, e.g., exopolysaccharides, are produced and secreted by the cells within the biofilm. Bacterial cells within a biofilm adhere to the extracellular matrix of the biofilm by molecules, e.g., proteins, expressed on the surface of the cells that bind to the biofilm EPS.

The term exopolysaccharide refers to a high-molecular-weight polysaccharide that is secreted by a microorganism. Typically, exopolysaccharides comprise a polymer of monosaccharides. Some exopolysaccharides, however, also comprise non-carbohydrate substituents (such as acetate, pyruvate, succinate, and phosphate). Exemplary exopolysaccharides include, without limitation acetan (*Acetobacter xylinum*), alginate (*Azotobacter vinelandii*), cellulose (*Acetobacter xylinum*), chitosan (*Mucorales* sp.), curdlan (*Alcaligenes faecalis* var. *myxogenes*), cyclosophorans (*Agrobacterium* sp., *Rhizobium* sp. and *Xanthomonas* sp.), dextran (*Leuconostoc mesenteroides*, *Leuconostoc dextranicum* and *Lactobacillus hilgardii*), emulsan (*Acinetobacter calcoaceticus*), galactoglucopolysaccharides (*Achromobacter* sp., *Agrobacterium radiobacter, Pseudomonas marginalis*, *Rhizobium* sp. and *Zooglea* sp.), gellan (*Aureomonas elodea* and *Sphingomonas paucimobilis*), glucuronan (*Sinorhizobium meliloti*), N-acetyl-glucosamine (*Staphylococcus epidermidis*), N-acetyl-heparosan (*Escherichia coli*), hyaluronic acid (*Streptococcus equi*), indican (*Beijerinckia indica*), kefiran (*Lactobacillus hilgardii*), lentinan (*Lentinus elodes*), levan (*Alcaligenes viscosus, Zymomonas mobilis, Bacillus subtilis*), pullulan (*Aureobasidium pullulans*), scleroglucan (*Sclerotium rolfsii, Sclerotium delfinii* and *Sclerotium glucanicum*), schizophyllan (*Schizophylum commune*), stewartan (*Pantoea stewartii* subsp. *stewartii*), succinoglycan (*Alcaligenes faecalis* var *myxogenes*, *Sinorhizobium meliloti*), xanthan (*Xanthomonas campestris*), and welan (*Alcaligenes* sp.).

The term exopolysaccharide-associated protein refers to a protein that binds to an exopolysaccharide via non-covalent interactions with a $K_D$ of $<10^{-5}$ M, $<10^{-6}$ M, $<10^{-7}$ M, $<10^{-8}$ M, $<10^{-9}$ M, $<10^{-10}$ M, $<10^{-11}$ M, or $<10^{-12}$ M. The term exopolysaccharide-binding fragment, in the context of exopolysaccharide-associated proteins, refers to a fragment of an exopolysaccharide-associated protein, wherein the fragment retains the exopolysaccharide binding characteristics of the parent protein, or binds the exopolysaccharide with a $K_D$ of $<10^{-5}$ M, $<10^{-6}$ M, $<10^{-7}$ M, $<10^{-8}$ M, $<10^{-9}$ M, $<10^{-10}$ M, $<10^{-11}$ M, or $<10^{-12}$ M. Exopolysaccharide-associated proteins are known to those of skill in the art. Some exemplary exopolysaccharide-associated proteins and exopolysaccharide-binding fragments thereof are described herein, including, but not limited to Bap1, RbmA, RbmC, and HlyA. Below are exemplary, representative sequences of Bap1, RbmA, RbmC, and HlyA from *Vibrio cholerae*. It is to be understood that these sequences are for illustration purposes only and are not meant to limit the scope of this disclosure. Those of skill in the art will know or will be able to ascertain additional sequences of Bap1, RbmA, RbmC, and HlyA, and of additional exopolysaccharide-binding proteins, both from *Vibrio* sp. and from other bacteria based on this disclosure and knowledge in the art. The disclosure is not limited in this respect.

```
Bap1
>vch: VC1888 hemolysin-like protein (A)
                                    (SEQ ID NO: 1)
MKQTKTLTAISVLALSHLMTQSTAFASSSSDIQTKLKWSWSTSVFHPESN

QVMAAPIVVQLNDDNGDGKIDEKDVADIIVVTFEGNKYANGGYIRALSGV

DGSELWSYSNGGVIADARYAPAAADLDGDGLIEIVSTSALTPYINILDHQ

GNIKKQLLKSASGWRSVGDIALADINGDGNIEILAADGVYSYESGLLFSH

DWAPSSIAFDSNGDGQREVFANGTLYQNNGAYLWQYQANDTVWFSSVANL

DGDDKPELVVSVPASLSTPENSEIAVLEHDGSVKWRVNNLSNPGGSVQAV

SSFLGKPSSSATTVDAQSAVYGYTDWAHQQRVLAENHQLAIRSGAVVDAI
```

-continued

```
GANSQNMIGGSGGSLSTIDTSKVRAIDVTYGKNKYTWKYGVLEMSFTLDN

GAKVTVGSKDSAFTYLGLEWKTKTVPYLGVEWRTKTVSYWFFGWHTKQVA

YLAPVWKEKTIPYAVPVTLSKSTTVRYDIPQGSQLLGMNVWSKEKHLFKH

KQQVNAVQFLVGKVTADQSHMGIVYAGYYAVDMYDAQGNKVWSVANDDLN

SGKIGVSAYDFTGDGIDEVLVQDRLRMRILDGQTGRVMGIIANSSGTLWE

YPVVADLEGNNNASLIMVANDYDRESQVNHGVFVYESANPSKPWRNATRI

WNQYAFNFSDINANGTIPTNAQPSWLTHNSFRSATIRVPLK
EF Hand domain: residues 63-78
VCBS domain: residues 77-135
PQQ enzyme repeat: residues 90-113
FG-GAP repeat: residues 119-13
VCBS domain: residues 125-184
FG-GAP repeat: residues 170-185
FG-GAP repeat: residues 246-267
FG-GAP repeat: residues 555-571

RbmA
>vch: VC0928 hypothetical protein (A)
                              (SEQ ID NO: 2)
MSNFKGSIMNKRHYYLASCLALLFSTASYAEVDCELQPVIEANLSLNQNQ

LASNGGYISSQLGIRNESCETVKFKYWLSIKGPEGIYFPAKAVVGVDTAQ

QESDALTDGRMLNVTRGFWVPEYMADGKYTVSLQVVAENGKVFKANQEFV

KGVDLNSLPELNGLTIDIKNQFGINSVESTGGFVPFTVDLNNGREGEANV

EFWMTAVGPDGLIIPVNAREKWVIASGDTYSKVRGINFDKSYPAGEYTIN

AQVVDIVSGERVEQSMTVVKK
Signal peptide: residues 1-30

RbmC
>vch: VC0930 hemolysin-like protein (A)
                              (SEQ ID NO: 3)
MTSHYIALAVGLLSLSSNVVQATTNEAEGCIISRLNGEKYCLKVGERSGY

SLPSWIYAHPVDVQAPSGVSVMLSDWDNLSYNRLAVFDRYTGNEDLKNVK

AYNGAYLDFSKPRSMRVLASETYPEACIVSRQTGERFCLKEGERSGYSLP

AYIYGHEVDVEAPLGLGVMLSDWDNLSYNRLAVFGGNTQNEQMRAVKAYN

GETLDFSKPRSMRVVPYDGDSSALNMKLKWSWQGSAFQPNSNQVMVTPIV

AQLNDDNGDGKIDEKDVADLIVVTFEGNKYANGGLVRALSGVDGSELWSY

ANGGVIADARYSPAVGDLDGDGIVEIVTTNNRDQFITILDNQGNIKKQIP

TTESGWRIVGDITLADLDHDGSVEILAADGVYNYHSGLVFNHPWAPSSIN

VDVDGDQQQEVFSGGTLFQNNGAINWQYQANDAVWFSSLVNLDNDAEPEI

VASVPATFATGDNARFAVLEHDGTIKWEINNTANPGGGVQAVSNFLGKAQ

AVETSEFSKVYGYQPNNNPASIALAVDGKISVRSGFAIDAIGASASTLVG

GTGGNLNAAVNVKDIKAIDLTWGKYYWGGYHLLALDFRMSNGSVISMGSK

NYAYSKQTERFTVPAGSRIKGIKAWTAGWLLDGVQFELATQNGTNDLDVK

GIVYAGYAAVDMYNSKGERVWSVANDDTGSGKIGVSAYDFDNDGIDEVLV

QDHARVRVLDGKTGKERASLAHSTATLWEYPIVVDLEGDNNAELIVAAND

FDRQYSINHGVYVYQSADSSKPWKNATRIWNQHAFHLTNINQDGTLPTFV

EPSWLSHNTYRSSTLRAAVGGESPIFGYSNTQQSQRVVTADNLMYLRSGF

AIDAIGTTVNNLVGGPVQGTNGGVLRAPIALDQLQSVEVTSGLYNWGGYH

IVAIKFTMKDGSSVLLGSTHYASNKKVETYTVPQGKRIKQINVWTGGWLV

EGFQFVY
Signal peptide: residues 1-20
FG-GAP repeat: residues 311-328
FG-GAP repeat: residues 684-709prism
Jacalin type lectin (beta prism) domain: residues
529-639
Jacalin type lectin (beta prism) domain: residues
832-957

HlyA
>vch: VCA0219 haemolysin; K10948 hemolysin (A)
                              (SEQ ID NO: 4)
MPKLNRCAIAIFTILSAISSPTLLANINEPSGEAADIISQVADSHAIKYY

NAADWQAEDNALPSLAELRDLVINQQKRVLVDFSQISDAEGQAEMQAQFR

KAYGVGFANQFIVITEHKGELLFTPFDQAEEVDPQLLEAPRTARLLARSG

FASPAPANSETNTLPHVAFYISVNRAISDEECTFNNSWLWKNEKGSRPFC

KDANISLIYRVNLERSLQYGIVGSATPDAKIVRISLDDDSTGAGIHLNDQ

LGYRQFGASYTTLDAYFREWSTDAIAQDYRFVFNASNNKAQILKTFPVDN

INEKFERKEVSGFELGVTGGVEVSGDGPKAKLEARASYTQSRWLTYNTQD

YRIERNAKNAQAVSFTWNRQQYATAESLLNRSTDALWVNTYPVDVNRISP

LSYASFVPKMDVIYKASATETGSTDFIIDSSVNIRPIYNGAYKHYYVVGA

HQFYHGFEDTPRRRITKSASFTVDWDHPVFTGGRPVNLQLASFNNRCIQV

DAQGRLAANTCDSQQSAQSFIYDQLGRYVSASNTKLCLDGEALDALQPCN

QNLTQRWEWRKGTDELTNVYSGESLGHDKQTGELGLYASSNDAVSLRTIT

AYTDVFNAQESSPILGYTQGKMNQQRVGQDHRLYVRAGAAIDALGSASDL

LVGGNGGSLSSVDLSGVKSITATSGDFQYGGQQLVALTFTYQDGRQQTVG

SKAYVTNAHEDRFDLPAAAKITQLKIWSDDWLVKGVQFDLN
Signal peptide: residues 1-24
Hemolysin N domain: residues 2-187
Leukocidin domain: residues 215-477
Ricin-type beta trefoil domain (a lectin domain):
residues 484-599
Jacalin-like = beta prism domain(a lectin domain):
residues 620-741
```

The term protein is used herein interchangeably with the term polypeptide, and refers to a polymer of amino acid residues linked together by peptide bonds. The term refers to proteins, polypeptides, and peptides of any size, structure, or function. A protein may be a naturally occurring protein, a fragment of a naturally occurring protein, or an engineered protein, for example, a recombinant protein, or a protein in which one or more amino acid residues are non-naturally occurring residues, e.g., modified amino acid residues, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. In some embodiments, the term protein refers to a polymer of three or more amino acids linked by a peptide bond, e.g., between 3 and 30, 12 and 60, or 30 and 300, or over 300 amino acids in length. In some embodiments, the protein includes one or more amino acids that does not occur in nature. In some embodiments, the polypeptide includes only natural amino acids. In some embodiments, a protein includes one or more post-translational or post-synthesis modifications, e.g., a glycosylation, amidation, phosphorylation, SUMOylation, PEGylation, or nitrosylation.

The terms conjugating, conjugated, and conjugation refer to an association of two entities, for example, of two molecules (e.g., two proteins), two domains (e.g., a binding domain and an catalytic domain), or a protein and an agent, e.g., a protein binding domain and a small molecule. The association can be, for example, via a direct or indirect (e.g., via a linker) covalent linkage or via non-covalent interactions. In some embodiments, the association is covalent. In some embodiments, two molecules are conjugated via a linker connecting both molecules. For example, in some embodiments where two proteins are conjugated to each other, e.g., an exopolysaccharide-associated protein and an antigen or enzyme, to form a protein fusion, the two proteins may be conjugated via a polypeptide linker, e.g., an amino acid sequence connecting the C-terminus of one protein to the N-terminus of the other protein.

The term fusion protein refers to a protein comprising two heterologous proteins, protein domains, or protein fragments, that are covalently bound to each other either directly or indirectly (e.g., via a linker), via a peptide bond. In some embodiments, a fusion protein is encoded by a nucleic acid comprising the coding region of a protein in frame with a coding region of an additional protein, without intervening stop codon, thus resulting in the translation of a single protein in which the proteins are fused together.

The term heterologous, in the context of molecules, e.g., of proteins, peptides, nucleic acids, and small molecules, refers to a molecule that is not in its natural context, e.g., in that it is conjugated with another molecule that it is not naturally conjugated to, or it is expressed in a cell that does not naturally express the molecule. For example, a heterologous protein in the context of a fusion protein is a protein that does not naturally occur as a fusion with the specific fusion partner. For example, an antigen that is not naturally conjugated to, or fused with, an exopolysaccharide-associated protein, e.g., Bpa1, RbmA, RbmC, or HlyA, is a heterologous protein in the context of conjugates or fusion proteins comprising the antigen and the exopolysaccharide-associated protein. Similarly, a nucleic acid that is not typically operably linked to another nucleic acid is heterologous in the context of a nucleic acid construct comprising both nucleic acids operably linked together.

The term secreted protein refers to a protein that is secreted from a cell, for example, from a bacterium. Accordingly, in some embodiments, a secreted protein is a protein that is synthesized within the cell and then released into the extracellular space surrounding the cell. In some embodiments, the protein comprises a signaling peptide, e.g., at the N-terminus of the protein, that targets the protein for secretion. Such signaling peptides, also sometimes referred to as signal peptides or signal sequences, are well known to those of skill in the art. Exemplary signal peptides include, but are not limited to those disclosed by the SPdb Signal Peptide Resource (see, e.g., Choo K H, Tan T W, Ranganathan S. 2005. SPdb—a signal peptide database. BMC Bioinformatics 6:249, accessible at "proline(.)bic(.)nus(.)edu(.)sg/spdb"—last accessed on Mar. 13, 2013: the entire contents of each of which are incorporated herein by reference); the Signal Peptide Database (see, e.g., Katja Kapp, *Signal Peptide Database.* Heidelberg & Thpr.net, accessible at "www(.)signalpeptide(.)de/index/php?m=listspdb_bacteria"—last accessed on Mar. 13, 2013, the entire contents of which are incorporated herein by reference). Exemplary signal suitable peptide sequences include, without limitation, signal peptide sequences from Lectin-like protein BA14k (MNIFKQTCVGAFAVIFGAT-SIAPTMA, SEQ ID NO: 6); Antigen 85-C (MKFLQQMRKLFGLAAKFPARLTIAVIGTAL-LAGLVGVVGDTAIAVA, SEQ ID NO: 7): Alginate biosynthesis protein algF (MNPMTRRHTWTRLA-CALSLGVAAFAAQA, SEQ ID NO: 8) Probable N-acetylmuramoyl-L-alanine amidase amiA (MSTFKLLKTLTSRRQVLKTGLAALTLSGMSHAVA, SEQ ID NO: 9); Alpha-amylase (MK-LAACFLTLLPGFAVA, SEQ ID NO: 10); Beta-lactamase (MHPSTSRPSRRTLLTATAGAALAAATLVPGTAHAS-SGGR; SEQ ID NO: 11); and Chitinase 63 (MRFRH-KAAALAATLALPLAGLVGLASPAQA, SEQ ID NO: 12). Additional suitable signal peptide sequences will be apparent to those of skill in the art, and the disclosure is not limited in this respect.

In some embodiments, a secreted protein is released from a cell into the extracellular space in a manner that no association between the cell and the protein remains after release. In some embodiments, a secreted protein is released from a cell into the extracellular space, but remains attached to the surface of the cell via non-covalent interaction.

The term extracytoplasmic protein refers to a protein of a cell that is expressed on the surface of the cell and abuts or protrudes into the surrounding extracellular space. In some embodiments, an extracytoplasmic protein is not a secreted protein. For example, in some embodiments, an extracytoplasmic protein comprises a transmembrane domain that spans the cell membrane, thus anchoring the protein on the surface of the cell.

The term protein domain refers to a conserved part of a protein sequence and structure that can evolve, fold, function, and/or exist independently of the rest of the protein chain. A domain typically forms a characteristic three-dimensional structure and often can fold independently and stably regardless of its sequence context. Many proteins consist of several structural domains. Typically, protein domains vary in length from between about 25 amino acids up to 500 amino acids in length, even though longer and shorter protein domains exist. Some of the shortest protein domains such as zinc fingers, are stabilized by metal ions or disulfide bridges. Protein domains often form structural or functional units, such as the calcium-binding EF hand domain of calmodulin. Independently stable protein domains can be recombined or fused to produce chimeric proteins having the characteristics of the fused protein domains. For example, an exopolysaccharide binding protein domain can be fused with a binding domain of an antibody to produce a divalent binding protein.

The term β-prism lectin domain is used interchangeably with the term jacalin-like lectin domain, and refers to a mannose-binding lectin domain with a beta-prism fold consisting of three 4-stranded beta-sheets, with an internal pseudo 3-fold symmetry. Some lectins comprising this domain stimulate distinct T- and B-cell functions, such as Jacalin, which binds to the T-antigen and acts as an agglutinin. This domain is found in 1 to 6 copies in lectins. The domain is also found in the salt-stress induced protein from rice and an animal prostatic spermine-binding protein. Proteins containing this domain include: Jacalin, a tetrameric plant seed lectin and agglutinin from *Artocarpus heterophyllus* (jackfruit), which is specific for galactose; Artocarpin, a tetrameric plant seed lectin from *A. heterophyllus*: Lectin MPA, a tetrameric plant seed lectin and agglutinin from *Maclura pomifera* (Osage orange); Heltuba lectin, a plant seed lectin and agglutinin from *Helianthus tuberosus* (Jerusalem artichoke); Agglutinin from *Calystegia sepium* (Hedge bindweed); and Griffithsin, an anti-viral lectin from red algae (*Griffithsia* species). See, e.g., Jeyaprakash et al., (2002) "Crystal structure of the jacalin-T-antigen complex and a comparative study of lectin-T-antigen complexes". J. Mol. Biol. 321 (4): 637-45; Jeyaprakash et al., (2004) "Structural basis for the carbohydrate specificities of artocarpin: variation in the length of a loop as a strategy for generating ligand specificity". J. Mol. Biol. 338 (4): 757-70; Lee et al., (1998) "Structure of the complex of *Maclura pomifera* agglutinin and the T-antigen disaccharide, Galbeta1,3GalNAc". J. Biol. Chem. 273 (11): 6312-8; Bourne et al., (1999) "*Helianthus tuberosus* lectin reveals a widespread scaffold for mannose-binding lectins". Structure 7 (12): 1473-82; Bourne et al., (2004) "The crystal structure of the *Calystegia sepium* agglutinin reveals a novel quaternary arrangement of lectin subunits with a beta-prism fold". J. Biol. Chem. 279 (1): 527-33; and Ziolkowska et al., (2006) "Domain-swapped structure of the potent antiviral protein griffithsin and its mode of carbohydrate binding". Structure 14 (7): 1127-35; the entire contents of each of which are incorporated herein by reference. Representative sequences and consensus sequences of β-prism lectin domains are well known to those of skill in the art, e.g., as published in Raval et al., *A database analysis of jacalin-like lectins: sequence-structure-function relationships* Glycobiology (2004) 14(12): 1247-1263; the entire contents of which are incorporated by reference. Based on the knowledge in the art, those of skill in the art will be able to ascertain whether a protein domain is a β-prism lectin domain and whether a protein comprises a β-prism lectin domain. Methods and algorithms for protein domain analysis and alignment are well known to those of skill in the art, and the disclosure is not limited in this respect.

The term FG-GAP domain is used interchangeably with the term FG-GAP repeat, and refers to an extracellular repeat that is found in up to seven copies in alpha integrins. The FG-GAP repeat has been predicted to fold into a beta propeller structure, and is called the FG-GAP repeat after two conserved motifs in the repeat. FG-GAP repeats are found in the N terminus of integrin alpha chains, a region that has been shown to be important for ligand binding. A putative Ca binding motif is found in some of the repeats. Representative sequences and consensus sequences of β-prism lectin domains are well known to those of skill in the art. See, e.g., Springer T A et al., Proc Natl Acad Sci USA 1997; 94:65-72. Folding of the N-terminal, ligand-binding region of integrin alpha-subunits into a beta-propeller domain, and Loftus J C, Smith J W, Ginsberg M H: J Biol Chem 1994; 269:25235-25238.: Integrin-mediated cell adhesion: the extracellular face; the entire contents of each of which are incorporated herein by reference. Based on the knowledge in the art, those of skill in the art will be able to ascertain whether a protein domain is an FG-GAP domain and whether a protein comprises an FG-GAP domain. Methods and algorithms for protein domain analysis and alignment are well known to those of skill in the art, and the disclosure is not limited in this respect.

The term linker refers to a chemical group or a molecule linking two adjacent molecules or moieties, e.g., a binding domain and a cleavage domain of a nuclease. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety.

The terms nucleic acid and nucleic acid molecule refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. The terms oligonucleotide and polynucleotide can be used interchangeably to refer to a polymer of nucleotides (e.g., a string of at least three nucleotides). In some embodiments, a nucleic acid encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms nucleic acid, DNA, RNA, and/or similar terms include nucleic acid analogs, e.g., analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications' A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases): intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term recombinant nucleic acid refers to a nucleic acid molecule that does not occur in nature, but has been engineered, e.g., in that it has been artificially synthesized, or produced from recombining or otherwise altering the nucleotide sequence of a naturally occurring nucleic acid. Suitable nucleic acid synthesis and engineering methods are well known to those of skill in the art.

The terms small molecule refers to an organic compound, whether naturally-occurring or artificially created (e.g., via chemical synthesis) that has a relatively low molecular weight. Typically, an organic compound contains carbon. An organic compound may contain multiple carbon-carbon bonds, stereocenters, and other functional groups (e.g., amines, hydroxyl, carbonyls, or heterocyclic rings). In some embodiments, small molecules are monomeric organic compounds that have a molecular weight of less than about 1500 g/mol. In certain embodiments, the molecular weight of the small molecule is less than about 1000 g/mol or less than about 500 g/mol. In certain embodiments, the small molecule is a drug, for example, a drug that has already been deemed safe and effective for use in humans or animals by the appropriate governmental agency or regulatory body. In certain embodiments, the organic molecule is known to bind and/or cleave a nucleic acid. In some embodiments, the organic compound is an enediyne. In some embodiments, the organic compound is an antibiotic drug, for example, an anticancer antibiotic such as dynemicin, neocarzinostatin, calicheamicin, esperamicin, bleomycin, or a derivative thereof.

The term covalent bond refers to a form of chemical bonding that is characterized by the sharing of one or more pairs of electrons between atoms. A covalent bond formed between two reactive moieties may, for example, be an amide bond, an acyl bond, a disulfide bond, an alkyl bond, an ether bond, or an ester bond. A covalent bond formed between two reactive moieties may be, for example, a carbon-carbon bond, a carbon-oxygen bond, a carbon-nitrogen bond, a carbon-sulfur bond, a sulfur-sulfur bond, a carbon-phosphorus bond, a phosphorus-oxygen bond, or a phosphorus-nitrogen bond.

The term non-covalent bond is used interchangeably with the term non-covalent interaction, and refers to a type of interaction between two molecules that does not involve the sharing of electrons between the molecules, but involves variations of electromagnetic, electrostatic, or hydrophobic interactions.

The term enzyme refers to a molecule, for example, a peptide, a protein, or a nucleic acid (for example, a ribozyme or DNAzyme) that catalyzes a chemical reaction. An enzyme may be a biomolecule (a molecule made by a living organism), a derivative of a biomolecule (e.g., a mutated biomolecule, a fragment of a biomolecule, and/or a fusion product of a biomolecule, or fragment thereof, with a second molecule), or an artificially made molecule (e.g., a synthetic protein or nucleic acid). An enzyme may be an oxidoreductase, transferase, polymerase, hydrolase lyase, synthase, isomerase, or ligase. Accordingly, a protease and a nuclease are non-limiting examples of enzymes. In certain embodiments, the enzyme is a protein. In certain embodiments, the enzyme is a nucleic acid. In certain embodiments, the enzyme is an RNA enzyme, also referred as a ribozyme. In certain embodiments, the enzyme is a DNA enzyme, also referred to as a DNAzyme.

The term enzyme substrate refers to a molecule upon which an enzyme acts. An enzyme substrate is bound by an enzyme and transformed into one or more products in a chemical reaction catalyzed by the enzyme. The reaction product or products are usually released from the enzyme. For example, a protease catalyzes the hydrolysis of an amide bond in a protease substrate peptide or protein. The substrate peptide of a protease is generally bound specifically, meaning that only a peptide of a certain amino acid sequence or with a sequence similar to a consensus sequence is bound by the protease and cleaved into two or more fragments in a hydrolysis reaction.

The term binding agent refers to a molecule that binds to another molecule. In some embodiments, the binding is through non-covalent interaction. In some embodiments, the binding is specific, meaning that the binding agent binds only one particular type of molecule, or a narrow class of highly similar molecules with high affinity. Non-limiting examples of binding agents are antibodies, antibody fragments, aptamers, and adnectins. In some embodiments, the term binding agent, refers to a molecule, for example, a protein, nucleic acid, carbohydrate, or small molecule, that binds another molecule, referred to herein as a target molecule, with high affinity, e.g., with a dissociation constant ($K_D$) of less than $10^{-6}$ M, of less than $10^{-7}$ M, of less than $10^{-8}$ M, of less than $10^{-9}$ M, or of less than $10^{-10}$ M. In some embodiments, a binding agent is or comprises a protein, a peptide, an antibody, an antibody fragment, a ligand, a receptor, or a small molecule, that binds to a target molecule with a $K_D$ as specified above. In some embodiments, the binding agent binds to the target molecule with high affinity, e.g. with a $K_D$ of less than $10^{-8}$, of less than $10^{-9}$ M of less than $10^{-10}$ M, of less than $10^{-11}$ M, or of less than $10^{-12}$ M. In some embodiments, the binding agent binds to the target molecule with high specificity, e.g., in that it does not bind to molecules other than the target molecule with a $K_D$ of less than $10^{-6}$ M, of less than $10^{-7}$ M, or of less than $10^{-8}$ M.

The term antibody refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term antibody encompasses antigen-binding fragments of antibodies (e.g., single chain antibodies: Fab, Fab', and sFab fragments; F(ab')$_2$ fragments; Fd fragments; Fv fragments: single-chain Fv antibodies (scFv); dAb fragments, and nanobodies) as well as complete antibodies.

The VH and VL regions can be further subdivided into regions of hypervanability, termed "complementarity determining regions" ("CDR"), interspersed with regions that are more conserved, termed "framework regions" ("FR"). The extent of the framework region and CDR's has been precisely defined (see, Kabat, E. A., et al. (1991) *Sequences of Proteins of Immunological Interest, Fifth Edition*, U.S. Department of Health and Human Services, NIH Publication No. 91-3242, and Chothia, C. et al. (1987) J. Mol. Biol. 196.901-917, see also www.hgmp.mrc.ac.uk). Kabat definitions are used herein. Each VH and VL is typically composed of three CDR's and four FR's, arranged from amino-terminus to carboxy-terminus in the following order: FR1, CDR1, FR2, CDR2, FR3, CDR3, FR4.

The term antibody fragment refers to any derivative of an antibody which is less than full-length. Preferably, the antibody fragment retains at least a significant portion of the full-length antibody's specific binding ability. Examples of antibody fragments include, but are not limited to, Fab, Fab', F(ab')2, scFv, Fv, dsFv, diabody, single variable domain, and Fd fragments. The antibody fragment may be produced by any means. For instance, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may optionally be a single chain antibody fragment. Alternatively, the fragment may comprise multiple chains which are linked together, for instance, by disulfide linkages. The fragment may also optionally be a multi-molecular complex. A functional antibody fragment will typically comprise at least about 50 amino acids and more typically will comprise at least about 200 amino acids. Single-chain Fvs (scFvs) are recombinant antibody fragments consisting of only the variable light chain (VL) and variable heavy chain (VH) covalently connected to one another by a polypeptide linker. Either VL or VH may be the NH2-terminal domain. The polypeptide linker may be of variable length and composition so long as the two variable domains are bridged without serious steric interference. Typically, the linkers are comprised primarily of stretches of glycine and serine residues with some glutamic acid or lysine residues interspersed for solubility. Diabodies are dimeric scFvs. The components of diabodies typically have shorter peptide linkers than most scFvs, and they show a preference for associating as dimers. An Fv fragment is an antibody fragment which consists of one VH and one VL domain held together by non-covalent interactions. The term dsFv is used herein to refer to an Fv with an engineered intermolecular disulfide bond to stabilize the VH-VL pair. An F(ab')2 fragment is an antibody fragment essentially equivalent to that obtained from immunoglobulins (typically IgG) by digestion with an enzyme pepsin at pH 4.0-4.5. The fragment may be recombinantly produced. A Fab' fragment is an antibody fragment essentially equivalent to that obtained by reduction of the disulfide bridge or bridges joining the two heavy chain pieces in the F(ab')2 fragment. The Fab' fragment may be recombinantly produced. A Fab fragment is an antibody fragment essentially equivalent to that obtained by digestion of immunoglobulins (typically IgG) with the enzyme papain. The heavy chain segment of the Fab fragment is the Fd piece.

The term antigen-binding fragment of an antibody refers to one or more antibody fragments that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains: (ii) a F(ab')2 fragment, a bivalent fragment including two Fab fragments linked by a disulfide bridge at the hinge region; (iii) a Fd fragment consisting of the VH and CH1 domains: (iv) a Fv fragment consisting of the VL and VH domains of a single arm of an antibody. (v) a dAb fragment (Ward et al., (1989) *Nature* 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) *Science* 242:423-426; and Huston et al. (1988) *Proc. Natl. Acad Sci. USA* 85:5879-5883.

Antibody fragments can be obtained using any appropriate technique including conventional techniques known to those with skill in the art. The term "monospecific antibody" refers to an antibody that displays a single binding specificity and affinity for a particular target, e.g., epitope. This term includes a monoclonal antibody or monoclonal antibody composition, which refer to a preparation of antibodies or fragments thereof of single molecular composition. The term isotype refers to the antibody class (e.g., IgM or IgG1) that is encoded by heavy chain constant region genes.

The term binding affinity refers to the apparent association constant or $K_A$. The $K_A$ is the reciprocal of the dissociation constant ($K_D$). A binding agent may, for example, have a binding affinity for a particular target molecule that is associated with a $K_D$ of $<10^{-6}$ M, $<10^{-7}$ M, $<10^{-8}$ M, $<10^{-9}$ M, $<10^{-10}$ M, or $<10^{-11}$ M, with lower $K_D$ values being associated with higher affinity. Higher affinity binding of a binding agent to a first target relative to a second target can be indicated by a higher $K_A$ (or a smaller numerical value $K_D$) for binding the first target than the $K_A$ (or numerical value $K_D$) for binding the second target. In such cases, the binding agent specifically binds the first target relative to the second target. Differences in binding affinity (e.g., for specificity or other comparisons) can be at least 1.5, 2, 3, 4, 5, 10, 15, 20, 50, 70, 80, 100, 500, 1000, 10000, 100000, or 1000000-fold.

Binding affinity can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in PBS (phosphate buffered saline) at pH 7.2 at 30° C. These techniques can be used to measure the concentration of bound and free binding protein as a function of binding protein (or target) concentration. The concentration of bound binding protein ([Bound]) is related to the concentration of free binding protein ([Free]) and the concentration of binding sites for the binding protein on the target where (N) is the number of binding sites per target molecule by the following equation:

$$[Bound] = N \cdot [Free]/((1/Ka) + [Free]).$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

The term epitope refers to the site on a target molecule that is bound by a binding agent (e.g., an antibody such as a Fab or full length antibody). In the case where the target molecule is a protein, the site can be entirely composed of amino acid components, entirely composed of chemical modifications of amino acids of the protein (e.g., glycosyl moieties), or composed of combinations thereof. Overlapping epitopes include at least one common amino acid residue.

One or more regions of an antibody can be human or effectively human. For example, one or more of the variable regions can be human or effectively human. For example, one or more of the CDRs can be human, e.g., HC CDR1, HC CDR2, HC CDR3, LC CDR1, LC CDR2, and LC CDR3. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human or effectively human. In one embodiment, at least 70, 75, 80, 85, 90, 92, 95, or 98% of, or the entire of, the antibody can be human or effectively human.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2- terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term ligand refers to a binding molecule that binds non-covalently to a second binding molecule with high affinity. In some embodiments, a high-affinity bond is characterized by a $K_D<10^{-6}$ M, a $K_D<10^{-7}$ M, a $K_D<10^{-8}$ M, a $K_D<10^{-9}$ M, a $K_D<10^{-10}$ M, a $K_D<10^{-11}$ M, or a $K_D<10^{-12}$ M. In some embodiments, the ligand is a small molecule. In some embodiments, the ligand is a peptide or protein. In some embodiments, the ligand is a nucleic acid.

The term isolated, in the context of a composition refers to a composition that is removed from at least 90% of at least one component of a natural sample from which the isolated composition can be obtained. In some embodiments, compositions produced artificially or engineered are also encompassed within the scope of the term isolated.

The terms therapeutically effective dosage, therapeutically ejective amount, or effective amount is an amount that, when administered to a subject, results in a desired clinical effect, e.g., in the vaccination or immunization of a subject, or in an amelioration of a symptom that is clinically manifest in the subject.

The term affinity tag refers to a tag, for example, a peptide tag that is N-terminally or C-terminally fused to a protein, e.g., an exopolysaccharide-associated protein, that binds to a ligand with high affinity and thus allows for the detection and/or isolation of the tagged protein. Affinity tags are well known to those of skill in the art and examples of suitable affinity tags include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. In some embodiments, the tag is a biotin tag or a biotin variant tag, for example, desthiobiotin (DTB). Some affinity tags and methods for the use of affinity tags are described herein and other suitable tags and methods will be apparent to those of skill in the art, e.g., as described in Lichty J J Malecki J L, Agnew H D, Michelson-Horowitz D J, Tan S. Comparison of affinity tags for protein purification. Protein Expr Purif. 2005:41:98-105; and Kimple, M. E., and Sondek, J. *Overview of affinity tags for protein purification.* Curr Protoc Protein Sci. 2004 September; Chapter 9:Unit 9.9: the contents of each of which are incorporated in their entirety herein for disclosure of affinity tags and related methods. Those of skill in the art will appreciate that the disclosure is not limited in this respect.

The term detection agent is used interchangeably with the term detectable label, and refers to a moiety that has at least one element, isotope, or a structural or functional group incorporated that enables detection of a molecule, e.g., a protein or polypeptide, or other entity, to which the detection agent is attached. A detection agent can be directly attached (e.g., via a bond) or can be attached by a tether or linker. A detection agent can also be conjugated to the molecule, e.g., via non-covalent interactions. It will be appreciated that a detection agent may be attached to or incorporated into a molecule, for example, an exopolysaccharide-associated protein, a fusion protein, a polypeptide, or other entity, at any position, but preferably in a manner that does not interfere with the structural or functional characteristics of the molecule, e.g., the binding of the molecule (e.g., a protein) to a binding partner (e.g., an exopolysaccharide). In general, a detection agent can fall into any one (or more) of five classes: a) an agent which contains isotopic moieties, which may be radioactive or heavy isotopes, including, but not limited to, 2H, 3H, 13C, 14C, 15N, 18F, 31P, 32P, 35S, 67Ga, 76Br, 99mTc (Tc-99m), 111In, 123I, 125I, 131I, 153Gd, 169Yb, and 186Re; b) an agent which contains an immune moiety, which may be an antibody or antigen, which may be bound to an enzyme (e.g., such as horseradish peroxidase): c) an agent comprising a colored, luminescent, phosphorescent, or fluorescent moiety (e.g., such as the fluorescent label fluoresceinisothiocyanat (FITC); d) an agent which has one or more photo affinity moieties; and e) an agent which is a ligand for one or more known binding partners (e.g., biotin-streptavidin, His-NiTNAFK506-FKBP). In certain embodiments, a detection agent comprises a radioactive isotope, preferably an isotope which emits detectable particles, such as R particles. In certain embodiments, a detection agent comprises a fluorescent moiety. In certain embodiments, the detection agent comprises a dye, e.g., a fluorescent dye, e.g., fluorescein isothiocyanate, TEXAS RED®, rhodamine, Cy3, Cy5, Cy5.5, ALEXA 647® and derivatives. In certain embodiments, the detection agent comprises a ligand moiety with one or more known binding partners. In certain embodiments, the detection agent comprises biotin. In some embodiments, a detection agent is a fluorescent polypeptide (e.g. GFP or a derivative thereof such as enhanced GFP (EGFP)) or a luciferase (e.g., a firefly, *Renilla*, or *Gaussia* luciferase). It will be appreciated that, in certain embodiments, a detection agent may react with a suitable substrate (e.g., a luciferin) to generate a detectable signal. Non-limiting examples of fluorescent proteins include GFP and derivatives thereof, proteins comprising chromophores that emit light of different colors such as red, yellow, and cyan fluorescent proteins, etc. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M, and Kain, S R (eds.) Green fluorescent protein: properties, applications, and protocols (Methods of biochemical analysis. v. 47). Wiley-Interscience, Hoboken, N.J., 2006, and/or Chudakov, D M, et al., Physiol Rev. 90(3):1103-63, 2010 for discussion of GFP and numerous other fluorescent or luminescent proteins. In some embodiments, a detection agent comprises a dark quencher, e.g., a substance that absorbs excitation energy from a fluorophore and dissipates the energy as heat.

The term antigen refers to a molecule or part of a molecule that is bound by the antigen-binding site of an antibody. In some embodiments, an antigen is a molecule or moiety that, when administered to a subject, activates or increases the production of antibodies that specifically bind the antigen. In some embodiments, an antigen is a protein or a polysaccharide. Antigens of pathogens are well known to those of skill in the art and include, but are not limited to parts (coats, capsules, cell walls, flagella, fimbriae, and toxins) of bacteria, viruses, and other microorganisms. A vaccine typically comprises an antigen, and is intentionally administered to a subject to induce an immune response in the recipient subject.

The term adjuvant refers to a pharmacological or immunological agent that modifies the effect of other agents, for example, of an antigen in a vaccine. Adjuvants are typically included in vaccines to enhance the recipient subject's immune response to an antigen. The use of adjuvants allows the induction of a greater immune response in a subject with the same dose of antigen, or the induction of a similar level of immune response with a lower dose of injected antigen. Many adjuvants suitable for use in the context of embodiments of this disclosure are known to those of skill in the art, including, but not limited to, aluminum salts, liposomes, lipopolysaccharide (LPS), molecular cages for antigen, components of bacterial cell walls, endocytosed nucleic acids such as double-stranded RNA (dsRNA), single-stranded DNA (ssDNA), and unmethylated CpG dinucleotide-containing DNA.

The term vaccine refers to a composition that activates or enhances a subject's immune response to an antigen after the vaccine is administered to the subject. In some embodiments, a vaccine typically contains an antigen characteristic for a pathogen, e.g., a pathogenic microorganism, such as a pathogenic bacterium. In some embodiments, a vaccine comprises a weakened (attenuated), inactivated, or killed pathogen. In some embodiments, a vaccine comprises an antigen found on a toxin or a surface protein of a pathogen. In some embodiments, a vaccine stimulates the subject's immune system to recognize the antigen as foreign, and enhances the subject's immune response if the subject is later exposed to the pathogen, whether attenuated, inactivated, killed, or not. Vaccines may be prophylactic, for example, preventing or ameliorating a detrimental effect of a future exposure to a pathogen, or therapeutic, for example, activating the subject's immune response to a pathogen after the subject has been exposed to the pathogen.

The terms immunizing and vaccinating a subject refer to a process of administering an immunogen, typically an antigen formulated into a vaccine, to the subject in an amount effective to increase or activate an immune response against the antigen and, thus, against a pathogen displaying the antigen. In some embodiments, the terms do not require the creation of complete immunity against the pathogen. In some embodiments, the terms encompass a clinically favorable enhancement of an immune response toward the antigen or pathogen. Methods for immunization, including formulation of a vaccine composition and selection of doses, routes of administration and the schedule of administration (e.g. primary dose and one or more booster doses), are well known in the art. In some cases, an evaluation of vaccine compositions can be performed in a subject, e.g., in human subjects. An immune response can, for example, be detected by an increased titer of circulating antibodies or by the presence of enhanced levels of circulating CTLs against bacterial cells bearing the antigen.

The term pharmaceutical composition refers to a composition that can be administrated to a subject in the context of treatment of a disease or disorder. In some embodiments, a pharmaceutical composition comprises an active ingredient, e.g. a nuclease or a nucleic acid encoding a nuclease, and a pharmaceutically acceptable excipient. In some embodiments, a pharmaceutical composition is sterile. In some embodiments, a pharmaceutical composition is free of undesired toxins, undesired allergens, undesired infectious agents, and/or undesired pathogens.

The term effective amount refers to an amount of a biologically active agent that is sufficient to elicit a desired biological response. For example, in some embodiments, an effective amount of a nuclease may refer to the amount of the nuclease that is sufficient to induce cleavage of a target site specifically bound and cleaved by the nuclease. As will be appreciated by the skilled artisan, the effective amount of an agent, e.g., a nuclease, a hybrid protein, or a polynucleotide, may van depending on various factors as, for example, on the desired biological response, the specific allele, genome, target site, cell, or tissue being targeted, and the agent being used.

The term subject refers to an individual organism. In some embodiments, is a mammal, for example, a human, a non-human primate, a mouse, a rat, a cat, a dog, a cattle, a goat, a pig, or a sheep. In some embodiments, the subject is a vertebrate.

The term target site refers to a site to which delivery of a molecule is desired, or that is targeted for delivery of a molecule. In some embodiments, the target site is an organ or a site of disease in a subject. In some embodiments, the target site is the gastrointestinal tract of a subject, e.g., a human. In some embodiments, the target site is the surface of a bioreactor or culture vessel adjacent to a culture medium within the bioreactor or the culture vessel. In some embodiments, the target site is a surface, e.g., a solid surface of a bioreactor or culture vessel that borders on a liquid phase, e.g., a culture medium in the bioreactor or culture vessel, or the surface of a body of water, e.g., a water/air interface.

The term surface, in the context of materials or target sites, refers to the exterior boundary or the outermost layer of a material. A surface typically constitutes the interface of a material with a different material and/or a different phase. For example, a surface may be the exterior boundary of a liquid material, for example, a culture medium in a bioreactor or culture dish, or liquid comprised in a body of water (e.g., a pond, a lake, an ocean), that is in contact with a solid material, e.g., a solid material comprised in the bioreactor or culture vessel, or a gaseous material, e.g., a gaseous phase overlaying the culture medium (e.g., air, oxygen, nitrogen, carbon dioxide, or a controlled mix of different gases (e.g., 5% Oxygen, 5% carbon dioxide, and 90% nitrogen), or overlaying the body of water (e.g., air). In some embodiments, a surface is an air/water interface, e.g., the region in which the outer layer of a body of water meets the outer layer of an adjacent body of air, or any material within 1 µm, 1 mm, 5 mm, 10 cm, 50 cm, 1 m, or 10 m from the air/water interface.

Engineered Exopolysaccharide-Associated Proteins

Some aspects of this disclosure provide engineered exopolysaccharide-associated proteins. Such proteins can embrace, for example, on secreted bacterial proteins that are retained in the bacterial biofilm matrix by association with the biofilm exopolysaccharide scaffold, as previously identified [1], or other exopolysaccharide-associated proteins, for example, as identified herein, or otherwise known to those of skill in the art.

Some aspects of this disclosure provide a composition comprising an exopolysaccharide-associated protein, or an exopolysaccharide-binding fragment thereof; and a heterologous molecule conjugated to the exopolysaccharide-associated protein, or an exopolysaccharide-binding fragment thereof. The exopolysaccharide-associated protein may be any exopolysaccharide-associated protein described herein or known to those of skill in the art. Similarly, the exopolysaccharide-binding fragment may be any such fragment described herein or known to those of skill in the art.

In some embodiments, the exopolysaccharide-associated protein is a secreted protein or an extracytoplasmic protein. In some embodiments, the exopolysaccharide associated protein remains attached to the cell after synthesis and cellular processing, for example, via noncovalent interactions with molecules on the surface of the cell in the case of a secreted protein, or by a tethering of a transmembrane domain to the cell membrane in the case of an extracytoplasmic protein. Accordingly, an engineered exopolysaccharide associated protein is provided herein, also remains attached to the cell after synthesis and cellular processing in such embodiments. In the case of an engineered secreted exopolysaccharide associated protein, the heterologous molecule conjugated to the exopolysaccharide associated protein will typically also be secreted. In the case of an engineered extracytoplasmic exopolysaccharide associated protein, it is preferable that the protein is engineered so that the heterologous molecule conjugated to the exopolysaccharide associated protein protrudes into the extracytoplasmic space after cellular processing of the engineered protein.

In some embodiments, an engineered exopolysaccharide-associated protein, as provided herein, comprises a known exopolysaccharide-associated protein, or fragment thereof, conjugated to a heterologous molecule. In some embodiments, the exopolysaccharide-associated protein is a type I β-prism lectin domain-containing protein, or an exopolysaccharide-binding fragment thereof. For example, in some embodiments, the exopolysaccharide-associated protein is Bap1 (SEQ ID NO: 1), RbmA (SEQ ID NO: 2), RbmC (SEQ ID NO: 3), or HlyA (SEQ ID NO:4). In some embodiments, the exopolysaccharide associated protein is an exopolysaccharide-binding fragment of Bap1 (SEQ ID NO: 1), RbmA (SEQ ID NO: 2), RbmC (SEQ ID NO: 3), or HlyA (SEQ ID NO:4). In some such embodiments, the fragment comprises a type I β-prism lectin domain contained in the respective full-length protein.

Exemplary known exopolysaccharide-associated proteins from *V. cholerae* are described in Table 1 and Table 2 below. Other exopolysaccharide-associated proteins from other bacteria strains, e.g., from other *Vibrio* sp. strains, other diarrheal pathogens, other pathogens, and other nonpathogenic organisms or molecules, are also useful according to some aspects of this disclosure. Homologous exopolysaccharide-associated proteins can be determined by those of skill in the art via homology determinations, e.g., based on sequence alignments. The sequences of some exemplary exopolysaccharide-associated proteins are provided elsewhere herein, including, the sequences of *V. cholerae* Bap1, RbmA, RbmC, and HlyA. Those of skill in the art will be able to identify homologous sequences in other *Vibrio* strains, other bacterial strains, and non-bacterial sources based on this sequence information, and will also be able to determine which of the identified proteins bind exopolysaccharides, e.g., based on the identified proteins comprising a polysaccharide-binding domain, such as, for example, a D-prism lectin domain or an FG-GAP domain.

TABLE 1

Secreted proteins identified in preparations of biofilm matrix.

| Genomic Locus | Annotation |
| --- | --- |
| VC0409 | MshA |
| VC0928 | RbmA |
| VC0930 | RbmC |
| VC2142 | FlaB |
| VC2143 | FlaD |
| VC2187 | FlaC |
| VC2188 | FlaA |
| VCA0027 | ChiA-2 |
| VCA0219 | HlyA |
| VCA0865 | HAP |

TABLE 2

Extracytoplasmic proteins of unknown location.

| Genomic Locus | Annotation |
| --- | --- |
| VC0174 | hypothetical |
| VC0430 | immunogenic protein |
| VC0483 | hypothetical |
| VC1101 | hypothetical |
| VC1154 | hypothetical |
| VC1334 | hypothetical |
| VC1384 | hypothetical |
| VC1523 | hypothetical |
| VC1834 | hypothetical |
| VC1853 | hypothetical |
| VC1887 | hypothetical |
| VC1894 | hypothetical |
| VC2168 | hypothetical |
| VC2517 | hypothetical |
| VCA0026 | hypothetical |
| VCA0058 | conserved, hypothetical |
| VCA0144 | immunogenic protein |
| VCA0900 | hypothetical |

Additional exopolysaccharide-associated proteins found in bacterial biofilms are well known to those of skill in the art and include, for example, those described in Oliver-Kozup et al., *The group A streptococcal collagen-like protein-1, Scl1, mediates biofilm formation by targeting the extra domain A-containing variant of cellular fibronectin expressed in wounded tissue.* Mol Microbiol. 2013; 87(3): 672-89; Diggle et al., *The galactophilic lectin, LecA, contributes to biofilm development in Pseudomonas aeruginosa.* Environ Microbiol. 2006 June; 8(6):1095-104; Johansson et al., *Inhibition and dispersion of Pseudomonas aeruginosa biofilms by glycopeptide dendrimers targeting the fucose-specific lectin LecB.* Chem Biol. 2008 Dec. 22:15(12):1249-57; and Abdian et al., *RapA2 Is a Calcium-binding Lectin Composed of Two Highly Conserved Cadherin-like Domains That Specifically Recognize Rhizobium leguminosarum Acidic Exopolysaccharides.* J Biol Chem. 2013 25:288(4):2893-904: the entire contents of each of which are incorporated herein by reference.

In some embodiments, an engineered exopolysaccharide-associated protein as provided herein comprises a β-prism lectin domain, or a fragment thereof, or an FG-GAP domain, or fragment thereof. In some embodiments, an exopolysaccharide-associated protein as provided herein comprises a β-prism lectin domain flanked by an FG-GAP domain. For example, in some embodiments, an engineered exopolysaccharide-associated protein provided herein comprises a structure N-[β-prism lectin domain]$_x$-[FG-GAP domain]$_y$-C;

N-[FG-GAP domain]$_n$-[β-prism lectin domain]$_m$-C;

N-[β-prism lectin domain]$_i$-[FG-GAP domain]$_{ii}$-[β-prism lectin domain]$_{iii}$-C N-[FG-GAP]$_a$-[β-prism lectin domain]$_b$-[FG-GAP domain]$_c$-C;

wherein N: N-terminus; C: C-terminus; and x, y, n, m, i, ii, iii, a, b, and c representing, independently, an integer between 0 and 25, and preferably an integer between 1 and 10. In some such embodiments, a heterologous molecule is conjugated to either the N terminus or the C terminus of the provided structure. In some embodiments, the β-prism lectin domain and/or the FG-GAP domain comprises or is encoded by a sequence found in or derived from a naturally occurring exopolysaccharide-associated protein, e.g., from RbMC, Bap1, or HlyA, which are described in more detail elsewhere herein. In some such embodiments, the engineered exopolysaccharide-associated protein can be generated by recombinant methods in which the naturally occurring coding sequences are recombined to form their respective structure. In some embodiments, the β-prism lectin domain and/or the FG-GAP domain comprise a non-naturally occurring sequence, for example a sequence determined to be the minimal sequence required for exopolysaccharide binding. In some embodiments, exopolysaccharide binding its binding to a known exopolysaccharide, for example, an N-glycan, with an affinity characterized by a $K_D$ of $\leq 10^{-6}$ M, $\leq 10^{-7}$ M, $\leq 10^{-8}$ M, $\leq 10^{-9}$ M, $\leq 10^{-10}$ M, $\leq 10^{-11}$ M, or $\leq 10^{-12}$ M. Some such minimal sequences are provided herein, and others are known to those of skill in the art, will be apparent to those of skill in the art based on the instant disclosure, or can be ascertained by those of skill in the art with no more than routine experimentation. For methods useful for the determination of the binding affinity of an exopolysaccharide-associated proteins or fragments thereof to an exopolysaccharide, see, e.g., Levan et al., *Vibrio cholerae Cytolysin Recognizes the Heptasaccharide Core of Complex N-Glycans with Nanomolar Affinity*. J Mol Biol. 2012 S0022-2836(12)00949-7: the entire contents of which are Incorporated herein by reference.

In some embodiments, the exopolysaccharide-associated protein of this disclosure is a RbmA protein from *Vibrio Cholerae*. In mature *V. Cholerae* biofilms, RbmA is present throughout the biofilms and retains daughter cells in the biofilm following division. Further, RbmA also facilitates micro-colony and cell cluster formation by stabilizing both cell-cell and cell-exopolysaccharide interactions. RbmA is expressed in *V. cholerae* cells and secreted to the matrix of the biofilm, where it remains attached to the cell surface. As illustrated in the drawings and examples of this disclosure, by fusing a heterologous molecule to RbmA. RbmA was able to deliver the heterologous molecule to the cell surface. A fusion protein comprising RbmA and cholera toxin B (CtxB) induced antigen-specific immune response in the host.

As used herein, the term "a RbmA protein," encompasses wild type RbmA protein and variants thereof. In some embodiments, the *V. Cholerae* RbmA protein comprises an amino acid sequence of SEQ ID NO: 2. Further provided herein are RbmA variants that may be used as the exopolysaccharide protein of this disclosure. A "variant" of a protein, e.g., RbmA, as used herein, refers to a protein that shares homology to the wild type protein, e.g., wild type RbmA, or a fragment thereof. For example, a RbmA variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to wild type RbmA. A RbmA variant may be made by deletion, insertion, amino acid substitution, or other recombinant protein techniques known by one skilled in the art. In some embodiments, the RbmA variants of this disclosure comprise amino acid substitution mutations.

As used herein, "substitution mutation" without the reference to a specific amino acid, may include any amino acid other than the wild type residue normally found at that position. Such substitutions may be replacement with non-polar (hydrophobic) amino acids, such as glycine, alanine, valine, leucine, isoleucine, methionine, phenylalanine, tryptophan, and proline. Substitutions may be replacement with polar (hydrophylic) amino acids such as serine, threonine, cysteine, tyrosine, asparagine, and glutamine. Substitutions may be replacement with electrically charged amino acids, e.g., negatively electrically charged amino acids such as aspartic acid and glutamic acid and positively electrically charged amino acids such as lysine, arginine, and histidine.

The substitution mutations described herein will typically be replacement with a different naturally occurring amino acid residue, but in some cases non-naturally occurring amino acid residues may also be substituted. Non-natural amino acids, as the term is used herein, are non-proteinogenic (i.e., non-protein coding) amino acids that either occur naturally or are chemically synthesized. Examples include but are not limited to β-amino acids (β3 and β2), homo-amino acids, proline and pyruvic acid derivatives, 3-substituted alanine derivatives, glycine derivatives, ring-substituted phenylalanine and tyrosine derivatives, linear core amino acids, diamino acids. D-amino acids, and N-methyl amino acids. In some embodiments, the amino acid can be substituted or unsubstituted. The substituted amino acid or substituent can be a halogenated aromatic or aliphatic amino acid, a halogenated aliphatic or aromatic modification on the hydrophobic side chain, or an aliphatic or aromatic modification.

In some embodiments, the RbmA variants comprise amino acid substitution mutations in a surface groove that is lined with several positively charged residues, e.g., lysine. Such surface groove is formed at the interface of a RbmA dimer, as described in Giglio et al; Journal of Bacteriology, July 2013 Volume 195 Number 14, p. 3277-3286, the entire contents of which is herein incorporated by reference. In some embodiments, the RbmA variant comprises one or more substitution mutations in positions R234, R219, or R116 in SEQ ID NO: 2. In some embodiments, the RbmA variant comprises one or more substitution mutations selected from R234A, R219A, or R116A in SEQ ID NO: 2. Possible combination of the mutations include: R234A, R219A, R116A, R234A/R219A R234A/R116A, and R219A/R116A. "/" indicates double mutations. In some embodiments, the RbmA variants comprise an amino acid sequence of any of SEQ ID NOs: 38-43.

RbmA R234A
(SEQ ID NO: 38)
MSNFKGSIMNKRHYYLASCLALLFSTASYAEVDCELQPVIEANLSLNQNQ

LASNGGYISSQLGIRNESCETVKFKYWLSIKGPEGIYFPAKAVVGVDTAQ

QESDALTDGRMLNVTRGFWVPEYMADGKYTVSLQVVAENGKVFKANQEFV

KGVDLNSLPELNGLTIDIKNQFGINSVESTGGFVPFTVDLNNGREGEANV

EFWMTAVGPDGLIIPVNAREKWVIASGDTYSKVAGINFDKSYPAGEYTIN

AQVVDIVSGERVEQSMTVVKK
Signal peptide: residues 1-30

RbmA R219A
(SEQ ID NO: 39)
MSNFKGSIMNKRHYYLASCLALLFSTASYAEVDCELQPVIEANLSLNQNQ

LASNGGYISSQLGIRNESCETVKFKYWLSIKGPEGIYFPAKAVVGVDTAQ

QESDALTDGRMLNVTRGFWVPEYMADGKYTVSLQVVAENGKVFKANQEFV

KGVDLNSLPELNGLTIDIKNQFGINSVESTGGFVPFTVDLNNGREGEANV

EFWMTAVGPDGLIIPVNAAEKWVIASGDTYSKVRGINFDKSYPAGEYTIN

AQVVDIVSGERVEQSMTVVKK
Signal peptide: residues 1-30

-continued

RbmA R116A
(SEQ ID NO: 40)
MSNFKGSIMNKRHYYLASCLALLFSTASYAEVDCELQPVIEANLSLNQNQ

LASNGGYISSQLGIRNESCETVKFKYWLSIKGPEGIYFPAKAVVGVDTAQ

QESDALTDGRMLNVTAGFWVPEYMADGKYTVSLQVVAENGKVFKANQEFV

KGVDLNSLPELNGLTIDIKNQFGINSVESTGGFVPFTVDLNNGREGEANV

EFWMTAVGPDGLIIPVNAREKWVIASGDTYSKVRGINFDKSYPAGEYTIN

AQVVDIVSGERVEQSMTVVKK
Signal peptide: residues 1-30

RbmA R234A/R219A
(SEQ ID NO: 41)
MSNFKGSIMNKRHYYLASCLALLFSTASYAEVDCELQPVIEANLSLNQNQ

LASNGGYISSQLGIRNESCETVKFKYWLSIKGPEGIYFPAKAVVGVDTAQ

QESDALTDGRMLNVTRGFWVPEYMADGKYTVSLQVVAENGKVFKANQEFV

KGVDLNSLPELNGLTIDIKNQFGINSVESTGGFVPFTVDLNNGREGEANV

EFWMTAVGPDGLIIPVNAAEKWVIASGDTYSKVAGINFDKSYPAGEYTIN

AQVVDIVSGERVEQSMTVVKK
Signal peptide: residues 1-30

RbmA R234A/R116A
(SEQ ID NO: 42)
MSNFKGSIMNKRHYYLASCLALLFSTASYAEVDCELQPVIEANLSLNQNQ

LASNGGYISSQLGIRNESCETVKFKYWLSIKGPEGIYFPAKAVVGVDTAQ

QESDALTDGRMLNVTAGFWVPEYMADGKYTVSLQVVAENGKVFKANQEFV

KGVDLNSLPELNGLTIDIKNQFGINSVESTGGFVPFTVDLNNGREGEANV

EFWMTAVGPDGLIIPVNAREKWVIASGDTYSKVAGINFDKSYPAGEYTIN

AQVVDIVSGERVEQSMTVVKK
Signal peptide: residues 1-30

RbmA R219A/R116A
(SEQ ID NO: 43)
MSNFKGSIMNKRHYYLASCLALLFSTASYAEVDCELQPVIEANLSLNQNQ

LASNGGYISSQLGIRNESCETVKFKYWLSIKGPEGIYFPAKAVVGVDTAQ

QESDALTDGRMLNVTAGFWVPEYMADGKYTVSLQVVAENGKVFKANQEFV

KGVDLNSLPELNGLTIDIKNQFGINSVESTGGFVPFTVDLNNGREGEANV

EFWMTAVGPDGLIIPVNAAEKWVIASGDTYSKVRGINFDKSYPAGEYTIN

AQVVDIVSGERVEQSMTVVKK
Signal peptide: residues 1-30

Both β-prism lectin domain and FG-GAP domain mediate protein adhesion to exopolysaccharides. In some embodiments, the heterologous molecule is conjugated to a fragment of an exopolysaccharide-associated protein that comprises a minimal exopolysaccharide-binding sequence. Exemplary minimal exopolysaccharide-binding sequences are described in more detail elsewhere herein, and additional minimal exopolysaccharide-binding sequences will be apparent to those of skill in the art based on the instant disclosure, or can be ascertained by those of skill in the art with no more than routine next fermentation.

The heterologous molecule may be any molecule that can be conjugated to an exopolysaccharide-associated protein, for example, a protein, a polypeptide, a nucleic acid, a lipid, a polysaccharide, a small molecule, a binding agent, or a detection agent. The heterologous molecule may be conjugated to the exopolysaccharide-associated protein, or fragment thereof, via covalent linkage, for example, direct covalent linkage, or indirectly via a linker. In some embodiments, the linker comprises a cleavage site, for example, a protease cleavage site. Inclusion of a cleavage site allows the controlled release of the heterologous molecule from the exopolysaccharide-associated protein, which is useful, among other instances, for the controlled release of the heterologous molecule from the exopolysaccharide-associated protein, for example, for isolation and/or purification of the heterologous molecule.

In some embodiments, the heterologous molecule comprises a heterologous protein, for example, an enzyme, or an antigen. In some such embodiments, the heterologous protein is fused to the exopolysaccharide-associated protein, or to the exopolysaccharide-binding fragment thereof, thus forming a fusion protein. The methods and compositions for the generation of fusion proteins are well known to those of skill in the art. In general, a fusion protein of an exopolysaccharide associated protein, or fragment thereof, and a heterologous protein can be created by generating a nucleic acid construct encoding both proteins in frame, optionally with a sequence encoding a linker sequence separating both protein-encoding sequences. Typically, such fusion protein encoding nucleic acid constructs are generated by recombinant technologies, which are well known to those of skill in the art. In some embodiments, a nucleic acid encoding a fusion protein, or a fusion protein itself, may also be synthesized de novo. Methods for synthesizing nucleic acids and proteins are also well known to those of skill in the art.

In some embodiments, the heterologous molecule comprises an antigen, for example, an antigen of a pathogen. Antigens, and, in particular, antigens of pathogens, are well known to those of skill in the art. Some antigens that are of particular interest in the context of some aspects of this disclosure, are antigens of diarrheal pathogens. Diarrheal pathogens include, without limitation, *V. cholerae, Salmonella* sp. (e.g., *Salmonella paratyphi*), *Campylobacter* sp. (e.g., *C. jejuni*) enterotoxic and enterophathogenic *E. coli* (e.g., EHEC, EPEC), and Norovirus. Immunogenic proteins and encoding genes or ORFs from various pathogens, including the diarrheal pathogens listed above, are well known to those of skill in the art, and include, without limitation, the antigens described in Adkins et al., *Bacteria and their toxins tamed for immunotherapy.* Curr Pharm Biotechnol. 2012 June; 13(8):1446-73; Nielsen et al., *Identification of immunogenic and virulence-associated Campylobacter jejuni proteins.* Clin Vaccine Immunol. 2012 February; 19(2):113-9; Yang et al., *Screening of the Salmonella paratyphi A CMCC 50973 strain outer membrane proteins for the identification of potential vaccine targets.* Mol Med Report. 2012 January; 5(1):78-83; Harro et al., *A combination vaccine consisting of three live attenuated enterotoxigenic Escherichia coli strains expressing a range of colonization factors and heal-labile toxin subunit B is well tolerated and immunogenic in a placebo-controlled double-blind phase I trial in healthy adults.* Clin Vaccine Immunol. 2011 December; 18(12):2118-27; Vasconcellos et al., *Generation of recombinant bacillus Calmette-Guerin and Mycobacterium smegmatis expressing BfpA and intimin as vaccine vectors against enteropathogenic Escherichia coli.* Vaccine. 2012 Sep. 7; 30(41):5999-6005; and Tan et al., *Norovirus P particle, a novel platform for vaccine development and antibody production.* J Virol. 2011 January; 85(2): 753-(4: the entire contents of each of which are Incorporated herein by reference. Some exemplary antigens suitable as heterologous molecules according to some aspects of this disclosure are provided in Tables 3 and 4 below.

TABLE 3 highly immunogenic ORFs cloned from *Campylobacter jejuni* (see Nielsen et al., *Identification of immunogenic and virulence-associated Campylobacter jejuni proteins*. Clin Vaccine Immunol. 2012 February; 19(2): 113-9, the entire contents of which are incorporated herein by reference).

| ORF (NCTC 11168)[a] | Annotation |
| --- | --- |
| Cj0014c | Putative integral membrane protein |
| Cj0034c (4) | Putative periplasmic protein |
| Cj0111 (3) | Putative periplasmic protein |
| Cj0203 | Putative transmembrane transport protein |
| Cj0383c | ribH, 6,7-dimethyl-8-ribityllumazine synthase |
| Cj0404 (3) | Putative transmembrane protein |
| Cj0408 | frdC, fumerate reductase cytochrome B subunit |
| Cj0477 | rplL, 50S ribosomal protein |
| Cj0525c (3) | pbpB, putative penicillin binding protein |
| Cj0645 (2) | Putative secreted tranglycosylase |
| Cj0774c (5) | ABC transport system ATP binding protein |
| Cj0811 | lpxK, tetrasyldisaccharide 4'-kinase |
| Cj0917c | cstA, carbon starvation protein A homolog |
| Cj0965c | Putative acyl coenzyme A thioester hydrolase |
| Cj1092c | secF, protein export membrane protein |
| Cj1094c | yajC, preprotein translocase subunit |
| Cj1163c (4) | Putative cation transport protein |
| Cj1174 (3) | Putative efflux protein |
| Cj1292 | dcd, dCTP deaminase |
| Cj1364c | fumC, fumerate hydratase |
| Cj1371 (2) | Putative periplasmic protein (vacJ homolog) |
| Cj1382c (4) | fldA, flavodoxin |
| Cj1529c (5) | purM, phosphoribosylaminoimidazole synthase |
| Cj1628 | exbB2, putative exbB/tolQ family transport protein |
| Cj1632c | Putative periplasmic protein |

TABLE 4 immunogenic proteins from *Salmonella paratyphi* (from Yang et al., *Screening of the Salmonella paratyphi A CMCC 50973 strain outer membrane proteins for the identification of potential vaccine targets*. Mol Med Report. 2012 January; 5(1): 78-83, the entire contents of which are incorporated herein by reference).

| NCBI GI identifier | Mass (Da) | pI (calc) | Protein | Gene |
| --- | --- | --- | --- | --- |
| 56416031 | 50640 | 4.87 | Maltoporin precursor | LamB |
| 56415127 | 553649 | 5.43 | Outer membrane channel precursor protein | tolC |
| 56412835 | 41214 | 4.63 | Outer membrane protein C | ompC |
| 56412712 | 47675 | 4.90 | Long-chain fatty acid transport protein precursor | fadL |
| 56415967 | 68470 | 5.40 | Vitamin B12 receptor protein | btuB |
| 56412364 | 89861 | 5.30 | Organic solvent tolerance protein | imp |
| 56413481 | 39655 | 4.66 | New outer membrane protein: predicted bacterial porin | nmpC |
| 56413763 | 20090 | 6.28 | Outer membrane invasion protein | pagC |
| 56413343 | 22990 | 5.64 | Putative outer membrane protein | ompW |
| 56413933 | 37583 | 5.47 | Outer membrane protein A | OmpA |
| 56413728 | 28035 | 5.51 | Putative outer membrane protein | mipA |
| 56414068 | 18540 | 5.74 | Outer membrane protein x precursor | OmpX |

In some embodiments, the heterologous molecule is a bacterial toxin, for example, *Bordetella pertussis* adenylate cyclase toxin, *Bacillus anthracis* lethal and edema toxins, *Shigella dysenteriae* shiga toxin, *Escherichia coli* shiga-like toxin, *E. coli* α-hemolysin, *Vibrio cholerae* cholera toxin (e.g., cholera toxin B), *E coli* heat-labile enterotoxin, *Bordetella pertussis* pertussis toxin, *Bacillus thuringiensis* Cry 1 A protein, *Clostridium perfringens* perfringolysin O, *Streptococcus intermedius* intermedilysin, *Streptococcus pneumoniae* pneumolysin, *Corynebacterium diphtheriae* diphtheria toxin, or a *Pseudomonas aeruginosa* exotoxin A-based immunotoxin. Bacterial toxins are well known to those of skill in the art, and while some exemplary suitable bacterial toxins are disclosed herein, this disclosure is not limited in this respect. Additional suitable toxins will be apparent to the skilled artisan based on the instant disclosure and the knowledge in the art, including, but not limited to, the toxins described in Adkins et al., *Bacteria and their toxins tamed for immunotherapy*. Curr Pharm Biotechnol. 2012 June; 13(8):1446-73, the entire contents of which are incorporated herein by reference.

In some embodiments, the heterologous molecule is a bacteria colonization factor antigen. A "bacteria colonization factor antigen," as used herein, are bacterial proteins that confer adhesive and colonizing properties for enteropathogenic strains of *E. coli* (ETEC) in the intestinal epithelium a host. Non-limiting examples of colonization factor antigens include ETEC exoproteins (e.g., EtpA), CFA-1 (fimbrial), KS 71A fimbrial antigen, colonization factor CS19, colonization factor CSS, colonization factor antigen-1,colonization factor antigen-2, colonization factor antigen-3, fimbrial antigen F7(1), and fimbrial colonization factor antigen-1. In some embodiments, the heterologous molecule is EtpA protein, or a fragment thereof. The EtpA protein was identified in ETEC H10407 in a recent search for candidate immunogens. The EtpA protein is a large glycosylated exoprotein secreted via two-partner secretion (TPS). Similar to structurally related molecules, EtpA functions in vitro as an adhesion (Fleckenstein et al., Infection and Immunity, 742245-2258.). The amino acid sequence of EtpA is provided in SEQ ID NO. 44.

ETEC EtpA (SEQ ID NO: 44)
MNRIYKLKFDKRRNELVVVSEITTGVGNAKATGSVEGEKSPRRGVRAMAL

SLLSGMMIMAHPAMSANLPTGGQIVAGSGSIQTPSGNQMNIHQNSQNMVA

NWNSFDIGKGNTVQFDQPSSSAVALNRVVGGGESQIMGNLKANGQVFLVN

PNGVLFGEGASVSTSGFVASTRDIKNDDFMNRRYTFSGGQKAGAAIVNQG

ELTTNAGGYIVLAADRVSNSGTIRTPGGKTVLAASERITLQLDNGGLMSV

QVTGDVVNALVENRGLVSARDGQVYLTALGRGMLMNTVLNVSGVVEASGM

HRQDGNIVLDGGDSGVVHLSGTLQADNASGQGGKVVVQGKNILLDKGSNI

TATGQGGGEVYVGGGWQGKDSNIRNADKVVMQGGARIDVSATQQGNGGT

AVLWSDSYTNFHGQISAKGGETGGNGGRVETSSHGNLQAFGTVSASAKKG

KAGNWLLDSADITIVNGSNVSKTETTQSPPHTQFAPTAAGSAVSNTSINN

RLNNGTSVTILTHRTRTGTAQGGNITVNAAINKSNGSDVNLTLQAGGNIT

VNNSITSTEGKLNVNLSGARTSNGSITISNNANITTNGGDITVGTTNTSN

RVNISINNTTLNASNGNIQLTGTGTDSGILFAGNNRLTASNIALTGNSTS

GNAINLTGTATLNATNNITLTGSSTSGNAINLKGNNTLTASNITLTGEST

SGNAINLTDTTGTTTLNATNNITMQGTRVQIKHSNITAGNFALNATVAGS

EISNTTLTATNNINLAAKTNSASSGVYLKDARITSTNGSITANGTATANG

KATHLDGNVTLNASNGRIKLTGNGHGSASGILFAGNNRLTASNIALTGNS

TSGNAINLTGTATLNATNDITLTGSSTSGNAINLTGTATLNATNNITLTG

SSTSGNAINLKGNNTLTASNITLTGESTSGNAINLTDTTGTTTLNATNNI

TMQGTRVQIKHSNITAGNFALNATVAGSEISNTTLTATNNINLAAKTNSA

SSGVYLKDARITSTNGSITANGTATANGKATHLDGNVTLNASNGRIKLTG

-continued

NGHGSASGILFAGNNRLTASNIALTGNSTSGNAINLTGTATLNATNDITL

TGSSTSGNAINLTGTATLNATNNITLTGSSTSGNAINLKGNNTLTASNIT

LTGESTSGNAINLTDTTGTTTLNATNNITMQGTRVQIKHSNITAGNFALN

ATVAGSEISNTTLTATNNINLAAKTNSASSGVYLKDARITSTNGSITANG

TATANGKATHLDGNVTLNASNGRIKLTGNGHGSASGILFAGNNRLTASNI

ALTGNSTSGNAINLTGTATLNATNDITLTGSSTSGNAINLTGTATLNATN

NITLTGSSTSGNAINLKGNNTLTASNITLTGESTSGNAINLTDTTGTTTL

NATNNITMQGTRVQIKHSNITAGNFALNATVAGSEISNTTLTATNNINLA

AKTNSASSGVYLKDARITSTNGSITTNGTATANGKATHLDGNVTLNASNG

RIKLTGNGHGSASGILFAGNNRLTASNIALTGNSTSGNAINLTGTATLNA

TNDITLTGSSTSGNAINLTGTATLNATNNITLTGSSTSGNAINLKGNNTL

TASNITLTGESTSGNAINLTDTTGTTTLNATNNITMQGTRVQIKHSNITA

GNFALNATVAGSEISNTTLTATNNINLAAKTNSASSGVYLKDARITSTNG

SITANGTAPANDNATYLDGNVTLNASNGSIKLTGNGNGSTSGILFAGNNT

LTASNITLTGNSEVYWQ

In some embodiments, the bacterial toxin is a non-toxic heat-stable toxoid (STa) variant and a B subunit of heat-labile toxin (LTB) from Enterotoxigenic *Escherichia coli* (ETEC). STa and heat-labile toxin (LT) contribute to the virulence of ETEC diarrhea caused by ETEC. LT antigens are often used in vaccine development, but STa has not been included because of its poor immunogenicity and potent toxicity. Toxic STa is not safe for vaccines, but only STa possessing toxicity is believed to be able to induce neutralizing antibodies.

However, recent studies demonstrated that nontoxic STa derivatives (toxoids) induced neutralizing antibodies, after being fused to an LT protein. Further, it has been shown that a A14H mutation in STa (the STa$^{A14H}$ variant) reduces its toxicity and improves its immunogenicity. As such, in some embodiments, the antigen used in the vaccines described herein is a STa$^{A14H}$ toxoid fused to subunit B of the LT protein (LTB).

In some embodiments, the STa$^{A14H}$ and LTB antigens are fused to RmbA to form a fusion protein having an order of RmbA-LTB-STa$^{A14H}$. In some embodiments, the fusion protein is encoded by a polynucleotide comprising the nucleotide sequence of SEQ ID No: 48 in Table 8. In some embodiments, the nucleotide sequence encoding the RmbA-LTB-STaA14H fusion protein is placed under control of the native RmbA promoter.

In some embodiments, the heterologous molecule is a bacterial lipopolysaccharide (LPS). "Lipopolysaccharides (LPS)," also known as lipoglycans and endotoxins, are large molecules consisting of a lipid and a polysaccharide composed of O-antigen, outer core and inner core joined by a covalent bond. LPS molecules are found in the outer membrane of Gram-negative bacteria, and elicit strong immune responses in animals. In some embodiments, the LPS is from *Vibrio cholerae*.

In some embodiments, the heterologous molecule is a virulence factor. A "virulence factor," as used herein, refers to a molecule produced by a pathogen (e.g., bacteria, virus, fungi, and protozoa) that contributes to the pathogenicity of the organism and enables them to colonize, evade and/or suppress host immune system, enter host cells. etc. Some virulence factors are enzymes that interfere with host cellular process and cause damage to host tissues, e.g., proteases, lipases, DNases, hemolysins, etc. In some embodiments, the virulence factor is a bacterial virulence factor. In some embodiments, the bacterial virulence factor is from *Shigella*. In some embodiments, the virulence factor is VirG from *Shigella*. The amino acid sequence of VirG is provided in SEQ ID NO: 45.

Shigella VirG
(SEQ ID NO: 45)
SFSPFVVGASLLLGGPIAFAIPLSGTQELHFSEDNYEKLLTPVDGLSPLG

AGEDGMDAWYITSSNPSHASRTKLRINSDIMISAGHGGAGDNNDGNSCGG

NGGDSITGSDLSIINQGMILGGSGGSGADHNGDGGEAVTGDNLFIINGEI

ISGGHGGDSYSDSDGGNGGDAVTGVNLPIINKGTISGGNGGNNYGEGDGG

NGGDAITGSSLSVINKGTFAGGNGGAAYGYGYDGYGGNAITGDNLSIINN

GAILGGNGGHWGDAINGSNMTIANSGYIISGKEDDGTQNVAGNAIHITGG

NNSLILHEGSVITGDVQVNNSSILKIINNDYTGTTPTIEGDLCAGDCTTV

SLSGNKFTVSGDVSFGENSSLNLAGISSLEASGNMSFGNNVKVEAIINNW

AQKDYKLLSADKGITSNISIINPLLTTGAIDYTKSYISDQNKLIYGLSWN

DTDGDSHGEFNLKENAELTVSTILADNLSHHNINSWDGKSLTKSGEGTLI

LAEKNTYSGFTNINAGILKMGTVEAMTRTAGVIVNKGATLNFSGMNQTVN

SLLNSGTVLINNINAPFLPDPVIVTGNMTLEKNGHVILNNSSSNVGQTYV

QKGNWHGKGGILSLGAVLGNDNSKTDRLEITGHASGITYVAVTNEGGSGD

KTLEGVQIISTDSSDKNAFIQKGRIVAGSYDYRLKQGTVSGLNTNKWYLT

SQMDNQESKQMSNQESTQMSSRRASSQLVSSLNLGEGSIHTWRPEAGSYI

ANLIAMNTMFSPSLYDRHGSTIVDPTTGQLSETTMWIRTVGGHNEHNLAD

RQLKTTANRMVYQIGGDILKTNFTDHDGLHVGIMGAYGYQDSKTHNKYTS

YSSRGTVSGYTAGLYSSWFQDEKERTGLYMDAWLQYGWFNNTVKGDGLTG

EKYSSKGITGALEAGYIYPTIRWTAHNNIDNALYLNPQVQITRHGVKAND

YIEHNGTMVTSSGVNNIQAKLGLRTSLISQSCIDKETLRKFEPFLEVNWK

WSSKQYGVIMNGMSNHQIGNRNVIELKTGVGGRLADNLSIWGNVSQQLV

In some embodiments, the heterologous molecule comprises an enzyme. Engineered exopolysaccharide-associated proteins comprising enzymes are useful for the generation of bacteria in biofilms that exhibits novel or increased enzymatic activities. Suitable enzymes for some embodiments of this disclosure, for example, oxidoreductases, transferases, polymerases, hydrolases, lyases, synthases, isomerases, and ligases. In some embodiments, the enzyme is a protein that is conjugated to the exopolysaccharide-associated protein by a covalent bond, thus forming a fusion protein. In certain embodiments, however, the enzyme is a non-protein enzyme, for example, a nucleic acid (e.g., a ribozyme or a DNAzyme). In some embodiments, the enzyme is a therapeutic enzyme. Therapeutic enzymes are well known to those of skill in the art and include, for example, digestive enzymes (e.g., proteases, lipases, carbohydrases, and nucleases). In some embodiments, the enzyme is selected from the group consisting of lactase, beta-galactosidase, a pancreatic enzyme, an oil-degrading enzyme, mucinase, cellulase, isomaltase, or alginase. In some embodiments, an engineered exopolysaccharide-associated protein is provided that comprises an exopolysaccharide-associated protein conjugated to a digestive enzyme expressed in the mammalian digestive tract. Suitable digestive enzymes for conjugation to exopolysaccharide-associated proteins include, but are not limited to, digestive lipases (e.g., lingual lipase, pancreatic lipase, phospholipase), amylases, cellulases, lysozyme, proteases (e.g., pepsin, trypsin, chymotrypsin, carboxypeptidase, elastase.), esterases (e.g. sterol esterase), disaccharidases (e.g., sucrase, lactase, beta-galactosidase, maltase, isomaltase), DNases, and RNases. Enzymes that are particularly suitable as heterologous molecules in some embodiments of this disclosure are enzymes expressed throughout the lining of the small intestine, which are also referred to sometimes as "brush border enzymes." This brush border enzymes include, but are not limited to the disaccharidases listed above. Other suitable digestive enzymes that can be used according to some aspects of the instant disclosure will be apparent to those of skill in the art and the disclosure is not limited in this respect.

Engineered exopolysaccharide-associated proteins comprising a therapeutic enzyme as the heterologous molecule are useful for various therapeutic applications. For example, such engineered proteins allow the targeted delivery of digestive enzymes to specific target sites within the gastrointestinal tract. For example, an engineered exopolysaccharide-associated protein comprising an exopolysaccharide-associated protein that binds to the biofilm matrix in the small intestine may be conjugated to a digestive enzyme catalyzing a digestive reaction taking place in the small intestine. The engineered protein, or a bacterium expressing the engineer protein, may then be administered to a subject having a deficiency in the respective digestive enzyme. For example, a bacterium expressing a fusion protein of exopolysaccharide associated protein and the digestive enzyme lactase may be administered to a subject with a lactose intolerance to improve lactose digestion and the small intestine.

Importantly, this disclosure is not limited to embodiments of enzyme replacement, but the technology disclosed herein can also be used to transfer entirely new functionalities to biofilms, for example biofilms within the gastrointestinal tract. For example, engineered exopolysaccharide-associated proteins comprising a digestive enzyme not naturally occurring in the intestinal tract of a subject, for example, cellulase, maybe deliberate to the gastrointestinal tract of the subject to enable the subject to digest a previously unknown digestible food source, in this case, cellulose. In an exemplary embodiment, a human subject may be administered a bacterium that can colonize the gastrointestinal tract of the subject, and that expresses an engineered exopolysaccharide-associated protein fused to a cellulase. Upon colonization of the gastrointestinal tract of the subject with the engineered bacteria, the subject will be able to digest cellulose. In preferred embodiments, the bacterium and/or the exopolysaccharide-associated protein are present, and their non-modified form, in the intestinal tract of the subject.

In some embodiments, the heterologous molecule comprises an enzyme that can digest an environmental pollutant. Engineered exopolysaccharide-associated proteins comprising such enzymes allow for the generation of engineered bacteria and biofilms that can help in the cleanup of environmental pollutants. For example, in some embodiments, the heterologous molecule comprises an enzyme that can digest mineral oil contaminations in the environment, for example, in the form of an oil spill into the ocean. Such enzymes include, for example, alkane 1-monooxygenase, naphthalene 1,2-dioxygenase, E-phenylitaconyl-CoA hydratase, benzylsuccinyl-CoA dehydrogenase, methane monooxygenase. In some embodiments, the heterologous molecule comprises an enzyme that protects a bacterium from detrimental effects of an environmental pollutant, or that catalyzes a reaction that increases the capability of a bacterium to break down an environmental pollutant. Such enzymes may include, in some embodiments, enzymes that catalyze sulfite, phosphorus, or iron reduction, or enzymes that confer metal resistance to a bacterium. Such enzymes include, without limitation, sulfite reductases, exopolyphosphatases, and metal reductases. The structure and sequence of many enzymes that can digest or help in the digestion of environmental pollutants, or confer protection against environmental pollutants, are well known to those of skill in the art. Such enzymes include, for example, those described in Hazen et al., *Deep-sea oil plume enriches indigenous oil-degrading bacteria*. Science. 2010 Oct. 8; 330(6001):204-8, including supplemental content (see, e.g., Table S6 of Hazen et al.); Lu et al., *Microbial gene functions enriched in the Deepwater Horizon deep-sea oil plume*. ISME J. 2012 February; 6(2):451-60; Kostka et al., *Hydrocarbon-degrading bacteria and the bacterial community response in gulf of Mexico beach sands impacted by the deepwater horizon oil spill*. Appl Environ Microbiol. 2011 November; 77(22): 7962-74; and Wood et al., *Engineering biofilm formation and dispersal*. Trends Biotechnol. 2011 February; 29(2):87-94: the entire contents of each of which are incorporated herein by reference.

In some embodiments, the heterologous molecule comprises a binding agent. Engineered exopolysaccharide-associated proteins comprising a binding agent are useful for the generation of bacteria and biofilms that exhibits novel or improved binding capabilities. In some embodiments, In some embodiments, this allows for the specific delivery of bacteria or biofilms to a target site of interest, which may be, for example an abiotic surface, such as the surface of a bioreactor, a solid support, a liquid-gas interface, the surface of an environmental pollutant, a biotic surface, e.g., the surface of a living cell or tissue, for example, of a cell or tissue exhibiting a structural or functional deficiency, or a diseased cell or tissue, or a specific region within the gastrointestinal tract. Suitable binding agents are well known to those of skill in the art, and include, but are not limited to, antibodies and antibody fragments. For the preparation of fusion proteins comprising an exopolysaccharide-associated protein and a binding agent specifically binding to antigen, single chain antibodies, such as nanobodies and scFvs are particularly useful. In some embodiments, the binding agent is an adnectin, a lectin, a ligand, or an affinity tag. In embodiments, where an engineered bacterium or an engineered by of time is to be targeted to a specific target site, the binding agent is chosen to bind a molecule or moiety present at the target site. Accordingly, the nature and specificity of the binding agent will depend on the nature and structural characteristics of the target site. For example, in embodiments where an engineered bacterium expressing the fusion protein comprising an exopolysaccharide-associated protein and an antigen-binding antibody fragment is to be delivered to a specific cell or tissue, the binding agent will be chosen to bind an antigen expressed on the surface of the respective cell or tissue.

In some embodiments, the heterologous molecule comprises a detection agent. The generation of engineered exopolysaccharide-associated proteins comprising a detection agent is useful for the detection of engineered bacteria or engineered biofilms expressing such an engineered protein. While any detection agent that can be conjugated to an exopolysaccharide-associated protein, or an exopolysaccharide-binding fragment thereof, is suitable, the use of detectable proteins, e.g., a fluorescent proteins, allows for the generation of fusion proteins comprising an exopolysaccharide-associated protein, or fragment thereof and the detectable protein. The use of detection agents, such as fluorescent proteins or affinity tags, is preferable in some embodiments, because the respective fusion proteins with exopolysaccharide-associated proteins or fragments thereof can easily be expressed in a host cell, e.g., a bacterial cell.

In some embodiments, the compositions further comprises a signal peptide fused to the exopolysaccharide-associated protein, or exopolysaccharide-binding fragment thereof, or to the heterologous molecule, wherein the signal peptide targets the exopolysaccharide-associated protein, or exopolysaccharide-binding fragment thereof, conjugated to the heterologous molecule for secretion. In some embodiments, the exopolysaccharide-associated protein or fragment thereof that is conjugated to the heterologous molecule comprises an endogenous signal peptide that is retained in the engineered protein, e.g., an engineered fusion protein comprising the respective exopolysaccharide-associated protein or fragment thereof fused to a heterologous protein. In particular, secreted exopolysaccharide-associated proteins comprise such signal peptides in their native sequences. In other embodiments, a heterologous signal peptide is fused to the engineered exopolysaccharide-associated protein, for example, at the N-terminus of the respective fusion protein. Suitable signal peptide sequences for expression of secreted proteins in bacteria are well known to those of skill in the art. Some exemplary signal peptides are described herein, and additional suitable signal peptide will be apparent to the skilled artisan based on the instant disclosure. The disclosure is not limited in this respect. Exemplary fusion proteins according to some aspects of this disclosure comprise a structure according to the general formula [signal peptide]–[exopolysaccharide-associated protein (or fragment)]–[heterologous molecule], wherein the hyphens represent a peptide bond or a linker. Methods and strategies for preparing such fusion proteins will be apparent to those of skill in the art in view of this disclosure, and exemplary suitable strategies for generating such fusion proteins are described in Absalon et al., The Bacterial Biofilm Matrix as a Platform for Protein Delivery. mBio 3(4): e00127-12, the entire contents of which are incorporated herein by reference.

Engineered Bacteria and Biofilms

Some aspects of this disclosure provide bacteria and biofilms comprising, or associated with, engineered exopolysaccharide-associated proteins. Some aspects of this disclosure provide a composition comprising a bacterium associated with an exopolysaccharide; an exopolysaccharide-associated protein, or an exopolysaccharide-binding fragment thereof; and a heterologous molecule conjugated to the exopolysaccharide-associated protein, or an exopolysaccharide-binding fragment thereof. For example, some aspects of this disclosure provide a bacterium associated with an exopolysaccharide, wherein the bacterium expresses or is associated with an engineered exopolysaccharide-associated protein, e.g., an exopolysaccharide-associated protein or an exopolysaccharide-binding fragment thereof conjugated to a heterologous molecule. In some embodiments, the bacterium expresses the engineered exopolysaccharide-associated protein, for example, from an expression construct encoding the engineered protein that is comprised within the bacterium, e.g., in the form of an expression vector, such as a plasmid. In some embodiments, a bacterium may be contacted with an isolated engineered exopolysaccharide-associated protein under conditions suitable for the protein to associate with the bacterium. In some embodiments, it is advantageous to express the engineered exopolysaccharide-associated protein from an expression vector within the bacterium, because this allows for constant or inducible production of the engineered exopolysaccharide-associated protein, which, in turn, circumvents the need for exogenous replacement of protein over time. This is particularly useful in embodiments where a bacterium is used to deliver a heterologous protein to a target site, e.g., to deliver a digestive enzyme to a cell, tissue, organ, or environmental target site. In such cases, a bacterium expressing the engineered exopolysaccharide-associated protein can, once at the target site, proliferate and replenish the engineered exopolysaccharide-associated protein, either continually or upon exposure to a molecular or environmental cue.

In some embodiments, an engineered exopolysaccharide-associated protein or exopolysaccharide-associated protein fragment described herein is expressed in a bacterium, for example, by contacting the bacterium with an expression construct encoding the engineered exopolysaccharide-associated protein or exopolysaccharide-associated protein fragment. Expression of such engineered proteins in bacteria will confer the engineered characteristics, e.g., engineered structural or functional characteristics, to the expressing bacteria. For example, if an engineered exopolysaccharide-associated protein or protein fragment comprising a fusion protein of an exopolysaccharide-associated protein and a digestive enzyme, e.g., lactase, is expressed in a bacterium, the bacterium will retain the fusion protein on its surface, and thus display lactase functionality. In some embodiments, the expression of an engineered exopolysaccharide-associated protein in a bacterium confers a structural or functional characteristic upon the bacterium that was not natively present in the bacterium, e.g., in the case of expression of the lactase-comprising fusion protein described above in a lactase-deficient bacterium. If such a bacterium can ferment the products of lactase digestion, the acquisition of lactase functionality will result in the bacterium being able to utilize lactose as a food source. Similarly, if the bacterium colonizes a site together with other bacteria that can ferment the products of lactase digestion, but cannot ferment lactose, the bacterial community can now utilize lactose as a food source. The same principle applies to other digestive enzymes, e.g., cellulases, amylases, disaccharidases, oil-degrading enzymes, and so forth.

The engineered exopolysaccharide-associated protein expressed by or contacted with the bacteria can be any engineered exopolysaccharide-associated protein provided herein, e.g., an engineered exopolysaccharide-associated protein comprising a heterologous protein, enzyme, antigen, binding agent, detection agent, small molecule, and so forth: an engineered exopolysaccharide-associated protein comprising an exopolysaccharide-associated protein or exopolysaccharide-binding fragment thereof, as described herein, e.g., as described in Table 1 or 2.

In some embodiments, the engineered bacterium can be any bacterium that can express an engineered exopolysaccharide-associated protein is suitable for use according to some aspects of this disclosure. In some embodiments, the bacterium is In some embodiments, the bacterium is a gram-negative bacterium. In some embodiments, the bacterium is a gram-positive bacterium. Gram-positive and gram-negative bacteria are well known to those of skill in the art. In addition, whether or not a bacterium is gram-positive or gram-negative can easily be determined without more than routine experimentation, e.g., by performing a routine gram staining procedure. In some embodiments, the bacterium is a non-pathogenic bacterium. The use of non-pathogenic bacteria is particularly useful in embodiments that include the delivery of a therapeutic heterologous molecule to a subject, and also in embodiments related to bioremediation, e.g., in embodiments that involve the cleanup of an environmental pollutant. In some embodiments, the bacterium is a pathogenic bacterium. The use of pathogenic bacteria is of particular use in some embodiments that involve or are related to the induction of an immune response, e.g., in embodiments involving the generation of a vaccine or a vaccination of a subject. Non-pathogenic and pathogenic bacteria are well known to those of skill in the art. Exemplary, non-limiting bacterial taxa, species, and strains, suitable for use in some embodiments of this disclosure, e.g., suitable for contacting with or for expression of an engineered exopolysaccharide-associated protein disclosed herein, are provided herein and include, without limitation, *Escherichia* sp., *Enterobacter* sp. (e.g., *Enterobacter cloacae*), *Salmonella* sp. (e.g., *Salmonella enteritidis, Salmonella typhi*), *Shigella* sp., *Pseudomonas* sp. (e.g., *Pseudomonas aeruginosa, Pseudomonas pachastrellae, Pseudomonas stulzeri*), *Moraxella* sp. (e.g., *Moraxella catarrhalis*), *Neisseria* sp. (e.g., *Neisseria gonorrhoeae Neisseria meningitidis*), *Helicobacter* sp., (e.g., *Helicobacter pylori*) *Stenotrophomonas* sp., *Vibrio* sp. (e.g., *Vibrio cholerae*), *Legionella* sp. (*Legionella pneumophila*), *Hemophilus* sp. (e.g., *Hemophilus influenzae*), *Klebsiella* sp. (e.g., *Klebsiella pneumoniae*), *Proteus* sp. (e.g., *Proteus mirabilis*), *Serratia* sp. (*Serratia marcescens*), *Streptococcus* sp., *Staphylococcus* sp., *Corynebacterium* sp., *Listeria* sp., and *Clostridium* sp., *Bacillus* sp. (e.g., *Bacillus anthracis*) *Bordetella* sp. (e.g., *Bordetella pertussis*); *Borrelia* sp. (e.g., *Borrelia burgdorferi*); *Brucella* sp. (e.g., *Brucella abortus, Brucella cants, Brucella melitensis, Brucella suis*); *Campylobacter* sp. (e.g., *Campylobacter jejuni*); *Chlamydia* sp. and *Chlamydophila* sp. (e.g., *Chlamydia pneumoniae, Chlamydia trachomatis, Chlamydophila psittaci*); *Clostridium* sp. (e.g., *Clostridium botulinum, Clostridium difficile, Clostridium perfringens, Clostridium tetani*); *Corynebacterium* sp. (e.g., *Corynebacterium diphtheriae*): *Enterococcus* sp. (e.g., *Enterococcus faecalis, Enterococcus faecium*); *Escherichia* sp. (e.g., *Escherichia coli*, Enterotoxic *E. coli*, enteropathogenic *E. coli; E. coli* O157:H7); *Francisella* sp. (e.g., *Francisella tularensis*); *Haemophilus* sp. (e.g., *Haemophilus influenzae*); *Helicobacter* sp. (e.g., *Helicobacter pylori*); *Legionella* sp. (e.g., *Legionella pneumophila*); *Leptospira* sp. (e.g., *Leptospira interrogans*); *Listeria* sp. (e.g., *Listeria monocytogenes*); *Mycobacterium* sp. (e.g., *Mycobacterium leprae, Mycobacterium tuberculosis, Mycobacterium ulcerans*); *Mycoplasma* sp. (e.g., *Mycoplasma pneumoniae*); *Neisseria* sp. (e.g., *Neisseria gonorrhoeae, Neisseria meningitidis*); *Pseudomonas* sp. (e.g., *Pseudomonas aeruginosa*); *Rickettsia* sp. (e.g., *Rickettsia rickettsii*); *Salmonella* sp. (e.g., *Salmonella typhi, Salmonella typhimurium*); *Shigella* sp. (e.g., *Shigella sonnei*); *Staphylococcus* sp. (e.g., *Staphylococcus aureus, Staphylococcus epidermidis, Staphylococcus saprophyticus*): *Streptococcus* sp. (e.g., *Streptococcus agalactiae, Streptococcus pneumoniae, Streptococcus pyogenes*); *Treponema* sp. (e.g., *Treponema pallidum*); *Pseudodiomarina* sp. (e.g., *P. maritima*): *Marinobacter* sp. (e.g., *Marinobacter hydrocarbonoclasticus, Marinobacter vinifirmus*) *Alcanivorax* sp. (e.g., *alcanivorax dieselolei*); *Acetinobacter* sp. (e.g., *A. venetianus*): *Halomonas* sp. (e.g., *H. shengliensis*): *Labrenzia* sp.; *Microbulifer* sp. (e.g., *M. schleiferi*); *Shewanella* sp. (e.g., *S. algae*): *Vibrio* sp. (e.g., *Vibrio cholerae, Vibrio alginolyticus, Vibrio hepatarius*); and *Yersinia* sp. (e.g., *Yersinia pestis*). In some embodiments, the bacterium is a *Vibrio* sp. bacterium. In some embodiments, the bacterium is a *Vibrio cholerae* bacterium. In some embodiments, the bacterium is an *E. coli* bacterium. Other bacterial taxa and strains that are suitable in embodiments of this disclosure will be apparent to those of skill in the art.

Some aspects of this disclosure provide a bacterial biofilm comprising an engineered bacterium as described herein, for example, a bacterium associated with an exopolysaccharide that is bound by an exopolysaccharide-associated protein (or an exopolysaccharide-binding fragment thereof) conjugated to a heterologous molecule. Depending on the structure and function of the heterologous molecule, such engineered biofilms exhibit novel functional or structural characteristics as compared to the native, non-engineered biofilms.

For example, if the heterologous molecule comprises a binding agent and is conjugated to an exopolysaccharide-associated protein, or exopolysaccharide-binding fragment thereof that is expressed at the surface of the biofilm, the biofilm can bind to a molecule or surface comprising a moiety bound by the binding agent. This allows the engineering of bacterial biofilms to bind to, e.g., surfaces that the respective native biofilm cannot or does not bind to. For another example, if the heterologous molecule comprises a an enzyme and is conjugated to an exopolysaccharide-associated protein, or exopolysaccharide-binding fragment thereof that is expressed at the surface of the biofilm, the biofilm will be able to digest the substrate of the enzyme, e.g., a substrate that was previously inaccessible to the bacteria within the biofilm, or an environmental pollutant.

In some embodiments, an engineered biofilm comprises a combination of engineered exopolysaccharide-associated proteins, e.g., an engineered protein in which the heterologous molecule is a binding agent and an engineered protein in which the heterologous molecule is an enzyme, allowing targeted delivery of the enzyme to a surface bound by the binding agent. In some embodiments, the biofilm comprises a detection agent, e.g., as part of an engineered exopolysaccharide-associated protein expressed by bacteria comprised in the biofilm. This allows the engineering of bacterial biofilms that can be detected, e.g., when bound to a surface, for example, if the detection agent is a fluorescent agent, by fluorescent imaging.

Vaccines

Some aspects of this disclosure provide that engineered exopolysaccharide-associated proteins, as provided herein, are useful for the generation of vaccines. A vaccine typically comprises an agent that mimics or comprises an antigen of a pathogen and, when administered to the subject, and uses an immune response in the subject. When subsequently exposed to the real pathogen, the subject's vaccine-primed immune system is able to recognize and destroy the pathogen with increased efficiency as compared to the immune system of a non-vaccinated subject.

Some aspects of this disclosure provide vaccines that comprise engineered exopolysaccharide-associated proteins that are conjugated to an antigen. In some embodiments, this disclosure provides vaccines that comprise a bacterium associated with an exopolysaccharide, an exopolysaccharide-associated protein, or an exopolysaccharide-binding fragment thereof, that binds the exopolysaccharide; and an antigen conjugated to the exopolysaccharide-associated protein, or an exopolysaccharide-binding fragment thereof. In some such embodiments, the bacterium expresses the engineered exopolysaccharide-associated protein. In some embodiments, the vaccines provided herein are advantageous over currently available vaccines, in that they are easier and cheaper to produce, particularly in a resource-poor setting.

For example, one licensed cholera vaccine comprises killed whole *V. cholerae* bacterial cells combined with the purified B subunit of cholera toxin (CtxB), which serves as both an antigen and an adjuvant [7]. While the purified CtxB component improves short term protection, its production and isolation is cost-intensive, and the use of isolated CtxB negatively affects ease of delivery of the vaccine. As a result, cholera vaccines manufactured in resource-poor settings typically omit this component [8,9], resulting in less-than-optimal vaccinations.

Some aspects of this disclosure provide an engineered vaccine, for example, an engineered *V. cholerae* vaccine, in which an engineered exopolysaccharide-associated protein conjugated to an antigen or adjuvant is expressed in a bacterial cell, resulting in a decoration of the bacterial cell's exopolysaccharide with the antigen or adjuvant. In some such embodiments, the bacterium comprises a recombinant nucleic acid encoding the engineered exopolysaccharide-associated protein conjugated to the antigen or adjuvant.

For example, in some embodiments, a *V. cholerae* vaccine is provided that comprises a bacterium, for example, a *Vibrio* sp. bacterium (e.g., *V. cholerae*) that expresses an engineered exopolysaccharide-associated protein, e.g., an isolated *V. cholerae* exopolysaccharide-associated protein (e.g., Bap1I, RbmA, RbmC, or HlyA), or an exopolysaccharide-binding fragment thereof, conjugated to an antigen or adjuvant, e.g., *V cholerae* CtxB. One advantage of this type of vaccine over conventional vaccines is its ease of production. Instead of having to grow the bacteria and, separately, having to produce the antigen and/or adjuvant, the bacteria in this type of vaccine express the antigen and/or adjuvant, display it on their surface, and retain it based on the conjugation of the antigen and/or adjuvant to the exopolysaccharide-associated protein. In some embodiments, the antigen and/or adjuvant is a protein or polypeptide that is expressed as a fusion protein with the exopolysaccharide-associated protein, or exopolysaccharide-binding fragment thereof.

As described in more detail in the Examples section, expression of an engineered exopolysaccharide-associated protein comprising CtxB (the B subunit of cholera toxin) as the heterologous agent in *V. cholerae* resulted in a decoration of the bacterial cell's biofilm exopolysaccharide scaffold with CtxB. This integrated decoration avoids the need for a separate production and isolation of CtxB, and could greatly simplify the production and administration of a vaccine including CtxB and also potentially improve vaccine efficacy. In the a proof of principle experiment, wild-type *V. cholerae* was engineered to express an engineered exopolysaccharide-associated protein comprising RbmA with either the CtxB subunit or a FLAG affinity tag fused to its C-terminus. Biofilms were formed with these strains and the RbmA-CtxB fusion protein was observed to be sequestered to the biofilm matrix.

In some embodiments, a vaccine is provided that comprises a bacterium that is not genetically engineered, e.g., wild-type bacterium such as a wild-type *Vibrio* sp. bacterium (e.g., a wild-type *V. cholerae* bacterium), but that is contacted with an isolated engineered exopolysaccharide-associated protein conjugated to an antigen and/or adjuvant, e.g., an isolated *V. cholerae* exopolysaccharide-associated protein (e.g., Bap1, RbmA, RbmC, or HlyA), or an exopolysaccharide-binding fragment thereof, that is conjugated to an antigen or adjuvant, e.g., *V. cholerae* CtxB. In some such embodiments, the engineered exopolysaccharide-associated protein conjugated to the antigen and/or adjuvant can be contacted or combined with the bacterium in a biofilm, and will associate with the exopolysaccharide scaffold of the biofilm. The biofilm can then be dispersed and used for the production of a vaccine. Alternatively, the engineered exopolysaccharide-associated protein conjugated to the antigen and/or adjuvant can be contacted or combined with the bacterium in planktonic form, and will associate with the surface of the bacterium based on the expression of exopolysaccharides on the surface of the bacterium.

The vaccines provided herein, comprising an exopolysaccharide-associated protein, or exopolysaccharide-binding fragment thereof, conjugated to an antigen and/or adjuvant can be produced according to methods of vaccine production known to those of skill in the art. In some embodiments, the bacterium is killed or attenuated, while in other embodiments, the bacterium is alive and/or not attenuated. In some embodiments, the vaccine comprises a pathogenic bacterium, for example, the pathogenic bacterium described herein. In some embodiments, the vaccine comprises a nonpathogenic bacterium, for example a nonpathogenic bacterium as described herein.

In some embodiments, the vaccine comprises a pathogenic bacterium, e.g., a pathogenic *Vibrio* sp. bacterium, such as *Vibrio cholerae* or *Vibrio haemolyticus*, and an engineered exopolysaccharide associated protein comprising an antigen expressed by the pathogenic bacterium as the heterologous molecule. In some embodiments, the vaccine comprises a nonpathogenic bacterium and engineered exopolysaccharide-associated protein comprising an antigen expressed by a pathogenic bacterium as the heterologous molecule. For example, in some embodiments, the vaccine comprises a nonpathogenic *Vibrio* sp. strain, such as *Vibrio alginolyticus, Vibrio harveyi, Vibrio anguillarum*, or *Vibrio fluvialis*, and an engineered exopolysaccharide associated protein comprising an antigen expressed by a pathogenic bacterium, e.g., *Vibrio cholerae* or *Vibrio haemolyticus*, as the heterologous molecule. In some embodiments, the antigen expressed by a pathogenic bacterium is *Vibrio cholerae* CtxB. In some embodiments, the pathogenic bacterium in the vaccine of this disclosure, e.g., a pathogenic *Vibrio* sp. bacterium, such as *Vibrio cholerae* or *Vibrio haemolyticus*, may be genetically modified. In some embodiments, the genetically modified pathogenic bacterium has reduced pathogenicity, i.e., is attenuated. In some embodiments, the genetically modified pathogenic bacterium is a *Vibrio Cholerae* with inactivated CtxA. In some embodiments, the CtxA gene is deleted from the *Vibrio Cholerae* genome (ΔctxA strain). Such ΔctxA strain may be used in the live attenuated vaccines of this disclosure.

In some embodiments, the exopolysaccharide-associated protein, or exopolysaccharide-binding fragment thereof, is fused to the antigen and/or adjuvant, thus forming a fusion protein. In some embodiments, the fusion protein is expressed by the bacterium, e.g., from a recombinant nucleic acid construct. In some embodiments, the exopolysaccharide-associated protein, or exopolysaccharide-binding fragment thereof that is conjugated to the antigen and/or adjuvant comprises a β-prism lectin domain and/or an FG-GAP domain. For example, in some embodiments, the exopolysaccharide-associated protein, or exopolysaccharide-binding fragment thereof that is conjugated to the antigen and/or adjuvant comprises a D-prism lectin domain flanked on one or both sides by an FG-GAP domain, and/or an FG-GAP domain flanked on one or both sides by a β-prism lectin domain. In some embodiments, the exopolysaccharide-associated protein is Bap1 (SEQ ID NO: 1), RbmA (SEQ ID NO: 2), RbmC (SEQ ID NO:3), or HlyA (SEQ ID NO: 4).

In some embodiments, the vaccine further comprises an adjuvant that is not comprised in the engineered exopolysaccharide-associated protein. Suitable adjuvants are known to those of skill in the art, include, without limitation, any adjuvants that are in use for vaccines known in the art. Exemplary suitable adjuvants include, without limitation, inorganic adjuvants, such as aluminium salts or gels (e.g., aluminium phosphate, aluminium hydroxide), alum, organic adjuvants, such as squalene (e.g., ASO₃), QS21, oil-based adjuvants (e.g., MF95), and virosomes (e.g., containing a membrane-bound hemagglutinin and neuraminidase derived from an influenza virus). Other adjuvants that are useful according to some aspects of this disclosure include imidazoquinoline amines, imidazopyridine amines, 6,7-fused cycloalkylimidazopyridine amines, 1,2-bridged imidazoquinoline amines, imiquimod and resiquimod, dsRNA, poly I:C, bacterial lipopolysacharide (LPS), VSV-G, and HMGB-1. Some aspects of this disclosure provide vaccines that comprise engineered exopolysaccharide-associated proteins that are conjugated to an antigen and that also comprise an adjuvant. Some aspects of this disclosure provide vaccines that comprise engineered exopolysaccharide-associated proteins that are conjugated to an adjuvant. Some aspects of this disclosure provide vaccines that comprise engineered exopolysaccharide-associated proteins that are conjugated to an antigen and an adjuvant. For example, in some embodiments, a vaccine is provided that comprises a fusion protein of the general structure [exopolysaccharide-associated protein (or fragment thereof)]-[antigen] and an adjuvant. In some embodiments, a vaccine is provided that comprises a fusion protein of the general structure [exopolysaccharide-associated protein (or fragment thereof)]-[antigen]-[adjuvant] or [exopolysaccharide-associated protein (or fragment thereof)]-[adjuvant]-[antigen]. In some embodiments, a composition, e.g., a vaccine, is provided that comprises a fusion protein of the general structure [exopolysaccharide-associated protein (or fragment thereof)]-[adjuvant]. In some embodiments, the adjuvant comprises a peptide. For example, in some embodiments, the adjuvant comprises a cholera toxin B peptide, or a fragment thereof. In some embodiments, the adjuvant comprises a host defense peptide, e.g., a host defense peptide or other immunostimulatory sequence as described in U.S. Patent Application Publication U.S. Pat. No. 2,010,023%11, entitled *Combination Adjuvant Formulation*, published on Sep. 23, 2010, or in Hancock et al., *Synthetic peptides as antigens for antibody production*. Methods Mol Biol. 2005:295:13-26: the entire contents of each of which are incorporated herein by reference. Exemplary suitable peptide adjuvants include, without limitation, ILPWKWPWWPWRR (SEQ ID NO: 13); VFLRRIRVIVIR (SEQ ID NO: 14): VFWRRIRVWVIR (SEQ ID NO: 15); VQLRAIRVRVIR (SEQ ID NO: 16): VQLRRIRVWVIR (SEQ ID NO: 17); VQWRAIRVRVIR (SEQ ID NO: 18): VQWRRIRVWVIR (SEQ ID NO: 19); GRFKR-FRKKFKKLFKKLSPVIPLLHLG (SEQ ID NO: 20); GGLRSLGRKILRAWKKYGPIIVPIIRIG (SEQ ID NO: 21): RLARIVVIRVAR LLGDFFRK-SKEKIGKEFKRIVQRIKDFLRNLVPRTES (SEQ ID NO: 22); VQLRIRVAVIRA (SEQ ID NO: 23); VQRWLIV-WRIRK (SEQ ID NO: 24): VRLIVAVRIWRR (SEQ ID NO: 25); IWVIWRR (SEQ ID NO: 26); I(Dhb)AI(Dha)LA(Abu)PGAK(Abu)GALMGANMK(Abu)A(Abu)ANAS-INV(Dha)L (SEQ ID NO: 27, Dhb: dehydrobutyrine, Dha: dehydroalanine, Abu: 2-aminobutyric acid): VXXRXIRVX-VIR (SEQ ID NO: 28); ILKWKWPWWPWRR (SEQ ID NO: 29): ILPWKKPWWPWRR (SEQ ID NO: 30); ILKWKWPWWKWRR (SEQ ID NO: 31); and ILRWKWRWWRWRR (SEQ ID NO: 32). For example, an exemplary fusion protein may comprise a structure as follows: [RbmA]-[CtxB]-[ILPWKWPWWPWRR (SEQ ID NO: 33)] or [RbmC]-[ILKWKWPWWPWRR (SEQ ID NO: 34)]. These two examples are merely to illustrate possible structures of fusion proteins provided herein, but are not limiting, as additional suitable combinations of exopolysaccharide-associated proteins or exopolysaccharide-binding fragments thereof with antigens and/or peptide adjuvants as provided herein will be apparent to those of skill in the art based on the instant disclosure.

In some embodiments, the adjuvant is a cholera toxin subunit A (CtxA) variant. The use of cholera toxin subunit A variants as vaccine adjuvants to harness their immunomodulating properties have been described in the art, e.g., in PCT publications WO2004083251 and WO2015004105, the entire contents of which are herein incorporated by reference. Wild-type CtxA amino acid sequence is provided as SEQ ID NO: 46. CtxA variants that have reduced activity are particular suitable for use as adjuvants. For example, CtxA variants comprising substitution mutations between amino acids corresponding to 189-211 in SEQ ID NO: 46 have significantly reduced activity, e.g., reduced by at least 2-100 fold. For example, the CtxA variant's activity may have been reduced by at least 2 fold, at least 3 fold, at least 4 fold, at least 5 fold, at least 10 fold, at least 20 fold, at least 30 fold, at least 40 fold, at least 50 fold, at least 60 fold, at least 70 fold, at least 80 fold, at least 90 fold, at least 100 fold, or more. Suitable mutations include mutations in positions correspond to N189, A190, P191, R192, S193, S194, M195, S196, N197, T 198, C199, D200, or L211 of SEQ ID NO: 46. In some embodiments, the mutations correspond to N189D, A190S, P191S, R192G, S193T, S1941, M195T, S196G, N1971, N197D, or L211A in SEQ ID NO: 46. The exemplary mutations are not meant to be limiting. Any CtxA variants that are known in the art to be suitable for use as an adjuvant may be used herein.

```
Cholera toxin subunit A (CtxA)
                                      (SEQ ID NO: 46)
NDDKLYRADSRPPDEIKQSGGLMPRGQSEYFDRGTQMNINLYDHARGTQT

GFVRHDDGYVSTSISLRSAHLVGQTILSGHSTYYIYVIATAPNMFNVNDV

LGAYSPHPDEQEVSALGGIPYSQIYGWYRVHFGVLDEQLHRNRGYRDRYY

SNLDIAPAADGYGLAGFPPEHRAWREEPWIHHAPPGCGNAPRSSMSNTCD

EKTQSLGVKFLDEYQSKVKRQIFSGYQSDIDTHNRIKDEL
```

In some embodiments, the CtxA variant adjuvant is encoded by a nucleic acid molecule and expressed in the bacterium in the vaccine of this this disclosure. In some embodiments, the CtxA variant adjuvant is constitutively expressed by the bacterium of the vaccine. In some embodiments, the CtxA variant adjuvant is added to the vaccine after it is made.

In some embodiments, the adjuvant is a multiple-mutated Cholera toxin (mmCT). The mmCT adjuvant has been described in the art, e.g., in Lebens et al., Vaccine. 2016 Apr. 19; 34(18):2121-8, incorporated herein by reference. In some embodiments, the mmCT adjuvant is produced by the bacterium associated with RmbA and the antigen (e.g., the LTB-STa$^{A14H}$ antigen). For example, the nucleotide sequence encoding the mmCT gene may be delivered to the bacterium, e.g., by any known methods of delivering nucleic acids to bacterial cells such as transformation. In some embodiments, the nucleotide sequence encoding the mmCT adjuvant may be integrated into the genome of the bacteria. In some embodiments, the nucleotide sequence encoding the mmCT adjuvant is placed under control of the LacZ promoter.

In some embodiments, the vaccine is formulated into a pharmaceutical composition for administration (e.g., orally, sublingually, intramuscularly, intradermally, or rectally) to a subject. In some embodiments, the vaccine is administered to a subject. Accordingly, some embodiments provide a method of vaccinating a subject against a pathogen. Typically, the method comprises administering to the subject an effective amount of a vaccine described herein. An effective amount, in some embodiments, is an amount that induces an immune reaction in the subject. For example, in some embodiments, an effective amount of a vaccine is an amount that, when administered to a subject, results in a measurable increase in immunity of the subject against a pathogen expressing an antigen comprised in the vaccine. In some embodiments, an effective amount of a vaccine is an amount that, when administered to a subject, results in a measurable immune response in the subject against a pathogen expressing an antigen comprised in the vaccine. For example, a measurable immune response may include an increased number or level of immunoglobulins (IgG and/or IgA) specifically binding the antigen, or an increased number of immune cells recognizing or producing antibodies directed towards the antigen. In some embodiments, the vaccine is administered in an amount sufficient to elicit an immune response against the bacterium and/or against the antigen. In some embodiments, the vaccine is administered in an amount sufficient to immunize the subject against the bacterium and/or against the antigen. While total immunization against the antigen may be desirable and feasible in some embodiment, partial immunization is also beneficial in many cases. For example, such partial immunization may ameliorate the clinical manifestation of an exposure to a pathogen, e.g., as evident in a shortened period of sickness or a decrease in the symptoms associated with the pathogen, as compared to an average subject within a population or to a non-vaccinated subject.

The inventive vaccines may be administered by a variety of routes of administration, including but not limited to parenteral (such as subcutaneous, intramuscular, intravenous, or intradermal); oral; transnasal, transmucosal, rectal; ophthalmic, or transdermal. The vaccines of this disclosure may induce systemic immune response or mucosal immune response. "Mucosal immune response," as used herein, refers the immune response elicited an organism's various mucous membranes upon invasion by potentially pathogenic microbes. Mucosal immune response provides three main functions: protecting the mucous membrane against infection; preventing the uptake of antigens, microorganisms, and other foreign materials; and moderating the organism's immune response to that material. At birth, the neonate's mucosal immune system is relatively undeveloped, but the colonization of intestinal flora accelerates its development. Because of its front-line status within the immune system, the mucosal immune system is being investigated for use in vaccines for various afflictions, including AIDS and allergies.

"Systemic immune response," as used herein, refers to the response elicited by the host's defense system, which may be categorized into two subsystems: the innate immune response and the adaptive immune response. The innate response is usually triggered when microbes are identified by pattern recognition receptors, which recognize components that are conserved among broad groups of microorganisms, or when damaged, injured or stressed cells send out alarm signals, many of which (but not all) are recognized by the same receptors as those that recognize pathogens. Innate immune defenses are non-specific, meaning these systems respond to pathogens in a generic way. This system does not confer long-lasting immunity against a pathogen. The innate immune system is the dominant system of host defense in most organisms. The adaptive immune response is antigen-specific and requires the recognition of specific "non-self" antigens during a process called antigen presentation. Antigen specificity allows for the generation of responses that are tailored to specific pathogens or pathogen-infected cells. The ability to mount these tailored responses is maintained in the body by "memory cells". Should a pathogen infect the body more than once, these specific memory cells are used to quickly eliminate it.

Since most enteric infections begin at mucosal surfaces, the first line of protection is likely provided by locally produced secretory IgA. Mucosal and systemic immune systems are, to a large extent, independent of one another. For example, monomeric IgA or polymeric IgA are produced independently by mucosal or systemic immune response, respectively. Adult levels of systemic IgA reach its maximum at adolescence, but younger children can respond well to exposure to bacterial and viral vaccines delivered mucosally. Thus, the vaccines of this disclosure may be particularly efficacious for young children, e.g., children before they reach adolescence. In some embodiments, the children may be 0-13 years of age. For example, the vaccines of this disclosure may be administered to children 0, 1, 2, 3, 4, 5, 6, 7, 8, 9, 10, 11, 12, or 13 years of age. In addition, the vaccines of this disclosure may also be administered to subjects more than 13 years of age, e.g., adolescents and adults.

Methods

Some aspects of this disclosure provide methods for delivering a molecule to a target site. In some embodiments, the method comprises delivering to the target site a bacterium associated with an exopolysaccharide that binds an exopolysaccharide-associated protein, or an exopolysaccharide-binding fragment thereof, wherein the exopolysaccharide-associated protein, or an exopolysaccharide-binding fragment thereof, binds the molecule. In some embodiments, the molecule is a heterologous molecule. In some embodiments, the molecule is conjugated to the exopolysaccharide-associated protein or the exopolysaccharide-binding fragment thereof, for example, via covalent bond or via non-covalent interaction. In some embodiments, the molecule is bound to the exopolysaccharide-associated protein, or the exopolysaccharide-binding fragment thereof, via a linker, for example via a linker comprising a sequence of immune acids that can be cleaved by a protease. In some embodiments, the molecule comprises a heterologous protein or polypeptide. In some embodiments, the polypeptide is fused to the exopolysaccharide-associated protein or the exopolysaccharide binding protein fragment. In some embodiments, the bacterium being delivered to the target site comprises a recombinant nucleic acid encoding the polypeptide fused to the exopolysaccharide-associated protein or the exopolysaccharide binding protein fragment.

In some embodiments, a method of delivering a protein of interest to a target site is disclosed herein can be used to deliver the protein to a target site that can be colonized by a bacterium expressing a fusion protein comprising the protein of interest and an exopolysaccharide-associated protein, or an exopolysaccharide-binding fragment thereof. In some embodiments, the protein of interest is a heterologous protein in relation to the exopolysaccharide-associated protein, or the exopolysaccharide-binding fragment thereof. In some embodiments, the heterologous protein comprises an antigen, an enzyme, a binding agent, a detection agent, a therapeutic agent, or an antibiotic agent. Any protein comprising an antigen, an enzyme, a binding agent, a detection agent, a therapeutic agent, or antibiotic agent described herein or otherwise known to those of skill in the art that can be fused to a exopolysaccharide-associated protein, or an exopolysaccharide-binding fragment thereof, can be delivered to a target site using the methods provided herein.

In some embodiments, the target site is a site within a subject that can be colonized by the bacterium. For example, in some embodiments, the target site is within the gastrointestinal tract, for example, within the stomach, the duodenum, the small intestine, the cecum, the appendix, or the colon, or within the oral cavity. In some embodiments, the target site is within the respiratory tract of the subject, for example, within the lung, within a primary bronchus, within a secondary bronchus, within a tertiary bronchus, within a bronchiole, within the trachea, or within the larynx. In some such embodiments, the method comprises administering to a subject a bacterium expressing a fusion protein comprising the protein of interest fused to an exopolysaccharide-associated protein or an exopolysaccharide-binding fragment thereof, in an amount sufficient for the bacterium to colonize the respective target site within the subject. In some embodiments, bacterial colonization of the target site refers to bacteria reaching the target site and proliferating and/or persisting at the target site for at least one day, at least two days, at least three days, at least four days, at least five days, at least six days, at least one week, at least two weeks, at least three weeks, at least four weeks, at least one month, at least two months, at least three months, at least four months, at least six months, at least one year, or at least two years.

For example, in some embodiments, a method is provided that comprises administering to a subject having a deficiency in and a digestive enzyme, for example, a lactase deficiency, a nonpathogenic bacterium that is able to colonize the gastrointestinal tract of the subject, for example, the small intestine, and that expresses a fusion protein comprising a digestive enzyme that the subject is deficient in, e.g., lactase, fused to an exopolysaccharide-associated protein or an exopolysaccharide-binding fragment thereof, in an amount sufficient for the bacterium to colonize the small intestines of the subject. In some embodiments, the bacterium is a bacterium that, in wild type form, colonizes the target site, for example the small intestine, of the subject, or is isolated from the target site, for example, from the small intestines, of the subject. In some embodiments, the subject is lactose intolerant, and the enzyme is lactase. In some embodiments, the subject has cystic fibrosis, and the enzyme is a pancreatic enzyme. In some embodiments, the bacterium is administered to the subject in the form of a probiotic. In some embodiments, administration route is oral or rectal.

In some embodiments, a method is provided that comprises administering to a subject having cystic fibrosis a nonpathogenic bacterium that is able to colonize the subject's respiratory tract, for example, the lung, the bronchi, the bronchioles, or the trachea, and that expresses a fusion protein comprising a mucus digesting enzyme, for example, a mucinase or alginase, fused to an exopolysaccharide-associated protein or an exopolysaccharide-binding fragment thereof, in an amount sufficient for the bacterium to colonize the respiratory tract of the subject. In some embodiments, the bacterium is a bacterium that, in wild type form, colonizes the respiratory tract, or part of the respiratory tract of the subject, or is a bacterium that is isolated from the pulmonary airway of a subject. In some embodiments, the bacterium is a nonpathogenic bacterium that can colonize the respiratory tract of a subject. In some embodiments, the bacterium is administered directly to the respiratory tract of the subject, e.g., via an aerosol or an inhalant. In some embodiments, the bacterium is of a nonpathogenic species that is found in the respiratory tract of a healthy subject, e.g., *Prevotella* sp., *Mesorhizobium* sp., *Microbacterium* sp., *Micrococcus* sp., *Veillonela* sp., *Rhizobium* sp., *Stenotrophomonas* sp., or *Lactococcus* sp. In some embodiments, the bacterium is a *Pseudomonas* sp. bacterium. In some embodiments, the bacterium is a nonpathogenic *Pseudomonas* bacterium, e.g., *Pseudomonas chlororaphis* or *Pseudomonas putida*.

In some embodiments, the target site is a surface. In some embodiments, the target site is an abiotic surface. In some embodiments, the surface is a liquid-gas interface, e.g., a water-air interface, or a culture media-air interface, for example, in a body of water, such as an ocean, a lake, or a pond, or in a bioreactor or culture vessel holding liquid media. In some embodiments, the target site is a liquid-solid interface, e.g., a water-soil interface, a water-metal interface, or a water-plastic interface. In some embodiments, the molecule to be delivered to the target site is an enzyme that can digest a substrate present at the target site. In some embodiments, the substrate is a contaminant that is present at the target site. For example, in some embodiments, the target site is a water-air interface and the substrate is an environmental pollutant, such as a toxic chemical or oil, for example, in the context of an oil spill. In some such embodiments, the enzyme expressed as a fusion protein with an exopolysaccharide-associated protein or exopolysaccharide-binding fragment thereof by a bacterium that forms a biofilm. The bacterium is then delivered to the target site, where it expresses the fusion protein and forms or integrates into a biofilm. The biofilm formed retains the fusion protein, and, thus, exhibits the functionality of the fusion protein, here an enzymatic activity directed towards the enzyme's substrate, e.g., a contaminant or an environmental pollutant.

Accordingly, the instantly disclosed technology can be used in the context of bioremediation, referring to the use of bacteria to remove, or aid in the removal of, pollutants from the environment. Engineered bacteria as provided herein can be delivered to sites of contamination and pollution and, through expression of an engineered exopolysaccharide-associated protein, e.g., a fusion protein comprising an enzyme that can break down the pollutant or contaminant.

In some embodiments related to bioremediation, the target site is an environmental surface. For example, in some embodiments, the target site is a polluted water-air interface, a polluted water-soil interface, or a polluted soil-air interface. In some embodiments, the molecule to be delivered to the target site is an enzyme that can break down a pollutant present at the target site. In some such embodiments, the enzyme is expressed as a fusion protein with an exopolysaccharide-associated protein or exopolysaccharide-binding fragment thereof by a bacterium that forms a biofilm. The bacterium is then delivered to the polluted target site, where it expresses the fusion protein and forms or integrates into a biofilm. The biofilm retains the fusion protein, and, thus, exhibits the functionality of the fusion protein, here an enzymatic activity that breaks down the pollutant.

For example, in some embodiments in the context of a marine oil spill, an engineered bacterium expressing an oil-degrading enzyme, e.g., an oil-degrading enzyme as described elsewhere herein, is delivered to the water-air interface of the contaminated body of water, where it proliferates and forms a biofilm expressing the oil-degrading enzyme functionality. Suitable enzymes that are useful in such embodiments include, without limitation, alkane 1-monooxygenase, naphthalene 1,2-dioxygenase, E-phenylitaconyl-CoA hydratase, benzylsuccinyl-CoA dehydrogenase, methane monooxygenase, and the enzymes described in Hazen et al., *Deep-sea oil plume enriches indigenous oil-degrading bacteria*. Science. 2010 Oct. 8; 330(6001):204-8, including supplemental content (see, e.g., Table S6 of Hazen et al.); Lu et al., *Microbial gene Junctions enriched in the Deepwater Horizon deep-sea oil plume*. ISME J. 2012 February; 6(2):451-60; Kostka et al., *Hydrocarbon-degrading bacteria and the bacterial community response in gulf of Mexico beach sands impacted by the deepwater horizon oil spill*. Appl Environ Microbiol. 2011 November; 77(22): 7962-74; and Wood et al., *Engineering biofilm formation and dispersal*. Trends Biotechnol. 2011 February; 29(2):87-94; the entire contents of each of which are incorporated herein by reference. Suitable bacterial genera and strains that are useful for expressing engineered exopolysaccharide-associated proteins as provided herein in the context of bioremediation scenarios, e.g., in the context of a marine oil spill, are known to those of skill in the art and include, without limitations, the bacterial taxa, genera, species, and strains described in Hazen et al., *Deep-sea oil plume enriches indigenous oil-degrading bacteria*. Science. 2010 Oct. 8:330(6001):204-8; Kostka et al., *Hydrocarbon-degrading bacteria and the bacterial community response in gulf of Mexico beach sands impacted by the deepwater horizon oil spill*. Appl Environ Microbiol. 2011 November; 77(22):7962-74; and Wood et al., *Engineering biofilm formation and dispersal*. Trends Biotechnol. 2011 February; 29(2):87-94: the entire contents of each of which are incorporated herein by reference. Additional suitable enzymes and bacterial genera will be apparent to those of skill in the art, and the disclosure is not limited in this respect.

In some embodiments related to bioremediation, or otherwise to the release of engineered bacteria into the environment, it is preferable that the bacteria also comprise a safeguard measure that prevents uncontrolled proliferation in the environment. For example, in some embodiments, the bacteria exhibit a dependency on a nutrient that does not exist or is extremely rare in the environment. This nutrient can be dispersed at the target site, e.g., at the water-air interface affected by a marine oil spill, to allow the bacteria to survive, proliferate, and form biofilms. Once the bioremediation task is done, dispersal of the nutrient is discontinued, resulting in the death of the released bacteria In some embodiments, the bacteria used are auxotrophs that require a nutrient not typically found at the site of release, or the environment exposed to the bacteria, for example, an amino acid (e.g., histidine), a vitamin (e.g., biotin), or a cell wall component (e.g., diaminopimelic acid).

Some aspects of this disclosure provide methods for using an engineered exopolysaccharide-associated protein, an engineered bacterium, or an engineered biofilm as provided herein for the purification of a product generated in a cell culture or in a bioreactor. In some such embodiments, engineered bacteria or biofilms function as a biocolumn, retaining and/or concentrating the product on their cell surface or within the biofilm. The bacteria or the biofilm can then be retrieved and the product isolated from the bacteria or the biofilm. The use of engineered bacteria or biofilms as provided herein as biocolumns is advantageous as compared to conventional strategies. Such conventional strategies typically rely on the desired product of a biofermentation being secreted by cells within a bioreactor into a liquid medium, separation of the cells from the liquid medium, and isolation of the product from the liquid medium. In many instances, this strategy required the processing of large amounts of liquid medium containing small amounts of the desired product. If the product is soluble, the subsequent isolation typically requires the use of binding agents conjugated to a solid support or the precipitation of the product from the liquid media.

In contrast, the methods for purifying a product from a bioreactor by using the engineered cells or biofilms provided herein as biocolumns allow for the separation of the product via a method that includes separating the bacteria or the biofilm from the liquid media in the bioreactor, and then isolating the product from the bacteria or biofilm. This obviates the use of binding agents for the isolation of the product from liquid media, and allows for a one-step purification method.

For example, in some embodiments, the product is a protein. In some such embodiments, the protein is expressed as a fusion protein with an exopolysaccharide-associated protein, or with an exopolysaccharide-binding fragment thereof. In some embodiments, the method of purifying the protein involves culturing a bacterium expressing the protein as a fusion protein with an exopolysaccharide-associated protein, or with an exopolysaccharide-binding fragment thereof in a liquid medium. In some embodiments, the fusion protein comprises a cleavable linker, e.g., a protease- or photocleavable linker. connecting the product protein to the exopolysaccharide-associated protein or the exopolysaccharide-binding fragment thereof. In some embodiments, the bacteria express the fusion protein. In some embodiments, the protein product is fused to the exopolysaccharide-associated protein or the exopolysaccharide-binding fragment thereof in manner that results in the product protein being located in the extracellular space. In some embodiments, the fusion protein is secreted by the bacteria. In some embodiments, the bacteria are in planktonic form and retain the product protein on their cell surface based on its fusion to an exopolysaccharide-associated protein, or with an exopolysaccharide-binding fragment thereof. In other embodiments, the bacteria form a biofilm and the product protein is retained within the biofilm based on its fusion to an exopolysaccharide-associated protein. In some embodiments, the method includes isolating the bacteria, e.g., by pelleting planktonic bacteria (e.g., by centrifugation), or by retrieving a biofilm from a surface within a bioreactor. In some embodiments, the method further includes separating the protein product from its fusion partner, e.g., the exopolysaccharide-associated protein or the exopolysaccharide-binding fragment thereof, for example, by cleavage of the cleavable linker. In some embodiments, the cleaved-off protein product is then eluted from the bacteria, which will retain the cleaved-off portion of the fusion protein that comprises the exopolysaccharide-associated protein or the exopolysaccharide-binding fragment thereof.

For example, in some embodiments, the product is a secreted molecule. In some such embodiments, the bacteria express the secreted molecule and a fusion protein comprising a protein binding agent that binds the secreted product molecule (e.g., an affinity tag, antibody fragment, adnectin, or aptamer) fused to an exopolysaccharide-associated protein or an exopolysaccharide-binding fragment thereof. In some embodiments, the method of purifying the protein involves culturing a bacterium expressing the secreted product and a protein binding agent that binds the secreted product molecule (e.g., an affinity tag, antibody fragment, adnectin, or aptamer) fused to an exopolysaccharide-associated protein or an exopolysaccharide-binding fragment thereof in a liquid medium. In some embodiments, the fusion protein comprises a cleavable linker, e.g., a protease- or photocleavable linker, connecting the binding agent to the exopolysaccharide-associated protein or the exopolysaccharide-binding fragment thereof. The binding agent in such embodiments is fused to the exopolysaccharide-associated protein or the exopolysaccharide-binding fragment thereof in manner that results in the binding agent being located in the extracellular space. In some embodiments, the fusion protein is secreted by the bacteria. In some embodiments, the bacteria are in planktonic form and retain the binding agent on their cell surface based on its fusion to an exopolysaccharide-associated protein or an exopolysaccharide-binding fragment thereof. In other embodiments, the bacteria form a biofilm and the binding agent is retained within the biofilm based on its fusion to an exopolysaccharide-associated protein or an exopolysaccharide-binding fragment thereof. The bacteria are cultured under conditions that permit the binding agent on the surface of the bacteria or within the biofilm to bind the product molecule. In some embodiments, the method includes isolating the bacteria, e.g., by pelleting planktonic bacteria (e.g., by centrifugation), or by retrieving a biofilm from a surface within a bioreactor. In some embodiments, the method further includes separating the product molecule from the binding agent, e.g., by eluting the product molecule. In some embodiments, the method includes cleaving the binding agent from its fusion partner, e.g., the exopolysaccharide-associated protein or the exopolysaccharide-binding fragment thereof, for example, by cleavage of the cleavable linker. In some embodiments, the cleaved-off binding agent, bound to the product molecule, is then separated from the bacteria, e.g., by elution, and subsequently the product molecule is isolated, e.g., eluted from the binding agent. The nature of the binding agent will depend on the product molecule to be purified. Binding agents for various product molecules are well known to those of skill in the art, and the disclosure is not limited in this respect.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLES

Materials and Methods

Bacterial strains, plasmids, and media. The bacterial strains and plasmids used in this study are listed in Table 5:

TABLE 5 bacterial strains and plasmids. All listed references (Ref.) are incorporated herein by reference in their entirety.

| Bacterial Strains | Genotype and/or phenotype | Ref. |
|---|---|---|
| *E. coli* strains | | |
| SM10λpir | thi thr leu tonA lacY supE recA::RP4-2-Tc::MuλpirR6K;Km$^r$ | [1] |
| *V. cholerae* strains | | |
| PW249 | MO10; Sm$^r$ | [2] |
| PW328 | MO10 ΔvpsL, Sm$^r$ | [3] |
| PW357 | MO10 lacZ::vpsLp→lacZ; Sm$^r$ | [3] |
| PW454 | MO10 ΔvpsL lacZ::gfp; Sm$^r$ | |
| PW707 | MO10 Δbap1ΔrbmC; lacZ::vpsLp→lacZ; Sm$^r$ | |
| PW1085 | MO10 rbmA-flag; lacZ::vpsLp→lacZ; Sm$^r$Ap$^r$ | |
| PW1086 | MO10 bap1-flag; lacZ::vpsLp→lacZ; Sm$^r$Ap$^r$ | |
| PW1087 | MO10 ΔrbmA; lacZ::vpsLp→lacZ; Sm$^r$ | |
| PW1088-90 | MO10 Δbap1ΔrbmC, Sm$^r$ | |
| Plasmids | | |
| pWM91 | oriR6KmobRP4 lacI pTac tnp miniTn10Km; Ap$^r$ | [4] |
| pWM91Δbap1 | pWM91 carrying a fragment of bap1 harboring an internal, unmarked deletion; Ap$^r$ | [5] |
| pWM91ΔrbmC | pWM91 carrying a fragment of rbmC harboring an internal, unmarked deletion; Ap$^r$ | |
| pWM91ΔrbmA | pWM91 carrying a fragment of rbmA harboring an internal, unmarked deletion; Ap$^r$ | |
| pGP704::bap1-flag | pGP704 carrying 3' end of bap1 fused to a flag tag; Ap$^r$ | |
| pGP704::rbmA-flag | pGP704 carrying 3' end of rbmA fused to a flag tag; Ap$^r$ | |
| pJZ111 | Plac::gfp::lacZ in pCVD442; Ap$^r$ | [6] |
| pBAD-TOPO-rbmA | pBAD-TOPO carrying the gene at locus VC0928 (rbmA); Ap$^r$ | |
| pFLAG-chiA-2 | pFLAG-CTC carrying the gene at locus VCA0027 (chiA-2); Ap$^r$ | |
| pFLAG-hlyA | pFLAG-CTC carrying the gene at locus VCA0219 (hlyA); Ap$^r$ | |
| pFLAG-hapA | pFLAG-CTC carrying the gene at locus VCA0865 (hapA); Ap$^r$ | |
| pFLAG-tcpG | pFLAG-CTC carrying the gene at locus VC0034 (tcpG); Ap$^r$ | |
| pFLAG-mshA | pFLAG-CTC carrying the gene at locus VC0409 (mshA); Ap$^r$ | |
| pFLAG-rbmA | pFLAG-CTC carrying the gene at locus VC0928 (rbmA); Ap$^r$ | |
| pFLAG-crr | pFLAG-CTC carrying the gene at locus VC0964 (crr); Ap$^r$ | |
| pFLAG-bap1 | pFLAG-CTC carrying the gene at locus VC1888 (bap1); Ap$^r$ | |

Vectors used for protein expression included an IPTG inducible promoter driving expression of the protein of interest with a C-terminal FLAGtag (pFLAG-CTC, Sigma-Aldrich). Bacteria were cultivated in Luria-Bertani broth (LB) supplemented with ampicillin (100 µg/ml). Because adequate protein expression was observed without induction, the growth medium was not supplemented with IPTG.

*V. cholerae* strain MO10 (serotype O139, streptomycin resistant) inactivated in ctxA and carrying a plasmid encoding the RbmA-CtxB fusion protein as previously described (ΔctxA/prbmA-ctxB) was maintained in Luria-Bertani medium (LB) with 25% glycerol at −80° C. Broth cultures were inoculated from the frozen stocks into LB and grown overnight for 18 hr at 37° C., 200 rpm. Ampicillin (100 µg/mL) was included at all times for plasmid maintenance.

Construction of plasmids for protein expression. The ORFs of interest were amplified by PCR using primers including the start and stop codons of each gene of interest. Kpn I restriction sites were included in the primers used for amplification of chiA-2. These restriction sites were used to insert chiA-2 between rbmA and the FLAG tag in expression vector pFLAG-rbmA [1]. Kpn I and Sal I restriction sites were used to fuse ctxB to the C-terminal end of rbmA pFLAG-rbmA. In this case, the FLAG tag was removed. All insertions were confirmed by sequence analysis. Before use, we confirmed that the RbmA-CtxB and RbmA-ChiA-2-FLAG fusion proteins did not interfere with formation of the wild-type *V. cholerae* biofilm.

Mutant construction. The *V. cholerae* Δbap1ΔrbmCΔrbmA mutant was constructed as previously described [14] using the strain *V. cholerae* Δbap1ΔrbmC mutant (PW707) and the suicide plasmid pWM91ΔrbmA [1].

Generation of the live-attenuated vaccine. Bacterial cultures grown overnight in LB were centrifuged for 5 min at 6,000×g, washed once with phosphate-buffered saline (PBS), and inoculated at a 1:100 dilution into 25 mL of fresh LB containing ampicillin. Protein production is induced with 0.1 mM of β-d-1-thiogalactopyranoside (IPTG). Following induction, cells were incubated for 8 hr at 37° C., and 200 rpm, then harvested by centrifuging for 20 min at 6000×g. Cell pellets were washed twice in PBS and finally resuspended in 2 mL of PBS. This constituted the vaccine suspension. From this suspension, 10 µL was removed for viable counts of colony forming units (CFU), 20 µL was removed and added to 180 µL of 4×Laemmli buffer. For each immunization, the vaccine suspension was prepared fresh and administered within 2 hr of preparation.

Generation of vaccines. Bacterial cultures were grown overnight from FS in 2 mL with ampicillin (100 µg/ml). They were shaken at 27C at 180 rpm for 14 hours. A 25 mL culture was inoculated with 1:100 dilution of the overnight culture, including ampicillin and IPTG (100 ug/ml ampicillin+0.5 mM IPTG added from start, in 250 mL-volume flasks). Following inoculation, the cultures were shaken at 27° C. at 180 rpm until the $OD_{600}$ reached 0.6. The cells were placed on ice for 10 minutes. The cells were then pelleted at 5000×G for 20 minutes at 4° C., and 100 uL of the supernatant was removed and added to 100 uL 2× Laemmli sample buffer for Western blot sample. The rest of the supernatant was discarded and the pellet was resuspended in 10 mL of PBS. The cells were pelleted at 5000×G for 20 minutes at 4C, and the resuspension and pelleting process was repeated for a total of three washes. The washed pellet was then resuspended in 5 mL of PBS and then 20 uL to 180 uL 2× Laemmli sample buffer were added for Western blot samples. Both Western blot samples were boiled for 5 minutes. Then, the samples were sonicated 15 s×2, with a 15 s rest in between. The samples were stored at −20° C. The vaccine was then stored on ice until administration. The vaccines were prepared fresh on the day of administration and were not stored overnight.

Once the vaccine was prepared, it was screened. Sterility was analyzed by adding LB culture to the vaccine and then streaking on a LB plate and measuring the OD at 600 nm. Cells were also counted using a hemocytometer and a BSA assay was performed to determine the protein concentration. Then, the presence of CtxB was assayed after formaldehyde, it was quantified by Western blot (see below) and the CtxB per cell was calculated.

Before the vaccine is shipped, it is diluted to match the cell levels required for the vaccine study. Purified CtxB is added to WT/pFLAG samples to match the concentration found in fusion protein samples.

Quantitative Western blot. Samples were boiled for 5 min, briefly centrifuged, sonicated twice for 15 s with one 10 s pulse (output approximately 10 W), and collected by brief centrifugation. Protein samples were resolved by 4-20% gradient Tris-glycine SDS-PAGE (BioRad). Aliquots of purified cholera toxin B subunit (List Laboratories) at known concentrations were included as standards for quantification. Proteins were transferred onto a polyvinylidene difluoride (PVDF) membrane using a semi-dry transfer method (BioRad). The membrane was incubated in a blocking solution consisting of Tris-buffered saline containing 0.1% TWEEN® 20 (TBS-TWEEN®) and 5% skim milk with gentle mixing for 2 hr at room temperature. Fresh blocking solution containing horseradish peroxidase (HRP)-conjugated antibody against CtxB (1:400) (Thermo Fisher) was added. Following overnight incubation at 4C with gentle mixing, the membrane was washed three times with TBS-TWEEN® and developed using ECL Western blotting substrate (Thermo Fisher). ImageJ was used to generate a standard curve based on CtxB standards. Concentration of the fusion protein in the sample was determined using the linear portion of the standard curve.

Biofilm assays. A single colony of *V. cholerae* was inoculated into 1 ml of LB broth and allowed to grow to mid exponential phase. The culture was then diluted in LB broth to yield an $OD_{655}$ of 0.05 and divided into three disposable glass culture tubes (10 mm×75 mm). These tubes were incubated statically at 27° C. After 24 hrs, planktonic cells were removed, and the $OD_{655}$ of the cells was measured. Remaining biofilms were washed with 0.1 M phosphate-buffered saline solution (PBS) (pH 7.0) and then disrupted with 1 mm beads (Biospec). The $OD_{655}$ of the resulting cell suspension was measured. For assays of biofilm integrity, biofilms were formed as described above in 24 well plates and then vortexed.

Immunofluorescence. Immunofluorescence experiments were performed as previously described with the following modifications [1]. To detect the RbmA-CtxB fusion protein, an anti-CtxB antibody (Sigma) (1:1000 dilution) followed with an ALEXA FLUOR® 488 Goat Anti-Rabbit Antibody (Invitrogen) was used. To detect ChiA-2-FLAG and RbmA-Chia-2-FLAG, an anti-FLAG M2 antibody (1:1000 dilution) (Sigma-Aldrich) was used followed by an incubation with DyLight 549 AffiniPure Rabbit Anti-Mouse IgG H+L (1:1000 dilution) (Jackson ImmunoResearch). Confocal images were acquired at the Children's Hospital, Boston Imaging Core with a LSM700 microscope (Zeiss) equipped with a 63× objective and 405, 488, and 555 nm laser lines. A computer equipped with ZEN 2009 software was used to acquire and process images.

Chitinase assays. For assays of protein activity, cells were cultured in LB broth supplemented with ampicillin at 27° C., for approximately 5 hours and then back-diluted in the same medium to yield an $OD_{655}$ of 0.05. For assays of activity within the biofilm, three 80 µl aliquots of each culture were transferred to the wells of a 96 well, black microtiter dish and three to wells of a polystyrene 96 well plate. Both plates were incubated statically at 27° C., for 24 hours. The planktonic fractions of the resulting cultures were removed, fractions from one well of the black plate and one well of the polystyrene plate were pooled, an $OD_{655}$ was recorded, and the cell suspensions were centrifuged. A 5 µl volume of the supernatant was removed and assayed for chitinase activity. Biofilms remaining in the black % well plates were rinsed twice with PBS and assayed directly for chitinase activity. For assays of the ΔbaplΔrbmAΔrbmC mutant, cells were cultured in 1 ml of LB broth at 27° C. with shaking overnight. An ODs was recorded. The cell suspension was pelleted, and the supernatant was removed. Cells were rinsed once with PBS and then resuspended in an equal volume of PBS. 5 µl of the cell suspension and supernatant were assayed for chitinase activity. Chitinase activity was measured using a fluorometric chitinase assay kit (Sigma-Aldrich) according to the manufacturer's protocol including the following steps. Bacterial cells, biofilms, or supernatants were incubated in substrate buffer containing 0.2 mg/ml 4-methylumbelliferyl N, N'-diacetylchitobioside hydrate chitobiose for 20 minutes at 37° C. in the dark prior to measurement of fluorescence with an Infinite 200 spectrophotometer (Tecan).

Sublingual immunization of mice. Female specific pathogen-free BALB/c mice (6-8 week) were obtained from Charles River Laboratories and housed in groups of five. The mice were given food and water ad libitum. Experimental procedures performed here have been previously approved by the Institutional Animal Care and Use Committee. To establish baseline values of antibodies reacting with CtxB prior to immunization, stool pellets were collected one day prior to the first vaccination and sera were obtained immediately before the first vaccination. The mice were immunized three times at 2 week intervals. Sera and stool samples were collected every 2 weeks after the first vaccination and analyzed with ELISA for the presence of CtxB-specific antibodies. For sublingual immunization, mice were anesthetized by intraperitoneal injection with ketamine (100 mg/kg) and xylazine (10 mg/kg), then held upright as 10 µL of the vaccine suspension is delivered under the tongue by a micropipette directed toward the floor of the mouth. The mice were held in the upright position for at least 2 min, then rested ventral side down for 30 min.

Measurement of antigen-specific antibodies. Blood was collected from the tail vein of the mice. Sera was obtained by incubating the samples for 45 min at room temperature, then centrifuging at 1,500 rpm for 15 min. Supernatant was removed into a new microcentrifuge tube and spun at 1,500 rpm for 5 min. Sera was stored at −20° C. until use. Stool pellets were resuspended in cold PBS containing 25 mM EDTA and 0.01% (w/v) soybean trypsin inhibitor. The suspension was centrifuged at 1,800 rpm for 10 min. The supernatant was removed and centrifuged once more at 12,000 rpm for 10 min at 4° C. Stool extracts were stored at −80° C. with 2 mM PMSF until use. Antibodies were detected by ELISA using monosialotetrahexosylganglioside $G_{M1}$ (10 µg/mL in 50 mM carbonate buffer, pH 9.5) followed by recombinant CtxB (1 µg/mL) for CtxB-specific antibodies and goat anti-mouse IgA (1 µg/mL) (Bethyl Laboratories) coating for total IgA in the stool samples. Presence of bound antibodies were detected with HRP-conjugated anti-IgA or anti-IgG (1 µg/mL) (Bethyl Laboratories). Plates were developed with 1-Step Ultra ELISA Turbo Substrate (Thermo Fisher) using a kinetic ELISA protocol, reading for 7 min at 10 s intervals with 3 s mixing. Standard curves were generated with mouse IgA (Bethyl Laboratories) or mouse anti-CtxB-IgG (Thermo Fisher).

Serum vibriocidal responses. Serum vibriocidal antibody titer was determined as previously described, with some modifications. Sera were serially diluted 2-fold in 5 µL with PBS. Wild-type MO10 was used as the indicator strain and grown to mid-logarithmic phase in brain heart infusion broth (BHI) containing streptomycin (100 µg/mL). The bacterial culture was diluted in PBS containing 10% guinea pig complement to 2×10 CFU/mL, and 5 µL of this suspension was added to the sera. The combination was incubated for 1 hr at 37° C. with shaking at 200 rpm. Viable cells were enumerated from sera dilution by CFU counts. Bactericidal titer was determined as the reciprocal of the sera dilution capable of killing 50% or more of the indicator strain compared with a control containing pre-immune sera.

Statistical analysis. Three experimental replicates were included in all quantitative experiments, and each experiment was repeated at least twice. Reported values represent the mean of the three experimental replicates, error bars represent the standard deviation, and statistical significance was calculated using a student's t-test.

Example 1

The bacterial biofilm matrix is comprised of exopolysaccharide, proteins, and DNA [2]. A model is emerging in which the biofilm exopolysaccharide is a scaffold to which adhesive proteins are anchored rather than the glue that holds the biofilm structure together [1,3]. We and others recently identified three such adhesive V. cholerae proteins, Bap1, RbmA, and RbmC [1,4-6]. Here we demonstrate the feasibility of using RbmA as a biofilm matrix targeting moiety for proteins of biological significance.

One licensed cholera vaccine includes killed whole V. cholerae cells combined with the purified B subunit of cholera toxin (CtxB), which serves as both an antigen and an adjuvant [7]. The purified CtxB component improves short term protection but also decreases affordability and ease of delivery. As a result, cholera vaccines manufactured in resource-poor settings have omitted this component [8,9]. We reasoned that engineering *V cholerae* to decorate its biofilm exopolysaccharide scaffold with CtxB could greatly simplify the production and administration of a vaccine including CtxB and also potentially improve vaccine efficacy. In a proof of principle experiment, we engineered wild-type *V. cholerae* to express RbmA with either the CtxB subunit or a FLAG affinity tag fused to its C-terminus. Biofilms were formed with these strains. To determine if the RbmA-CtxB fusion protein was sequestered to the biofilm matrix, we subjected these biofilms to immunofluorescence using an antibody recognizing CtxB.

As a control, a biofilm formed by wild-type *V. cholerae* carrying an empty vector was also subjected to immunofluorescence using an anti-CtxB antibody. As shown in FIG. 1, the RbmA-CtxB fusion was visualized in the biofilm in a distribution similar to that of RbmA-FLAG. However, the anti-CtxB antibody did not associate with the biofilm in the absence of the RbmA-CtxB fusion protein. This result suggests that bacteria can be engineered to deliver and concentrate antigens or adjuvants at their surfaces by fusion to biofilm matrix-associated proteins. Such engineered bacterial strains could be candidates for live-attenuated or killed whole cell vaccines. Exemplary sequences of the respective fusions are provided below:

RbmA-FLAG:
(SEQ ID NO: 35)
MSNFKGSIMNKRHYYLASCLALLFSTASYAEVDCELQPVIEANLSLNQNQ

LASNGGYISSQLGIRNESCETVKFKYWLSIKGPEGIYFPAKAVVGVDTAQ

QESDALTDGRMLNVTRGFWVPEYMADGKYTVSLQVVAENGKVFKANQEFV

KGVDLNSLPELNGLTIDIKNQFGINSVESTGGFVPFTVDLNNGREGEANV

EFWMTAVGPDGLIIPVNAREKWVIASGDTYSKVRGINFDKSYPAGEYTIN

AQVVDIVSGERVEQSMTVVKKDYKDDDDK

RbmA-CtxB
(SEQ ID NO: 36)
MSNFKGSIMNKRHYYLASCLALLFSTASYAEVDCELQPVIEANLSLNQNQ

LASNGGYISSQLGIRNESCETVKFKYWLSIKGPEGIYFPAKAVVGVDTAQ

QESDALTDGRMLNVTRGFWVPEYMADGKYTVSLQVVAENGKVFKANQEFV

KGVDLNSLPELNGLTIDIKNQFGINSVESTGGFVPFTVDLNNGREGEANV

EFWMTAVGPDGLIIPVNAREKWVIASGDTYSKVRGINFDKSYPAGEYTIN

AQVVDIVSGERVEQSMTVVKKMIKLKFGVFFTVLLSSAYAHGTPQNITDL

CAEYHNTQIYTLNDKIFSYTESLAGKREMAIITFKNGAIFQVEVPGSQHI

DSQKKAIERMKDTLRIAYLTEAKVEKLCVWNNKTPHAIAAISMAN

RbmA-ChiA-FLAG
(SEQ ID NO: 37)
MSNFKGSIMNKRHYYLASCLALLFSTASYAEVDCELQPVIEANLSLNQNQ

LASNGGYISSQLGIRNESCETVKFKYWLSIKGPEGIYFPAKAVVGVDTAQ

QESDALTDGRMLNVTRGFWVPEYMADGKYTVSLQVVAENGKVFKANQEFV

KGVDLNSLPELNGLTIDIKNQFGINSVESTGGFVPFTVDLNNGREGEANV

EFWMTAVGPDGLIIPVNAREKWVIASGDTYSKVRGINFDKSYPAGEYTIN

AQVVDIVSGERVEQSMTVVKKMNRMTLCAASIACALASTAMAAPSAPSVD

VYGSNNLQFSKIELAMETTAGYNQMVKYHEEAPITLKFNQWSGVTGNTYK

IYFDGVEVATGPISGSQTTAQFTYPKGGVYQLVIEACDATGCTKSAPSEI

TIADTDGSHLKPLKMNVDPNNKSYTIPQNTVIGTYFVEWSIYDRKFTVDN

IPGQNLTHILYGFIPICGPNESLKSVGGNSFNALQTACKGVPDFEVVIHD

PWAAYQKSFPQAGHQYSSPIKGNYAMLMALKKTYPDLKIIPSIGGWTLSD

PFFSFTDKAKRDVFVASVKRFLKTWKFYDGVDIDWEYPGGGGQAADLGDP

VKDGPAYVALMAELRAMLDELEAETGRKYELTSAIGVGHDKIEDVNYGQA

VQYMDYIFAMTYDFYGGWNNVLGHQTALYCGSFMRPGQCDGKGVDENGEP

YKGPAYTTDNGIQLLLAQGVPPSKLVVGAAMYGRGWEGVTPASLKDPNDP

MTGVGNGKLKGTTAQGVWEAGVIDYKGVKNFMLGANKTGVNGFEYGYDEQ

AEAPWVWNRTTGQLVTFDDDRSVKAKGAYVRNLGLAGLFSWEIDADNGDI

LNAMHEGLAGGTTTPPVNKAPVANAGADITVTGPAAVSLDGSASKDSDGS

IASYLWEQTAGPAVTLTGANSAKASFNAAEVTEKQTFTFKLTVTDNKGAT

ATDTVVVTVNPKSTTPVNTAPVAALSAPASVKAGATVVVDASASSDADQD

PLSFTWDLPVGVNATVQGAKVTFVAGEYTQDTTLDFTVTVSDGKATSKAS

ASVLVEKKAGTGGDACTNLWNAESIYTGGQQVTWAGKTWEAKWWTRGEDP

SKSGQWGVWKDLGAASCSTHDYKDDDDK

Figure 2:
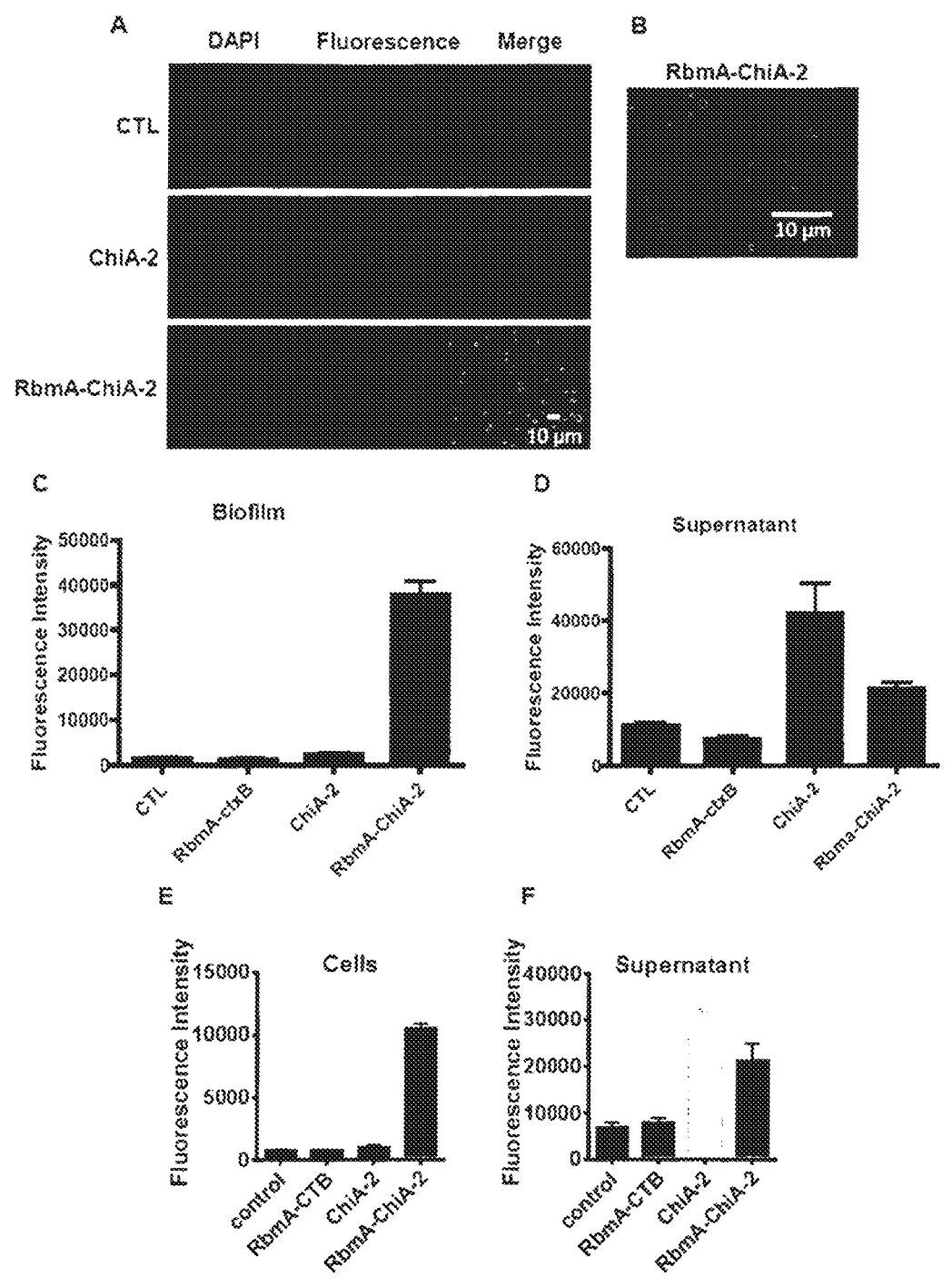

Additionally, we reasoned that this technology might be used to deliver a functional enzyme to a surface. To model this, we inserted a secreted *V. cholerae* chitinase between RbmA and a C-terminal FLAG tag (RbmA-ChiA-2-FLAG) and expressed this fusion protein from a plasmid in wild-type *V. cholerae*. As controls, we also generated wild-type *V. cholerae* carrying an empty vector or the same vector encoding ChiA-2-FLAG. Biofilms were formed with these three strains, and immunofluorescence was performed using an anti-FLAG antibody. As shown in FIGS. 2A and B, the RbmAChiA-2-FLAG fusion was concentrated in the biofilm, whereas the ChiA-2-FLAG protein alone was not.

To be useful in surface modification, enzymes directed to the biofilm matrix must retain their activity. Therefore, we assessed whether the biofilm-associated RbmA-ChiA-2 fusion protein retained enzymatic activity. We formed biofilms with wild-type *V cholerae* expressing RbmA-CtxB, ChiA-2-FLAG, or RbmA-ChiA-2-FLAG from a plasmid. As an additional control, a wild-type strain carrying an empty vector was included. Planktonic cells were removed, the biofilms were rinsed, and the chitinase activity of the biofilms and cell supernatants was tested. As shown in FIG. 2C, chitinase activity was approximately 15 times greater in the biofilm formed by the strain expressing the RbmAChiA-2-FLAG fusion than in any of the other biofilms tested. Because chitinase is a secreted protein native to *V. cholerae*, chitinase activity was high in all the cell supernatants, particularly those expressing either ChiA-2-FLAG alone or the RbmA-ChiA-2-FLAG fusion protein (FIG. 2D). These experiments show that the biofilm matrix can be used to deliver active enzymes to surfaces.

For some applications, it may be advantageous to anchor proteins to planktonic cells. Bap1 and RbmC are found at the biofilm-surface interface and are important for anchoring the biofilm to surfaces. When biofilms are formed under static growth conditions, a *V. cholerae* Δbap1ΔrbmC mutant forms a multicellular structure or pellicle at the air-water interface, but this structure does not adhere to the walls of the well.

Therefore, in quantitative assays of biofilm association, the Δbap1ΔrbmC mutant pellicle is easily dislodged, and the resulting measurement is indistinguishable from that of an exopolysaccharide mutant [1,5]. In contrast, RbmA is distributed throughout the biofilm and cements intercellular interactions. The ΔrbmA mutant biofilm forms a pellicle at the air-water interface that remains strongly attached to the surface. However, the pellicle is easily dispersed by vortexing [1,4]. The biofilm defects of both the Δbap1ΔrbmC mutant and the ΔrbmA mutant can rescued by addition of these purified proteins to the culture medium 1. This suggests that the exopolysaccharide scaffold is synthesized and exported in the absence of matrix protein synthesis.

Figure 1A:
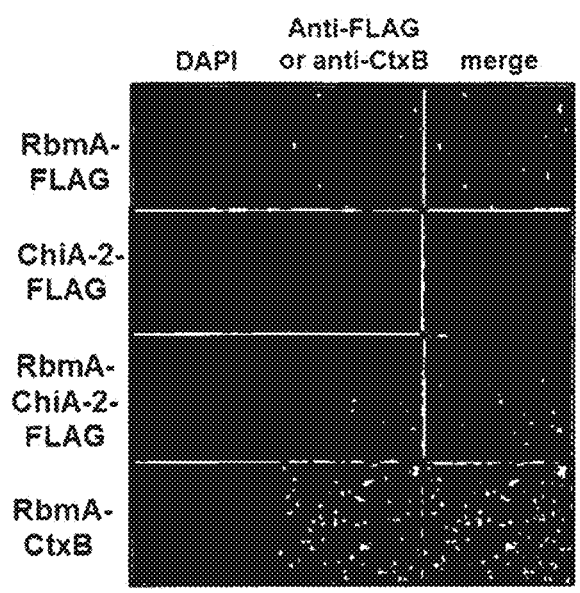
FIGS. 1A to 1B. An RbmA-CtxB fusion protein is retained in the biofilm matrix.
Figure 1B:
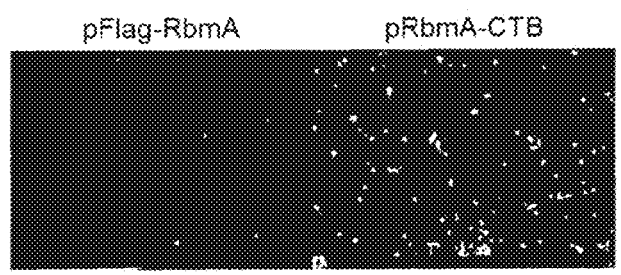
Figure 3:
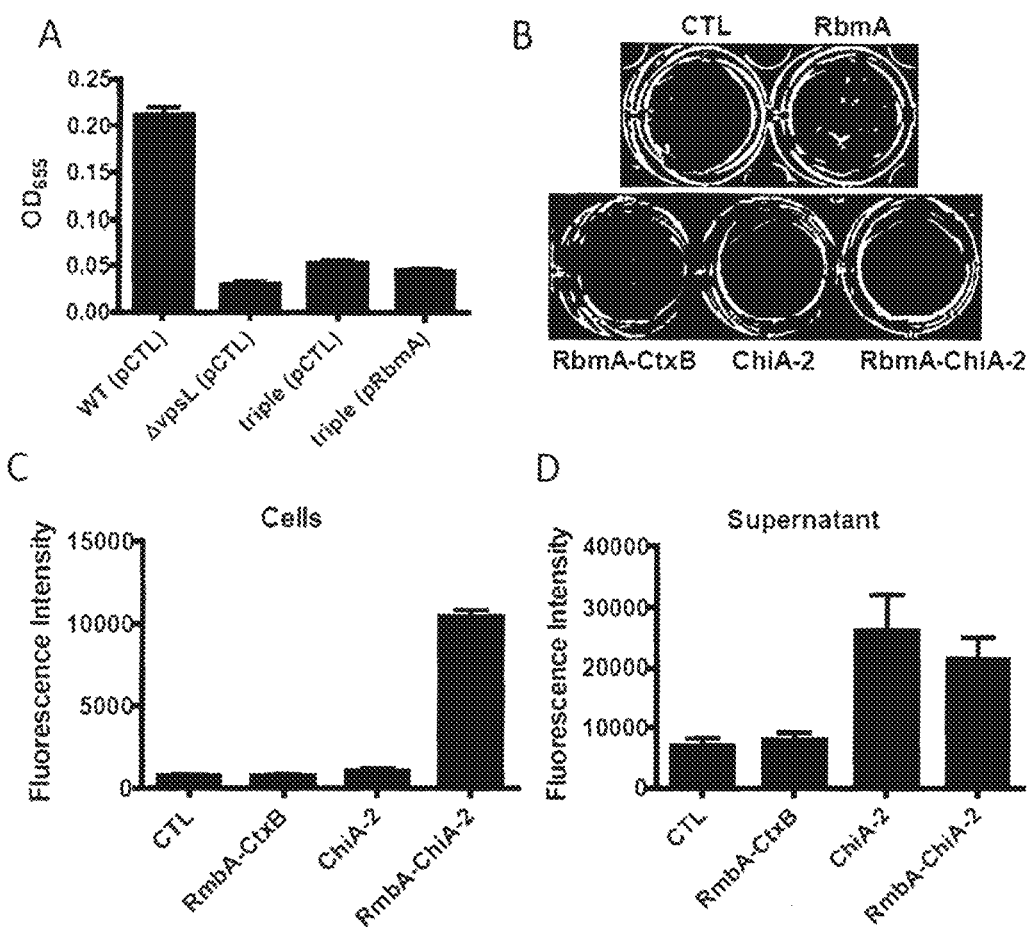

We hypothesized that a Δbap1 ΔrbmA ΔrbmC mutant would be defective in cell-surface and cell-cell interactions and, therefore, unable to form a biofilm. To test this, we created this triple mutant and assessed biofilm formation. As shown in FIGS. 3A and B, the triple mutant did not associate with the surfaces in quantitative assays and did not form a pellicle. Pellicle formation was rescued, however, by a plasmid encoding RbmA-FLAG or RbmA-CtxB (FIG. 3B). Expression of ChiA-2-FLAG and the RbmAChiA-2-FLAG from a plasmid did not rescue pellicle formation by the triple mutant. This suggests that, unlike RbmA and RbmA-CtxB, the RbmA-ChiA-2-FLAG protein is unable to mediate intercellular interactions.

To determine whether the RbmA-ChiA2-FLAG fusion remained associated with cells in the absence of biofilm formation, a triple mutant expressing RbmA-ChiA-2-FLAG was cultured with agitation, cells were pelleted, and the chitinase activity of both the cellular fraction and the supernatant was assayed. As shown in FIGS. 3C and D chitinase activity was sequestered to cells expressing the RbmA-ChiA-2-FLAG fusion but not to cells expressing ChiA-2-FLAG or RbmA-CtxB. This suggests that RbmA-ChiA-2-FLAG is cell-associated even in the absence of a biofilm structure. We hypothesize that the biofilm matrix exopolysaccharide is produced and exported by the triple mutant.

Furthermore, although RbmA-ChiA-2-FLAG is unable to mediate intercellular interactions, it likely retains the ability to associate with this matrix exopolysaccharide and remains functional on the cell surface. These experiments suggest that this protein presentation platform can also be adapted for use in planktonic bacterial cells.

Example 2

Like other bacteria, Vibrio cholerae synthesizes a highly regulated extracellular matrix that enables attachment to surfaces in a complex, three-dimensional multicellular structure known as a biofilm. Components of the biofilm matrix include exopolysaccharide, protein, and DNA. The polysaccharide component of the biofilm matrix has often been thought of as the glue that stabilizes the biofilm structure. We have recently completed the first proteomic analysis of a Gram-negative bacterial biofilm matrix [1]. Our findings suggest that the V. cholerae biofilm exopolysaccharide is tightly associated with the cell of origin, while secreted matrix-associated proteins are a communal resource required for cell-cell and cell-surface interactions. Furthermore, once secreted, these proteins segregate to distinct regions of the biofilm matrix to maintain the structural integrity of the biofilm.

Biofilm matrix-associated proteins can be harnessed to target enzymes or antigens of interest to specific regions of the biofilm matrix of Gram-negative bacteria. Engineered peptides that attach to the biofilm matrix in distinct distributions are provided herein. Proof of principle experiments in which a heterologous molecule (e.g., the enzyme chitinase or the cholera toxin B subunit) conjugated to an exopolysaccharide-associated protein or protein fragment is delivered to a biofilm comprising the exopolysaccharide, either uniformly or in a specific spatial distribution are also described herein. As described in more detail herein, engineered biofilm matrix-associated proteins for antigen presentation and targeting of enzymes to surfaces can be used for antigen presentation in vaccine development and to expand the enzymatic functionality of the bacterial biofilm matrix for therapeutic and bioengineering applications.

Proteins associated with the biofilm matrix. A recently published study represents the first comprehensive analysis of proteins associated with the Gram-negative biofilm matrix. [1] The experiments described here will advance the understanding of the mechanisms by which proteins are retained in the biofilm matrix, the spectrum of functions carried out by biofilm matrix-associated proteins, and the mechanisms by which proteins maintain spatial segregation in the biofilm.

In contrast to current views of the biofilm matrix proteins as the "glue" that holds the biofilm together, in which the biofilm matrix polysaccharide is depicted as a secreted, continuous matrix in which biofilm-associated bacteria are embedded, the preliminary results provided herein suggest that the V. cholerae matrix exopolysaccharide is tightly associated with cells and provides a scaffold for biofilm matrix-associated proteins. It is these proteins that mediate the intercellular and cell-surface contacts that provide structure to the biofilm.

Based on this understanding, different uses of bacterial biofilm matrix proteins and of biofilm matrix-associated proteins or protein fragments in novel applications is envisioned. For example, as described herein, biofilm matrix-associated proteins are spatially localized. For another example, the use of the biofilm matrix as a platform for presentation of antigens and delivery of functional enzymes to surfaces is envisioned. Heterologous molecules of interest, e.g., heterologous antigens or enzymes, can be strategically targeted to specific parts of a biofilm by conjugating them to proteins or protein fragments that associate with particular regions of the biofilm matrix.

Bacterial biofilm formation. Biofilm formation is the process by which bacteria attach to a living or non-living surface. In biofilms comprised of multiple layers of bacteria, cell-cell and cell-surface interactions are mediated by a secreted matrix of natural polymers that may include exopolysaccharides, protein, and DNA. This matrix is secreted in response to specific environmental cues.

The Vibrio cholerae multilayer biofilm matrix. V. cholerae is an epidemic diarrheal pathogen of humans and a natural inhabitant of estuarine environments. When environmental conditions are favorable, V. cholerae forms a multilayer biofilm by elaborating a matrix that contains several proteins as well as the VPS polysaccharide, whose synthesis is largely encoded by the vps genes. It was recently demonstrated that the VPS polysaccharide is tightly associated with cells. Preliminary results suggest that it does not mediate biofilm formation directly. Rather, secreted biofilm matrix-associated proteins mediate the cell-cell and cell-surface interactions. [1].

Proteins in the V. cholerae biofilm matrix. The first complete proteomic analysis of a bacterial biofilm matrix was recently published [1]. In that study, 10 proteins that are known to be secreted into the extracellular space were identified (Table 1) as well as 18 proteins that are predicted to be extracytoplasmic (Table 2).

Figure 4:
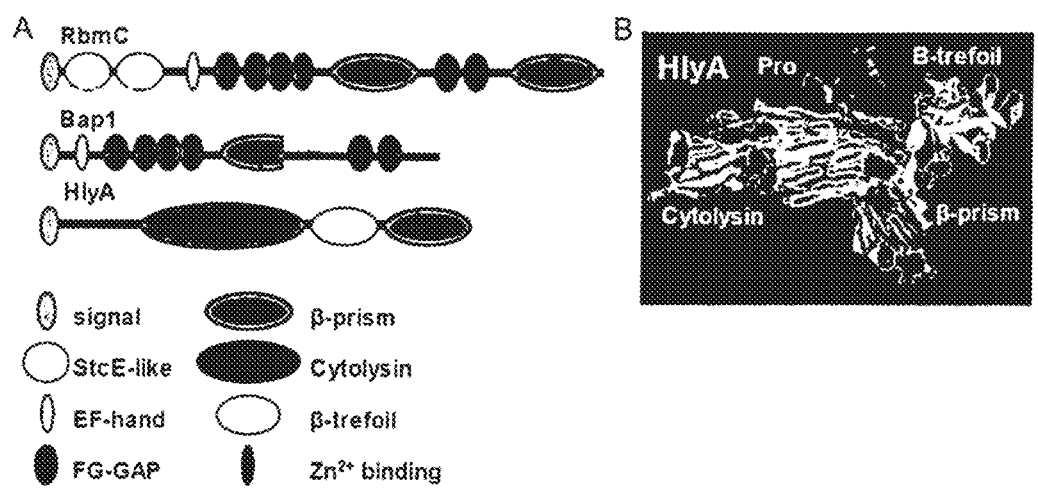

Type I β-prism domain-containing proteins in the V. cholerae biofilm matrix. Bap1, RbmC, and HlyA, three biofilm matrix-associated proteins identified, form a paralogous family of Type 1 β-prism lectin domain-containing proteins. Type I β-prism domains were first described in jacalin, a lectin found in the seeds of the Jack Fruit [15, 16]. Bap1 and RbmC are highly similar proteins with overlapping functions that are essential for biofilm formation [1, 6, 5]. These proteins contain multiple, conserved FG-GAP domains surrounding a β-prism domain (FIG. 4A). As a result, the β-prism domain is predicted to be part of a larger, β-propeller-like structure. While RbmC has conserved N and C terminal domains not found in Bap1, Bap1 represents the minimal peptide required to rescue the biofilm defect of a Δbap1ΔrbmC mutant. HlyA, a pore-forming toxin, is secreted as a protoxin and is activated by cleavage of the 5 kDa N-terminal chaperone-like domain. Activated HlyA consists of spatially separated cytolysin, β-trefoil, and β-prism domains (FIG. 4B) [17]. This protein forms heptameric pores in cholesterol and sphingolipid-rich cell membranes leading to membrane depolarization and/or hemoloysis [18, 19, 20]. There is evidence that HlyA associates with the V. cholerae biofilm matrix [1]. RbmA is a novel biofilm matrix-associated protein. RbmA is a secreted protein encoded in the VPS island. It has no conserved domains. Deletion of RbmA was originally noted to result in a weakened biofilm structure [4].

Figure 5:
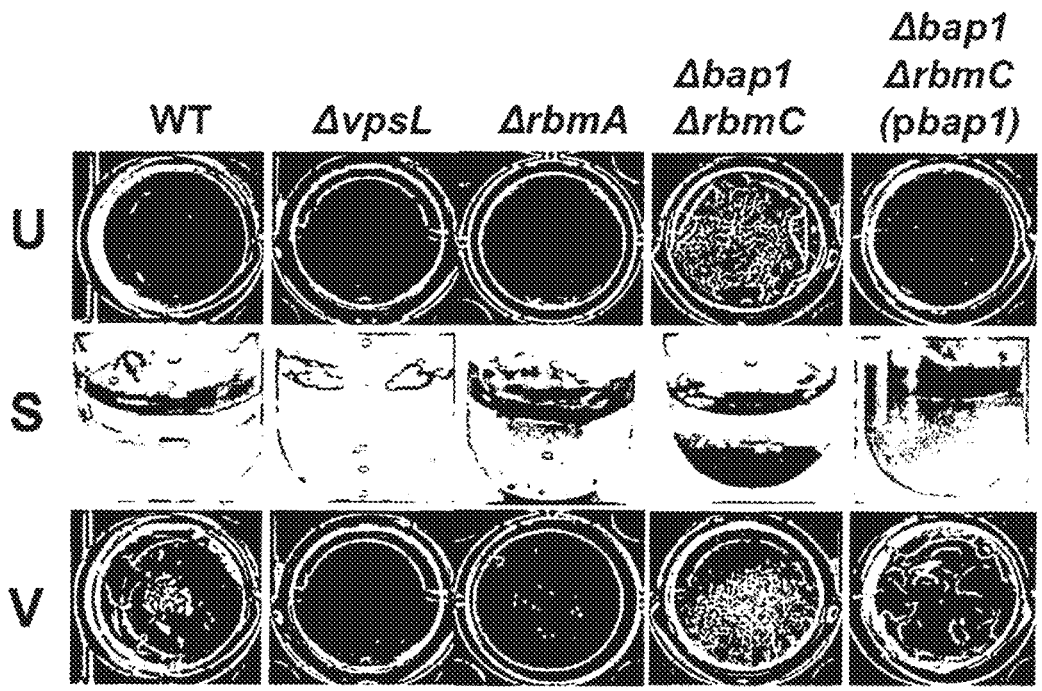

Bap1 reinforces the attachment of the biofilm to the surface, while RbmA strengthens intercellular contacts. The results shown herein suggest that RbmA plays a role in biofilm formation that is distinct from that of Bap1 and RbmC. As shown in FIG. 5, the ΔbaplΔrbmC mutant is able to form a pellicle, which is a biofilm structure found at the air-water interface. However, this pellicle is only weakly attached to the surrounding solid surface and, therefore, can be easily dissociated from the surface by gentle shaking. In contrast, ΔRbmA mutants form strong attachments to the surface that are not disrupted by shaking. However, when vortexed, the ΔrbmA mutant biofilm disperses into much smaller particles than the Δbap1ΔrbmC mutant biofilm, suggesting that RbmA reinforces intercellular contacts. The biofilm made by a Δbap1ΔrbmAΔrbmC mutant is indistinguishable from that made by a ΔvpsL mutant (data not shown).

Figure 6:
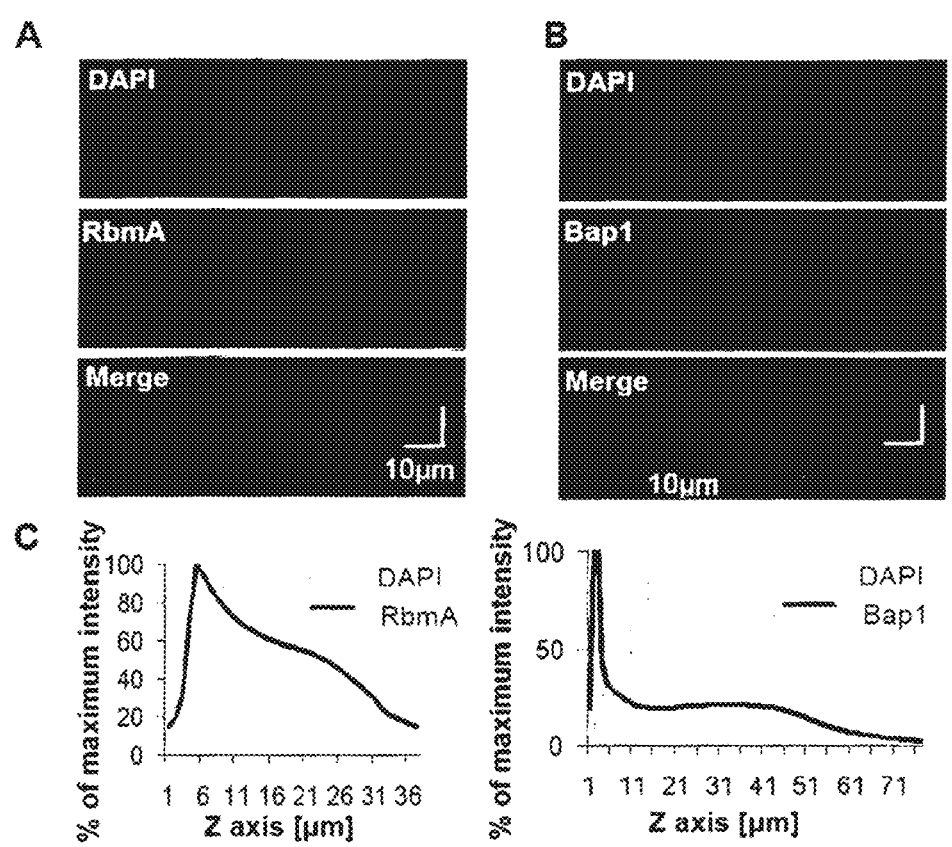
Figure 7:
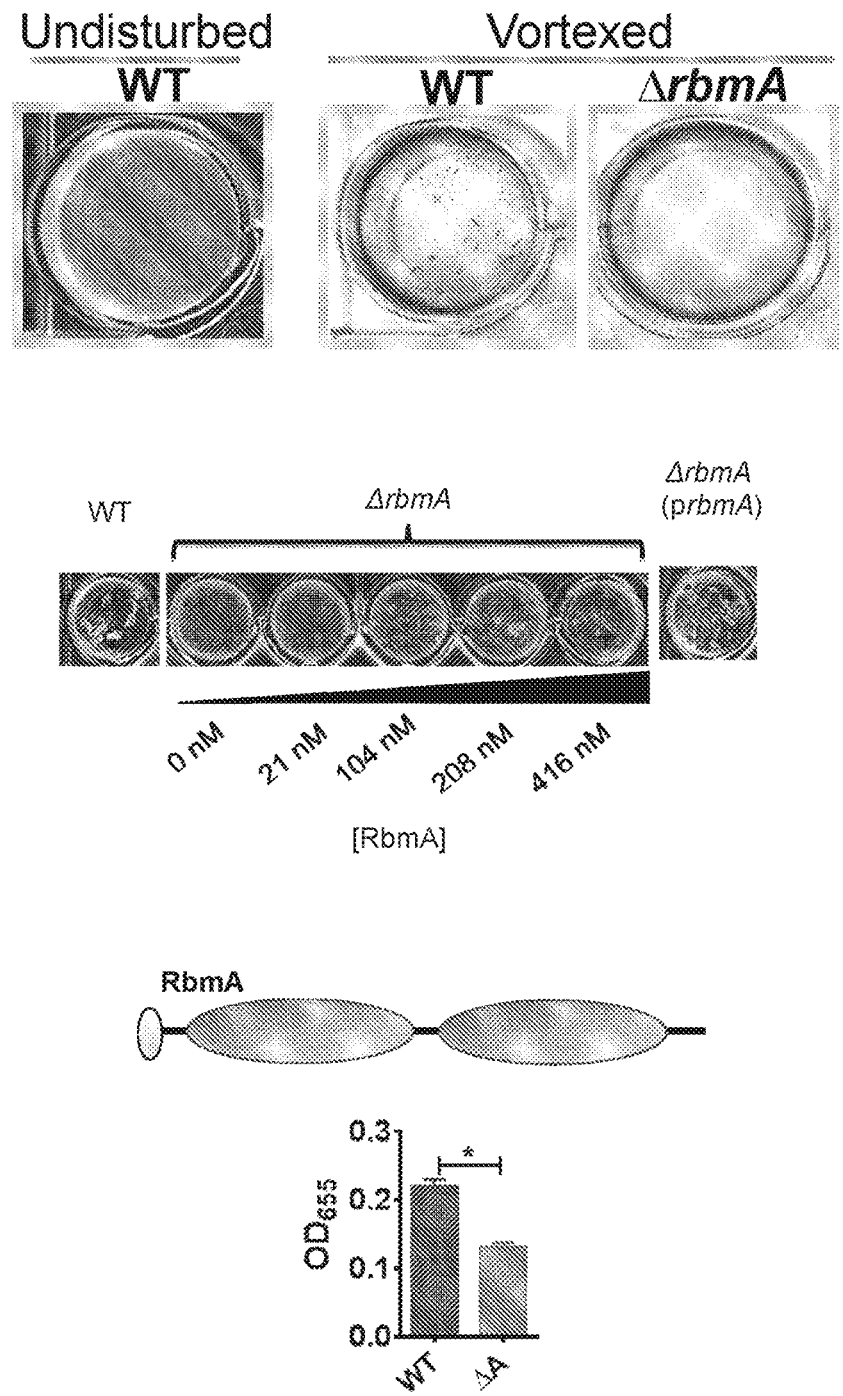
Figure 8:
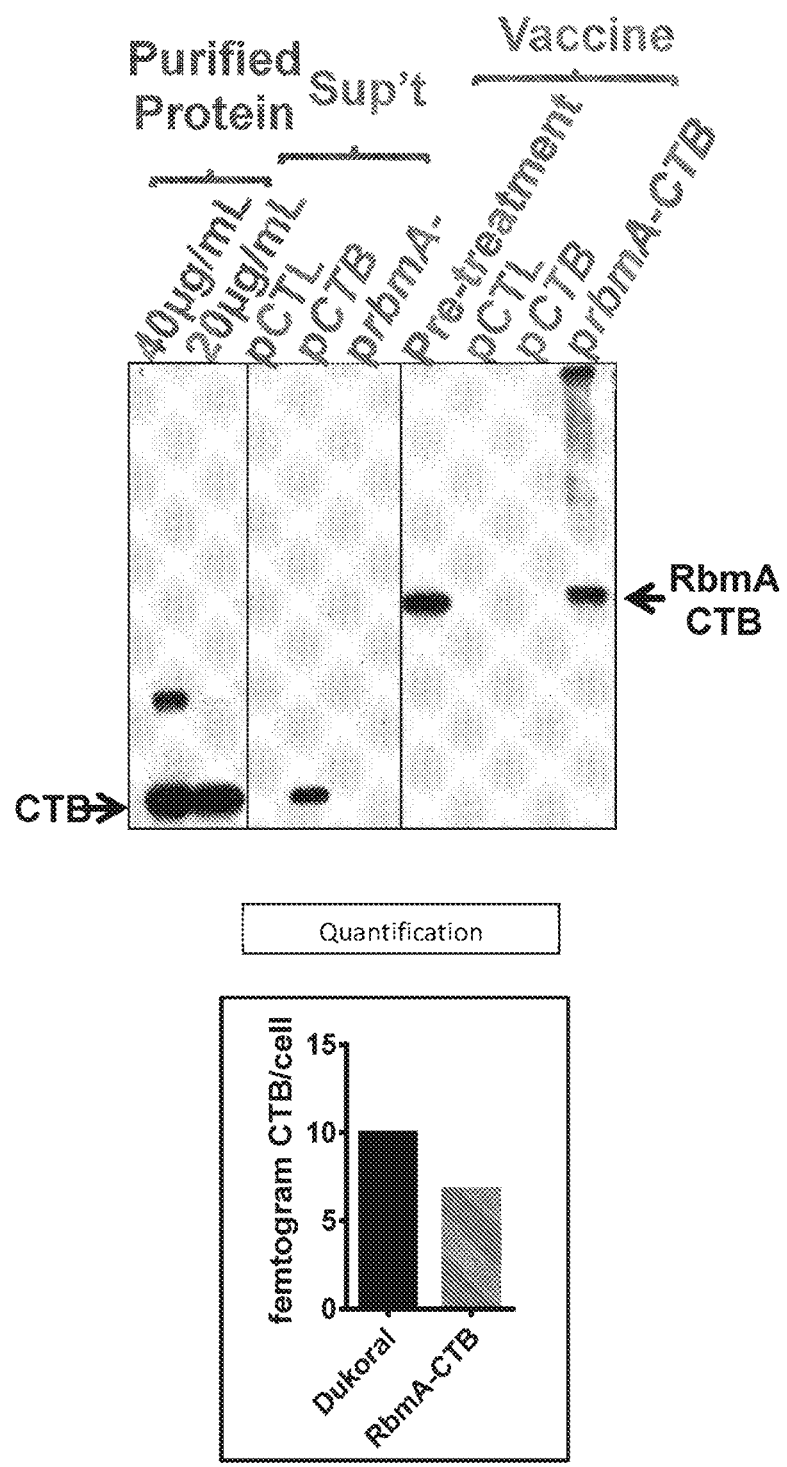

Bap1 and RbmC localize to the base of the biofilm, while RbmA is distributed throughout the biofilm. To correlate the observed biofilm formation defects of Δbap1 ΔrbmC and ΔrbmA mutants with the distribution of these proteins in native biofilms, we added a FLAG affinity tag to the C-terminal end of Bap1, RbmC, and RbmA expressed from their native promoters and performed immunofluorescence microscopy on intact, viable biofilms (FIGS. 6A and B). To quantify the protein distribution, we measured the total fluorescence in each transverse section as a function of distance from the substratum (FIG. 6C). Controls were performed to demonstrate that: (i) all proteins were well-expressed and secreted, (ii) FLAG-tagged proteins did not disrupt biofilm formation, and (iii) cytoplasmic, periplasmic proteins, and other unrelated secreted proteins were NOT visible by this method.

Bap1 and RbmC were noted to localize to the biofilm-surface interface, while RbmA was distributed throughout the biofilm ([1] and data not shown). A similar protein distribution was observed when expression of these proteins was driven by a constitutive promoter on a plasmid, suggesting that spatial localization of proteins in the biofilm is not the result of differential transcription [1].

Addition of purified Bap1 or RbmA can restore wild-type biofilm formation to a Δbap1ΔrbmC or ΔrbmA mutant, respectively. Affinity-tagged Bap1 and RbmA were purified from the supernatants of V. cholerae strains. Each mutant was allowed to form a biofilm in the presence of the purified protein that it lacked. Addition of purified Bap1 or RbmA rescued the biofilm defect of the corresponding mutant [1].

Four biofilm matrix-associated proteins, Bap1, RbmA, RbmC, and HlyA were characterized. The resulting data suggest that these proteins are spatially segregated in the biofilm and adhere to the exopolysaccharide component of the matrix. Accordingly, these proteins can be used to target heterologous molecules, such as functional proteins to specific regions of the biofilm matrix.

Example 3

Structure-Function analysis of HlyA. Of the β-prism domain-containing proteins specifically discussed herein, HlyA has been most intensively studied because of its hemolytic activity [17, 18, 19]. Although it has not previously been implicated in biofilm formation, researchers have postulated a role for HlyA in the environment because it is well-represented in environmental strains of V. cholerae [21, 22]. In this experiment, the role of HlyA in biofilm formation is characterized and the minimal HlyA peptide required for association with the biofilm, or, in other words, the minimal exopolysaccharide-binding HlyA fragment, is identified.

Characterization of the role of full length HA in biofilm formation. First, an in-frame deletion of HlyA in a wild-type genetic background is constructed to determine if HlyA plays a role in biofilm surface attachment and/or structure. The impact of HlyA deletion in a Δbap1ΔrbmC mutant background is also assessed in order to determine if the function of HlyA overlaps at all with that of Bap1 and RbmC. Surface attachment is quantified and the resistance of ΔhlyA and ΔhlyA Δbap1ΔrbmC biofilms to shaking and vortexing is analyzed in analogy to the analyses performed for ΔrbmA and Δbap1ΔrbmC biofilms. If a biofilm phenotype is observed, rescue experiments are performed with an HlyA-FLAG construct encoded on a plasmid. Adequate protein expression is confirmed by Western analysis.

Distribution of HlyA in the biofilm matrix. In this experiment, the transverse and vertical distributions of HlyA in the V. cholerae biofilm matrix are defined. The goal of this experiment is two-fold: first, to better understand the roles of the conserved domains of HlyA in spatial localization within the biofilm; and second, to identify additional proteins with distinct matrix distributions within the biofilm that may be useful to target proteins to different regions within the biofilm matrix. To this end, strains are constructed that express HlyA-FLAG both from its native promoter on the chromosome and from a constitutive promoter on a plasmid. After these tagged HlyA constructs are confirmed to be well expressed by Western analysis, the distribution of these proteins in the biofilm are examined by coupling confocal microscopy with immunofluorescence. The distribution of HlyA in the biofilm matrix is compared to that of Bap1, RbmA, and RbmC.

Role of the HlyA cytolysin, β-trefoil, and β-prism domains in biofilm matrix association. As illustrated in the crystal structure shown in FIG. 4, the domains of HlyA are spatially separated. The minimal peptide required for attachment to the V. cholerae biofilm matrix is identified. From a plasmid, a series of six FLAG-tagged, HlyA-based peptides are constitutively expressed. These engineered peptides include either one or two conserved domains of HlyA. After establishing expression and stability, association of these peptides with the biofilm matrix is assessed by immunofluorescence. A negative result is not informative as it might reflect severe compromise of the three-dimensional domain structure. However, a positive result allows to assign roles in biofilm association to one or more domains of HlyA. If HlyA plays an essential role in biofilm formation, these experiments are performed in a wild-type genetic background only. Otherwise, these experiments are performed in ΔhlyA and Δbap1ΔrbmC mutant g backgrounds as well as in wild-type V. cholerae.

Functional analysis of HlyA point mutants. If the β-trefoil and β-prism domains are required for biofilm matrix association, mutation of the conserved sugar-binding residues within these domains will decrease protein retention within the biofilm. In this experiment, residues in the β-trefoil and β-prism lectin domains of HlyA that are predicted to be critical for binding to the polysaccharide component of the biofilm matrix are mutated.

The D-trefoil domain of HlyA contains two out of three QXW sugar-binding motifs that are conserved in ricin-like lectins (Q537/F539 and Q574/W576). In the crystal structures of β-prism domains of jacalin-like lectins, several conserved amino acids are known to make contacts with the bound sugar. These include an aspartate in a GXXXD motif that forms a hydrogen bond with the sugar and two aromatic residues that form stacking interactions with the bound sugar [23]. The β-prism domain of HlyA contains these conserved putative sugar binding residues (G647, D651, Y698, and Y723). FLAG-tagged versions of full length HlyA and HlyA peptides found to be matrix-associated in the experiment above are constructed with one or more of the conserved residues replaced by alanine. Mutant proteins are expressed from a plasmid along with a C-terminal FLAG-tag in wild-type *V. cholerae* as well as in ΔhlyA and Δbap1ΔrbmC mutants. After ascertaining that these mutant proteins are adequately expressed and stable by Western analysis, their biofilm retention and spatial localization within the pellicle or biofilm matrix is assessed by immunofluorescence. The creation of point mutations by alanine substitution is unlikely to disturb the protein structure. If a mutation of a residue has no effect on matrix binding, it can be concluded that this residue is not essential for matrix binding function.

Example 4

Identification of additional biofilm matrix-binding proteins. Eighteen additional candidate matrix-associated proteins that were identified in a preliminary proteomic analysis are characterized (see Table 2). While all of these proteins are predicted to be secreted, their function and role in biofilm formation has not been characterized. The preliminary results are validated by characterizing the role and distribution of confirmed biofilm matrix-associated proteins using an approach that has been successful in characterization of Bap1, RbmA, and RbmC [1].

Confirmation of protein secretion. To establish that the proteins listed in Table 2 are secreted outside the cell, the relevant gene is cloned along with its native signal sequence and a C-terminal FLAG affinity tag into an IPTG-inducible expression vector. These vectors are electroporated into wild-type *V. cholerae*. The engineered strains are grown to mid-log phase in the presence and absence of inducer (IPTG). Cells are pelleted and separated from the supernatant. Western analysis is carried out on both the cell pellet and supernatant to determine if the proteins are expressed and secreted. Similarly treated strains expressing FLAG-tagged cytoplasmic and periplasmic proteins are used as controls to establish that the experimental treatment does not release cytoplasmic and periplasmic contents into the medium. Importantly, the controls behaved appropriately in previous experiments that are now published [1].

Assessment of biofilm matrix association. To determine whether secreted proteins are selectively retained in the matrix, biofilms are formed with strains expressing the FLAG-tagged proteins and the proteins are visualized in the biofilm matrix using immunofluorescence. Similarly expressed cytoplasmic and periplasmic proteins are used as controls. Only proteins that are secreted and visualized in the biofilm matrix are pursued further.

Native distribution of proteins in the biofilm matrix. The native distributions of proteins found to associate with the biofilm matrix is characterized. Strains are constructed in which the protein of interest is expressed from its native promoter with the addition of a C-terminal FLAG affinity tag. Biofilms are formed with these strains, and immunofluorescence is used to image the distribution of the protein in the biofilm.

Role of biofilm matrix-associated proteins in biofilm formation. In order to determine the function of biofilm matrix-associated proteins in biofilm formation. *V. cholerae* carrying in-frame deletions in the genes encoding these proteins are created. Biofilm formation by these mutants is quantified and compared to that by wild-type *V. cholerae*. The resistance of mutant biofilms to surface dissociation and dispersal is also tested by shaking and vortexing. If no phenotype is observed, it is concluded that the respective protein does not play a structural role in biofilm formation.

Identification of minimum biofilm-association peptides. For any multi-domain proteins that are identified in these experiments, experiments similar to those described for HlyA are performed to identify the minimal peptide required for association with the biofilm.

Example 5

There is evidence that matrix-associated proteins fulfill similar roles in the biofilms of other organisms [12, 13, 24, 25]. While *V. cholerae* may not be a suitable host for some applications, the "proof of principle" experiments described herein serve as a model for application development in other bacteria.

Targeting a secreted, active enzyme to a specific location within the biofilm matrix. ChiA-2 is an efficiently secreted chitinase that is not concentrated in the biofilm matrix [1]. In this experiment, ChiA-2 is targeted to the biofilm matrix via conjugation to an exopolysaccharide-associated protein. The tagged versions of each of the exopolysaccharide-associated proteins described herein are fused to the C-terminus of ChiA-2 via recombinant technology, and the recombinant nucleic acids encoding the resulting chimeric proteins are placed in a neutral chromosomal location such as the lacZ gene of wild-type *V. cholerae*. Immunofluorescence is used to compare the levels and distribution of ChiA-2 in the biofilm matrix in the presence and absence of the recombinant proteins. For all chimeric proteins that successfully localize ChiA-2 in the biofilm matrix, a fluorescent chitinase substrate is used to compare biofilm-associated chitinase activity in the presence and absence of matrix-associated ChiA-2.

It is expected that it is possible to target a protein, e.g., ChiA-2 to either the substrate-biofilm interface or the biofilm apex by using specific exopolysaccharide-associated proteins as fusion partners for the protein. In some embodiments, surface-active proteins (e.g., proteins with antibacterial, glycolytic, lipolytic, or proteolytic activity) are targeted to concentrate at the biofilm matrix-surface interface for purposes of medical treatment or bioremediation.

Targeting a secreted antigen to the biofilm matrix. The oral cholera vaccine currently licensed in Europe consists of whole cell, killed *V. cholerae* strains combined with the purified cholera toxin B subunit (CtxB) [26]. This vaccine affords some protection against cholera and traveler's diarrhea but is expensive to produce and administer. Therefore, simpler whole cell, killed vaccines have been developed in Vietnam and India 191.

A whole cell, killed vaccine strain that concentrates CtxB in the biofilm matrix would be less expensive to administer and produce and could be more immunogenic. Furthermore, one could engineer a strain that also incorporated protein antigens affording protection against other diarrheal diseases, thus generating a broad spectrum diarrhea vaccine.

To explore this application, a strain of *V. cholerae* is engineered in which CtxB is targeted to the biofilm matrix via fusion to an exopolysaccharide-associated protein. The resulting biofilm is processed into a killed-cell vaccine according to methods known to those of skill in the art. The vaccine is administered to a human subject, resulting in an immune response similar to that of a currently licensed *V. cholerae* vaccine.

REFERENCES

1. Absalon, C., Van Dellen, K. & Watnick, P. I. A communal bacterial adhesin anchors biofilm and bystander cells to surfaces. PLoS Pathog 7, e1002210 (2011).

2. Karatan, E. & Watnick, P. Signals, regulatory networks, and materials that build and break bacterial biofilms. Microbiol Mol Biol Rev 73, 310-347 (2009).
3. Nadell, C. D. & Bassler, B. L. A fitness trade-off between local competition and dispersal in *Vibrio cholerae* biofilms. Proc Natl Acad Sci USA 108, 14181-14185 (2011).
4. Fong, J. C., Karplus, K., Schoolnik, G. K. & Yildiz, F. H. Identification and characterization of RbmA, a novel protein required for the development of rugose colony morphology and biofilm structure in *Vibrio cholerae*. J Bacteriol 188, 1049-1059 (2006).
5. Fong, J. C. & Yildiz, F. H. The rbmBCDEF gene cluster modulates development of rugose colony morphology and biofilm formation in *Vibrio cholerae*. J Bacteriol 189, 2319-2330 (2007).
6. Moorthy, S. & Watnick, P. I. Identification of novel stage-specific genetic requirements through whole genome transcription profiling of *Vibrio cholerae* biofilm development. Mol Microbiol 57, 1623-1635 (2005).
7. Svennerholm, A. M. From cholera to enterotoxigenic *Escherichia coli* (ETEC) vaccine development. Indian J Med Res 133, 188-196 (2011).
8. Saha, A., et al. Safety and immunogenicity study of a killed bivalent (O1 and O139) whole-cell oral cholera vaccine Shanchol, in Bangladeshi adults and children as young as 1 year of age. Vaccine 29, 8285-8292 (2011).
9. Lopez-Gigosos, R. M., Plaza, E., Diez-Diaz, R. M. & Calvo, M. J. Vaccination strategies to combat an infectious globe: oral cholera vaccines. J Glob Infect Dis 3, 56-62 (2011).
10. Romero, D., Aguilar, C., Losick, R. & Kolter, R. Amyloid fibers provide structural integrity to *Bacillus subtilis* biofilms. Proc Natl Acad Sci USA 107, 2230-2234.
11. Vidal, O., et al. Isolation of an *Escherichia coli* K-12 mutant strain able to form biofilms on inert surfaces: involvement of a new ompR allele that increases curli expression. J Bacteriol 180, 2442-2449 (1998).
12. Diggle, S. P., et al. The galactophilic lectin. LecA, contributes to biofilm development in *Pseudomonas aeruginosa*. Environ Microbiol 8, 1095-1104 (2006).
13. Tielker, D., et al. *Pseudomonas aeruginosa* lectin LecB is located in the outer membrane and is involved in biofilm formation. Microbiology 151, 1313-1323 (2005).
14. Haugo, A. J. & Watnick, P., *Vibrio cholerae* CytR is a repressor of biofilm development. Mol Microbiol 45, 471-483 (2002).
15. Sankaranarayanan R, Sekar K, Banerjee R. Sharma V, Surolia A, et al. (1996) A novel mode of carbohydrate recognition in jacalin, a Moraceae plant lectin with a beta-prism fold. Nat Struct Biol 3: 596-603.
16. Roque-Barreira M C, Campos-Neto A (1985) Jacalin: an IgA-binding lectin. J Immunol 134: 1740-1743.
17. Olson R, Gouaux E (2005) Crystal structure of the *Vibrio cholerae* cytolysin (VCC) pro-toxin and its assembly into a heptameric transmembrane pore. J Mol Biol 350: 997-1016.
18. Krasilnikov O V, Merzlyak P G, Lima V L, Zitzer A O, Valeva A. et al. (2007) Pore formation by *Vibrio cholerae* cytolysin requires cholesterol in both monolayers of the target membrane. Biochimie 89: 271-277.
19. Zitzer A, Zitzer O, Bhakdi S, Palmer M (1999) Oligomerization of *Vibrio cholerae* cytolysin yields a pentameric pore and has a dual specificity for cholesterol and sphingolipids in the target membrane. J Biol Chem 274: 1375-1380.
20. Singh D V, Matte M H, Matte G R, Jiang S, Sabeena F. et al. (2001) Molecular analysis of *Vibrio cholerae* O1, O139, non-O1, and non-O139 strains: clonal relationships between clinical and environmental isolates. Appl Environ Microbiol 67: 910-921.
21. Rahman M H, Biswas K, Hossain M A, Sack R B, Mekalanos J J, et al. (2008) Distribution of genes for virulence and ecological fitness among diverse *Vibrio cholerae* population in a cholera endemic area: tracking the evolution of pathogenic strains. DNA Cell Biol 27: 347-355.
22. Goel A K, Jain M, Kumar P, Kamboj D V, Singh L Virulence profile and clonal relationship among the *Vibrio cholerae* isolates from ground and surface water in a cholera endemic area during rainy season. Folia Microbiol (Praha) 55: 69-74.
23. Raval S, Gowda S B, Singh D D, Chandra N R (2004) A database analysis of jacalin-like lectins: sequence-structure-function relationships. Glycobiology 14: 1247-1263.
24. Borlee B R, Goldman A D, Murakami K, Samudrala R, Wozniak D J, et al. *Pseudomonas aeruginosa* uses a cyclic-di-GMP-regulated adhesin to reinforce the biofilm extracellular matrix. Mol Microbiol 75: 827-842.
25. Danese P N, Pratt L A, Dove S L, Kolter R (2000) The outer membrane protein, antigen 43, mediates cell-to-cell interactions within *Escherichia coli* biofilms. Mol Microbiol 37: 424-432.
26. Lopez-Gigosos R. Garcia-Fortea P, Reina-Dona E, Plaza-Martin E (2007) Effectiveness in prevention of travelers' diarrhea by an oral cholera vaccine WC/rBS. Travel Med Infect Dis 5: 380-384.
27. Attridge, Stephen R., et al. "Susceptibility of *Vibrio cholerae O*139 to antibody-dependent, complement-mediated bacteriolysis." Clinical and Diagnostic Laboratory Immunology 7.3 (2000): 444450.

Example 6 A Self-Assembling, Self-Adjuvanting Whole Cell Vaccine Targeting Diarrheal Disease In low-income countries, severe diarrhea caused by intestinal pathogens is the primary cause of morbidity in children under the age of five. Vaccines are a cost-effective means of disease prevention. However, vaccines targeting the most common intestinal pathogens are lacking, and the highest incidence of childhood diarrheal disease occurs in regions that are unable to fund immunization campaigns without financial assistance. Therefore, there is a great need for a multi-valent diarrheal vaccine that is inexpensive to prepare and simple to administer. Described herein is a self-assembling vaccine platform based on *Vibrio cholera*. A multivalent, live-attenuated vaccine was developed based on this platform that elicits a robust immune response against enterotoxigenic *E. coli* and *Vibrio cholerae* antigens when administered sublingually.

Figure 15A:
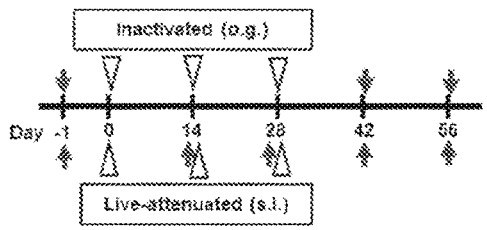
Figure 15B:
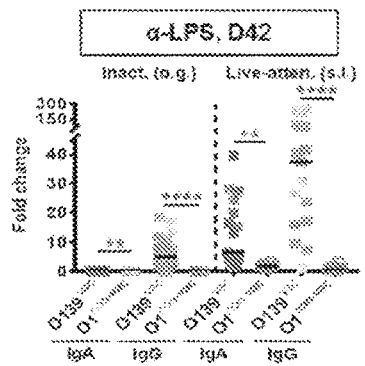
Figure 15C:
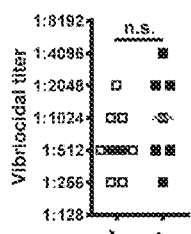
Figure 15D:
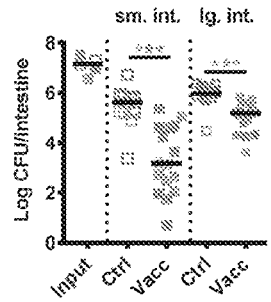
Figure 15E:
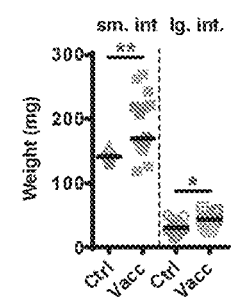
Figure 15F:
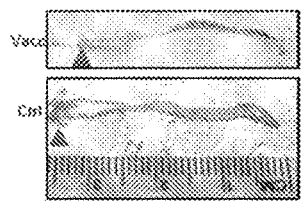
Figure 15G:
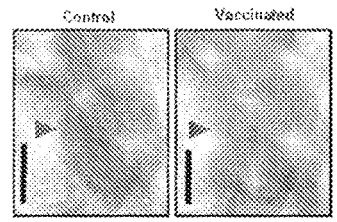
Figures 15H, 15I, 15J:
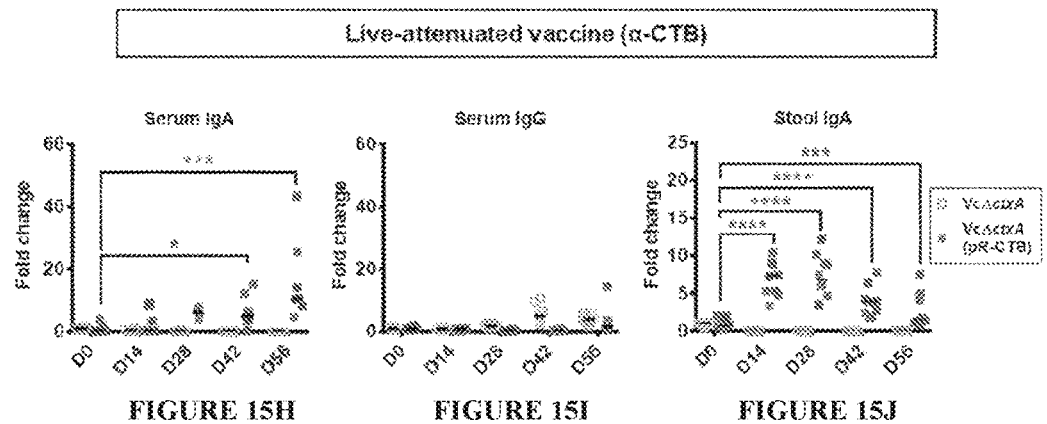
Figures 15K, 15L, 15M, 15N:
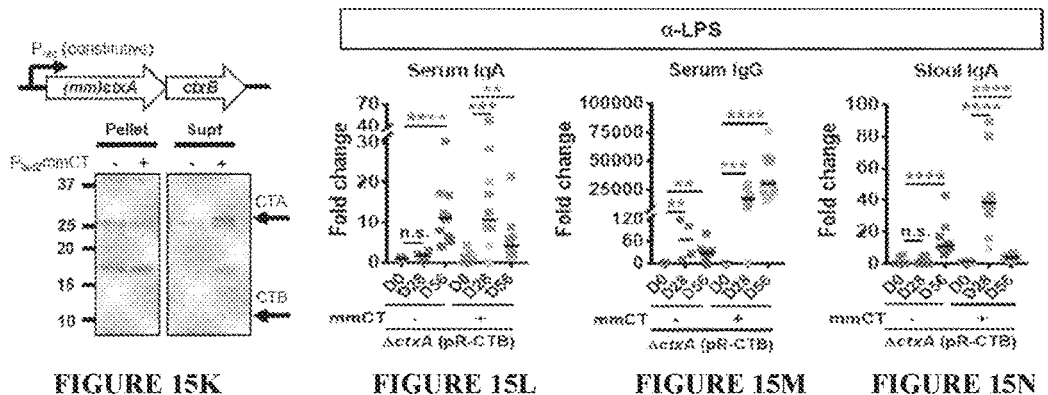

In low-income countries, severe diarrhea caused by intestinal pathogens is the primary cause of morbidity, leading to 1.7 billion cases of childhood disease annually with profound consequences for physical and mental development[1]. Treatment of infection is essential for survival, but prevention is preferable as it allows these children to escape life-altering developmental sequelae. In the absence of improved sanitation, vaccination is an excellent means of prevention. The *Vibrio cholerae* biofilm matrix has previously been proposed to be able to be used to link secreted proteins to the cell surface. It is demonstrated herein that fusion of an enterotoxigenic *E. coli*-derived heat-stable toxoid (STa$^{414H}$) and the B subunit of the heat-labile toxin (LTB) to the *Vibrio cholerae* biofilm matrix protein RbmA results in decoration of whole cells with these antigens and a robust immune response when administered sublingually as a live-attenuated, whole cell vaccine. The immune response to this vaccine can be boosted by inclusion of a chromosomally-encoded, constitutively expressed, non-toxic cholera toxin variant mmCT[3,4]. A self-assembling, flexible protein antigen presentation platform was developed that can be used to create an affordable combination vaccine targeting diarrheal disease.

Results

RbmA, a lectin that spontaneously associates with the biofilm matrix polysaccharide VPS after secretion from the cell, consists of two tandem fibronectin III domains. These domains are presumed to bind to VPS as an antiparallel homodimer to mediate cell-to-cell adhesions[5-7] (FIG. 14A). While RbmA is essential for biofilm structure and development8, some strains of *V. cholerae* express VPS and RbmA in the free-swimming or planktonic state[2]. It was previously shown that proteins of interest could be anchored to VPS by genetic fusion to the C terminus of RbmA and hypothesized that cells expressing RbmA-antigen fusion proteins could serve as antigen presentation vehicles for mucosal vaccination.

Dukoral, a currently licensed cholera vaccine, consists of killed, whole *V. cholerae* cells combined with the purified B subunit of cholera toxin (CTB). This vaccine is costly and must be administered with sodium bicarbonate resuspended in a large volume of potable water to ensure presentation of intact CTB to the intestinal immune system. Due to the higher cost and requirement for potable water. Dukoral is mainly a vaccine of travelers. To determine whether a vaccine presenting a comparable amount of CTB could be developed without the need for purification or administration with bicarbonate, a prototype strain was generated harboring a plasmid expressing CTB fused to the C terminus of RbmA under the control of an inducible promoter (Vc (pR-CTB)) (FIG. 14B). A similar strain harboring a plasmid encoding native CTB was used as a control. Western blot analysis was used to assess association of CTB to cells. It was found that R-CTB was efficiently anchored to the bacterial cell, whereas CTB expressed alone was found exclusively in the culture supernatant (FIG. 14C). In fact, the amount of CTB associated with the cell pellet compared favorably to that incorporated in the Dukoral vaccine (FIG. 14D).

Planktonic Vc(pR-CTB) was tested as a formalin-inactivated whole cell vaccine. While formalin treatment led to some protein cross-linking, CTB remained cell-associated (FIG. 17). The fixed vaccine preparation was administered to mice by orogastric gavage (o. g.) with boosters 2 and 4 weeks later (FIG. 15A) and measured the immune response. As a positive control, a Dukoral-like vaccine consisting of formalin-fixed wild-type *V. cholerae* combined with purified CTB was prepared. Although not required for the fixed vaccine, both Vc(pR-CTB) and the positive control were administered with bicarbonate to allow a direct comparison. Negative controls included PBS alone and formalin-fixed wild-type *V. cholerae*. While the Dukoral-like vaccine induced production of CTB-specific serum IgA and IgG, the formalin-treated Vc(pR-CTB) vaccine elicited no antigen-specific antibodies (FIGS. 18A-18C). It was hypothesized that this was the result of formalin fixation of CTB, which has been reported to alter protein structure and abrogate antigenicity[9]. Therefore, formalin fixation was eliminated and a live-attenuated formulation of Vc(pR-CTB) was used.

Several live-attenuated *V. cholerae* vaccines are either under development or licensed[10-12]. However, these vaccines have disadvantages. Because *V. cholerae* is extremely acid-sensitive and colonization of the intestine is thought to be essential for a robust immune response, such vaccines must be administered with bicarbonate to maintain viability during transit through the stomach. Furthermore, the intestinal colonization required for immunogenicity increases the risk of acquisition of the phage carrying cholera toxin and dissemination into the environment[13]. To minimize these disadvantages, pR-CTB was introduced into a ΔctxA strain (VcΔctxA (pR-CTB)) and administered via the sublingual route (s.l.) according to the vaccination schedule shown in FIG. 15A. Sublingual immunization with live *V. cholerae*, given without bicarbonate, resulted in low level shedding of live bacteria that ceased after 24 hours (FIG. 19). Next, the antibody response to the *V. cholerae* O-antigen carbohydrate of the lipopolysaccharide (LPS) was examined. Although generation of protective anti-*V. cholerae* O-antigen antibodies by oral vaccines is well-described, the immune response to a sublingually administered, live-attenuated *V. cholerae* vaccine has not been determined[14-17]. It was found that, for both the oral, inactivated Vc(pR-CTB) and the sublingual, live-attenuated VcΔctxA (pR-CTB) vaccine, O-antigen specific IgA and IgG antibodies were detected in serum two weeks after the final immunization (FIG. 15B). Furthermore, the serum vibriocidal titers, a measurement of antibody-mediated activation of serum complement and a predictive marker for protection against disease, did not differ between the two vaccine groups (FIG. 15C). Finally, the level of O-specific IgA in serum was significantly higher in the group that received the sublingual, live-attenuated vaccine as compared with the group that received the inactivated vaccine. Because robust immune responses to the O-antigen and high vibriocidal titers are correlated with protection against infection, it was tested whether the live-attenuated, sublingual vaccine afforded passive immunity using an infant mouse model. Suckling mice born to immunized or unimmunized dams were challenged with wild-type *V. cholerae* and assessed for disease outcome after 24 hours[18, 19]. Pups born to vaccinated dams had significantly decreased *V. cholerae* colonization (FIG. 15D). Furthermore, animals in the unvaccinated group exhibited signs of cholera including weight loss, fluid accumulation in the large intestine and cecum, and reduced skin turgor indicative of dehydration (FIGS. 15E-15G). The results show that sublingual immunization with a live-attenuated *V. cholerae* vaccine stimulates a robust immune response comparable to that provided by the currently licensed, oral inactivated vaccine and provides passive protection against cholera in a murine model.

Next, the generation of CTB-specific antibodies in serum and stool was evaluated. CTB-specific serum IgA was significantly increased six weeks after the initial vaccine dose, while serum IgG was not detected throughout the study period (FIGS. 15H and 151). Secretory IgA in stool was significantly increased two weeks after the first vaccine dose and remained elevated throughout the study period (FIG. 153). This was consistent with a previous report that sublingual immunization with a live bacteria vector generated antigen-specific fecal IgA but not serum IgG[20]. These results demonstrate for the first time that a protein antigen anchored on RbmA can be delivered sublingually to stimulate a robust antigen-specific mucosal immune response.

Inspired by the success of the VcΔctxA(pR-CTB) vaccine, the vaccine strain was engineered to produce its own adjuvant by introducing the cholera toxin-based adjuvant mmCT[3] onto the chromosome under control of the lacZ promoter (PlacZmmCT) (FIG. 15K). First, the secretion of the mmCT components was confirmed by Western blot (FIG. 15K). The vaccine was then administered to mice following the immunization and sample collection scheme shown in FIG. 15A. Inclusion of mmCT greatly enhanced the systemic and mucosal immune responses to the O-antigen (FIG. 15L-15N, FIGS. 20A-20C), but abrogated the mucosal immune response to CTB (FIGS. 21A-21C). It was hypothesized that delivery of CTB within mmCT in addition to that affixed to RbmA might have stimulated tolerance. To assess this possibility, the amount of mmCT secreted during the approximate period the vaccine remains in the murine sublingual site and the amount of CTB delivered as R-CTB in a single vaccine dose were compared. As shown in FIG. 22, mmCT contributed minimally to the total level of CTB. This suggests that mmCT may induce tolerance to protein antigens such as CTB when delivered via the sublingual route. To minimize this effect, we decreased the amount of antigen delivered in subsequent vaccine trials by expression of fusion proteins from the native RbmA promoter rather than from a multi-copy plasmid. In addition, three improvements (FIG. 16A) were instituted. First, the whole cell platform was transferred to the *V. cholerae* vaccine strain Bengal-2, in which all elements of the CTX phage responsible for horizontal transfer of cholera toxin are absent[21]. Second, because the robust immune response obtained with sublingual vaccination suggested that intestinal colonization was not essential, the gene encoding the major subunit of the principal colonization factor, tcpA was deleted. Third, the heterologous antigens from enterotoxigenic *Escherichia coli* (ETEC), a major cause of childhood diarrhea worldwide[1], was introduced. Based on previous studies[22,23,24], the genes encoding LTB and an immunogenic STa point mutant were linked to that encoding RbmA on the chromosome at the native RbmA locus (R-LTB/STa$^{A14H}$).

The performance of the multi-valent, improved diarrheal vaccine was then assessed. Secretion and cell-association of R-LTB/STa$^{A4}$H were documented by Western blot (FIG. 16B), and it was estimated that each vaccine dose delivered approximately 30 femtomoles of cell-associated R-LTB/STa$^{A14H}$ (FIG. 23). This vaccine was administered to mice (FIG. 16C). Levels of LTB- or CTB-specific IgA and IgG in the serum after one vaccine dose were comparable between the mice that received the adjuvanted vaccine with ETEC antigens and those that received the adjuvanted vaccine alone. Furthermore, STa-specific IgG was strongly induced in the serum between two to four weeks after the first vaccine dose (FIG. 16H). There was also a trend towards increased STa-specific IgA in serum but this did not reach statistical significance (FIG. 16G). Stool IgA was not detected (FIG. 16I). STa is known to be poorly immunogenic. To determine whether it is possible to increase the immune response, a second vaccine dose was delivered after 36 days (FIG. 16C). A boosting effect was seen in the group that received the control vaccine, while an immune suppressive effect was found in the R-LTB/STa$^{A14H}$ vaccine group after the second dose (FIGS. 16D-16I). This supports the hypothesis that co-administration of mmCT and a protein antigen leads to immune tolerance and that delivery of smaller quantities of this antigen mitigate this effect. Taken together, the results suggest that an optimized vaccine would include mmCT alone combined with RbmA fused to additional copies of STa, which has previously been shown to improve immunogenicity[25].

ST-producing enterotoxigenic *E. coli. Shigella* spp., *Aeromonas* spp., *V. cholerae*, and *Campylobacter jejuni*, have been identified as the five most common bacterial causes of severe childhood diarrhea in the developing world1. Yet currently a vaccine against only one of these pathogens, *V. cholerae*, is licensed for pediatric use. Described herein is the development of a self-assembling, multi-valent, self-adjuvanting sublingual vaccine that generates immunity against both *V. cholerae* and ETEC antigens. The platform described herein simplifies manufacturing and administration costs and provide a path to affordable, efficacious combination vaccines against diarrheal pathogens for use in resource-poor settings.

TABLE 6

Vaccine Constructs

| Strains/Plasmid | Description | Reference |
|---|---|---|
| *V. cholerae* | | |
| PW17 | N16961 (El Tor, Inaba); Sm$^r$ | 1 |
| PW724 | MO10; Sm$^r$ | 2 |
| PW839 | MO10ΔctxA; Sm$^r$ | 3 |
| PW1947 | MO10ΔctxA, $P_{lacZ}$mmCT; Sm$^r$ | This study |
| PW139 (Bengal-2) | MO10ΔattRS1; Sm$^r$ | 2 |
| PW1159 | MO10ΔattRS1ΔtcpA; Sm$^r$ | This study |
| PW1938 | MO10ΔattRS1ΔtcpA, $P_{lacZ}$mmCT; Sm$^r$ | This study |
| PW1934 | MO10AattRS1ΔtcpA, $P_{lacZ}$mmCT, $P_{rbmA}$-rbmA-LTb-STa$^{A14H}$; Sm$^r$ | This study |
| *E. Coli* | | |
| SM10λpir | thi thr leu tonA lacY supE recA::RP4-2-Tc::Mu (λpirR6K); Km$^r$ | 4 |
| Plasmids | | |
| pWM91 | oriR6K mobRP4 lacI pTac tnp mini-Tn10; Km$^r$ Ap$^r$ | 5 |
| pFLAG-CTC-rbmA-ctxB | IPTG-inducible expression of RbmA-CTB fusion protein; Ap$^r$ | 6 |
| pWM91-lacZ::mmCT | pWM91 carrying in-frame mmCT insertion into lacZ for homologous recombination; Ap$^r$ | This study |
| pWM91-rbmA-LTb-STa$^{A14H}$ | pWM91 carrying in-frame insertion of LTb-STa$^{A14H}$ fusion protein between the 3' end of rbmA and downstream sequence; Ap$^r$ | This study |

TABLE 6-continued

Vaccine Constructs

| Strains/Plasmid | Description | Reference |
|---|---|---|
| pHT3 | pCVD442 carrying unmarked, in-frame deletion of tcpA; Ap$^r$ | 7 |

TABLE 7

Primer Sequences

| Primer | Sequence | Note |
|---|---|---|
| | $P_{lacZ}$mmCT | |
| mmCT_1F | GATCATTTGGTAATAGGTATCGATTAAATAAGGAGG (SEQ ID NO: 49) | Stop codons bold and underlined; RBS underlined |
| mmCT_1R | TGCTTTATTTCGTCGGGCGGGCGACTATC (SEQ ID NO: 50) | |
| mmCT_2F | CCGCCCGACGAAATAAAGCAGTCAGGTGGTCTTATGC (SEQ ID NO: 51) | |
| mmCT_2R | ATAACCATCTGCTGCTGGAGCAATATCTAAGTTACTG (SEQ ID NO: 52) | |
| mmCT_3F | ATTGCTCCAGCAGCAGATGGTTATGGATTGGCAGGTTTC (SEQ ID NO: 53) | |
| mmCT_3R | ATCACCCGTGATTGTTCCGCTACTATCCCCACAACCCGGCGGTGCATGATG (SEQ ID NO: 54) | LT189-197 bold and underlined, R192G double underlined |
| mmCT_4F | GATAGTAGCGGAACAATCACGGGTGATACTTGCGATGAAA AAACCCAAAGTC (SEQ ID NO: 55) | |
| mmCT_4R | GATTGGTATTCAGCGTCGAATTTTACACCTAGACTTTG (SEQ ID NO: 56) | L211A double underlined |
| mmCT_5F | GTAAAATTCGCTGACGAATACCAATCTAAAGTTAAAAGAC (SEQ ID NO: 57) | |
| mmCT_5R | GTATTGCACAGGTTAATTTGCCATACTAATTGCG (SEQ ID NO: 58) | |
| lacZ_1F | GCGCGCGCGAGCTCAAGCCTTACATACAGGCCAGCG (SEQ ID NO: 59) | SacI site underlined |
| lacZ_1R | CGATACCTATTACCAAATGATCACACAAGGGTG (SEQ ID NO: 60) | Stop codons bold and underlined |
| lacZ_2F | GCAAATTAACCTGTGCAATACGAAGGGGC (SEQ ID NO : 61) | |
| lacZ_2R | GCGCGCGCGAGCTCGCTGGACTTTTTTGACTTCATGTAATG (SEQ ID NO: 62) | SacI site underlined |
| | rbmA-LTb-STa$^{A14H}$ | |
| rbmA_1F | ATTGGGTACCGGGCCCCCCCCTCTTACTGATGGTCGTATG (SEQ ID NO: 63) | |
| rbmA_1R | CCACTGTCATTGACTGTTCC (SEQ ID NO: 64) | |
| rbmA_2F | GTCGTATGTATAAAAAACCG (SEQ ID NO: 65) | |
| rbmA_2R | CTTATCGATACCGTCGACCTCGATAGCATCAATGACCCAAAC (SEQ ID NO: 66) | |

TABLE 8

Adjuvant and Antigen Nucleotide Sequences

| Construct | Sequence synthesized | Note |
|---|---|---|
| P$_{lacZ}$mmCT | GTATCGATTAAATAAGGAGGAATAAACCATGGTAAAGATAATC<br>TTCGTGTTCTTCATCTTCCTGAGCAGCTTTTCGTACGCTAACGAT<br>GATAAGCTCTATCGCGCAGATAGTCGCCCGCCCGACG (SEQ ID NO: 47) | RBS underlined |
| rbmA-LTBS Ta$^{414H}$ | GAGTGGAACAGTCAATGACAGTGGTAAAGAAGATGAATAAAG<br>TAAAATGTTATGTTTTATTTACGGCGTTACTATCCTCTCTATGTG<br>CATACGGAGCTCCCCAGTCTATTACAGAACTATGTTCGGAATAT<br>CGCAACACACAAATATATACGATAAATGACAAGATACTATCAT<br>ATACGGAATCGATGGCAGGCAAAAGAGAAATGGTTATCATTAC<br>ATTTAAGAGCGGCGCAACATTTCAGGTCGAAGTCCCGGGCAGTC<br>AACATATAGACTCCCAAAAAAAAGCCATTGAAAGGATGAAGGACA<br>CATTAAGAATCACATATCTGACCGAGACCAAAATTGATAAATT<br>ATGTGTATGGAATAATAAAACCCCCAATTCAATTGCGGCAATCAG<br>TATGGAAAAC<u>GATCCCCGGGTACCGAGCTCG</u>aatagtagcaattactgctgtgaa<br>ttgtgttgtaatcct<u>CAT</u>tgtaccgggtgctatTAAATTTACCTAGTCACTTAGTCG<br>TATGTATAAAAAACCG (SEQ ID NO: 48) | AAA to AAG degenerate codon change bold and underlined Start and stop codons bold Linker between LTb and STa underlined A14H change double underlined |

Methods

Bacterial strains and culture conditions. *Vibrio cholerae* strains were cultured in Luria-Bertani (LB) broth supplemented with 100 µg/mL streptomycin at 27° C., with shaking at 200 rpm. *Escherichia coli* was grown in LB broth at 37° C. with shaking. Where necessary, plasmids were maintained with 100 µg/mL of ampicillin in the culture medium. Protein production was induced with 0.5 mM IPTG (D-d-1-thiogalactopyranoside). Frozen stocks were maintained in 15% glycerol at −80° C. Strains used in this study are listed in Table 6.

DNA manipulations and strain construction. All oligonucleotides were synthesized by Integrated DNA Technologies and detailed in Tables 7 and 8. Restriction enzymes were purchased from New England Biolabs (NEB) and used according to manufacturer's instructions. Gibson assembly of DNA fragments was carried out with the NEBuilder HiFi DNA Assembly kit (NEB). PCR reactions were performed with GoTaq polymerase (Promega) for screening and Q5 High-Fidelity polymerase (NEB) for cloning. Genomic DNA from wild-type MO10, a *V. cholerae* O139 serotype strain, was used as the PCR template unless otherwise noted.

Construction of the prototype vaccine expressing pR-CTB. The previously described pFLAG-CTC derivative carrying the gene encoding the B subunit of cholera toxin (CTB) fused to the gene encoding RbmA (R-CTB)2 or CTB alone under an IPTG-inducible promoter was introduced into wild-type MO10 or ΔctxA by electroporation. Protein production in positive transformants was verified by Western blot analysis using an anti-CTB antibody as described below.

Construction of PlacZmmCT in *V. cholerae*. The mmCT sequence was obtained by Gibson assembly of PCR fragments amplified from genomic DNA with exception of the first 97 bases, which were amplified from an oligonucleotide synthesized to contain the proximal ribosome binding motif from the Ptrc promoter and the first 97 nucleotides of the ctxA gene. Mutations of mmCT4 and stop codons distal to the ribosome binding site were introduced on primers and confirmed in the assembled product by sequencing. This was then ligated between two PCR fragments of the lacZ gene by Gibson assembly to obtain the final construct. The lacZ-mmCT construct was digested using SacI and ligated into the sacB-encoding suicide plasmid pWM91. Plasmids from positive clones were isolated, and the sequence of the inserted DNA was confirmed by sequencing with M13 primers. Homologous recombination into the chromosomal lacZ gene and positive clone selection was carried out as previously described[26,27].

Construction of R-LTB/STa$^{414H}$ vaccine strain. A synthetic oligonucleotide containing the sequence of a fusion peptide between the B subunit of the *E. coli* heat-labile toxin (LTB) and the heat-stable toxin (STa) with an A14H point mutation that abrogated toxicity[22] was custom synthesized (Integrated Gene Technologies). The two sequences were connected by a heptapeptide linker28. The 5' and 3' ends of the oligonucleotide included 32 bp at the 3' end of rbmA excluding the stop codon and 37 bp just downstream of rbmA, respectively. The rbmA stop codon was removed to allow read-through translation of the ETEC antigens. The nucleotides encoding the last two amino acid residues of RbmA were altered from AAA to the degenerate codon AAG to facilitate oligonucleotide synthesis. The STa sequence encoded only the 19 structural amino acid residues and did not include sequences encoding the N terminal residues processed in the pre-pro-peptide. Gibson assembly was used to ligate this fragment, two PCR fragments including ~500 bp encoding the C-terminus of RbmA and ~500 bp downstream of rbmA, respectively, and XhoI-linearized suicide plasmid pWM91. Plasmids from positive clones were confirmed by sequencing. Homologous recombination was carried out as described above. Positive clones were selected through screening by PCR.

Vaccine Preparation

Protein induction. Frozen stocks were inoculated into 3 mL of LB supplemented with streptomycin and ampicillin (LB-Sm/Amp) and cultured at 27° C. overnight. This starter culture was collected by centrifugation, washed once with LB-Sm/Amp, and sub-cultured into 25 mL of fresh LB-Sm/Amp in a 250-mL flask. After incubating for 6-8 h at 27° C. with shaking, IPTG was added to a final concentration of 0.5 mM, and the culture was incubated for an additional 2 h at 27° C. with shaking.

Trichloroacetic acid (TCA) precipitation of secreted proteins. Proteins secreted into the supernatant was precipitated with TCA and washed with acetone. Briefly, spent supernatant was passed through a 0.2 µm filter to remove bacterial cells. TCA was added to the cell-free supernatant to a final concentration of 10% and the supernatant was incubated overnight at 4° C. with gentle mixing. Precipitated proteins were collected by centrifugation and washed three times with ice-cold acetone. Residual acetone was evaporated by brief incubation at 95° C. The protein pellet was resuspended in 4× Laemmli buffer containing β-mercaptoethanol and prepared for Western blot as described below.

Preparation of whole cell vaccines. After protein induction for strains carrying pR-CTB or after overnight culture for the strains encoding chromosomal vaccine constructs, the bacterial culture was centrifuged at 5,000×g for 15 min at 4° C. to collect cells. The supernatant was passed through a 0.2 µm filter, and the resulting cell-free supernatant was used for Western blot analysis. The remaining bacterial pellet was washed three times with 12 mL of sterile PBS and finally resuspended in 1 mL of PBS. This constituted the live, whole cell vaccine. For each vaccine preparation, 10 µL was removed to quantify colony forming units (CFU), and 20 µL was reserved for Western blot analysis. For each immunization, the vaccine was prepared and used within 2 h.

Preparation of the formalin-inactivated whole cell vaccine. An equal volume of freshly prepared 1% formaldehyde was added to the live vaccine suspension and gently mixed overnight at room temperature while protected from light. The following day, cells from the formaldehyde-treated suspension were collected by centrifugation at 5,000×g for 20 min and washed 3 times with 12 mL of PBS. The final cell pellet was resuspended in 5 mL of PBS to obtain the killed whole cell vaccine. From this preparation, 20 µL were reserved for Western blot analysis, 10 µL were cultured in LB medium to test for sterility, and 10 µL were used for cell count in a hemocytometer. Purified CTB was added, where necessary, to match the protein concentration in the Dukoral vaccine.

Western blot analysis. Supernatants and cell pellet samples were separated by centrifugation. TCA precipitation of the supernatant was performed prior to detection of mmCT. These samples were combined with 4× Laemmli buffer containing β-mercaptoethanol, sonicated in an ice bath, boiled for 5 min, and finally briefly centrifuged to remove particulates. Proteins were resolved on a denaturing 4-20% gradient Tris-HCl gel and then transferred onto a polyvinylidene difluoride membrane by semi-dry transfer (BioRad). The membrane was blocked in tris-buffered saline with 0.1% TWEEN® (TBS-T) and 5% skim milk for 2 h at room temperature with gentle shaking. Fresh blocking solution containing primary antibody was added in a 1:1000 dilution. An anti-CTB polyclonal antibody conjugated to horseradish peroxidase (HRP) (Pierce, PA1-85293) was used to detect RbmA-CTB in cell pellets and native CTB in supernatants. Rabbit-derived serum raised against both the A and B subunits of cholera toxin (Sigma) was used to detect mmCT. Anti-STa antibody (Fitzgerald Industries, clone 30) was used to detect the R-LT/ST fusion protein. After overnight incubation with primary antibodies, the membrane was washed 3 times with TBS-T. For anti-CT and anti-STa antibodies, membranes were then incubated for 2 h at room temperature with 1:5,000 diluted HRP-conjugated anti-rabbit secondary antibody (Cell Signaling) or anti-mouse antibody (Sigma). All membranes were developed using an ECL Western blotting substrate (Pierce).

Quantification of R-CTB by densitometry. Known concentrations of purified CTB (List Laboratories) were resolved by SDS-PAGE alongside R-CTB samples and used as standards for quantification. ImageJ was used to generate a standard curve fitted to the intensities of bands corresponding to the CTB standards. Concentration of R-CTB was calculated using the linear portion of the standard curve.

Quantification of R-LT/STa by Enzyme-linked immunosorbent assay (ELISA). Because unconjugated STa cannot be detected by Western blot, the amount of cell-associated R-LTB/STa$^{A14H}$ was determined from whole cell lysates using ELISA. Lysates of R-CTB and R-LTB/STa$^{A14H}$ vaccines were prepared by resuspending whole cells in 50 mM sodium carbonate binding buffer (pH 9.6) and sonicating in an ice bath for 2 min with 15 s burst and 10 s pulse cycles. Duplicate samples of lysates were serially diluted in binding buffer and placed into wells of microtiter plates (Nunc, Maxisorp). Dilutions ranged from 1:2 to 1:128,000. A standard curve was generated with purified STa diluted to 1 µg/mL and serially diluted onto the plate.

The plates were incubated overnight at room temperature, washed three times in phosphate-buffered saline containing 0.1% TWEEN® (PBS-T), and blocked with PBS containing 1% bovine serum albumin (PBS-BSA). Anti-STa antibody diluted to 1 µg/mL in PBS-T containing 0.1% BSA (PBS-T-BSA), added to the plates, and incubated overnight. Plates were washed in PBS-T, incubated for 1 h at 37° C. with goat anti-mouse IgG conjugated to horseradish peroxidase (HRP, 1 µg/mL in PBS-T-BSA) (Bethyl Laboratories). and developed with TMB (3,3',5,5'-tetramethylbenzidine). Absorbance at 650 nm was recorded on a Biorad Benchmark Plus plate reader using a kinetic ELISA protocol.

Quantification of supernatant mmCT by ELISA. The amount of mmCT secreted into the supernatant by the live vaccine suspension was quantified by GM1 ELISA as previously described29. The VcΔctxA(pR-CTB) vaccine was prepared and then incubated at room temperature for 30 min. The cells were collected by centrifuging at 5,000×g for 10 min and 300 µL of the supernatant was removed for quantification. The supernatant of a wild-type strain that does not express mmCT was similarly prepared and used as a negative control.

One hundred ng of bovine monosialoganglioside GM1 (Sigma) in sodium carbonate buffer was added to each well of a % well microtiter plate (Nunc, Maxisorp) incubated overnight at room temperature, and then washed in PBS-T. Serial dilutions of cell-free supernatants in PBS were applied to GM1-coated wells. Purified CTB was prepared in a 1 µg/mL concentration in PBS, and serial dilutions were also applied to GM1-coated wells to generate a standard curve. The plates were incubated overnight at room temperature, washed in PBS-T, and blocked in PBS-BSA. Monoclonal anti-CTB IgG (Fisher, PIMA 183519) diluted to 1 µg/mL in PBS-T-BSA was added to the plates and incubated overnight. The plates were probed with HRP-conjugated goat anti-mouse antibodies (Bethyl Laboratories) and developed as described above.

Immunization and Sample Collection

Animals. Female, 6-8-week old BALB/c mice were used in all immunization experiments. For sublingual immunizations, mice were purchased from Charles River Laboratories and housed in a biosafety level two facility at Boston Children's Hospital with food and water ad libitum. Mice were acclimatized for 5 days. All procedures had been previously approved by the Institutional Animal Care and Use Committee. Animals used for inactivated vaccine immunizations were housed at Cocalico Biologicals.

Orogastric administration of killed, whole cell vaccine. The formalin-inactivated whole cell vaccine was administered by orogastric gavage. Briefly, $5\times10^9$ cells per milliliter of the vaccine was prepared as described above and mixed with an equal volume of 6% sodium bicarbonate and administered immediately. Each inoculation delivered 200 μL of the mixture, corresponding to $5\times10^8$ inactivated cells.

Sublingual administration of live, attenuated vaccine. Mice were anesthetized by intraperitoneal injection with a cocktail of ketamine (100 mg/kg) and xylazine (10 mg/kg), then held upright while 10 μL of the vaccine was delivered under the tongue by a micropipette directed toward the floor of the mouth. Mice were maintained in the upright position for 2 min before resting, ventral side down, for at least 30 min until regaining consciousness.

Collection of blood and stool samples. Blood and stool samples were collected one day before vaccination and at the designated time points throughout the study period. Fresh stool pellets were frozen at −80° C. until use. Blood was collected from the tail vein using capillary tubes with clot activator (Sarstedt). Sera were obtained by clearing the clotted blood with centrifugation at 10,000×g for 5 min at room temperature and stored at −20° C. Stool samples were prepared as previously described29. Briefly, pellets were thawed on ice, transferred to 15-mL conical tubes containing 3 mL of chilled resuspension solution (0.1 mg/mL soybean trypsin inhibitor, 3:1 mixture of PBS to 0.1 M EDTA), thoroughly homogenized, and centrifuged at 650×g for 10 min at room temperature. The supernatant was collected and centrifuged once more at 15,300×g for 10 min at 4° C. PMSF (phenylmethane sulfonyl fluoride) was added to the supernatant to a final concentration of 2 mM. Stool samples were kept at −20° C., or at −80° C., for long term storage.

Enumeration of *V. cholerae* in fecal pellets. A fresh stool pellet was collected from each mouse 24 h and 48 h after sublingual immunization. The pellet was weighed, homogenized in 1 mL sterile PBS, and serially diluted. One hundred μl of the undiluted and diluted stool suspensions were plated on LB agar containing 100 μg/mL streptomycin and incubated at 37° C. overnight. The number of colony forming units (CFU) was recorded and normalized to the weight of the pellet to calculate CFU per gram stool. Because 1/10 of the total stool suspension was plated containing approximately 22.7 mg stool/ml, the lower limit of detection was estimated to be approximately 440 CFU/g.

Enzyme-Linked Immunosorbent Assays

Quantification of CTB- and LTB-specific antibodies by ELISA. CTB and LTB are more than 80% identical at the amino acid level and share the same mechanism of action. Anti-LTB and anti-CTB antibodies recognize both proteins. Therefore, we used the same ELISA protocol, described below, to measure anti-CTB and anti-LTB antibodies.

Standard curve: IgA anti-CTB IgA antibodies were not available for use in a standard curve. Therefore, to assess linearity, standard curves were generated by capturing IgA and IgG in reference mouse serum with goat anti-mouse IgG or IgA. Microtiter plate wells were incubated overnight with 100 μg of goat anti-mouse IgG or IgA diluted in sodium carbonate buffer. The wells were washed in PBS-T and blocked with PBS-BSA. Reference mouse serum (Bethyl Laboratory) was diluted to 1 μg/mL of total IgG or IgA and applied to the wells. The wells were washed after overnight incubation, then probed with HRP-conjugated goat anti-mouse antibodies and developed as described above for quantification of mmCT.

Test samples: Microtiter plates were coated with GM1 followed by purified CTB as described above. The plates were blocked in PBS-BSA and washed in PBS-T. Serially diluted sera or stool samples were applied to the wells and incubated overnight. Serum dilutions ranged from 1:50 to 1:6400, and stool dilutions ranged from 1:2 to 1:128. The plates were probed and developed as described above.

Quantification of STa-specific antibodies by ELISA. Antibodies to STa in the sera and stool were measured using the protocol described for CTB-specific antibodies using microtiter plates coated with 100 ng/mL of purified STa in sodium carbonate buffer in each well. Standard curves were generated using the procedure described above.

Quantification of total stool IgA by ELISA. Total fecal IgA was used to normalize antigen-specific IgA in the stool. Each well of a microtiter plate was coated with 100 ng of goat anti-mouse IgA antibody in sodium bicarbonate buffer and incubated overnight. Plates were washed in PBS-T and blocked in PBS-BSA. Stool samples were serially diluted from 1:200 to 1:25,600 in PBS-T-BSA and added to the plates. The plates were incubated overnight and then probed and developed as described above. Standard curves were generated as described for CTB/LTB-specific antibodies.

Lipopolysaccharide extraction and O-antigen (LPS) specific antibodies. Lipopolysaccharide (LPS) was extracted from 50 mL of *Vibrio cholerae* MO10 (serotype O139) and N16961 (serotype O1) overnight cultures using a commercial kit (Bulldog Bio). Serum and stool antibodies recognizing the O-antigen of lipopolysaccharide were quantified as previously described30. A 1:1,000 dilution of LPS in sodium carbonate buffer was applied to microtiter plates and incubated overnight. The plates were washed in PBS-T and blocked for 40 min at 37° C. in PBS-BSA. Serum and stool samples were applied to the plates in dilutions similar to those used to measure CTB-specific antibodies. The plates were incubated for 90 min at 37° C. and then washed in PBS-T. Plates were incubated for 90 min at 37° C. after addition of 100 ng of HRP-conjugated goat anti-mouse antibodies per well. Plates were developed using the same protocol described for quantification of CTB-specific antibodies.

Serum Vibriocidal Titers.

Serum vibriocidal antibody titers were determined as previously described with the following modifications31. Immunized mouse sera were incubating at 56° C., for 1 h to inactivate endogenous complement, serially diluted two-fold in PBS in 0.5-μL tubes, and kept on ice. Wild-type MO10 was grown to mid-logarithmic phase in brain heart infusion broth containing 100 μg/mL streptomycin and diluted in PBS containing 20% guinea pig complement to $4\times10^6$ CFU/mL. An equal volume of this suspension was added to the serum dilutions to obtain a final concentration of 10% complement and $2\times10^6$ CFU/mL *V. cholerae*, the mixture was incubated for 1 h at 37° C. with shaking at 200 rpm, and viable cells were enumerated by plating. Bactericidal titer was determined as the reciprocal of the serum dilution capable of killing 50% or more of the indicator strain compared with a control containing pre-immune or PBS-immunized serum. Sera from mice that received the inactivated vaccine were randomly pooled into groups of three for determination of vibriocidal titers.

Infant Mouse Challenge Model

Orogastric challenge of infant mice. At the end of the study period (between 60 to 70 days after the initial immunization), vaccinated female mice were mated with age-matched male. Non-vaccinated, non-timed pregnant mice were purchased from Charles River Laboratories and housed in the same facility as vaccinated mice. When pups were born, wild-type MO10 was grown overnight in LB broth with 100 µg/mL streptomycin at 27° C. The cell density was adjusted to 5×10$^9$ CFU/mL. Bacteria were collected by centrifugation at 6,000×g for 5 min and resuspended in 2.5% sodium bicarbonate (0.29 M). Four- to five-day-old pups were challenged with 2.5×10$^7$ CFU of wild-type MO10 delivered in 50 µL of sodium bicarbonate solution by oral gavage. Pups were monitored for immediate signs of distress and then returned to the dam. All pups were sacrificed 24 h after infection, and signs of disease were documented.

Quantification of bacterial colonization. The small and large intestines were weighed, added to sterile conical tubes containing 1 mL of PBS, and homogenized. The homogenates were serially spread plated on LB agar supplemented with 100 µg/mL of streptomycin. Plates were incubated overnight at 37° C. The limit of detection for each spread plate is 10 CFU per intestine.

Statistical analysis. Statistical analyses were performed in GraphPad Prism 7. Two-tailed Mann-Whitney rank-sum test was used. All vaccine groups consisted of ten mice. Error bars indicate standard deviations unless otherwise noted. Western blot images are representative of experimental triplicates.

REFERENCES

1. Kotloff, K. L. et al. Burden and aetiology of diarrhoeal disease in infants and young children in developing countries (the Global Enteric Multicenter Study, GEMS): a prospective, case-control study. The Lancet 382, 209-222 (2013).
2. Absalon, C., Ymele-Leki, P. & Watnick, P. I. The bacterial biofilm matrix as a platform for protein delivery. mBio 3, e00127-00112-e00127-00112 (2012).
3. Larena. M., Holmgren, J., Lebens, M., Terrinoni, M. & Lundgren, A. Cholera toxin, and the related nontoxic adjuvants mmCT and dmLT, promote human Th17 responses via cyclic AMP-protein kinase A and inflammasome-dependent IL-1 signaling. The Journal of Immunology 194, 3829-3839 (2015).
4. Lebens, M. et al. Construction and preclinical evaluation of mmCT, a novel mutant cholera toxin adjuvant that can be efficiently produced in genetically manipulated *Vibrio cholerae*. Vaccine 34, 2121-2128 (2016).
5. Fong, J. C. N., Karplus, K., Schoolnik, G. K. & Yildiz, F. H. Identification and characterization of RbmA, a novel protein required for the development of rugose colony morphology and biofilm structure in *Vibrio cholerae*. Journal of Bacteriology 188, 1049-1059 (2006).
6. Absalon, C., van Dellen, K. & Watnick, P. I. A communal bacterial adhesin anchors biofilm and bystander cells to surfaces. PLoS Pathogens 7, e1002210. (2011).
7. Giglio, K. M., Fong, J. C., Yildiz, F. H. & Sondermann, H. Structural basis for biofilm formation via the *Vibrio cholerae* matrix protein RbmA. Journal of Bacteriology 195, 3277-3286(2013).
8. Smith, D. R. et al. In situ proteolysis of the *Vibrio cholerae* matrix protein RbmA promotes biofilm recruitment. Proceedings of the National Academy of Sciences 112, 10491-10496 (2015).
9. Aguilar, P. V. et al. Formalin inactivation of Japanese encephalitis virus vaccine alters the antigenicity and immunogenicity of a neutralization epitope in envelope protein domain III. PLOS Neglected Tropical Diseases 9, e0004167 (2015).
10. Perez, J. L. et al. Passive protection of serum from volunteers inoculated with attenuated strain 638 of *Vibrio cholerae* 01 in animal models. Vaccine 19, 376-384 (2001).
11. Talavera. A. et al. Process development for a Cuban cholera vaccine based on the attenuated strain *Vibrio cholerae* 638. Vaccine 24, 3746-3749 (2006).
12. Chen, W. H. et al. Single-dose live oral cholera vaccine CVD 103-HgR protects against human experimental infection with *Vibrio cholerae* O1 El Tor. Clin Infect Dis 62, 1329-1335 (2016).
13. Waldor, M. K. & Mekalanos, J. Lysogenic conversion by a filamentous phage encoding cholera toxin. Science 272, 1910-1914 (1996).
14. Bishop, A. L., Schild. S., Patimalla, B., Klein, B. & Camilli, A. Mucosal immunization with *Vibrio cholerae* outer membrane vesicles provides material protection mediated by antilipopolysaccharide antibodies that inhibit bacterial motility. Infection and Immunity 78, 4402-4420 (2010).
15. Benitez. J. A. et al. Preliminary assessment of the safety and immunogenicity of a new CTXf-negative, hemagglutinin/protease-defective El Tor strain as a cholera vaccine candidate. Infection and Immunity 67, 539-545 (1999).
16. Losonsky, G. A., Tacket, C. O., Wasserman, S. S., Kaper, J. B. & Levine, M. M. Secondary *Vibrio cholerae*-specific cellular antibody responses following wild-type homologous challenge in people vaccinated with CVD 103-HgR live oral cholera vaccine: changes with time and lack of correlation with protection. Infection and Immunity 61, 729-733(1993).
17. Svennerholm, A. M. Experimental studies on cholera immunization 4. The antibody response to formalized *Vibrio cholerae* and purified endotoxin with special reference to protective capacity. International Archives of Allergy and Immunology 49, 434-452 (1975).
18. Guentzel, M. N. & Berry, L. J. Protection of suckling mice from experimental cholera by maternal immunization: comparison of the efficacy of whole-cell, ribosomal-derived, and enterotoxin immunogens. Infection and Immunity 10, 167-172 (1974).
19. Sengupta, D. K., Boesman-Finkelstein, M. & Finkelstein, R. A. Antibody against the capsule of *Vibrio cholerae O*139 protects against experimental challenge Infection and Immunity 64, 343-345 (1996).
20. Ferreira, P. C. D. et al. Immunization of mice with *Lactobacillus casei* expressing a beta-intimin fragment reduces intestinal colonization by *Citrobacter rodentium*. Clinical and Vaccine Immunology 18, 1823-1833 (2011).
21. Waldor, M. K. & Mekalanos, J. J. Emergence of a new cholera pandemic: molecular analysis of virulence determinants in *Vibrio cholerae O*139 and development of a live vaccine prototype. The Journal of Infectious Diseases 170, 278-283 (1994).
22. Taxt, A. M. et al. Towards rational design of a toxoid vaccine against the heat-stable toxin of *Escherichia coli*. Infection and Immunity 84, 1239-1249 (2016).
23. Ruan, X., Robertson. D. C., Nataro, J. P., Clements, J. D. & Zhang, W. Characterization of heat-stable (STa) toxoids of enterotoxigenic *Escherichia coli* fused to double mutant heat-labile toxin peptide in inducing neutralizing anti-STa antibodies. Infection and Immunity 82, 1823-1832 (2014).

24. Liu, M. et al. Modified heat-stable toxins (hSTa) of enterotoxigenic *Escherichia coli* lose toxicity but display antigenicity after being genetically fused to heat-labile toxoid LT(R192G). Toxins 3, 1146-1162 (2011).
25. Zhang, C. et al. Toxicity and immunogenicity of enterotoxigenic *Escherichia coli* heat-labile and heat-stable toxoid fusion $3\times ST^{A14Q}$-LTS63K/R192G/L211A in a murine model. PLoS ONE 8, e77386 (2013).
26. Metcalf, W. W. et al. Conditionally replicative and conjugative plasmids carrying lacZa for cloning, mutagenesis, and allele replacement in bacteria. Plasmid 35, 1-13 (1996).
27. Butterton, J. R. et al. Heterologous antigen expression in *Vibrio cholerae* vector strains. Infection and Immunity 63, 2689-2696 (1995).
28. Clements, J. D. Construction of a nontoxic fusion peptide for immunization against *Escherichia coli* strains that produce heat-labile and heat-stable enterotoxins. Infection and Immunity 58, 1159-1166 (1990).
29. Ryan, E. T. et al. Oral immunization with attenuated vaccine strains of *Vibrio cholerae* expressing a dodecapeptide repeat of the serine-rich *Entamoeba histolytica* protein fused to the cholera toxin B subunit induces systemic and mucosal antiamebic and anti-*V. cholerae* antibody responses in mice. Infect Immun 65, 3118-3125 (1997).
30. Rollenhagen, J. E. et al. Transcutaneous immunization with a synthetic hexasaccharide-protein conjugate induces anti-*Vibrio cholerae* lipopolysaccharide responses in mice. Vaccine 27, 4917-4922 (2009).
31. Qadri, F. et al. Comparison of the vibriocidal antibody response in cholera due to *Vibrio cholerae* O139 Bengal with the response in cholera due to *Vibrio cholerae* O1. Clin Diagn Lab Immunol 2, 685-688 (1995).

All publications, patents, patent applications, publication, and database entries (e.g., sequence database entries) mentioned herein, e.g., in the Background, Summary, Detailed Description, Examples, and/or References sections, are hereby incorporated by reference in their entirety as if each individual publication, patent, patent application, publication, and database entry was specifically and individually incorporated herein by reference. In case of conflict, the present application, including any definitions herein, will control.

EQUIVALENTS AND SCOPE

Those skilled in the art will recognize, or be able to ascertain using no more than routine experimentation, many equivalents of the embodiments described herein. The scope of the present disclosure is not intended to be limited to the above description, but rather is as set forth in the appended claims.

Articles such as "a," "an," and "the" may mean one or more than one unless indicated to the contrary or otherwise evident from the context. Claims or descriptions that include "or" between two or more members of a group are considered satisfied if one, more than one, or all of the group members are present, unless indicated to the contrary or otherwise evident from the context. The disclosure of a group that includes "or" between two or more group members provides embodiments in which exactly one member of the group is present, embodiments in which more than one members of the group are present, and embodiments in which all of the group members are present. For purposes of brevity those embodiments have not been individually spelled out herein, but it will be understood that each of these embodiments is provided herein and may be specifically claimed or disclaimed.

It is to be understood that the disclosure encompasses all variations, combinations, and permutations in which one or more limitation, element, clause, or descriptive term, from one or more of the claims or from one or more relevant portion of the description, is introduced into another claim. For example, a claim that is dependent on another claim can be modified to include one or more of the limitations found in any other claim that is dependent on the same base claim. Furthermore, where the claims recite a composition, it is to be understood that methods of making or using the composition according to any of the methods of making or using disclosed herein or according to methods known in the art, if any, are included, unless otherwise indicated or unless it would be evident to one of ordinary skill in the art that a contradiction or inconsistency would arise.

Where elements are presented as lists, e.g., in Markush group format, it is to be understood that every possible subgroup of the elements is also disclosed, and that any element or subgroup of elements can be removed from the group. It is also noted that the term "comprising" is intended to be open and permits the inclusion of additional elements or steps. It should be understood that, in general, where an embodiment, product, or method is referred to as comprising particular elements, features, or steps, embodiments, products, or methods that consist, or consist essentially of, such elements, features, or steps, are provided as well. For purposes of brevity those embodiments have not been individually spelled out herein, but it will be understood that each of these embodiments is provided herein and may be specifically claimed or disclaimed.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in some embodiments, to the tenth of the unit of the lower limit of the range, unless the context clearly dictates otherwise. For purposes of brevity, the values in each range have not been individually spelled out herein, but it will be understood that each of these values is provided herein and may be specifically claimed or disclaimed. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

Where websites are provided, URL addresses are provided as non-browser-executable codes, with periods of the respective web address in parentheses. The actual web addresses do not contain the parentheses.

In addition, it is to be understood that any particular embodiment of the present disclosure may be explicitly excluded from any one or more of the claims. Where ranges are given, any value within the range may explicitly be excluded from any one or more of the claims. Any embodiment, element, feature, application, or aspect of the compositions and/or methods of the disclosure, can be excluded from any one or more claims. For purposes of brevity, all of the embodiments in which one or more elements, features, purposes, or aspects is excluded are not set forth explicitly herein.

What is claimed is:

1. A composition comprising
   (i) a *Vibrio cholerae* that produces an exopolysaccharide;
   (ii) a RbmA protein comprising the amino acid sequence of SEQ ID NO: 2 with amino acids at one or more of positions R234, R219, or R116 substituted with a non-polar amino acid; and (iii) a heterologous protein antigen conjugated or fused to the RbmA protein.

2. The composition of claim 1, wherein the heterologous protein antigen is fused to the RbmA protein thus forming a fusion protein.

3. The composition of claim 1, wherein the one or more amino acid substitutions are selected from the group consisting of R234A, R219A, or R116A.

4. A composition comprising (i) a RbmA protein comprising the amino acid sequence of SEQ ID NO: 2 with amino acids at one or more of positions R234, R219, or R116 substituted with a non-polar amino acid; and (ii) a heterologous protein antigen conjugated to the RbmA protein.

5. The composition of claim 1, which is an immunogenic composition.

6. The immunogenic composition of claim 5, wherein the exopolysaccharide is an exopolysaccharide secreted by the *Vibrio cholerae*, the exopolysaccharide is bound by the *Vibrio cholerae*, and/or the heterologous protein antigen conjugated or fused to the RbmA protein is bound by the exoolysaccharide.

7. The immunogenic composition of claim 5, further comprising an adjuvant.

8. The immunogenic composition of claim 7, wherein the adjuvant is a Cholera toxin subunit A (CtxA) variant comprising mutations N189D, A190S, P191S, R192G, S193T, S194I, M195T, S196G, N197I, N197D, or L211A in SEQ ID NO: 46.

9. The immunogenic composition of claim 5, wherein the *Vibrio cholerae* is live attenuated or killed whole cell.

10. A bacterial biofilm comprising the composition of claim 1.

11. The immunogenic composition of claim 5, wherein the heterologous protein antigen is a protein antigen of a pathogen.

12. A method of eliciting an immune response in a mammalian subject against a pathogen, the method comprising administering to the subject an amount of the immunogenic composition of claim 11 sufficient to elicit an immune response to the heterologous protein antigen of the pathogen in the subject.

* * * * *

UNITED STATES PATENT AND TRADEMARK OFFICE
CERTIFICATE OF CORRECTION

PATENT NO. : 11,071,779 B2  
APPLICATION NO. : 16/310544  
DATED : July 27, 2021  
INVENTOR(S) : Paula I. Watnick et al.

Page 1 of 1

It is certified that error appears in the above-identified patent and that said Letters Patent is hereby corrected as shown below:

In the Claims

At Column 156, Line 62, Claim 6, the word "cholerae" should read --cholera--

At Column 156, Line 63, Claim 6, the word "cholerae" should read --cholera--

At Column 156, Line 65, Claim 6, the word "exoolysaccharide" should read --exopolysaccharide--

At Column 157, Line 4, Claim 8, "S1941" should read --S194I--

At Column 157, Line 4, Claim 8, "N1971" should read --N197I--

At Column 157, Line 7, Claim 9, the word "cholerae" should read --cholera--

Signed and Sealed this  
Sixteenth Day of November, 2021

Drew Hirshfeld  
*Performing the Functions and Duties of the  
Under Secretary of Commerce for Intellectual Property and  
Director of the United States Patent and Trademark Office*